United States Patent
Orimoto et al.

(10) Patent No.: US 11,490,622 B2
(45) Date of Patent: Nov. 8, 2022

(54) SUBSTITUTED HETEROCYCLES AS HARMFUL ARTHROPOD CONTROLLING AGENTS

(71) Applicant: SUMITOMO CHEMICAL COMPANY, LIMITED, Chuo-ku (JP)

(72) Inventors: Kohei Orimoto, Takarazuka (JP); Yuji Nakajima, Takarazuka (JP); Risa Kono, Chuo-ku (JP); Ryota Maehata, Takarazuka (JP); Masayuki Tashiro, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 82 days.

(21) Appl. No.: 16/954,871

(22) PCT Filed: Dec. 21, 2018

(86) PCT No.: PCT/JP2018/047243
§ 371 (c)(1),
(2) Date: Jun. 17, 2020

(87) PCT Pub. No.: WO2019/124548
PCT Pub. Date: Jun. 27, 2019

(65) Prior Publication Data
US 2021/0084903 A1    Mar. 25, 2021

(30) Foreign Application Priority Data

Dec. 22, 2017 (JP) .............................. JP2017-245959
Aug. 9, 2018 (JP) .............................. JP2018-150184

(51) Int. Cl.

| | | |
|---|---|---|
| A61K 31/4184 | (2006.01) | |
| A61K 31/4188 | (2006.01) | |
| C07D 403/02 | (2006.01) | |
| C07D 417/02 | (2006.01) | |
| A01N 43/90 | (2006.01) | |
| A01C 1/06 | (2006.01) | |
| A01N 25/00 | (2006.01) | |
| A01N 25/04 | (2006.01) | |
| A01N 25/06 | (2006.01) | |
| A01N 25/10 | (2006.01) | |
| A01N 25/12 | (2006.01) | |
| A01N 25/18 | (2006.01) | |
| A61K 9/00 | (2006.01) | |
| C07D 471/04 | (2006.01) | |
| C07D 487/04 | (2006.01) | |
| C07D 513/04 | (2006.01) | |

(52) U.S. Cl.
CPC .............. *A01N 43/90* (2013.01); *A01C 1/06* (2013.01); *A01N 25/002* (2013.01); *A01N 25/04* (2013.01);
(Continued)

(58) Field of Classification Search
CPC ............ A61K 31/4184; A61K 31/4188; C07D 403/02; C07D 417/02
(Continued)

(56) References Cited

U.S. PATENT DOCUMENTS

| | | |
|---|---|---|
| 2017/0267672 A1 | 9/2017 | Andrew et al. |
| 2018/0022760 A1 | 1/2018 | Masaki et al. |
| 2019/0127328 A1 | 5/2019 | Orimoto et al. |

FOREIGN PATENT DOCUMENTS

| | | |
|---|---|---|
| CN | 106604922 A | 4/2017 |
| CN | 107074781 A | 8/2017 |

(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
(Continued)

*Primary Examiner* — Douglas M Willis
(74) *Attorney, Agent, or Firm* — Oblon, McClelland, Maier & Neustadt, L.L.P.

(57) ABSTRACT

The present invention provides a compound substituted with an excellent control effect against a harmful arthropod, which is represented by formula (I)

Het-Q    (I)

wherein Q represents a group represented by Q1, etc., Het represents a group represented by Het1, etc., $R^2$ represents a C1-C6 alkyl group, etc., $G^1$ represents a nitrogen atom or $CR^{3a}$, $G^2$ represents a nitrogen atom or $CR^{3b}$, $G^3$ represents a nitrogen atom or $CR^{3c}$, $G^4$ represents a nitrogen atom or $CR^{3d}$, $R^{3a}$, $R^{3b}$, $R^{3c}$, and $R^{3d}$ are identical to or different from each other and represent a C1-C6 chain hydrocarbon group, etc., n represents 0, 1, or 2, T represents a C1-C10 chain hydrocarbon group substituted with one or more halogen atoms, etc., $A^2$ represents a nitrogen atom or $CR^{4a}$, $A^3$ represents a nitrogen atom or $CR^{4b}$, $R^{4a}$ and $R^{4b}$ are identical to or different from each other and represent a C1-C6 chain hydrocarbon group, $W^1$ represents an oxygen atom, etc., and $R^6$ represents a C1-C6 chain hydrocarbon group, etc.

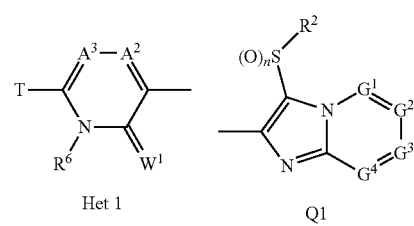

18 Claims, No Drawings

(52) U.S. Cl.
CPC ............ *A01N 25/06* (2013.01); *A01N 25/10* (2013.01); *A01N 25/12* (2013.01); *A01N 25/18* (2013.01); *A61K 9/0056* (2013.01); *C07D 471/04* (2013.01); *C07D 487/04* (2013.01); *C07D 513/04* (2013.01)

(58) Field of Classification Search
USPC ...................................... 514/393; 548/302.7
See application file for complete search history.

(56) References Cited

FOREIGN PATENT DOCUMENTS

| | | |
|---|---|---|
| CN | 107207506 A | 9/2017 |
| EP | 2 862 853 A1 | 4/2015 |
| EP | 3 257 853 A1 | 12/2017 |
| JP | 2017-36339 A | 2/2017 |
| WO | WO 2016/030229 A1 | 3/2016 |
| WO | WO 2016/129684 A1 | 8/2016 |
| WO | WO 2017/050654 A1 | 6/2017 |
| WO | WO 2017/175613 A1 | 10/2017 |
| WO | WO-2019124548 A1 * | 6/2019 ............... A01C 1/06 |

OTHER PUBLICATIONS

Office Action dated Nov. 12, 2021 in corresponding Indian Patent Application No. 202047024764 (with English Translation), 6 pages.
International Search Report dated Mar. 12, 2019 in PCT/JP2018/047243, citing documents AP-AR therein, 1 page.
International Preliminary Report on Patentability and Written Opinion dated Jun. 23, 2020 in PCT/JP2018/047243, citing documents AP-AR therein, 4 pages.
Combined Chinese Office Action and Search Report dated Jul. 20, 2021 in Chinese Patent Application No. 201880089069.2 (with English translation), citing documents AO through AR therein, 16 pages.
Extended European Search Report dated Oct. 6, 2021 in European Patent Application No. 18891596.1, citing documents AO and AP therein, 6 pages.

* cited by examiner

SUBSTITUTED HETEROCYCLES AS HARMFUL ARTHROPOD CONTROLLING AGENTS

CROSS REFERENCE TO RELATED APPLICATION

This application is a National Stage entry under 35 USC 371 of PCT/JP2018/047243, filed on Dec. 21, 2018, and claims priority to Japanese Patent Application No. 2018-150184, filed on August 9, 2018, and Japanese Patent Application No. 2017-245959, filed on Dec. 22, 2017, the entire contents of which are incorporated herein by reference.

TECHNICAL FIELD

This application claims priorities to and the benefits of Japanese Patent Application No. 2017-245959 filed on Dec. 22, 2017 and Japanese Patent Application No. 2018-150184 filed on Aug. 9, 2018 the entire contents of which are incorporated herein by reference.

The present invention relates to a certain type of heterocyclic compounds and an agent for controlling harmful arthropods comprising said compound.

BACKGROUND ART

To date, some compounds for controlling harmful arthropods have been developed and come into practical use.

Further, it is known that a certain type of compounds has an efficacy for controlling harmful arthropods (see, for example, Patent Document 1).

CITATION LIST

Patent Document

Patent Document 1: WO 2016/129684

SUMMARY OF THE INVENTION

Problems to be Solved by Invention

An object of the present invention is to provide a compound that has an excellent efficacy for controlling harmful arthropods.

DETAILED DESCRIPTION OF THE INVENTION

The present invention is as follows.

[1] A compound represented by formula (I):

Het-Q     (I)

wherein,

Q represents a group represented by Q1, a group represented by Q2, or a group represented by Q3,

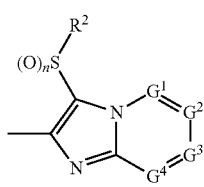
Q1

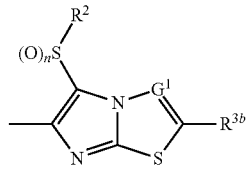
Q2

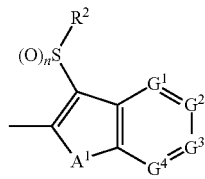
Q3

$R^2$ represents a C1-C6 alkyl group optionally substituted with one or more halogen atoms, a cyclopropyl group, or a cyclopropylmethyl group, n represents 0, 1, or 2,
$G^1$ represents a nitrogen atom or $CR^{3a}$,
$G^2$ represents a nitrogen atom or $CR^{3b}$,
$G^3$ represents a nitrogen atom or $CR^{3c}$,
$G^4$ represents a nitrogen atom or $CR^{3d}$,
$R^{3a}$, $R^{3b}$, $R^{3c}$, and $R^{3d}$ are identical to or different from each other and represent a C1-C6 chain hydrocarbon group optionally substituted with one or more substituents selected from Group B, a C3-C7 cycloalkyl group optionally substituted with one or more substituents selected from Group E, a phenyl group optionally substituted with one or more substituents selected from Group H, a 5 or 6 membered aromatic heterocyclic group optionally substituted with one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{11}R^{32}$, $NR^{24}NR^{11}C(O)NR^{31}R^{32}$, $N=CHNR^{31}R^{32}$, $N=S(O)_pR^{15}R^{16}$, $C(O)R^{13}$, $C(O)OR^{17}$, $C(O)NR^{31}R^{32}$, $C(O)NR^{11}S(O)_2R^{23}$, $CR^{30}=NOR^{17}$, $NR^{11}CR^{24}=NOR^{17}$, a cyano group, a nitro group, a hydrogen atom, or a halogen atom, p represents 0 or 1,
$A^1$ represents $NR^5$, an oxygen atom, or a sulfur atom,
Het represents a group represented by Het1, a group represented by Het2, or a group represented by Het3,

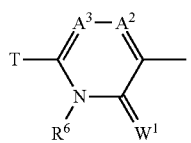
Het1

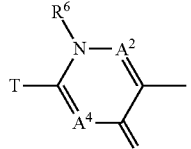
Het2

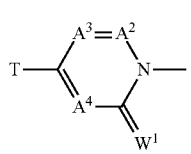
Het3

$A^2$ represents a nitrogen atom or $CR^{4a}$, $A^3$ represents a nitrogen atom or $CR^{4b}$, $A^4$ represents a nitrogen atom or $CR^{4c}$, $W^1$ represents an oxygen atom or a sulfur atom, $R^{4a}$, $R^{4b}$, and $R^{4c}$ are identical to or different from each other and represent a C1-C6 chain hydrocarbon group optionally substituted with one or more halogen atoms, a nitro group, $OR^{18}$, $NR^{18}R^{19}$, a cyano group, an amino group, a halogen atom, or a hydrogen atom, $R^6$ represents a C1-C6 chain hydrocarbon group optionally substituted with one or more substituents selected from Group F, a C3-C6 cycloalkyl group optionally substituted with one or more substituents selected from Group J, a phenyl group optionally substituted with one or more substituents selected from Group H, or a 5 or 6 membered aromatic heterocyclic group optionally substituted with one or more substituents selected from Group H, T represents a C1-C10 chain hydrocarbon group; a (C1-C5 alkoxy)C2-C5 alkyl group; a (C3-C5 alkenyloxy)C2-C5 alkyl group; a (C3-C5 alkynyloxy)C2-C5 alkyl group; a (C1-C5 alkyl)-S(O)$_w$—(C2-C5 alkyl) group; a (C3-C5 alkenyl)-S(O)$_w$—(C2-C5 alkyl) group; a (C3-C5 alkynyl)-S(O)$_w$—(C2-C5 alkyl) group; a (C1-C5 alkyl)-C(O)—(C1-C5 alkyl) group (wherein the C1-C10 chain hydrocarbon group, the (C1-C5 alkoxy)C2-C5 alkyl group, the (C3-C5 alkenyloxy)C2-C5 alkyl group, the (C3-C5 alkynyloxy)C2-C5 alkyl group, the (C1-C5 alkyl)-S(O)$_w$—(C2-C5 alkyl) group, the (C3-C5 alkenyl)-S(O)$_w$—(C2-C5 alkyl) group, the (C3-C5 alkynyl)-S(O)$_w$—(C2-C5 alkyl) group, and the (C1-C5 alkyl)-C(O)—(C1-C5 alkyl) group are substituted with one or more substituents selected from the group consisting of a cyano group and a halogen atom}; a (C3-C7 cycloalkyl)C1-C3 alkyl group substituted with one or more substituents selected from Group G; a C3-C7 cycloalkyl group substituted with one or more substituents selected from Group G; $OR^1$; $S(O)_vR^1$; $OS(O)_2R^1$; $CH_2OR^1$; $NR^1R^{29}$; $C(O)R^1$; $C(O)NR^1R^{29}$; $NR^{29}C(O)R^1$; $N=CR^1R^{30}$; a group represented by T-1; a group represented by T-2; a group represented by T-3; a group represented by T-4; a group represented by T-5; a group represented by T-6; a group represented by T-7; a group represented by T-8; a group represented by T-9; a group represented by T-10; a group represented by T-11; or a group represented by T-12:

T-1

T-2

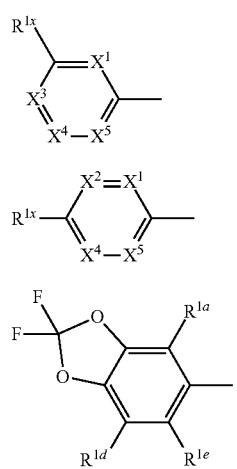

T-3

T-4

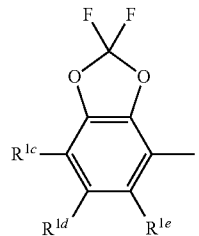

T-5

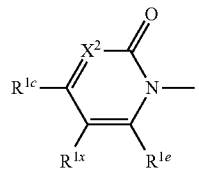

T-6

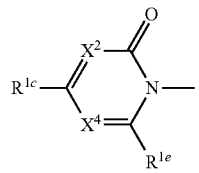

T-7

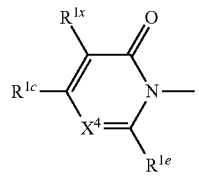

T-8

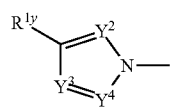

T-9

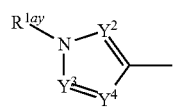

T-10

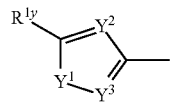

T-11

T-12

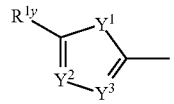

$X^1$ represents a nitrogen atom or $CR^{1a}$, $X^2$ represents a nitrogen atom or $CR^{1b}$, $X^3$ represents a nitrogen atom or $CR^{1c}$, $X^4$ represents a nitrogen atom or $CR^{1d}$, $X^5$ represents a nitrogen atom or $CR^{1e}$, $R^{1x}$ represents a C1-C5 chain hydrocarbon group substituted with one or more halogen atoms, $OR^7$, $OS(O)_2R^7$, $S(O)_2R^7$, $NR^8S(O)_2R^7$, or a halogen atom, $R^{1a}$, $R^{1b}$, $R^{1c}$, $R^{1d}$, and $R^{1e}$ are identical to or different from each other and represent a C1-C6 chain hydrocarbon group optionally substituted with one or more halogen atoms, a C3-C6 cycloalkyl group optionally substituted with one or more halogen atoms, a halogen atom, or a hydrogen atom, $Y^1$ represents $NR^{25}$, an oxygen atom, or a sulfur atom, $Y^2$ represents a nitrogen atom or $CR^{28}$ $Y^3$ represents a nitrogen atom or $CR^{27}$, $Y^4$ represents a nitrogen atom or $CR^{28}$, $R^5$ and $R^{25}$ are identical to or different from each other and represent a C1-C6 chain hydrocarbon group optionally substituted with one or more halogen atoms, a C1-C6 alkoxy group optionally substituted with one or more halogen atoms, a C3-C7 cycloalkyl group optionally substituted with one or more halogen atoms, a (C3-C7 cycloalkyl)C1-C6 alkyl group optionally substituted with one or more halogen atoms, or a hydrogen atom, $R^{26}$, $R^{27}$, and $R^{28}$ are identical to or different from each other and represent a C1-C6 chain hydrocarbon group optionally substituted with one or more halogen atoms, a C3-C6 cycloalkyl group optionally substituted with one or more halogen atoms, a halogen atom, or a hydrogen atom, $R^{1y}$ represents a C1-C5 chain hydrocarbon group substituted with one or more halogen atoms, $OR^7$, $OS(O)_2R^7$, $S(O)_mR^7$, $NR^8S(O)_2R^7$, a cyano group, or a halogen atom, $R^{1ay}$ and $R^7$ are identical to or different from each other and represent a C1-C6 chain hydrocarbon group substituted with one or more halogen atoms, m and v are identical to or different from each other and represent 0, 1, or 2, w and t are identical to or different from each other and represent 0, 1, or 2, $R^1$ represents a C1-C10 chain hydrocarbon group; a (C1-C5 alkoxy)C2-C5 alkyl group; a (C3-C5 alkenyloxy)C2-C5 alkyl group; a (C3-C5 alkynyloxy)C2-C5 alkyl group; a (C1-C5 alkyl)-S(O)$_t$—(C2-C5 alkyl) group; a (C3-C5 alkenyl)-S(O)$_t$—(C2-C5 alkyl) group; a (C3-C5 alkynyl)-S(O)$_t$—(C2-C5 alkyl) group; a (C1-C5 alkyl)-C(O)—(C1-C5 alkyl) group (wherein the C1-C10 chain hydrocarbon group, the (C1-C5 alkoxy)C2-C5 alkyl group, the (C3-C5 alkenyloxy)C2-C5 alkyl group, the (C3-C5 alkynyloxy)C2-C5 alkyl group, the (C1-C5 alkyl)-S(O)$_t$—(C2-C5 alkyl) group, the (C3-C5 alkenyl)-S(O)$_t$—(C2-C5 alkyl) group, the (C3-C5 alkynyl)-S(O)$_t$—(C2-C5 alkyl) group, and the (C1-C5 alkyl)-C(O)—(C1-C5 alkyl) group are substituted with one or more substituents selected from the group consisting of a cyano group and a halogen atom}; a (C3-C7 cycloalkyl)C1-C3 alkyl group substituted with one or more substituents selected from Group G; or a C3-C7 cycloalkyl group substituted with one or more substituents selected from Group G, $R^{30}$ represents a C1-C6 chain hydrocarbon group optionally substituted with one or more halogen atoms, a halogen atom, $OR^{35}$, $NR^{36}R^{37}$, or a hydrogen atom, $R^{18}$ and $R^{35}$ are identical to or different from each other and represent a C1-C6 chain hydrocarbon group optionally substituted with one or more halogen atoms, $R^{17}$ represents a C1-C6 chain hydrocarbon group optionally substituted with one or more halogen atoms, a phenyl group optionally substituted with one or more substituents selected from Group D, or a hydrogen atom, $R^8$, $R^{11}$, $R^{19}$, $R^{24}$, $R^{29}$, $R^{36}$, and $R^{37}$ are identical to or different from each other and represent a C1-C6 chain hydrocarbon group optionally substituted with one or more halogen atoms, or a hydrogen atom, $R^{12}$ represents a C1-C6 chain hydrocarbon group optionally substituted with one or more halogen atoms, a C1-C6 chain hydrocarbon group optionally substituted with one or more substituents selected from Group F, a C3-C7 cycloalkyl group optionally substituted with one or more substituents selected from Group J, a C3-C7 cycloalkenyl group optionally substituted with one or more substituents selected from Group J, a phenyl group optionally substituted with one or more substituents selected from Group D, a 6 membered aromatic heterocyclic group optionally substituted with one or more substituents selected from Group D, a hydrogen atom, or $S(O)_2R^{23}$, $R^{23}$ represents a C1-C6 chain hydrocarbon group optionally substituted with one or more halogen atoms, or a phenyl group optionally substituted with one or more substituents selected from Group D, $R^{11a}$ and $R^{12a}$ are taken together with the nitrogen atom to which they are attached to form a 3 to 7 membered non-aromatic heterocyclic group optionally substituted with one or more substituents selected from Group E, $R^{13}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, a 5 or 6 membered aromatic heterocyclic group optionally substituted with one or more substituents selected from Group D, or a hydrogen atom, $R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenyl C1-C3 alkyl group wherein the phenyl moiety in the phenyl C1-C3 alkyl group may optionally be substituted with one or more substituents selected from Group D, $R^{15}$ and $R^{16}$ are identical to or different from each other and represent a C1-C6 alkyl group optionally substituted with one or more halogen atoms, $R^{31}$ represents a C1-C6 alkyl group optionally substituted with one or more halogen atoms, or a hydrogen atom, $R^{32}$ represents a C1-C6 chain hydrocarbon group optionally substituted with one or more substituents selected from Group F, a C3-C7 cycloalkyl group optionally substituted with one or more substituents selected from Group J, $S(O)_2R^{23}$, or a hydrogen atom, Group B: the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, a hydroxy group, and a halogen atom, Group C: the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom, Group D: the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, an amino group, $NHR^{21}$, $NR^{21}R^{22}$, $C(O)R^2$, $OC(O)R^{21}$, $C(O)OR^{21}$, a cyano group, a nitro group, and a halogen atom, wherein $R^{21}$ and $R^{22}$ are identical to or different from each other and represent a C1-C6 alkyl group optionally substituted with one or more halogen atoms, Group E: the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group, Group F: the group consisting of a C1-C6 alkoxy group optionally substituted with one or more halogen atoms, a phenyl group optionally substituted with one or more substituents selected from Group D, a 5 or 6 membered aromatic heterocyclic group optionally substituted with one or more substituents selected from Group D, a C3-C7 cycloalkyl group optionally substituted with one or more halogen atoms, a 3 to 7 membered nonaromatic heterocyclic group optionally substituted with one or more substituents selected from Group C, an amino group, $NHR^{21}$, $NR^{21}R^{22}$, a halogen atom, and a cyano group, Group G: the group consisting of a halogen atom, a C1-C6 haloalkyl group, and a cyano group, Group H: the group consisting of a C1-C6 alkyl group optionally substituted with one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, an amino group, and a 5 or 6 membered aromatic heterocyclic group, wherein $R^9$ represents a C1-C6 alkyl group optionally substituted with one or more halogen atoms, or a C3-C6 cycloalkyl group optionally substituted with one or more halogen atoms, $R^{10}$ represents a C1-C6 alkyl group optionally substituted with one or more halogen atoms, a C3-C6 cycloalkyl group optionally substituted with one or more halogen atoms, or a hydrogen atom, Group J: the group consisting of a C1-C6 alkyl group optionally substituted with one or more halogen atoms, a halogen atom, and a cyano group, or its N-oxide compound (hereinafter, a compound represented by formula (I) or its N-oxide compound is referred to as "present compound X").

[2] The compound according to [1], wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, $OR^1$, $S(O)_xR^1$, $OS(O)_2R^1$, $CH_2OR^1$, $NR^1R^{29}$, $C(O)R^1$, $C(O)NR^1R^{29}$, $NR^{29}C(O)R^1$, $N=CR^1R^{30}$, a group represented by T-1, a group represented by T-2, a group represented by T-3, a group represented by T-4, a group represented by T-5, a group represented by T-6, a group represented by T-7, a group represented by T-8, a group represented by T-9, a group represented by T-10, a group represented by T-11, or a group represented by T-12, $R^1$ represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, or a C3-C7 cycloalkyl group substituted with one or more substituents selected from Group G, Group F is the group consisting of a C1-C6 alkoxy group optionally substituted with one or more halogen atoms, a phenyl group optionally substituted with one or more substituents selected from Group D, a 5 or 6 membered aromatic heterocyclic group optionally substituted with one or more substituents selected from Group D, a C3-C7 cycloalkyl group optionally substituted with one or more halogen atoms, a 3 to 7 membered nonaromatic heterocyclic group optionally substituted with one or more substituents selected from Group C, an amino group, $NHR^{21}$, $NR^{21}R^{22}$, and a cyano group, Group G is the group consisting of a halogen atom and a C1-C6 haloalkyl group (hereinafter, referred to as "present compound").

[3] The compound according to [1] or [2], wherein Q represents a group represented by Q1 or a group represented by Q2.

[4] The compound according to [1] or [2], wherein Q represents a group represented by Q1.

[5] The compound according to any one of [1] to [4], wherein Het represents a group represented by Het1 or a group represented by Het2.

[6] The compound according to any one of [1] to [4], wherein Het represents a group represented by Het1, $A^2$ represents $CR^{4a}$, $A^3$ represents $CR^{4b}$.

[7] The compound according to any one of [1] to [4], wherein Het represents a group represented by Het1, $A^2$ represents $CR^{4a}$, $A^3$ represents a nitrogen atom.

[8] The compound according to any one of [1] to [7], wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, $OR^1$, $S(O)_xR^1$, $OS(O)_2R^1$, or $NR^1R^{29}$.

[9] The compound according to any one of [1] to [7], wherein T represents $OR^1$, $R^1$ represents a C1-C5 alkyl group substituted with three or more fluorine atoms.

[10] The compound according to any one of [1] to [9], wherein $R^{3a}$, $R^{3b}$, $R^{3c}$, and $R^{3d}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a phenyl group; a pyridyl group; a pyrimidinyl group {wherein the phenyl group, the pyridyl group, and the pyrimidinyl group may be substituted with one or more substituents selected from Group J}; $OR^{12}$; $CR^{30}=NOR^{17}$; a hydrogen atom; or a halogen atom, $R^{4a}$, $R^{4b}$, and $R^{4c}$ are identical to or different from each other and represent a C1-C3 alkyl group, $OR^{18}$, a cyano group, a halogen atom, or a hydrogen atom, $R^{18}$ represents a C1-C3 alkyl group.

[11] The compound according to any one of [1] to [9], wherein $G^1$ represents a nitrogen atom or CH, $G^2$ represents $CR^{3b}$, $G^3$ represents $CR^{3c}$, $G^4$ represents CH, $R^{3b}$ and $R^{3c}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; $OR^{12}$; a hydrogen atom; or a halogen atom, $R^{4a}$, $R^{4b}$, and $R^{4c}$ represent a hydrogen atom.

[12] The compound according to any one of [1] to [9], wherein $G^1$ represents a nitrogen atom or CH, $G^2$ represents $CR^{3b}$, $G^3$ represents $CR^{3c}$, $G^4$ represents CH, $R^{3b}$ and $R^{3c}$ are identical to or different from each other and represent a C1-C6 alkyl group optionally substituted with one or more halogen atoms, or a hydrogen atom.

[13] The compound according to any one of [1] to [12], wherein $R^2$ represents an ethyl group.

[14] A composition for controlling a harmful arthropod, comprising the compound according to any one of [1] to [13], and an inert carrier.

[15] A method for controlling a harmful arthropod, which comprises applying an effective amount of the compound according to any one of [1] to [13] to a harmful arthropod or a habitat where the harmful arthropod lives.

[16] A composition, comprising one or more ingredients selected from the group consisting of Group (a) and Group (b), and the compound according to any one of [1] to [13]:

Group (a): the group consisting of an insecticidal ingredient, a miticidal ingredient, and a nematicidal ingredient;
Group (b): a fungicidal ingredient.

[17] A method for controlling a harmful arthropod, which comprises applying an effective amount of the composition according to [14] or [16] to a harmful arthropod or a habitat where the harmful arthropod lives.

[18] A seed or vegetative reproductive organ carrying an effective amount of the compound according to any one of [1] to [13] or an effective amount of the composition according to [14] or [16].

[19] A compound represented by formula (X)

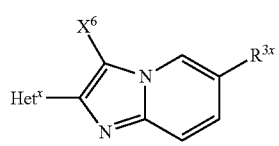

(X)

wherein,
$X^6$ represents a chlorine atom, a bromine atom, an iodine atom, or a hydrogen atom,
$R^{3x}$ represents a chlorine atom, a bromine atom, or an iodine atom, $Het^x$ represents a group represented by Het4, a group represented by Het5, or a group represented by Het6,

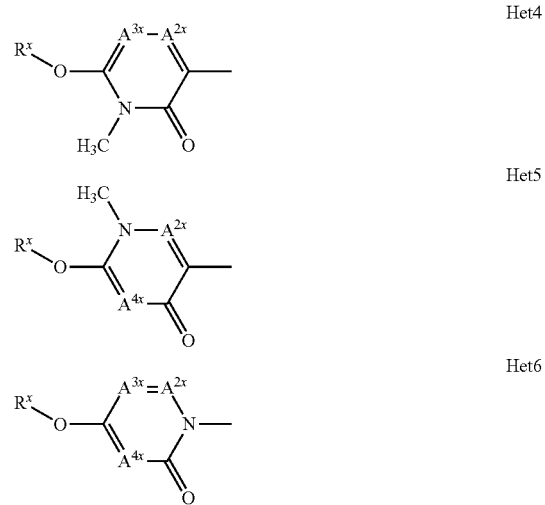

$A^{2x}$ represents a nitrogen atom or CH,
$A^{3x}$ represents a nitrogen atom or CH,
$A^{4x}$ represents a nitrogen atom or CH,
$R^x$ represents a C1-C5 alkyl group substituted with three or more fluorine atoms.

A compound represented by formula (Y)

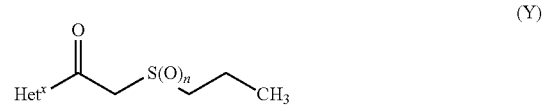

(Y)

wherein,
n represents, 0, 1, or 2,
$Het^x$ represents a group represented by Het4, a group represented by Het5, or a group represented by Het6,

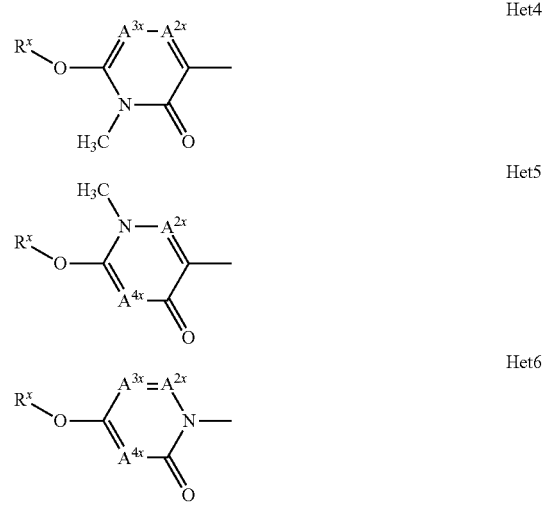

$A^{2x}$ represents a nitrogen atom or CH,
$A^{3x}$ represents a nitrogen atom or CH, $A^{4x}$ represents a nitrogen atom or CH, $R^x$ represents a C1-C5 alkyl group substituted with three or more fluorine atoms.

Effect of Invention

The present compound can control harmful arthropods.

MODE FOR CARRYING OUT THE INVENTION

The groups as used herein are explained as follows.

The term "halogen atom" represents a fluorine atom, a chlorine atom, a bromine atom, or an iodine atom.

When a substituent has two or more halogen atoms, the halogen atoms may be identical to or different from each other.

The expression "CX-CY" as used herein represents that the number of carbon atoms is from X to Y. For example, the expression "C1-C6" represents that the number of carbon atoms is from 1 to 6.

The term "chain hydrocarbon group" represents an alkyl group, an alkenyl group, or an alkynyl group.

Examples of the alkyl group include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group, hexyl group, octyl group, nonyl group, and decyl group.

Examples of the alkenyl group include vinyl group, 1-propenyl group, 2-propenyl group, 1-methyl-1-propenyl group, 1-methyl-2-propenyl group, 1,2-dimethyl-1-propenyl group, 1-ethyl-2-propenyl group, 3-butenyl group, 4-pentenyl group, 5-hexenyl group, 7-octenyl group, nonenyl group, and decenyl group.

Examples of the alkynyl group include ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, 5-hexynyl group, 7-octynyl group, nonynyl group, and decynyl group.

Examples of the haloalkyl group include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Examples of the alkoxy group include methoxy group, ethoxy group, isopropoxy group, 1,1-dimethylpropoxy group, 1,2-dimethylpropoxy group, 1-ethylpropoxy group, 1-butoxy group, tert-butoxy group, pentoxy group, hexyloxy group, heptyloxy group, octyloxy group, nonyloxy group, decyloxy group, and benzyloxy group.

Examples of the cycloalkyl group include cyclopropyl group, cyclobutyl group, cyclopentyl group, cyclohexyl group, and cycloheptyl group.

Examples of the cycloalkenyl group include cyclopropenyl group, cyclobutenyl group, cyclopentenyl group, cyclohexenyl group, and cycloheptenyl group.

The "3 to 7 membered nonaromatic heterocyclic group" represents aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxadinane ring, morpholine ring, 1,4-oxazepane ring, thiazolidine ring, isothiazolidine ring, 1,3-thiazinane ring, thiomorpholine ring, or 1,4-thiazepane ring. Examples of the "3 to 7 membered nonaromatic heterocyclic group optionally substituted with one or more substituents selected from Group E" include the groups as shown below.

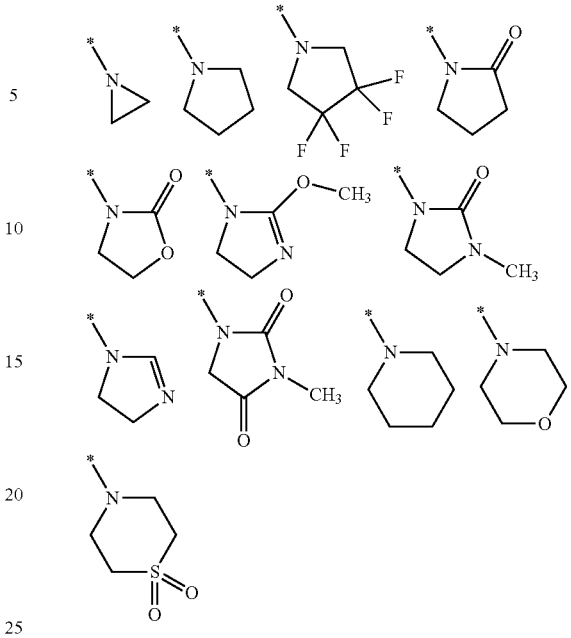

The "(C1-C5 alkoxy)C2-C5 alkyl group substituted with one or more halogen atoms" represents a group wherein the (C1-C5 alkoxy) and/or (C2-C5 alkyl) have one or more halogen atoms, and includes, for example, 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The "(C1-C5 alkylsulfanyl)C2-C5 alkyl group substituted with one or more halogen atoms" represents a group wherein the (C1-C5 alkylsulfanyl) and/or (C2-C5 alkyl) have one or more halogen atoms, and includes, for example, 2,2-difluoro-2-(trifluoromethylthio)ethyl group.

The "(C1-C5 alkylsulfinyl)C2-C5 alkyl group substituted with one or more halogen atoms" represents a group wherein the (C1-C5 alkylsulfinyl) and/or (C2-C5 alkyl) have one or more halogen atoms, and includes, for example, 2,2-difluoro-2-(trifluoromethanesulfinyl)ethyl group.

The "(C1-C5 alkylsulfonyl)C2-C5 alkyl group substituted with one or more halogen atoms" represents a group wherein the (C1-C5 alkylsulfonyl) and/or (C2-C5 alkyl) have one or more halogen atoms, and includes, for example, 2,2-difluoro-2-(trifluoromethanesulfonyl)ethyl group.

The "(C3-C7 cycloalkyl)C1-C6 alkyl group optionally substituted with one or more halogen atoms" represents a group wherein the (C3-C7 cycloalkyl) and/or (C1-C6 alkyl) may optionally have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The "(C3-C6 cycloalkyl)C1-C3 alkyl group optionally substituted with one or more halogen atoms" represents a group wherein the (C3-C6 cycloalkyl) and/or (C1-C3 alkyl) may optionally have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The "(C3-C7 cycloalkyl)C1-C3 alkyl group substituted with one or more substituents selected from Group G" represents a group wherein the (C3-C7 cycloalkyl) and/or (C1-C3 alkyl) have one or more substituents selected from Group G, and includes, for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

Examples of the "phenyl C1-C3 alkyl group wherein the phenyl moiety in the phenyl C1-C3 alkyl group may optionally have one or more substituents selected from Group D" include benzyl group, 2-fluorobenzyl group, 4-chlorobenzyl group, 4-(trifluoromethyl)benzyl group, and 2-[4-(trifluoromethyl)phenyl]ethyl group.

The "5 or 6 membered aromatic heterocyclic group" represents a 5 membered aromatic heterocyclic group or a 6 membered aromatic heterocyclic group, and the "5 membered aromatic heterocyclic group" represents pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, or thiadiazolyl group. The "6 membered aromatic heterocyclic group" represents pyridyl group, pyridazinyl group, pyrimidinyl group, pyrazinyl group, triazinyl group, or tetrazinyl group.

Examples of the alkylsulfanyl group include methylsulfanyl group, ethylsulfanyl group, propylsulfanyl group, and isopropylsulfanyl group.

Examples of the alkylsulfinyl group include methylsulfinyl group, ethylsulfinyl group, propylsulfinyl group, and isopropylsulfinyl group.

Examples of the alkylsulfonyl group include methylsulfonyl group, ethylsulfonyl group, propylsulfonyl group, and isopropylsulfonyl group The present compound may have one or more stereoisomer(s). Examples of the stereoisomer include enantiomer, diastereomer, and geometric isomer, etc. The present compound includes its each stereoisomer and a mixture of stereoisomers in any ratio.

The present compound may form an acid addition salt. Examples of an acid to form the acid addition salt include inorganic acids such as hydrogen chloride, phosphoric acid and sulfuric acid, and organic acids such as acetic acid, trifluoroacetic acid, benzoic acid and p-toluenesulfonic acid. The acid addition salt can be prepared by mixing the present compound with the acid.

Embodiments of the present compound include the following compounds.

Embodiment 1

The present compound, wherein $R^2$ represents a C1-C6 alkyl group optionally substituted with one or more halogen atoms, $R^{3a}$, $R^{3b}$, $R^{3c}$, and $R^{3d}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano atom}; a phenyl group; a pyridyl group; a pyrimidinyl group {wherein the phenyl group, the pyridyl group, and the pyrimidinyl group may be substituted with one or more substituents selected from Group J}; $OR^{12}$; $CR^{30}=NOR^{17}$; a hydrogen atom; or a halogen atom, $R^{4a}$, $R^{4b}$, and $R^{4c}$ are identical to or different from each other and represent a halogen atom or a hydrogen atom, $W^1$ represents an oxygen atom, $R^6$ represents a C1-C6 chain hydrocarbon group optionally substituted with one or more substituents from Group F.

Embodiment 2

The compound according to Embodiment 1, wherein Q represents a group represented by Q1, or a group represented by Q2.

Embodiment 3

The compound according to Embodiment 1, wherein Q represents a group represented by Q1.

Embodiment 4

The present compound, wherein $R^2$ represents an ethyl group, $R^{4a}$, $R^{4b}$, and $R^{4c}$ represent a hydrogen atom, $W^1$ represents an oxygen atom, $R^6$ represents a methyl group or an ethyl group.

Embodiment 5

The compound according to Embodiment 4, wherein Q represents a group represented by Q1, $R^{3a}$, $R^{3b}$, $R^{3c}$, and $R^{3d}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a hydrogen atom; or a halogen atom.

Embodiment 6

The compound according to Embodiment 4, wherein Q represents a group represented by Q1, $G^1$ represents a nitrogen atom or CH, $G^2$ represents $CR^{3b}$, $G^3$ represents $CR^{3c}$, $G^4$ represents CH, $R^{3b}$ and $R^{3c}$ are identical to or different from each other and represent a C1-C6 alkyl group optionally substituted with one or more halogen atoms, or a halogen atom.

Embodiment 7

The compound according to Embodiment 4, wherein Q represents a group represented by Q1, $G^1$ represents CH, $G^2$ represents $CR^{3b}$, $G^3$ represents $CR^{3c}$, $G^4$ represents CH, $R^{3b}$ and $R^{3c}$ are identical to or different from each other and represent a C1-C6 alkyl group optionally substituted with one or more halogen atoms, or a halogen atom.

Embodiment 8

The compound according to Embodiment 4, wherein Q represents a group represented by Q1, $G^1$ represents a nitrogen atom or CH, $G^2$ represents $CR^{3b}$, $G^3$ and $G^4$ represent CH, $R^{3b}$ represents a C1-C6 alkyl group substituted with three or more fluorine atoms.

Embodiment 9

The compound according to Embodiment 4, wherein Q represents a group represented by Q1, $G^1$ represents CH, $G^2$ represents $CR^{3b}$, $G^3$ and $G^4$ represent CH, $R^{3b}$ represents a C1-C6 alkyl group substituted with three or more fluorine atoms.

Embodiment 10

The compound according to Embodiment 4, wherein Q represents a group represented by Q2, $R^{3a}$ and $R^{3b}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a hydrogen atom; or a halogen atom.

Embodiment 11

The compound according to Embodiment 4, wherein Q represents a group represented by Q3, $R^{3a}$, $R^{3b}$, $R^{3c}$, and $R^{3d}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a hydrogen atom; or a halogen atom.

Embodiment 12

The present compound, wherein Het represents a group represented by Het1, or a group represented by Het2.

Embodiment 13

The compound according to Embodiment 1, wherein Het represents a group represented by Het1, or a group represented by Het2.

Embodiment 14

The compound according to Embodiment 2, wherein Het represents a group represented by Het1, or a group represented by Het2.

Embodiment 15

The compound according to Embodiment 3, wherein Het represents a group represented by Het1, or a group represented by Het2.

Embodiment 16

The compound according to Embodiment 4, wherein Het represents a group represented by Het1, or a group represented by Het2.

Embodiment 17

The compound according to Embodiment 5, wherein Het represents a group represented by Het1, or a group represented by Het2.

Embodiment 18

The compound according to Embodiment 6, wherein Het represents a group represented by Het1, or a group represented by Het2.

Embodiment 19

The compound according to Embodiment 7, wherein Het represents a group represented by Het1, or a group represented by Het2.

Embodiment 20

The compound according to Embodiment 8, wherein Het represents a group represented by Het1, or a group represented by Het2.

Embodiment 21

The compound according to Embodiment 9, wherein Het represents a group represented by Het1, or a group represented by Het2.

Embodiment 22

The compound according to Embodiment 10, wherein Het represents a group represented by Het1, or a group represented by Het2.

Embodiment 23

The compound according to Embodiment 11, wherein Het represents a group represented by Het1, or a group represented by Het2.

Embodiment 24

The present compound, wherein Het represents a group represented by Het1.

Embodiment 25

The compound according to Embodiment 1, wherein Het represents a group represented by Het1.

Embodiment 26

The compound according to Embodiment 2, wherein Het represents a group represented by Het1.

Embodiment 27

The compound according to Embodiment 3, wherein Het represents a group represented by Het1.

Embodiment 28

The compound according to Embodiment 4, wherein Het represents a group represented by Het1.

Embodiment 29

The compound according to Embodiment 5, wherein Het represents a group represented by Het1.

Embodiment 30

The compound according to Embodiment 6, wherein Het represents a group represented by Het1.

Embodiment 31

The compound according to Embodiment 7, wherein Het represents a group represented by Het1.

Embodiment 32

The compound according to Embodiment 8, wherein Het represents a group represented by Het1.

Embodiment 33

The compound according to Embodiment 9, wherein Het represents a group represented by Het1.

Embodiment 34

The compound according to Embodiment 10, wherein Het represents a group represented by Het1.

Embodiment 35

The compound according to Embodiment 11, wherein Het represents a group represented by Het1.

Embodiment 36

A present compound, wherein Het represents a group represented by Het1, $A^2$ represents $CR^{4a}$, $A^3$ represents a nitrogen atom or $CR^{4b}$.

Embodiment 37

The compound according to Embodiment 1, wherein Het represents a group represented by Het1, $A^2$ represents $CR^{4a}$, $A^3$ represents a nitrogen atom or $CR^{4b}$.

Embodiment 38

The compound according to Embodiment 2, wherein Het represents a group represented by Het1, $A^2$ represents $CR^{4a}$, $A^3$ represents a nitrogen atom or $CR^{4b}$.

Embodiment 39

The compound according to Embodiment 3, wherein Het represents a group represented by Het1, $A^2$ represents $CR^{4a}$, $A^3$ represents a nitrogen atom or $CR^{4b}$.

Embodiment 40

The compound according to Embodiment 4, wherein Het represents a group represented by Het1, $A^2$ represents $CR^{4a}$, $A^3$ represents a nitrogen atom or $CR^{4b}$.

Embodiment 41

The compound according to Embodiment 5, wherein Het represents a group represented by Het1, $A^2$ represents $CR^{4a}$, $A^3$ represents a nitrogen atom or $CR^{4b}$.

Embodiment 42

The compound according to Embodiment 6, wherein Het represents a group represented by Het1, $A^2$ represents $CR^{4a}$, $A^3$ represents a nitrogen atom or $CR^{4b}$.

Embodiment 43

The compound according to Embodiment 7, wherein Het represents a group represented by Het1, $A^2$ represents $CR^{4a}$, $A^3$ represents a nitrogen atom or $CR^{4b}$.

Embodiment 44

The compound according to Embodiment 8, wherein Het represents a group represented by Het1, $A^2$ represents $CR^{4a}$, $A^3$ represents a nitrogen atom or $CR^{4b}$.

Embodiment 45

The compound according to Embodiment 9, wherein Het represents a group represented by Het1, $A^2$ represents $CR^{4a}$, $A^3$ represents a nitrogen atom or $CR^{4b}$.

Embodiment 46

The compound according to Embodiment 10, wherein Het represents a group represented by Het1, $A^2$ represents $CR^{4a}$, $A^3$ represents a nitrogen atom or $CR^{4b}$.

Embodiment 47

The compound according to Embodiment 11, wherein Het represents a group represented by Het1, $A^2$ represents $CR^{4a}$, $A^3$ represents a nitrogen atom or $CR^{4b}$.

Embodiment 48

The present compound, wherein Het represents a group represented by Het1, $A^2$ represents $CR^{4a}$, $A^3$ represents $CR^{4b}$.

Embodiment 49

The compound according to Embodiment 1, wherein Het represents a group represented by Het1, $A^2$ represents $CR^{4a}$, $A^3$ represents $CR^{4b}$.

Embodiment 50

The compound according to Embodiment 2, wherein Het represents a group represented by Het1, $A^2$ represents $CR^{4a}$, $A^3$ represents $CR^{4b}$.

Embodiment 51

The compound according to Embodiment 3, wherein Het represents a group represented by Het1, $A^2$ represents $CR^{4a}$, $A^3$ represents $CR^{4b}$.

Embodiment 52

The compound according to Embodiment 4, wherein Het represents a group represented by Het1, $A^2$ represents $CR^{4a}$, $A^3$ represents $CR^{4b}$.

Embodiment 53

The compound according to Embodiment 5, wherein Het represents a group represented by Het1, $A^2$ represents $CR^{4a}$, $A^3$ represents $CR^{4b}$.

Embodiment 54

The compound according to Embodiment 6, wherein Het represents a group represented by Het1, $A^2$ represents $CR^{4a}$, $A^3$ represents $CR^{4b}$.

Embodiment 55

The compound according to Embodiment 7, wherein Het represents a group represented by Het1, $A^2$ represents $CR^{4a}$, $A^3$ represents $CR^{4b}$.

Embodiment 56

The compound according to Embodiment 8, wherein Het represents a group represented by Het1, $A^2$ represents $CR^{4a}$, $A^3$ represents $CR^{4b}$.

Embodiment 57

The compound according to Embodiment 9, wherein Het represents a group represented by Het1, $A^2$ represents $CR^{4a}$, $A^3$ represents $CR^{4b}$

Embodiment 58

The compound according to Embodiment 10, wherein Het represents a group represented by Het1, $A^2$ represents $CR^{4a}$, $A^3$ represents $CR^{4b}$.

Embodiment 59

The compound according to Embodiment 11, wherein Het represents a group represented by Het1, $A^2$ represents $CR^{4a}$, $A^3$ represents $CR^{4b}$.

Embodiment 60

The present compound, wherein Het represents a group represented by Het1, $A^2$ represents $CR^{4a}$, $A^3$ represents a nitrogen atom.

Embodiment 61

The compound according to Embodiment 1, wherein Het represents a group represented by Het1, $A^2$ represents $CR^{4a}$, $A^3$ represents a nitrogen atom.

Embodiment 62

The compound according to Embodiment 2, wherein Het represents a group represented by Het1, $A^2$ represents $CR^{4a}$, $A^3$ represents a nitrogen atom.

Embodiment 63

The compound according to Embodiment 3, wherein Het represents a group represented by Het1, $A^2$ represents $CR^{4}$, $A^3$ represents a nitrogen atom.

Embodiment 64

The compound according to Embodiment 4, wherein Het represents a group represented by Het1, $A^2$ represents $CR^{4a}$, $A^3$ represents a nitrogen atom.

Embodiment 65

The compound according to Embodiment 5, wherein Het represents a group represented by Het1, $A^2$ represents $CR^{4a}$, $A^3$ represents a nitrogen atom.

Embodiment 66

The compound according to Embodiment 6, wherein Het represents a group represented by Het1, $A^2$ represents $CR^{4a}$, $A^3$ represents a nitrogen atom.

Embodiment 67

The compound according to Embodiment 7, wherein Het represents a group represented by Het1, $A^2$ represents $CR^4a$ $A^3$ represents a nitrogen atom.

Embodiment 68

The compound according to Embodiment 8, wherein Het represents a group represented by Het1, $A^2$ represents $CR^{4a}$, $A^3$ represents a nitrogen atom.

Embodiment 69

The compound according to Embodiment 9, wherein Het represents a group represented by Het1, $A^2$ represents $CR^{4a}$, $A^3$ represents a nitrogen atom.

Embodiment 70

The compound according to Embodiment 10, wherein Het represents a group represented by Het1, $A^2$ represents $CR^{4a}$, $A^3$ represents a nitrogen atom.

Embodiment 71

The compound according to Embodiment 11, wherein Het represents a group represented by Het1, $A^2$ represents $CR^{4a}$, $A^3$ represents a nitrogen atom.

Embodiment 72

The present compound, wherein Het represents a group represented by Het2.

Embodiment 73

The compound according to Embodiment 2, wherein Het represents a group represented by Het2.

Embodiment 74

The compound according to Embodiment 3, wherein Het represents a group represented by Het2.

Embodiment 75

The compound according to Embodiment 5, wherein Het represents a group represented by Het2.

Embodiment 76

The compound according to Embodiment 10, wherein Het represents a group represented by Het2.

Embodiment 77

The compound according to Embodiment 11, wherein Het represents a group represented by Het2.

Embodiment 78

The present compound, wherein Het represents a group represented by Het2, $A^2$ represents $CR^{4a}$. $A^4$ represents $CR^{4c}$.

Embodiment 79

The compound according to Embodiment 2, wherein Het represents a group represented by Het2, $A^2$ represents $CR^{4a}$, $A^4$ represents $CR^{4c}$.

Embodiment 80

The compound according to Embodiment 3, wherein Het represents a group represented by Het2, $A^2$ represents $CR^{4a}$, $A^4$ represents $CR^{4c}$.

Embodiment 81

The compound according to Embodiment 5, wherein Het represents a group represented by Het2, $A^2$ represents $CR^{4a}$, $A^4$ represents $CR^{4c}$.

Embodiment 82

The compound according to Embodiment 10, wherein Het represents a group represented by Het2, $A^2$ represents $CR^{4a}$, $A^4$ represents $CR^{4c}$.

Embodiment 83

The compound according to Embodiment 11, wherein Het represents a group represented by Het2, $A^2$ represents $CR^{4a}$, $A^4$ represents $CR^{4c}$.

Embodiment 84

The present compound, wherein Het represents a group represented by Het2, $A^2$ represents $CR^{4a}$, $A^4$ represents a nitrogen atom.

Embodiment 85

The compound according to Embodiment 2, wherein Het represents a group represented by Het2, $A^2$ represents $CR^{4a}$, $A^4$ represents a nitrogen atom.

Embodiment 86

The compound according to Embodiment 3, wherein Het represents a group represented by Het2, $A^2$ represents $CR^{4a}$, $A^4$ represents a nitrogen atom.

Embodiment 87

The compound according to Embodiment 5, wherein Het represents a group represented by Het2, $A^2$ represents $CR^{4a}$, $A^4$ represents a nitrogen atom.

Embodiment 88

The compound according to Embodiment 10, wherein Het represents a group represented by Het2, $A^2$ represents $CR^{4a}$, $A^4$ represents a nitrogen atom.

Embodiment 89

The compound according to Embodiment 11, wherein Het represents a group represented by Het2, $A^2$ represents $CR^{4a}$, $A^4$ represents a nitrogen atom.

Embodiment 90

The present compound, wherein Het represents a group represented by Het3.

Embodiment 91

The compound according to Embodiment 2, wherein Het represents a group represented by Het3.

Embodiment 92

The compound according to Embodiment 3, wherein Het represents a group represented by Het3.

Embodiment 93

The compound according to Embodiment 5, wherein Het represents a group represented by Het3.

Embodiment 94

The compound according to Embodiment 10, wherein Het represents a group represented by Het3.

Embodiment 95

The compound according to Embodiment 11, wherein Het represents a group represented by Het3.

Embodiment 96

The present compound, wherein Het represents a group represented by Het3, $A^2$ represents $CR^{4a}$, $A^3$ represents a nitrogen or $CR^{4b}$, $A^4$ represents $CR^{4c}$.

Embodiment 97

The compound according to Embodiment 2, wherein Het represents a group represented by Het3, $A^2$ represents $CR^{4a}$, $A^3$ represents a nitrogen or $CR^{4b}$, $A^4$ represents $CR^{4c}$.

Embodiment 98

The compound according to Embodiment 3, wherein Het represents a group represented by Het3, $A^2$ represents $CR^{4a}$, $A^3$ represents a nitrogen or $CR^{4b}$, $A^4$ represents $CR^{4c}$.

Embodiment 99

The compound according to Embodiment 5, wherein Het represents a group represented by Het3, $A^2$ represents $CR^{4a}$, $A^3$ represents a nitrogen or $CR^{4b}$, $A^4$ represents $CR^{4c}$.

Embodiment 100

The compound according to Embodiment 10, wherein Het represents a group represented by Het3, $A^2$ represents $CR^{4a}$, $A^3$ represents a nitrogen or $CR^{4b}$, $A^4$ represents $CR^4c$.

Embodiment 101

The compound according to Embodiment 11, wherein Het represents a group represented by Het3, $A^2$ represents $CR^{4a}$, $A^3$ represents a nitrogen or $CR^{4b}$, $A^4$ represents $CR^{4c}$.

Embodiment 102

The present compound, wherein Het represents a group represented by Het3, $A^2$ represents $CR^{4a}$, $A^3$ represents $CR^{4b}$, $A^4$ represents $CR^{4c}$.

Embodiment 103

The compound according to Embodiment 2, wherein Het represents a group represented by Het3, $A^2$ represents $CR^{4a}$, $A^3$ represents $CR^{4b}$, $A^4$ represents $CR^{4c}$.

Embodiment 104

The compound according to Embodiment 3, wherein Het represents a group represented by Het3, $A^2$ represents $CR^{4a}$, $A^3$ represents $CR^{4b}$, $A^4$ represents $CR^{4c}$.

Embodiment 105

The compound according to Embodiment 5, wherein Het represents a group represented by Het3, $A^2$ represents $CR^{4a}$, $A^3$ represents $CR^{4b}$, $A^4$ represents $CR^{4c}$.

Embodiment 106

The compound according to Embodiment 10, wherein Het represents a group represented by Het3, $A^2$ represents $CR^{4a}$, $A^3$ represents $CR^{4b}$, $A^4$ represents $CR^{4b}$.

Embodiment 107

The compound according to Embodiment 11, wherein Het represents a group represented by Het3, $A^2$ represents $CR^{4b}$, $A^3$ represents $CR^{4b}$, $A^4$ represents $CR^{4c}$.

Embodiment 108

The present compound, wherein Het represents a group represented by Het3, $A^2$ represents $CR^{4a}$, $A^3$ represents a nitrogen atom, $A^4$ represents $CR^{4c}$.

Embodiment 109

The compound according to Embodiment 2, wherein Het represents a group represented by Het3, $A^2$ represents $CR^{4a}$, $A^3$ represents a nitrogen atom, $A^4$ represents $CR^{4c}$.

Embodiment 110

The compound according to Embodiment 3, wherein Het represents a group represented by Het3, $A^2$ represents $CR^4$, $A^3$ represents a nitrogen atom, $A^4$ represents $CR^{4a}$.

Embodiment 111

The compound according to Embodiment 5, wherein Het represents a group represented by Het3, $A^2$ represents $CR^{4a}$, $A^3$ represents a nitrogen atom, $A^4$ represents $CR^{4c}$.

Embodiment 112

The compound according to Embodiment 10, wherein Het represents a group represented by Het3, $A^2$ represents $CR^{4a}$, $A^3$ represents a nitrogen atom, $A^4$ represents $CR^{4c}$.

Embodiment 113

The compound according to Embodiment 11, wherein Het represents a group represented by Het3, $A^2$ represents $CR^{4a}$, $A^3$ represents a nitrogen atom, $A^4$ represents $CR^{4b}$.

Embodiment 114

The compound according to any of Embodiment 1 to Embodiment 113, wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, $OR^1$, $S(O)_vR^1$, $OS(O)_2R^1$, $NR^1R^{29}$, a group represented by T-1, a group represented by T-2, a group represented by T-3, a group represented by T-4, or a group represented by T-8, $R^1$, $R^{1x}$, and $R^{1y}$ are identical to or different from each other and represent a C1-C5 chain hydrocarbon group substituted with one or more halogen atoms.

Embodiment 115

The compound according to any of Embodiment 1 to Embodiment 113, wherein T represents a group represented by T-1, a group represented by T-2, a group represented by T-3, a group represented by T-4, a group represented by T-5, a group represented by T-6, a group represented by T-7, a group represented by T-8, a group represented by T-9, a group represented by T-10, a group represented by T-11, or a group represented by T-12, $R^{1x}$, $R^{1y}$, and $R^{1ay}$ are identical to or different from each other and represent a C1-C5 chain hydrocarbon group substituted with one or more halogen atoms.

Embodiment 116

The compound according to any of Embodiment 1 to Embodiment 113, wherein T represents a group represented by T-1, a group represented by T-2, a group represented by T-3, a group represented by T-4, or a group represented by T-8, $R^{1x}$ and $R^{1y}$ are identical to or different from each other and represent a C1-C5 alkyl group substituted with three or more fluorine atoms.

Embodiment 117

The compound according to any of Embodiment 1 to Embodiment 113, wherein T represents a group represented by T-1, a group represented by T-2, a group represented by T-3, or a group represented by T-4, $R^1$ represents a C1-C5 alkyl group substituted with three or more fluorine atoms.

Embodiment 118

The compound according to any of Embodiment 1 to Embodiment 113, wherein T represents a group represented by T-8, $R^{1y}$ represents a C1-C5 alkyl group substituted with three or more fluorine atoms.

Embodiment 119

The compound according to any of Embodiment 1 to Embodiment 113, wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, $OR^1$, $S(O)_xR^1$, $OS(O)_2R^1$, or $NR^1R^{29}$, $R^1$ represents a C1-C5 chain hydrocarbon group substituted with one or more halogen atoms.

Embodiment 120

The compound according to any of Embodiment 1 to Embodiment 113, wherein T represents $OR^1$, $R^1$ represents a C1-C5 chain hydrocarbon group substituted with one or more halogen atoms.

Embodiment 121

The compound according to any of Embodiment 1 to Embodiment 113, wherein T represents $OR^1$, $R^1$ represents a C1-C5 alkyl group substituted with three or more fluorine atoms.

Embodiments of the present compound X include the following compounds.

Embodiment 122

The present compound X, wherein Het represents a group represented by Het1, or a group represented by Het2.

Embodiment 123

The compound according to Embodiment 122, wherein $R^2$ represents an ethyl group, $R^{4a}$, $R^{4b}$, and $R^{4c}$ represent a hydrogen atom, $W^1$ represents an oxygen atom, $R^6$ represents a methyl group or an ethyl group.

Embodiment 124

The compound according to Embodiment 123, wherein Q represents a group represented by Q1, or a group represented by Q2.

Embodiment 125

The compound according to Embodiment 124, wherein $R^{3a}$, $R^{3b}$, $R^{3c}$, and $R^{3d}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a hydrogen atom; or a halogen atom.

Embodiment 126

The compound according to Embodiment 124, wherein $G^1$ represents a nitrogen atom or CH, $G^2$ represents $CR^{3b}$, $G^3$ represents $CR^{3c}$, $G^4$ represents CH, $R^{3b}$ and $R^{3c}$ are identical to or different from each other and represent a C1-C6 alkyl group optionally substituted with one or more halogen atoms, or a halogen atom.

Embodiment 127

The compound according to Embodiment 124, wherein $G^1$ represents CH, $G^2$ represents $CR^{3b}$, $G^3$ represents $CR^{3c}$, $G^4$ represents CH, $R^{3b}$ and $R^{3c}$ are identical to or different from each other and represent a C1-C6 alkyl group optionally substituted with one or more halogen atoms, or a halogen atom.

Embodiment 128

The compound according to Embodiment 124, wherein $G^1$ represents a nitrogen atom or CH, $G^2$ represents $CR^{3b}$, $G^3$ and $G^4$ represent CH, $R^{3b}$ represents a C1-C6 alkyl group substituted with three or more fluorine atoms.

Embodiment 129

The compound according to Embodiment 124, wherein $G^1$ represents CH, $G^2$ represents $CR^{3b}$, $G^3$ and $G^4$ represent CH, $R^{3b}$ represents a C1-C6 alkyl group substituted with three or more fluorine atoms.

Embodiment 130

The compound according to Embodiment 124, wherein $G^1$ represents a nitrogen atom or CH, $G^2$ represents $CR^{3b}$, $G^3$ and $G^4$ represent CH, $R^{3b}$ represents a halogen atom.

Embodiment 131

The compound according to Embodiment 129, wherein Q represents a group represented by Q1.

Embodiment 132

The compound according to Embodiment 130, wherein Q represents a group represented by Q1.

Embodiment 133

The compound according to Embodiment 123, wherein Q represents a group represented by Q2, $R^{38}$ and $R^{3b}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a hydrogen atom; or a halogen atom.

Embodiment 134

The compound according to Embodiment 123, wherein Q represents a group represented by Q3, $R^{3a}$, $R^{3b}$, $R^{3c}$, and $R^{3d}$ are identical to or different from each other and represent a C1-C6 alkyl group; a C3-C7 cycloalkyl group {wherein the C1-C6 alkyl group and the C3-C7 cycloalkyl group may be substituted with one or more substituents selected from the group consisting of a halogen atom and a cyano group}; a hydrogen atom; or a halogen atom.

Embodiment 135

The compound according to Embodiment 122, wherein, when Het represents a group represented by Het1, $A^2$

Embodiment 136

The compound according to Embodiment 123, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 137

The compound according to Embodiment 124, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 138

The compound according to Embodiment 125, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 139

The compound according to Embodiment 126, wherein, when Het represents a group represented by Het1, $A^2$ represents $CR^{4a}$, $A^3$ represents a nitrogen atom or $CR^{b}$, when Het represents a group represented by Het2, $A^2$ represents $CR^{4a}$, $A^4$ represents $CR^{4c}$.

Embodiment 140

The compound according to Embodiment 127, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 141

The compound according to Embodiment 128, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 142

The compound according to Embodiment 129, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 143

The compound according to Embodiment 130, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 144

The compound according to Embodiment 131, wherein, when Het represents a group represented by Het1, $A^2$ represents $CR^{4a}$, $A^3$ represents a nitrogen atom or $CR^{b}$, when Het represents a group represented by Het2, $A^2$ represents $CR^{4a}$, $A^4$ represents $CR^{4c}$.

Embodiment 145

The compound according to Embodiment 132, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 146

The compound according to Embodiment 133, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 147

The compound according to Embodiment 134, wherein, when Het represents a group represented by Het1, $A^2$ represents $CR^{4a}$, $A^3$ represents a nitrogen atom or $CR^{4b}$, when Het represents a group represented by Het2, $A^2$ represents $CR^{4a}$, $A^4$ represents $CR^{4c}$.

Embodiment 148

The compound according to any of Embodiment 135 to Embodiment 147, wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, $OR^1$, $S(O)_vR^1$, $OS(O)_2R^1$, $NR^1R^{29}$, a group represented by T-1, a group represented by T-2, a group represented by T-3, a group represented by T-4, or a group represented by T-8, $R^1$, $R^{1x}$, and $R^{1y}$ are identical to or different from each other and represent a C1-C5 chain hydrocarbon group substituted with one or more halogen atoms.

Embodiment 149

The compound according to any of Embodiment 135 to Embodiment 147, wherein T represents a group represented by T-1, a group represented by T-2, a group represented by T-3, a group represented by T-4, a group represented by T-5, a group represented by T-6, a group represented by T-7, a group represented by T-8, a group represented by T-9, a group represented by T-10, a group represented by T-11, or a group represented by T-12, $R^{1x}$, $R^{1y}$, and $R^{1ay}$ are identical to or different from each other and represent a C1-C5 chain hydrocarbon group substituted with one or more halogen atoms.

Embodiment 150

The compound according to any of Embodiment 135 to Embodiment 147, wherein T represents a group represented by T-1, a group represented by T-2, a group represented by T-3, a group represented by T-4, or a group represented by T-8, $R^{1x}$ and $R^{1y}$ are identical to or different from each other and represent a C1-C5 alkyl group substituted with three or more fluorine atoms.

Embodiment 151

The compound according to any of Embodiment 135 to Embodiment 147, wherein T represents a group represented by T-1, a group represented by T-2, a group represented by T-3, or a group represented by T-4, $R^1$ represents a C1-C5 alkyl group substituted with three or more fluorine atoms.

Embodiment 152

The compound according to any of Embodiment 135 to Embodiment 147, wherein T represents a group represented by T-8, $R^{1y}$ represents a C1-C5 alkyl group substituted with three or more fluorine atoms.

Embodiment 153

The compound according to any of Embodiment 135 to Embodiment 147, wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, $OR^1$, $S(O)_xR^1$, $OS(O)_2R^1$, or $NR^1R^{29}$, $R^1$ represents a C1-C5 chain hydrocarbon group substituted with one or more halogen atoms.

Embodiment 154

The compound according to any of Embodiment 135 to Embodiment 147, wherein T represents $OR^1$, $R^1$ represents a C1-C5 chain hydrocarbon group substituted with one or more halogen atoms.

Embodiment 155

The compound according to any of Embodiment 135 to Embodiment 147, wherein T represents $OR^1$, $R^1$ represents a C1-C5 alkyl group substituted with three or more fluorine atoms.

Next, a process for preparing the present compound X is described.

Process 1

A compound represented by formula (II-1b) (hereinafter, referred to as "compound (II-1b)") or a compound represented by formula (II-1c) (hereinafter, referred to as "compound (II-1c)") can be prepared by reacting a compound represented by formula (II-1a) (hereinafter, referred to as "compound (II-1a)") with an oxidizing agent.

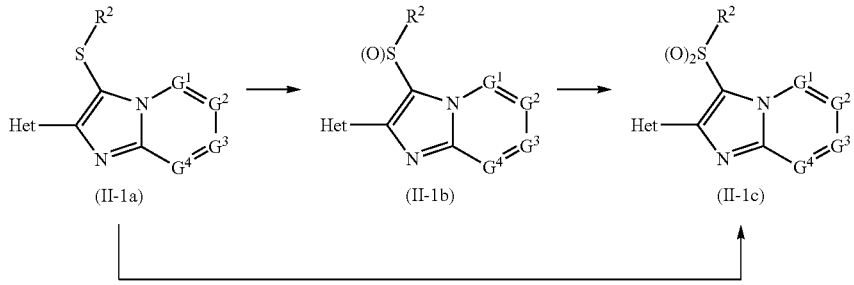

wherein the symbols are the same as those defined above.

Firstly, a process for preparing the compound (II-1b) from the compound (II-1a) is described.

The reaction is usually carried out in a solvent. Examples of the solvent to be used in the reaction include halogenated hydrocarbons (hereinafter, referred to as "halogenated hydrocarbons") such as dichloromethane and chloroform; nitriles (hereinafter, referred to as "nitriles") such as acetonitrile; alcohols (hereinafter, referred to as "alcohols") such as methanol and ethanol; acetic acid; water, and two or more mixed solvents thereof.

Examples of the oxidizing agent to be used in the reaction include sodium periodate, m-chloroperoxybenzoic acid (hereinafter, referred to as "mCPBA"), and hydrogen peroxide.

When hydrogen peroxide is used as the oxidizing agent, a base or a catalyst may be added as needed.

Examples of the base include sodium carbonate. When the base is used in the reaction, the base is used usually within a range of 0.01 to 1 molar ratio(s) relative to 1 mole of the compound (II-1a).

Examples of the catalyst include tungstic acid and sodium tungstate. When the catalyst is used in the reaction, the catalyst is used usually within a range of 0.01 to 0.5 molar ratios relative to 1 mole of the compound (II-1a).

In the reaction, the oxidizing agent is used usually within a range of 1 to 1.2 molar ratio(s) relative to 1 mole of the compound (II-1a).

A reaction temperature in the reaction is usually within a range of −20 to 80° C. A reaction period in the reaction is usually within a range of 0.1 to 12 hours.

When the reaction is completed, to the reaction mixture is added water, and the reaction mixture is extracted with an organic solvent. The organic layer is sequentially washed with an aqueous solution of a reducing agent such as sodium sulfite and sodium thiosulfate, and an aqueous solution of a base such as sodium hydrogen carbonate as needed. The resulting organic layer can be dried and concentrated to give the compound (II-1b).

Next, a process for preparing the compound (II-1c) from the compound (II-1b) is described.

The reaction is usually carried out in a solvent. Examples of the solvent to be used in the reaction include halogenated hydrocarbons, nitriles, alcohols, acetic acid, water, and two or more mixed solvents thereof.

(II-b) using the oxidizing agent usually within a range of 2 to 5 molar ratios relative to 1 mole of the compound (II-1a).

Process 2

A compound represented by formula (II-2b) and a compound represented by formula (II-2c) can be prepared by reacting a compound represented by formula (II-2a) with an oxidizing agent.

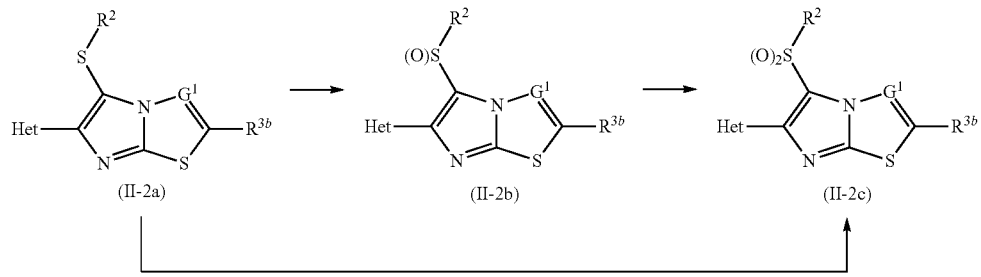

Examples of the oxidizing agent to be used in the reaction include mCPBA and hydrogen peroxide.

When hydrogen peroxide is used as the oxidizing agent, a base or a catalyst may be added as needed.

Examples of the base include sodium carbonate. When the base is used in the reaction, the base is used usually within a range of 0.01 to 1 molar ratio(s) relative to 1 mole of the compound (II-1b).

wherein the symbols are the same as those defined above.

The reactions may be carried out according to a similar method to that described in the Process 1.

Process 3

A compound represented by formula (II-3b) and a compound represented by formula (II-3c) can be prepared by reacting a compound represented by formula (II-3a) with an oxidizing agent.

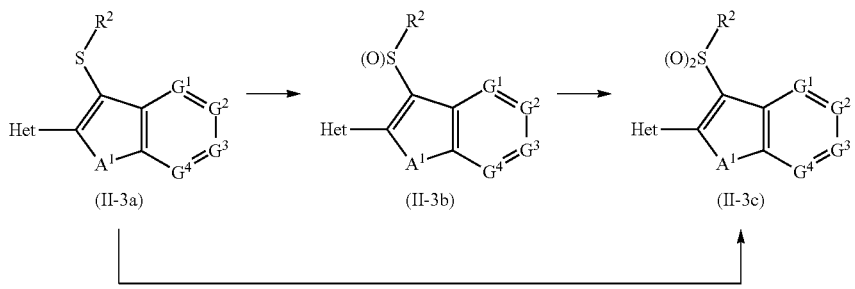

Examples of the catalyst include sodium tungstate. When the catalyst is used in the reaction, the catalyst is used usually within a range of 0.01 to 0.5 molar ratios relative to 1 mole of the compound (II-1b).

In the reaction, the oxidizing agent is used usually within a range of 1 to 2 molar ratio(s) relative to 1 mole of the compound (II-1b).

A reaction temperature in the reaction is usually within a range of −20 to 120° C. A reaction period in the reaction is usually within a range of 0.1 to 12 hours.

When the reaction is completed, to the reaction mixture is added water, and the reaction mixture is extracted with an organic solvent. The organic layer is sequentially washed with an aqueous solution of a reducing agent such as sodium sulfite and sodium thiosulfate, and an aqueous solution of a base such as sodium hydrogen carbonate as needed. The resulting organic layer can be dried and concentrated to give the compound (II-1c).

Further, the compound (II-1c) can be prepared in one step (one-pot) by reacting the compound (II-1a) with an oxidizing agent.

The reaction can be carried out according to the process for preparing the compound (II-1c) from the compound wherein the symbols are the same as those defined above.

The reactions may be carried out according to a similar method to that described in the Process 1.

Process 4

A compound represented by formula (III-1aa) (hereinafter, referred to as "compound (III-1aa)") can be prepared by reacting a compound represented by formula (III-M1a) (hereinafter, referred to as "compound (III-M1a)") with a compound represented by formula (R-1a) (hereinafter, referred to as "compound (R-1a)") in the presence of a base.

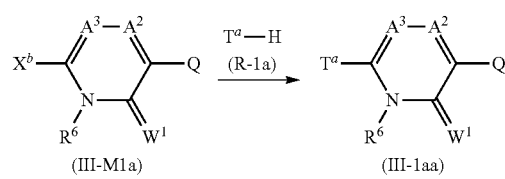

wherein $X^b$ represents a chlorine atom or a bromine atom, $T^a$ represents $OR^1$, $NR^1R^{29}$, a group represented by T-5, a group represented by T-6, a group represented by T-7, or a group represented by T-8, and the other symbols are the same as those defined above.

The reaction is usually carried out in a solvent. Examples of the solvent to be used in the reaction include ethers (hereinafter, collectively referred to as "ethers") such as tetrahydrofuran (hereinafter, referred to as "THF") and methyl tert-butyl ether (hereinafter, referred to as "MTBE"); aromatic hydrocarbons (hereinafter, collectively referred to as "aromatic hydrocarbons") such as toluene and xylene; nitriles; N-methyl pyrrolidone (hereinafter, referred to as "NMP"); polar aprotic solvents (hereinafter, collectively referred to as "polar aprotic solvents") such as N,N-dimethylformamide (hereinafter, referred to as "DMF") and dimethylsulfoxide (hereinafter, referred to as "DMSO"), and two or more mixed solvents thereof.

Examples of the base to be used in the reaction include alkali metal carbonates (hereinafter, referred to as "alkali metal carbonates") such as potassium carbonate, or alkali metal hydrides (hereinafter, referred to as "alkali metal hydrides") such as sodium hydride.

In the reaction, the compound (R-1a) is used usually within a range of 1 to 2 molar ratio(s), and the base is used usually within a range of 1 to 10 molar ratio(s), relative to 1 mole of the compound (III-M1a).

A reaction temperature in the reaction is usually within a range of −20 to 150° C. A reaction period in the reaction is usually within a range of 0.5 to 24 hours.

When the reaction is completed, to the reaction mixture is added water, and the reaction mixture is extracted with an organic solvent. The organic layer can be worked up (for example, drying and concentration) to give the compound (III-1aa).

The compound (R-1a) is commercially-available or can be prepared according a known method.

Process 5

A compound represented by formula (III-1ba) can be prepared by reacting a compound represented by formula (III-M1b) (hereinafter, referred to as "compound (III-M1b)") with the compound (R-1a) in the presence of a base.

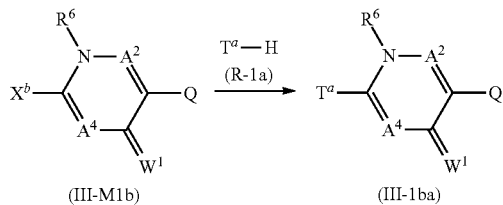

wherein the symbols are the same as those defined above.

The reaction can be carried out according to a similar method to that described in the Process 4.

Process 6

A compound represented by formula (III-1ab) (hereinafter, referred to as "compound (III-1ab)") can be prepared by reacting the compound (III-M1a) with a compound represented by formula (R-1b) (hereinafter, referred to as "compound (R-1b)") in the presence of a metal catalyst.

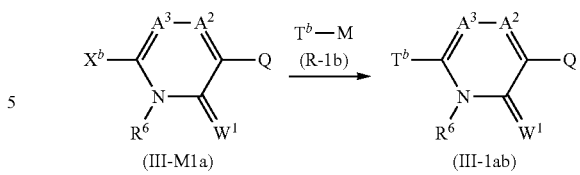

wherein $T^b$ represents a group represented by T-1, a group represented by T-2, a group represented by T-3, a group represented by T-4, a group represented by T-9, a group represented by T-10, a group represented by T-11, or a group represented by T-12, M represents a 9-borabicyclo[3.3.1]nonane-9-yl group, a borono group, a 4,4,5,5-tetramethyl-1,3,2-dioxaborolan-2-yl group, a tributylstannyl group, ZnCl, MgCl, or MgBr, and the other symbols are the same as those defined above.

The reaction is usually carried out in a solvent. Examples of the solvent to be used in the reaction include ethers, aromatic hydrocarbons, polar aprotic solvents, water, and two or more mixed solvents thereof.

Examples of the metal catalyst to be used in the reaction include palladium catalysts such as tetrakis(triphenylphosphine)palladium(0), [1,1'-bis(diphenylphosphino)ferrocene]palladium(II) dichloride, tris(dibenzylideneacetone)dipalladium(0) and palladium(II) acetate; nickel catalysts such as bis(cyclooctadiene)nickel(0) and nickel(II) chloride; and copper catalysts such as copper(I) iodide and copper(I) chloride.

A ligand, a base, and/or an alkali metal halide may be used in the reaction as needed.

Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. When the ligand is used in the reaction, the ligand is used usually within a range of 0.01 to 1 molar ratio(s) relative to 1 mole of the compound (III-M1a).

Examples of the base include alkali metal hydrides, alkali metal carbonates, and organic bases (hereinafter, referred to as "organic bases") such as triethylamine, diisopropylethylamine, pyridine and 4-(dimethylamino)pyridine. When the base is used in the reaction, the base is used usually within a range of 0.1 to 5 molar ratios relative to 1 mole of the compound (III-M1a)

Examples of the alkali metal halide include potassium fluoride, sodium fluoride, lithium chloride and sodium chloride. When the alkali metal halide is used in the reaction, the alkali metal halide is used usually within a range of 0.1 to 5 molar ratios relative to 1 mole of the compound (III-M1a).

In the reaction, the compound (R-1b) is used usually within a range of 1 to 10 molar ratio(s), and the metal catalyst is used usually within a range of 0.01 to 0.5 molar ratios, relative to 1 mole of the compound (III-M1a).

A reaction temperature in the reaction is usually within a range of −20 to 200° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-1ab).

The compound (R-1b) is commercially available, or can be prepared according to a known method.

Process 7

A compound represented by formula (III-1bb) can be prepared by reacting the compound (III-M1b) with the compound (R-1b) in the presence of a metal catalyst.

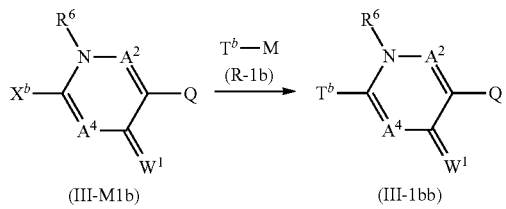

wherein the symbols are the same as those defined above.

The reaction can be carried out according to a similar method to that described in the Process 6.

Process 8

A compound represented by formula (III-1ac) (hereinafter, referred to as "compound (III-1ac)") can be prepared by reacting the compound (III-M1a) with a compound represented by formula (R-1c) (hereinafter, referred to as "compound (R-1c)") in the presence of copper.

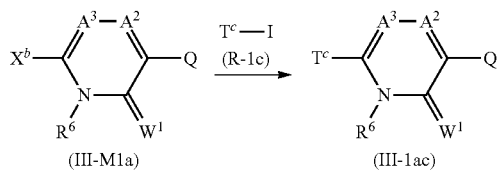

wherein $T^c$ represents a C1-C10 chain hydrocarbon group; a (C1-C5 alkoxy)C2-C5 alkyl group; a (C3-C5 alkenyloxy)C2-C5 alkyl group; a (C3-C5 alkynyloxy)C2-C5 alkyl group; a (C1-C5 alkyl)-S(O)$_w$—(C2-C5 alkyl) group; a (C3-C5 alkenyl)-S(O)$_w$—(C2-C5 alkyl) group; a (C3-C5 alkynyl)-S(O)$_w$—(C2-C5 alkyl) group; a (C1-C5 alkyl)-C(O)—(C1-C5 alkyl) group {wherein the C1-C10 chain hydrocarbon group, the (C1-C5 alkoxy)C2-C5 alkyl group, the (C3-C5 alkenyloxy)C2-C5 alkyl group, the (C3-C5 alkynyloxy)C2-C5 alkyl group, the (C1-C5 alkyl)-S(O)$_w$—(C2-C5 alkyl) group, the (C3-C5 alkenyl)-S(O)$_w$—(C2-C5 alkyl) group, the (C3-C5 alkynyl)-S(O)$_w$—(C2-C5 alkyl) group, and the (C1-C5 alkyl)-C(O)—(C1-C5 alkyl) group are substituted with one or more substituents selected from the group consisting of a cyano group and a halogen atom}; or a C3-C7 cycloalkyl group substituted with one or more substituents selected from Group G, and the other symbols are the same as those defined above.

The reaction is usually carried out in a solvent. Examples of the solvent to be used in the reaction include aromatic hydrocarbons, polar aprotic solvents, and two or more mixed solvents thereof.

The copper to be used in the reaction is preferably a copper powder.

In the reaction, the compound (R-1c) is used usually within a range of 1 to 10 molar ratio(s), and copper is used usually within a range of 1 to 10 molar ratio(s), relative to 1 mole of the compound (III-M1a).

A reaction temperature in the reaction is usually within a range of 40 to 200° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-1ac).

The compound (R-1c) is commercially-available or can be prepared according a known method.

Process 9

A compound represented by formula (III-1bc) can be prepared by reacting the compound (III-M1b) with the compound (R-1c) in the presence of copper.

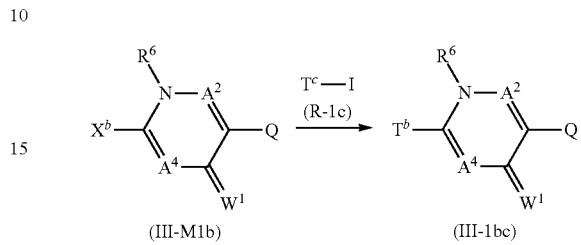

wherein the symbols are the same as those defined above.

The reaction can be carried out according to a similar method to that described in the Process 8.

Process 10

A compound represented by formula (III-1ad) (hereinafter, referred to as "compound (III-1ad)") can be prepared by reacting the compound (III-M1a) with a compound represented by formula (R-1d) (hereinafter, referred to as "compound (R-1d)") in the presence of a base.

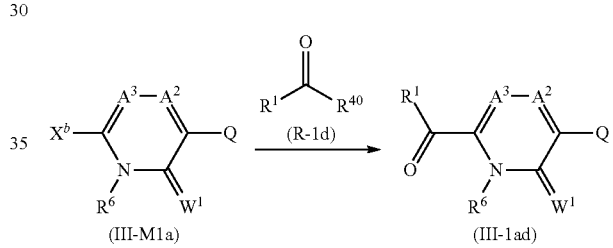

wherein $R^{40}$ represents a methoxy group, an ethoxy group, a phenoxy group, or $N(CH_3)OCH_3$, and the other symbols are the same as those defined above.

The reaction is usually carried out in a solvent. Examples of the solvent to be used in the reaction include ethers, and aromatic hydrocarbons.

Examples of the base to be used in the reaction include butyllithium, lithium diisopropylamide, lithium 2,2,6,6-tetramethylpiperidide, and lithium bis(trimethylsilyl)amide.

In the reaction, the compound (R-1d) is used usually within a range of 1 to 10 molar ratio(s), and the base is used usually within a range of 1.0 to 2.0 molar ratio(s), relative to 1 mole of the compound (III-M1a).

A reaction temperature in the reaction is usually within a range of −100 to 30° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-1ad).

The compound (R-1d) is commercially-available or can be prepared according a known method.

Process 11

A compound represented by formula (III-1bd) can be prepared by reacting the compound (III-M1b) with the compound (R-1d) in the presence of a base.

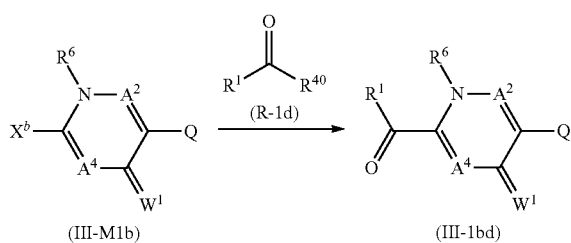

wherein the symbols are the same as those defined above.

The reaction can be carried out according to a similar method to that described in the Process 10.

Process 12

A compound represented by formula (III-2a) can be prepared by reacting a compound represented by formula (III-M2a) (hereinafter, referred to as "compound (III-M2a)") with a compound represented by formula (R-2) (hereinafter, referred to as "compound (R-2)") in the presence of a base.

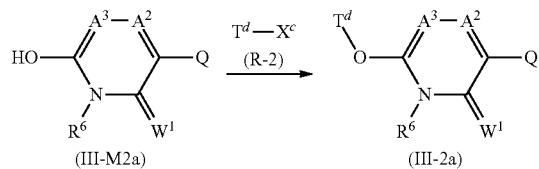

wherein $X^c$ represents a chlorine atom, a bromine atom, or an iodine atom, $T^d$ represents a C1-C10 chain hydrocarbon group; a (C1-C5 alkoxy)C2-C5 alkyl group; a (C3-C5 alkenyloxy)C2-C5 alkyl group; a (C3-C5 alkynyloxy)C2-C5 alkyl group; a (C1-C5 alkyl)-S(O)$_w$—(C2-C5 alkyl) group; a (C3-C5 alkenyl)-S(O)$_N$—(C2-C5 alkyl) group; a (C3-C5 alkynyl)-S(O)$_w$—(C2-C5 alkyl) group; a (C1-C5 alkyl)-C(O)—(C1-C5 alkyl) group {wherein the C1-C10 chain hydrocarbon group, the (C1-C5 alkoxy)C2-C5 alkyl group, the (C3-C5 alkenyloxy)C2-C5 alkyl group, the (C3-C5 alkynyloxy)C2-C5 alkyl group, the (C1-C5 alkyl)-S(O)$_w$—(C2-C5 alkyl) group, the (C3-C5 alkenyl)-S(O)$_w$—(C2-C5 alkyl) group, the (C3-C5 alkynyl)-S(O)$_w$—(C2-C5 alkyl) group, and the (C1-C5 alkyl)-C(O)—(C1-C5 alkyl) group are substituted with one or more substituents selected from the group consisting of a cyano group and a halogen atom}; a (C3-C7 cycloalkyl)C1-C3 alkyl group substituted with one or more substituents selected from Group G; a C3-C7 cycloalkyl group substituted with one or more substituents selected from Group G; or S(O)$_2$R$^1$, and the other symbols are the same as those defined above.

The reaction is usually carried out in a solvent. Examples of the solvent to be used in the reaction include ethers, aromatic hydrocarbons, polar aprotic solvents, and two or more mixed solvents thereof.

Examples of the base to be used in the reaction include organic bases, alkali metal hydrides, and alkali metal carbonates.

In the reaction, the compound (R-2) is used usually within a range of 1 to 10 molar ratio(s), and the base is used usually within a range of 0.1 to 5 molar ratios, relative to 1 mole of the compound (III-M2a).

A reaction temperature in the reaction is usually within a range of −20 to 120° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-2a).

The compound (R-2) is commercially available, or can be prepared according to a known method.

Process 13

A compound represented by formula (III-2b) can be prepared by reacting a compound represented by formula (III-M2b) (hereinafter, referred to as "compound (III-M2b)") with the compound (R-2) in the presence of a base.

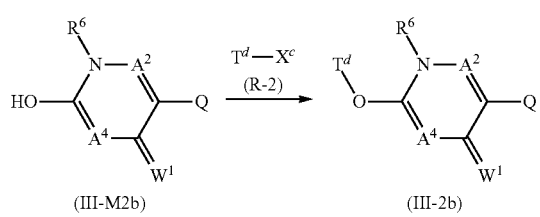

wherein the symbols are the same as those defined above.

The reaction can be carried out according to a similar method to that described in the Process 12.

Process 14

A compound represented by formula (III-3a) (hereinafter, referred to as "compound (III-3a)") can be prepared by reacting a compound represented by formula (III-M3a) (hereinafter, referred to as "compound (III-M3a)") with a compound represented by formula (R-3) (hereinafter, referred to as "compound (R-3)") in the presence of a condensing agent.

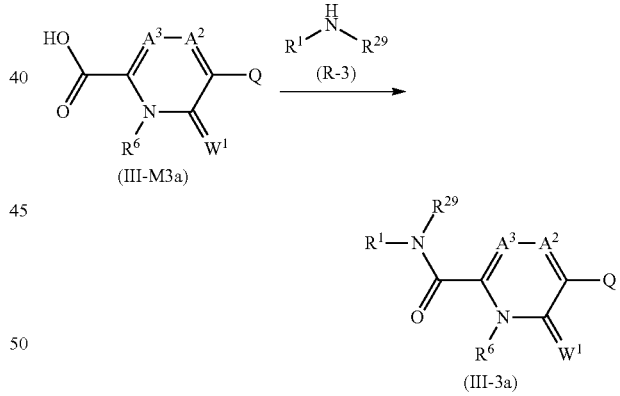

wherein the symbols are the same as those defined above.

The reaction is usually carried out in a solvent. Examples of the solvent to be used in the reaction include ethers, halogenated aliphatic hydrocarbons, aromatic hydrocarbons, polar aprotic solvents, and two or more mixed solvents thereof.

Examples of the condensing agent to be used in the reaction include 1-ethyl-3-(3-dimethylaminopropyl)carbodiimide hydrochloride.

A base may be used in the reaction as needed, and examples of the base include organic bases. When the base is used in the reaction, the base is used usually within a range of 0.1 to 10 molar ratios relative to 1 mole of the compound (III-M3a).

In the reaction, the compound (R-3) is used usually within a range of 1 to 10 molar ratio(s), and the condensing agent is used usually within a range of 1 to 5 molar ratio(s), relative to 1 mole of the compound (III-M3a).

A reaction temperature in the reaction is usually within a range of −20 to 120° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-3a).

The compound (R-3) is commercially-available or can be prepared according a known method.

Process 15

A compound represented by formula (III-3b) can be prepared by reacting a compound represented by formula (III-M3b) (hereinafter, referred to as "compound (III-M3b)") with the compound (R-3) in the presence of a condensing agent.

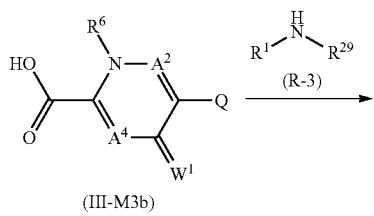

(III-M3b)

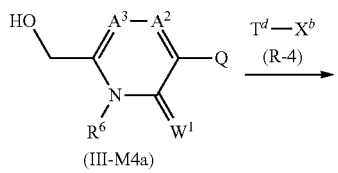

(III-3b)

wherein the symbols are the same as those defined above.

The reaction can be carried out according to a similar method to that described in the Process 14.

Process 16

A compound represented by formula (III-4a) (hereinafter, referred to as "compound (III-4a)") can be prepared by reacting a compound represented by formula (III-M4a) (hereinafter, referred to as "compound (III-M4a)") with a compound represented by formula (R-4) (hereinafter, referred to as "compound (R-4)") in the presence of a base.

The reaction can be carried out according to a similar method to that described in the Process 12 using the compound (III-M4a) instead of the compound (III-M2a) and using the compound (R-4) instead of the compound (R-2).

The compound (R-4) is commercially-available or can be prepared according a known method.

Process 17

A compound represented by formula (III-4b) can be prepared by reacting a compound represented by formula (III-M4b) (hereinafter, referred to as "compound (III-M4b)") with the compound (R-4) in the presence of a base.

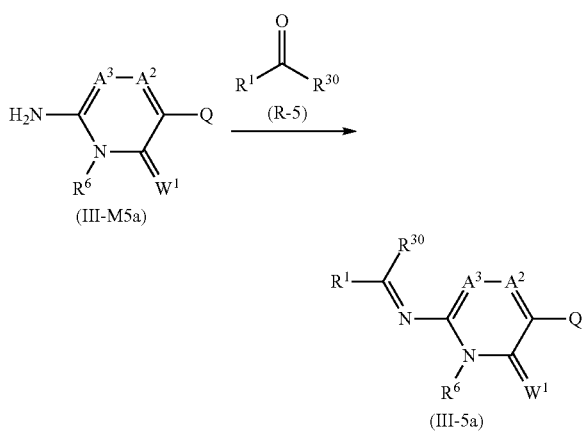

wherein the symbols are the same as those defined above.

The reaction can be carried out according to a similar method to that described in the Process 16.

Process 18

A compound represented by formula (III-5a) (hereinafter, referred to as "compound (III-5a)") can be prepared by reacting a compound represented by formula (III-M5a) (hereinafter, referred to as "compound (III-M5a)") with a compound represented by formula (R-5) (hereinafter, referred to as "compound (R-5)").

wherein the symbols are the same as those defined above.

The reaction is usually carried out in a solvent. Examples of the solvent to be used in the reaction include ethers, halogenated aliphatic hydrocarbons, aromatic hydrocarbons, polar aprotic solvents, and two or more mixed solvents thereof.

An acid may be used in the reaction as needed, and examples of the acid include p-toluenesulfonic acid and 10-camphorsulfonic acid. When the acid is used in the reaction, the acid is used usually within a range of 0.1 to 10 molar ratios relative to 1 mole of the compound (III-M5a).

In the reaction, the compound (R-5) is used usually within a range of 1 to 10 molar ratio(s) relative to 1 mole of the compound (III-M5a).

A reaction temperature in the reaction is usually within a range of −20 to 180° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-5a).

The compound (R-5) is commercially-available or can be prepared according a known method.

Process 19

A compound represented by formula (III-5b) can be prepared by reacting a compound represented by formula (III-M5b) (hereinafter, referred to as "compound (III-M5b)") with the compound (R-5).

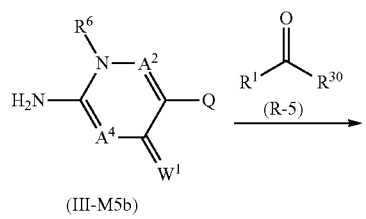

(III-M5b)

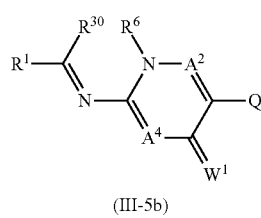

(III-5b)

wherein the symbols are the same as those defined above.

The reaction can be carried out according to a similar method to that described in the Process 18.

Process 20

A compound represented by formula (III-6a) (hereinafter, referred to as "compound (III-6a)") can be prepared by reacting a compound represented by formula (III-M6a) (hereinafter, referred to as "compound (III-M6a)") with a compound represented by formula (R-6) (hereinafter, referred to as "compound (R-6)").

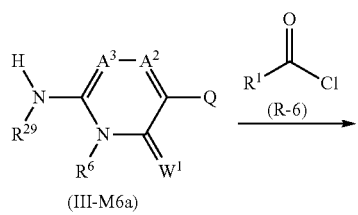

(III-M6a)

-continued

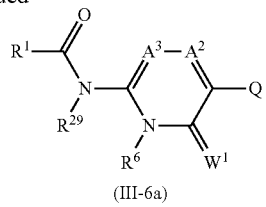

(III-6a)

wherein the symbols are the same as those defined above.

The reaction is usually carried out in a solvent. Examples of the solvent to be used in the reaction include ethers, halogenated hydrocarbons, aromatic hydrocarbons, polar aprotic solvents, and two or more mixed solvents thereof.

A base may be used in the reaction as needed, and examples of the base include organic bases. When a base is used in the reaction, the base is used usually within a range of 0.1 to 10 molar ratio(s) relative to 1 mole of the compound (III-M6a).

In the reaction, the compound (R-6) is used usually within a range of 1 to 10 molar ratio(s) relative to 1 mole of the compound (III-M6a).

A reaction temperature in the reaction is usually within a range of −20 to 120° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-6a).

The compound (R-6) is commercially-available or can be prepared according a known method.

Process 21

A compound represented by formula (III-6b) can be prepared by reacting a compound represented by formula (III-M6b) (hereinafter, referred to as "compound (III-M6b)") with the compound (R-6).

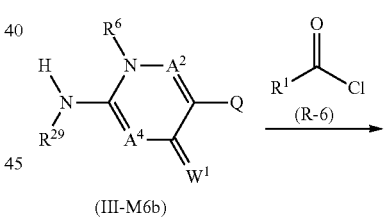

(III-M6b)

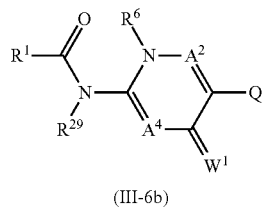

(III-6b)

wherein the symbols are the same as those defined above.

The reaction can be carried out according to a similar method to that described in the Process 20.

Process 22

A compound represented by formula (III-7aa) (hereinafter, referred to as "compound (III-7aa)"), a compound represented by formula (III-7ab) (hereinafter, referred to as "compound (III-7ab)"), and a compound represented by formula (III-7ac) (hereinafter, referred to as "compound (III-7ac)") can be prepared according to the following process.

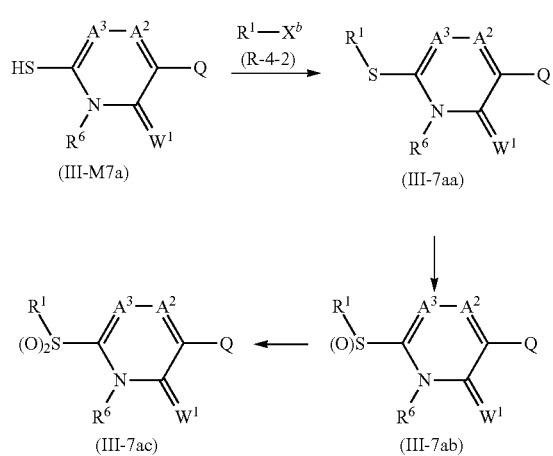

(III-M7a) → (III-7aa) → (III-7ab) → (III-7ac)

wherein the symbols are the same as those defined above.

Firstly, a process for preparing the compound (III-7aa) is described.

The compound (III-7aa) can be prepared according to a similar method to that described in the Process 16 using a compound represented by formula (III-M7a) (hereinafter, referred to as "compound (III-M7a)") instead of the compound (III-M4a) and using a compound represented by formula (R-4-2) (hereinafter, referred to as "compound (R-4-2)") instead of the compound (R-4).

The compound (R-4-2) is commercially-available or can be prepared according a known method.

Next, a process for preparing the compound (III-7ab) is described.

The compound (III-7ab) can be prepared according to a similar method to that described in the Process 1 using the compound (III-7aa) instead of the compound (II-1a).

Then, a process for preparing the compound (III-7ac) is described.

The compound (III-7ac) can be prepared according to a similar method to that described in the Process 1 using the compound (III-7ab) instead of the compound (II-1b).

Process 23

A compound represented by formula (III-7ba) (hereinafter, referred to as "compound (III-7ba)"), a compound represented by formula (III-7bb) (hereinafter, referred to as "compound (III-7bb)"), and a compound represented by formula (III-7bc) (hereinafter, referred to as "compound (III-7bc)") can be prepared according to the following process.

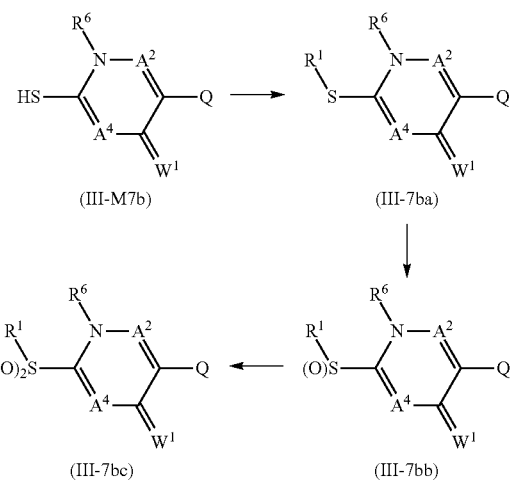

wherein the symbols are the same as those defined above.

The reaction can be carried out according to a similar method to that described in the Process 22.

Process 24

A compound represented by formula (III-8a) (hereinafter, referred to as "compound (III-8a)") can be prepared according to the following scheme.

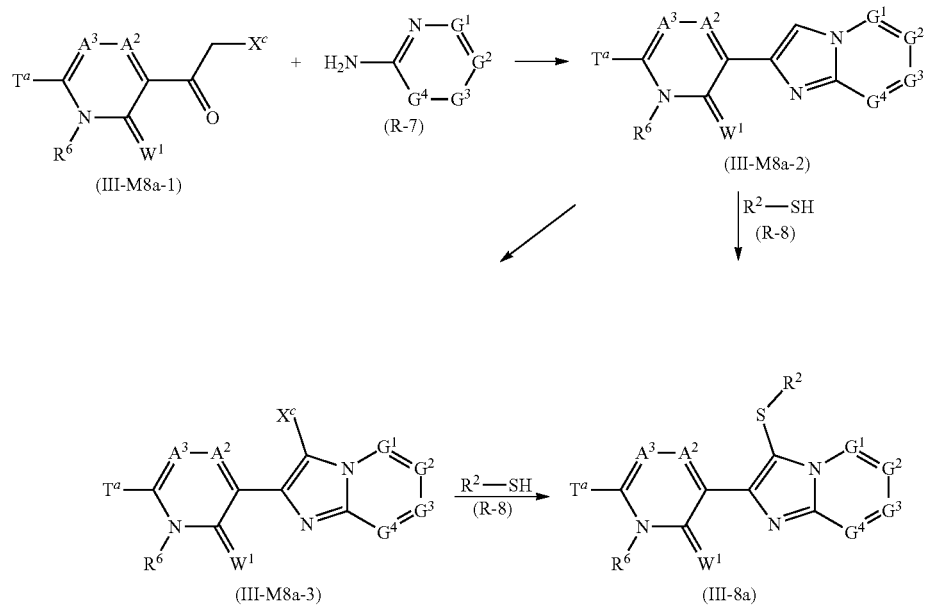

wherein the symbols are the same as those defined above.

Firstly, a process for preparing a compound represented by formula (III-M8a-2) (hereinafter, referred to as "compound (III-M8a-2)") is described.

The compound (III-M8a-2) can be prepared by a compound represented by formula (III-M8a-1) (hereinafter, referred to as "compound (III-M8a-1)") with a compound represented by formula (R-7) (hereinafter, referred to as "compound (R-7)").

The reaction is usually carried out in a solvent. Examples of the solvent to be used in the reaction include ethers, aromatic hydrocarbons, polar aprotic solvents, alcohols, nitriles, water, and two or more mixed solvents thereof.

A base can be used in the reaction as needed. Examples of the base to be used in the reaction include organic bases and alkali metal carbonates.

In the reaction, the compound (R-7) is used usually within a range of 1 to 10 molar ratio(s), and the base is used usually within a range of 0.1 to 5 molar ratios, relative to 1 mole of the compound (III-M8a-1).

A reaction temperature in the reaction is usually within a range of −20 to 200° C. A reaction period in the reaction is usually within a range of 0.1 to 48 hours.

When the reaction is completed, to the reaction mixture is added water, and the reaction mixture is extracted with an organic solvent. The organic layer can be worked up (for example, drying and concentration) to give the compound (III-M8a-2).

The compound (R-7) is commercially available, or can be prepared according to a known method.

Next, a process for preparing a compound represented by formula (III-M8a-3) (hereinafter, referred to as "compound (III-M8a-3)") is described.

The compound (III-M8a-3) can be prepared by reacting the compound (III-M8a-2) with a halogenating agent.

The reaction is usually carried out in a solvent. Examples of the solvent to be used in the reaction include alcohols, nitriles, ethers, aromatic hydrocarbons, polar aprotic solvents, halogenated hydrocarbons, water, and two or more mixed solvents thereof.

Examples of the halogenating agent include chlorine, bromine, iodine, N-chlorosuccinimide, N-bromosuccinimide, and N-iodosuccinimide.

In the reaction, the halogenating agent is used usually within a range of 1 to 20 molar ratio(s) relative to 1 mole of the compound (III-M8a-2).

A reaction temperature in the reaction is usually within a range of −20 to 200° C. A reaction period in the reaction is usually within a range of 0.1 to 72 hours.

When the reaction is completed, to the reaction mixture is added water, and the reaction mixture is extracted with an organic solvent. The organic layer can be worked up (for example, drying and concentration) to give the compound (III-M8a-3).

Next, a process for preparing the compound (III-8a) from the compound (III-M8a-2) is described.

The compound (III-8a) can be prepared by reacting the compound (III-M8a-2), a compound represented by formula (R-8) (hereinafter, referred to as "compound (R-8)"), and a halogenating agent.

The reaction is usually carried out in a solvent. Examples of the solvent to be used in the reaction include alcohols, nitriles, ethers, aromatic hydrocarbons, polar aprotic solvents, halogenated hydrocarbons, water, and two or more mixed solvents thereof.

Examples of the halogenating agent include chlorine, bromine, iodine, N-chlorosuccinimide, N-bromosuccinimide, and N-iodosuccinimide.

In the reaction, the compound (R-8) is used usually within a range of 1 to 20 molar ratio(s), and the halogenating agent is used usually within a range of 1 to 20 molar ratio(s), relative to 1 mole of the compound (III-M8a-2).

A reaction temperature in the reaction is usually within a range of −20 to 200° C. A reaction period in the reaction is usually within a range of 0.1 to 72 hours.

When the reaction is completed, to the reaction mixture is added water, and the reaction mixture is extracted with an organic solvent. The organic layer can be worked up (for example, drying and concentration) to give the compound (III-8a).

The compound (R-8) is commercially available, or can be prepared according to a known method.

Next, a process for preparing the compound (III-8a) from the compound (III-M8a-3) is described.

The compound (III-8a) can be also prepared by reacting the compound (III-M8a-3) with the compound (R-8) in the presence of a metal catalyst and a base.

The reaction is usually carried out in a solvent. Examples of the solvent to be used in the reaction include alcohols, nitriles, ethers, aromatic hydrocarbons, polar aprotic solvents, water, and two or more mixed solvents thereof.

Examples of the metal catalyst to be used in the reaction include palladium catalysts such as tetrakis(triphenylphosphine)palladium(0), [1,1'-bis(diphenylphosphino)ferrocene]palladium(II) dichloride, tris(dibenzylideneacetone)dipalladium(0) and palladium(II) acetate; nickel catalysts such as bis(cyclooctadiene)nickel(0) and nickel(II) chloride; and copper catalysts such as copper(I) iodide and copper(I) chloride.

Examples of the base to be used in the reaction include alkali metal hydrides, alkali metal carbonates, and organic bases.

A ligand can be used in the reaction. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. When the ligand is used in the reaction, the ligand is used usually within a range of 0.01 to 1 molar ratio(s) relative to 1 mole of the compound (III-M8a-3).

In the reaction, the compound (R-8) is used usually within a range of 1 to 20 molar ratio(s), the metal catalyst is used usually within a range of 0.01 to 0.5 molar ratios, and the base is used usually within a range of 0.1 to 5 molar ratios, relative to 1 mole of the compound (III-M8a-3).

A reaction temperature in the reaction is usually within a range of −20 to 200° C. A reaction period in the reaction is usually within a range of 0.1 to 72 hours.

When the reaction is completed, to the reaction mixture is added water, and the reaction mixture is extracted with an organic solvent. The organic layer can be worked up (for example, drying and concentration) to give the compound (III-8a).

Process 25

The compound (III-8a) can be prepared by reacting the compound (R-7) with a compound represented by formula (III-M8a-4) (hereinafter, referred to as "compound (III-M8a-4)").

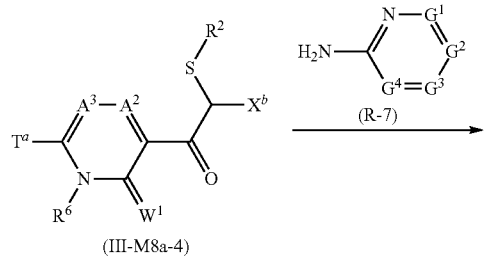

(III-M8a-4)

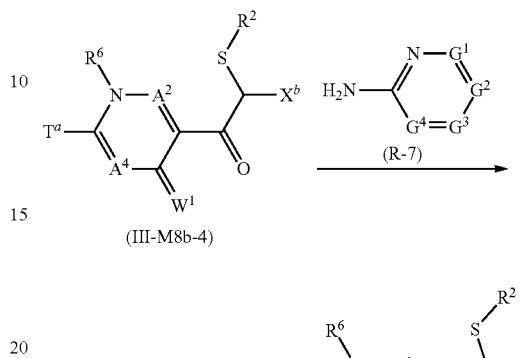

(III-8a)

wherein the symbols are the same as those defined above.

The reaction can be carried out according to a similar method to that described in the process for preparing the compound (III-M8a-2) from the compound (III-M8a-1) in the Process 24.

Process 26

A compound represented by formula (III-8b) (hereinafter, referred to as "compound (III-8b)"), a compound represented by formula (III-M8b-2), and a compound represented by formula (III-M8b-3) can be prepared according to the following scheme.

Process 27

The compound (III-8b) can be prepared by reacting the compound (R-7) with a compound represented by formula (III-M8b-4) (hereinafter, referred to as "compound (III-M8b-4)").

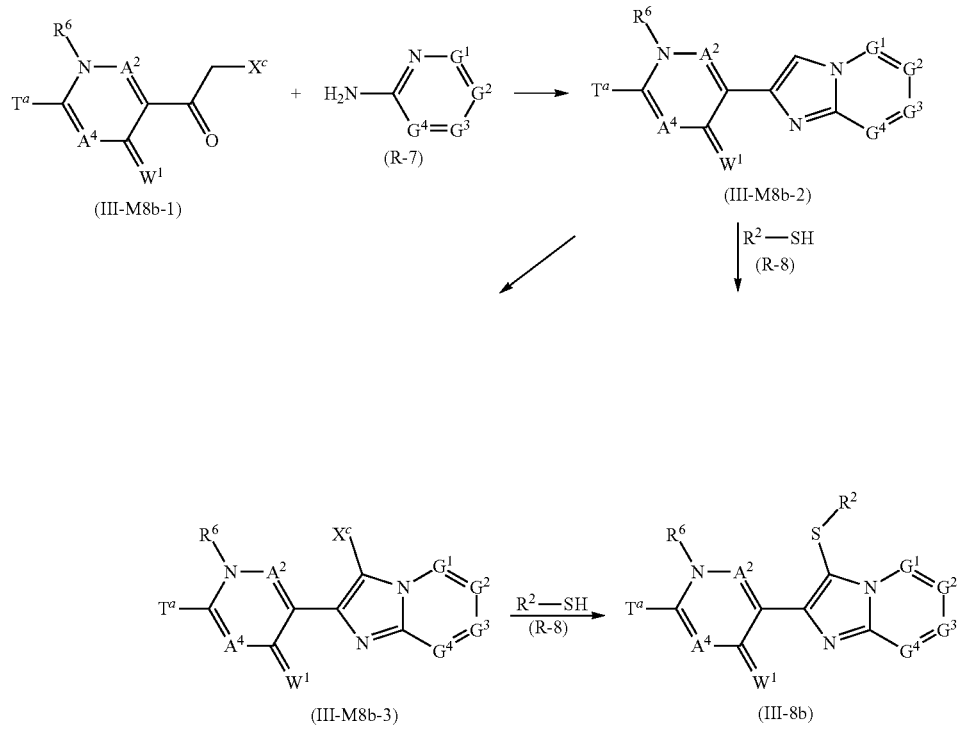

wherein the symbols are the same as those defined above.

The reaction can be carried out according to a similar method to that described in the process for preparing the compound (III-M8a-2) from the compound (III-M8a-1) in the Process 24.

wherein the symbols are the same as those defined above.

The reaction can be carried out according to a similar method to that described in the Process 24.

Process 28

A compound represented by formula (IV-1a) (hereinafter, referred to as "compound (IV-1a)") can be prepared by reacting a compound represented by formula (IV-M1) (hereinafter, referred to as "compound (IV-M1)") with a compound represented by formula (Q1a) (hereinafter, referred to as "compound (Q1a)") in the presence of a base.

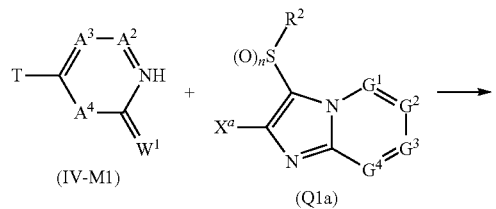

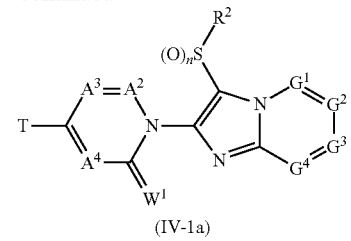

(IV-1a)

wherein $X^a$ represents a fluorine atom or a chlorine atom, and the other symbols are the same as those defined above.

The reaction is usually carried out in a solvent. Examples of the solvent to be used in the reaction include ethers, aromatic hydrocarbons, nitriles, polar aprotic solvents, and two or more mixed solvents thereof.

Examples of the base to be used in the reaction include alkali metal carbonates, and alkali metal hydrides.

In the reaction, the compound (IV-M1) is used usually within a range of 1 to 2 molar ratio(s), and the base is used usually within a range of 1 to 10 molar ratio(s), relative to 1 mole of the compound (Q1a).

A reaction temperature in the reaction is usually within a range of −20 to 150° C. A reaction period in the reaction is usually within a range of 0.5 to 24 hours.

When the reaction is completed, to the reaction mixture is added water, and the reaction mixture is extracted with an organic solvent. The organic layer can be worked up (for example, drying and concentration) to give the compound (IV-1a).

The compound (IV-M1) is known, or can be prepared according to the method described in WO 2005/018557, WO 2009/149188, WO 2010/104818, and WO 2015/153304, etc.

Process 29

The compound (IV-1a) can be prepared by reacting the compound (IV-M1) with a compound represented by formula (Q1c) (hereinafter, referred to as "compound (Q1c)") in the presence of a metal catalyst and a base.

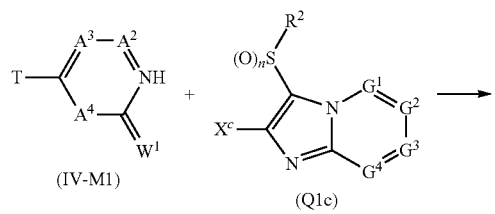

-continued wherein the symbols are the same as those defined above.

The reaction is usually carried out in a solvent. Examples of the solvent to be used in the reaction include ethers, aromatic hydrocarbons, polar aprotic solvents, water, and two or more mixed solvents thereof.

Examples of the metal catalyst to be used in the reaction include copper catalysts such as copper(I) iodide, copper(I) bromide, copper(I) chloride, copper(I) oxide, copper(I) trifluoromethanesulfonate benzene complex, tetrakis(acetonitrile)copper(I) hexafluorophosphate and copper(I) 2-thiophenecarboxylate; and nickel catalysts such as bis(cyclooctadiene)nickel(0) and nickel(II) chloride.

A ligand, a base, or an alkali metal halide may be used in the reaction as needed.

Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, 1,10-phenanthroline, trans-1,2-cyclohexanediamine, trans-N,N'-dimethylcyclohexane-1,2-diamine, and N,N'-dimethylethylenediamine. When the ligand is used in the reaction, the ligand is used usually within a range of 0.01 to 1 molar ratio(s) relative to 1 mole of the compound (Q1c).

Examples of the base include organic bases, alkali metal hydrides, and alkali metal carbonates. When the base is used in the reaction, the base is used usually within a range of 0.1 to 5 molar ratios relative to 1 mole of the compound (Q1c).

Examples of the alkali metal halide include potassium fluoride, sodium fluoride, lithium chloride, and sodium chloride. When the alkali metal halide is used in the reaction, the alkali metal halide is used usually within a range of 0.1 to 5 molar ratios relative to 1 mole of the compound (Q1c).

In the reaction, the compound (IV-M1) is used usually within a range of 1 to 10 molar ratio(s), and the metal catalyst is used usually within a range of 0.01 to 2 molar ratios, relative to 1 mole of the compound (Q1c).

A reaction temperature in the reaction is usually within a range of −20 to 200° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (IV-1a).

Process 29-1

A compound represented by formula (IV-1a-1) can be prepared according to the following scheme.

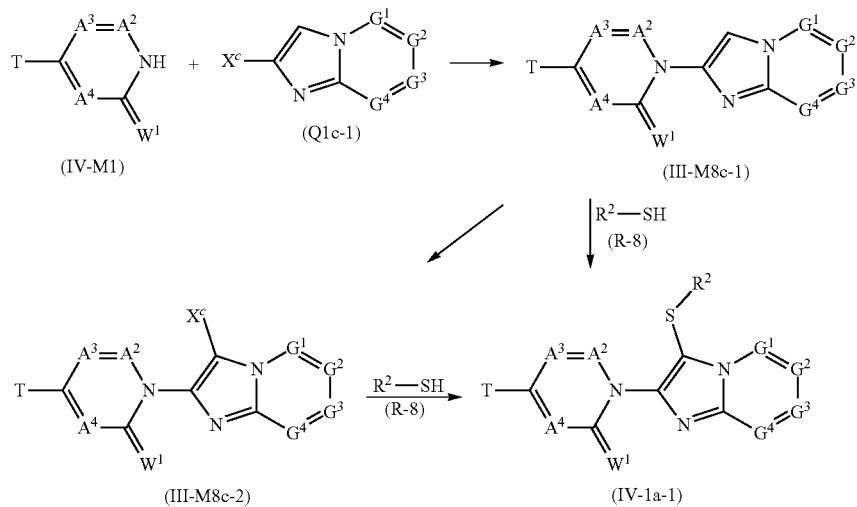

(IV-M1)  (Q1c-1)  (III-M8c-1)
(III-M8c-2)  (IV-1a-1)

wherein the symbols are the same as those defined above.

The reaction can be carried out according to a similar method to those described in the Processes 24 and 29.

Process 30

A compound represented by formula (IV-2a) (hereinafter, referred to as "compound (IV-2a)") can be prepared by reacting the compound (IV-M1) with a compound represented by formula (Q2a) (hereinafter, referred to as "compound (Q2a)") in the presence of a base.

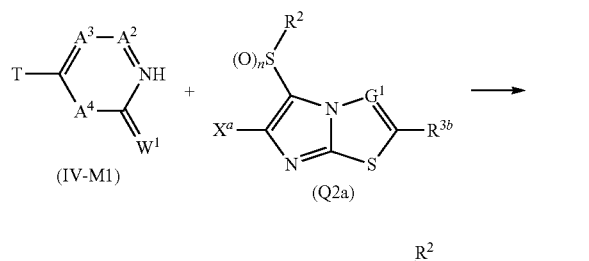

(IV-M1)  (Q2a)

(IV-2a)

wherein the symbols are the same as those defined above.

The reaction can be carried out according to a similar method to that described in the Process 28.

Process 31

The compound (IV-2a) can be prepared by reacting the compound (IV-M1) with a compound represented by formula (Q2c) (hereinafter, referred to as "compound (Q2c)") in the presence of a metal catalyst and a base.

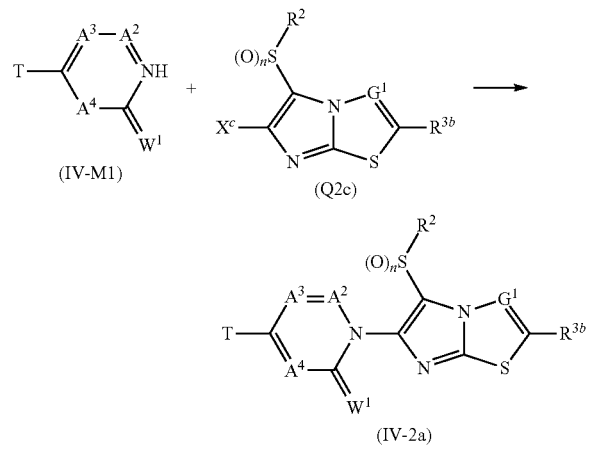

(IV-M1)  (Q2c)

(IV-2a)

wherein the symbols are the same as those defined above.

The reaction can be carried out according to a similar method to that described in the Process 29.

Process 32

A compound represented by formula (IV-3a) (hereinafter, referred to as "compound (IV-3a)") can be prepared by reacting the compound (IV-M1) with a compound represented by formula (Q3a) (hereinafter, referred to as "compound (Q3a)") in the presence of a base.

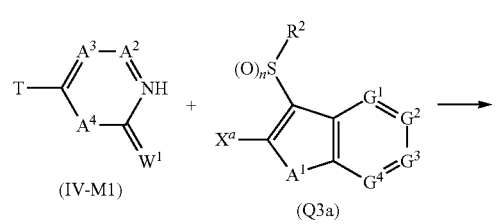

(IV-M1)  (Q3a)

-continued

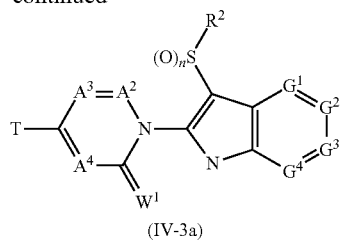

(IV-3a)

wherein the symbols are the same as those defined above.

The reaction can be carried out according to a similar method to that described in the Process 28.

Process 33

The compound (IV-3a) can be prepared by reacting the compound (IV-M1) with a compound represented by formula (Q3c) (hereinafter, referred to as "compound (Q3c)") in the presence of a metal catalyst and a base.

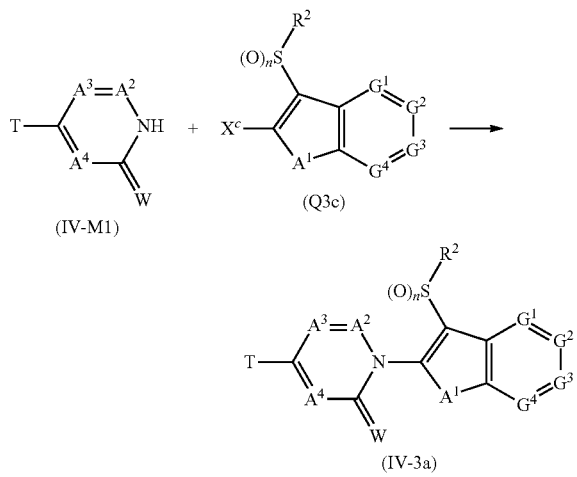

wherein the symbols are the same as those defined above.

The reaction can be carried out according to a similar method to that described in the Process 29.

Process 34

A compound represented by formula (V-2a) (hereinafter, referred to as "compound (V-2a)") can be prepared by reacting a compound represented by formula (V-M2a) (hereinafter, referred to as "compound (V-M2a)") with the compound (R-1a) in the presence of a base.

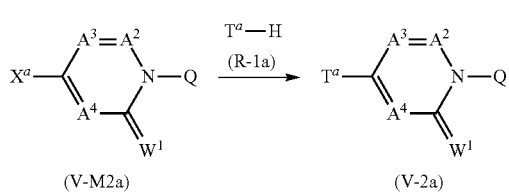

wherein the symbols are the same as those defined above.

The reaction can be carried out according to a similar method to that described in the Process 4.

Process 35

A compound represented by formula (V-2b) (hereinafter, referred to as "compound (V-2b)") can be prepared by reacting a compound represented by formula (V-M2b) (hereinafter, referred to as "compound (V-M2b)") with the compound (R-1b) in the presence of a metal catalyst.

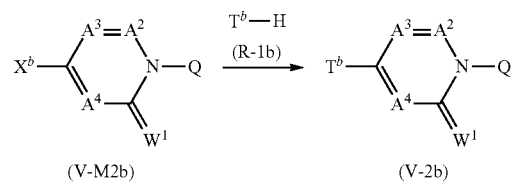

wherein the symbols are the same as those defined above.

The reaction can be carried out according to a similar method to that described in the Process 6.

Process 36

A compound represented by formula (V-2c) can be prepared by reacting a compound represented by formula (V-M2c) (hereinafter, referred to as "compound (V-M2c)") with a compound represented by formula (R-1e) (hereinafter, referred to as "compound (R-1e)") in the presence of a base.

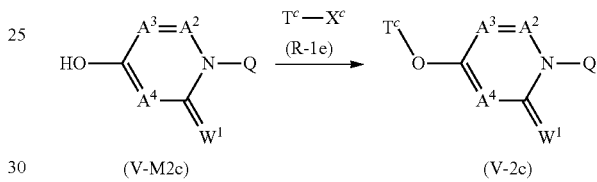

wherein the symbols are the same as those defined above.

The reaction can be carried out according to a similar method to that described in the Process 12.

The compound (R-1e) is commercially-available or can be prepared according a known method.

Process 37

An N-oxide of a compound represented by Formula (I) can be prepared by reacting a compound represented by Formula (I) with an oxidizing agent. The reaction can be carried out according to, for example, the Process 1, the method described in US patent application publication No. 2018/0009778, or the method described in WO 2016/121970.

A process for preparing an intermediate compound is described as follows.

Reference Process 1

The compound (III-M8a-1) and the compound (III-M8a-4) can be prepared according to the following scheme.

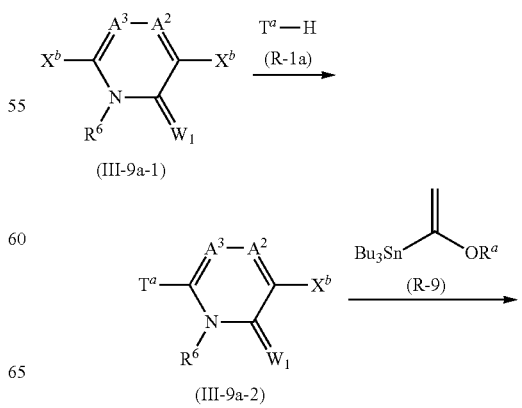

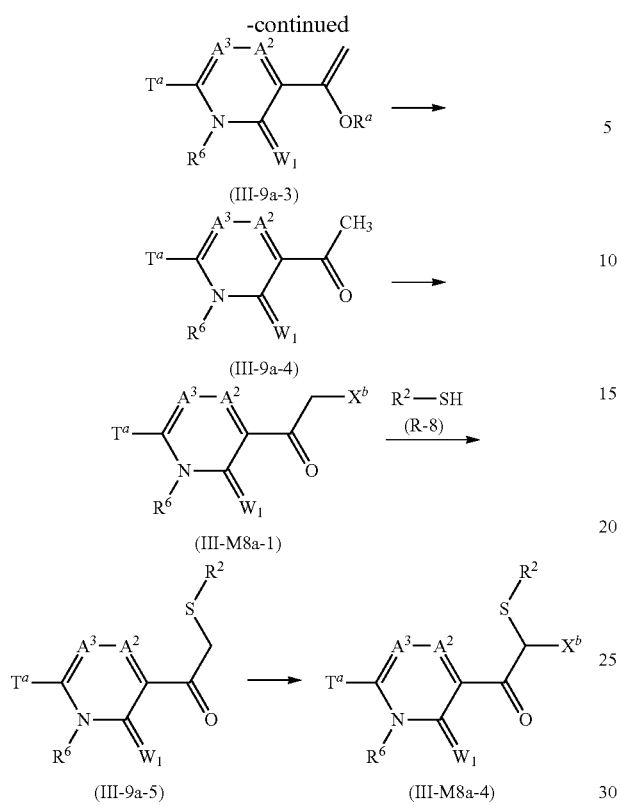

wherein $R^a$ represents a methyl group or an ethyl group, and the other symbols are the same as those defined above.

A compound represented by formula (III-9a-2) (hereinafter, referred to as "compound (III-9a-2)") can be prepared by reacting a compound represented by formula (III-9a-1) (hereinafter, referred to as "compound (III-9a-1)") with the compound (R-1a) in the presence of a base. The reaction can be carried out according to a similar method to that described in the Process 4.

The compound (III-9a-1) can be prepared according to, for example, the method described in WO 2007/146824 or the method described in WO 2007/103308.

Next, a process for preparing a compound represented by formula (III-9a-3) (hereinafter, referred to as "compound (III-9a-3)") is described.

The compound (III-9a-3) can be prepared by reacting the compound (III-9a-2) with a compound represented by formula (R-9) (hereinafter, referred to as "compound (R-9)"). The reaction can be carried out according to, for example, the method described in WO 2016/123253.

The compound (R-9) is known, or can be prepared according to a known method.

A compound represented by formula (III-9a-4) (hereinafter, referred to as "compound (III-9a-4)") can be prepared by reacting the compound (III-9a-3) with an acid. The reaction can be carried out according to, for example, the method described in WO 2016/123253.

The compound (III-M8a-1) can be prepared by reacting the compound (III-9a-4) with a halogenating agent. The reaction can be carried out according to, for example, the method described in WO 2013/191113.

A compound represented by formula (III-9a-5) (hereinafter, referred to as "compound (III-9a-5)") can be prepared by reacting the compound (III-M8a-1) with the compound (R-8) in the presence of a base. The reaction can be carried out according to the method described in Tetrahedron Letters, 64, 7419 (2008).

The compound (III-M8a-4) can be prepared by reacting the compound (III-9a-5) with a halogenating agent. The reaction can be carried out according to the method described in WO 2013/191113.

Reference Process 2

The compound (III-M8b-1) and the compound (III-M8b-4) can be prepared according to the following scheme.

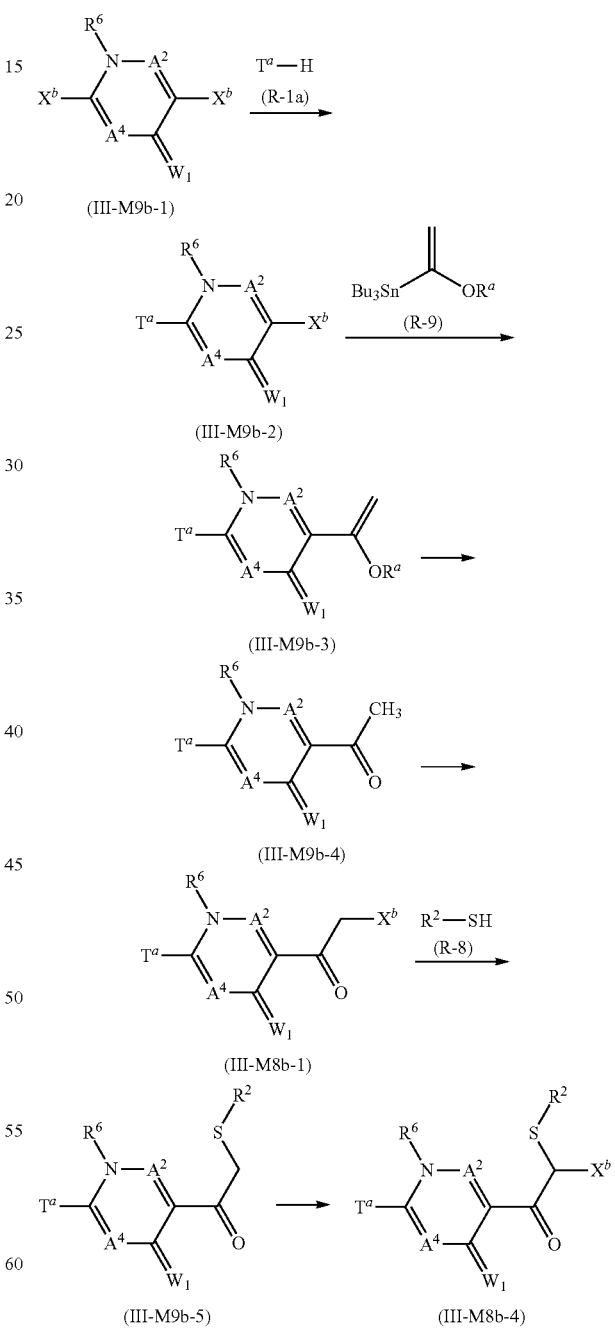

wherein the symbols are the same as those defined above.

The reactions can be carried out according to a similar method to that described in the Reference process 1.

A compound represented by formula (III-9b-1) can be prepared according to the method described in WO 2007/146824 or the method described in WO 2007/103308.

Reference Process 3

A compound represented by formula (III-M1a-a) (hereinafter, referred to as "compound (III-M1a-a)") can be prepared by reacting a compound represented by formula (III-M1a-1) (hereinafter, referred to as "compound (III-M1a-1)") with a compound represented by formula (R-10) (hereinafter, referred to as "compound (R-10)") in the presence of a base.

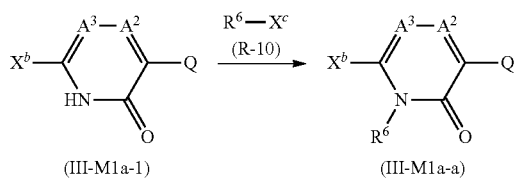

wherein the symbols are the same as those defined above.

The reaction can be carried out according to a similar method to that described in the Process 12 using the compound (III-M1a-1) instead of the compound (III-M2a) and using the compound (R-10) instead of the compound (R-2).

The compound (R-10) is commercially available, or can be prepared according to a known method.

Reference Process 4

The compound (III-M1a-1) can be prepared according the following scheme.

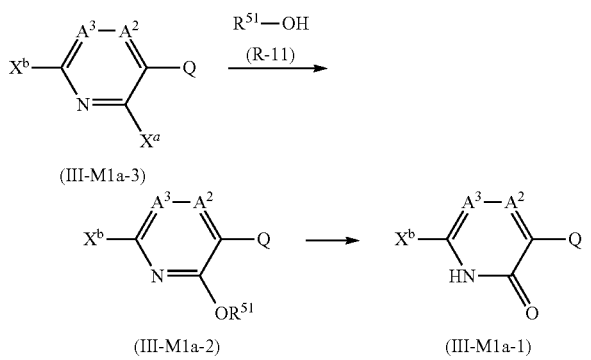

wherein $R^{51}$ represents a methyl group, an ethyl group, or a benzyl group, and the other symbols are the same as those defined above.

A compound represented by formula (III-M1a-2) (hereinafter, referred to as "compound (III-M1a-2)") can be prepared by reacting a compound represented by formula (III-M1a-3) (hereinafter, referred to as "compound (III-M1a-3)") with a compound represented by formula (R-11) (hereinafter, referred to as "compound (R-11)") in the presence of a base. The reaction can be carried out according to a similar method to that described in the Process 4.

The compound (III-M1a-1) can be prepared by reacting the compound (III-M1a-2) with an acid. The reaction can be carried out according to, for example, the method described in WO 2016/052455.

The compound (R-11) is commercially available, or can be prepared according to a known method.

Reference Process 5

A compound represented by formula (III-Q1a-1) (hereinafter, referred to as "compound (III-Q1a-1)") can be prepared by reacting a compound represented by formula (R-12) (hereinafter, referred to as "compound (R-12)") with a compound represented by formula (Q1b) (hereinafter, referred to as "compound (Q1b)") in the presence of a metal catalyst.

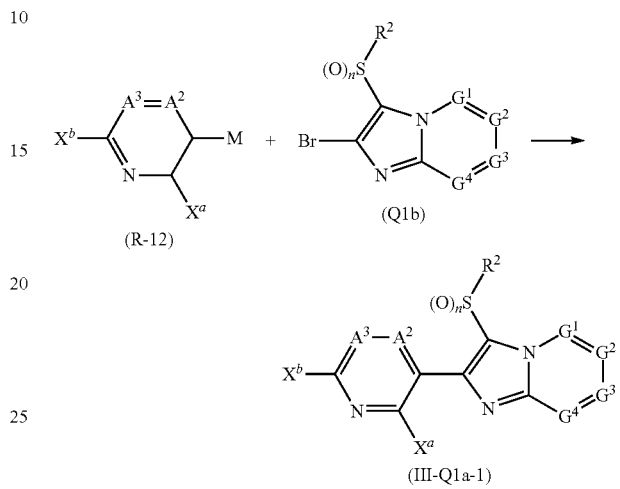

wherein the symbols are the same as those defined above.

The reaction can be carried out according to a similar method to that described in the Process 6 using the compound (Q1b) instead of the compound (III-M1a) and using the compound (R-12) instead of the compound (R-1b).

The compound (R-12) is commercially available, or can be prepared according to a known method.

Reference Process 6

A compound represented by formula (III-Q2a-1) (hereinafter, referred to as "compound (III-Q2a-1)") can be prepared by reacting the compound (R-12) with a compound represented by formula (Q2b) (hereinafter, referred to as "compound (Q2b)") in the presence of a metal catalyst.

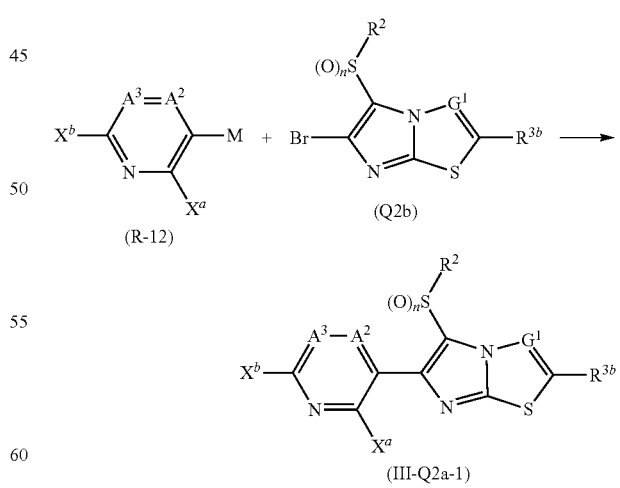

wherein the symbols are the same as those defined above.

The reaction can be carried out according to a similar method to that described in the Process 6 using the compound (Q2b) instead of the compound (III-M1a) and using the compound (R-12) instead of the compound (R-1b).

Reference Process 7

A compound represented by formula (III-Q3a-1) (hereinafter, referred to as "compound (III-Q3a-1)") can be prepared by reacting the compound (R-12) with a compound represented by formula (Q3b) (hereinafter, referred to as "compound (Q3b)") in the presence of a metal catalyst.

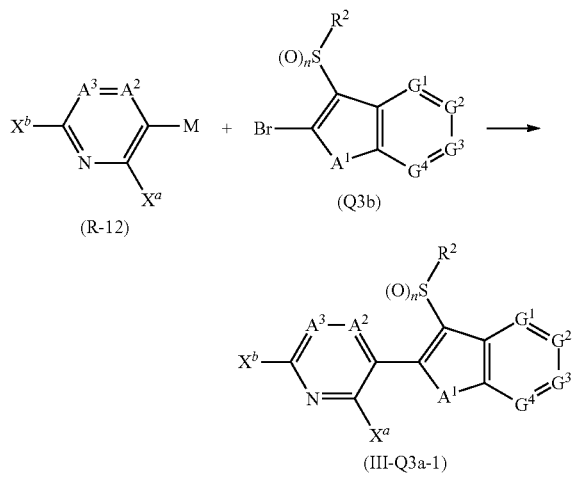

wherein the symbols are the same as those defined above.

The reaction can be carried out according to a similar method to that described in the Process 6 using the compound (Q3b) instead of the compound (III-M1a) and using the compound (R-12) instead of the compound (R-1b).

Reference Process 8

The compound (III-M1b) can be prepared by reacting a compound represented by formula (III-M1b-1) (hereinafter, referred to as "compound (III-M1b-1)") with the compound (R-10) in the presence of a base.

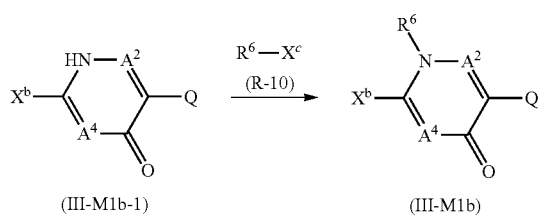

wherein the symbols are the same as those defined above.

The reaction can be carried out according to a similar method to that described in the Reference process 3.

Reference Process 9

The compound (III-M1b-1) can be prepared according to the following scheme.

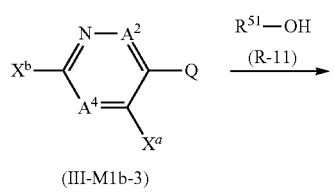

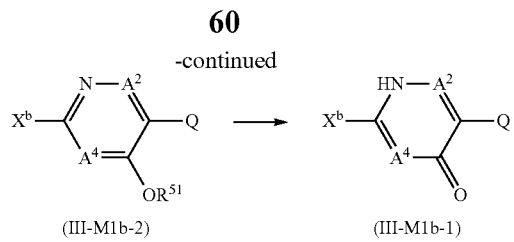

wherein the symbols are the same as those defined above.

The reactions can be carried out according to a similar method to that described in the Reference process 4.

Reference Process 10

A compound represented by formula (III-Q1a-2) can be prepared by reacting a compound represented by formula (R-13) (hereinafter, referred to as "compound (R-13)") with the compound (Q1b) in the presence of a metal catalyst.

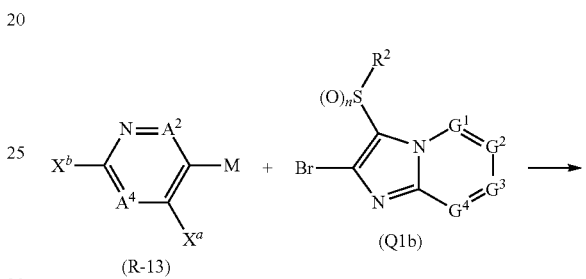

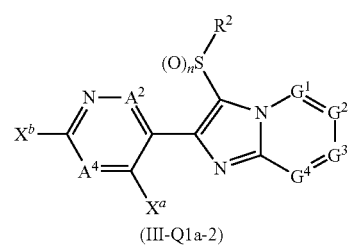

wherein the symbols are the same as those defined above.

The reaction can be carried out according to a similar method to that described in the Reference process 5.

The compound (R-13) is commercially available, or can be prepared according to a known method.

Reference Process 11

A compound represented by formula (III-Q2a-2) can be prepared by reacting the compound (R-13) with the compound (Q2b) in the presence of a metal catalyst.

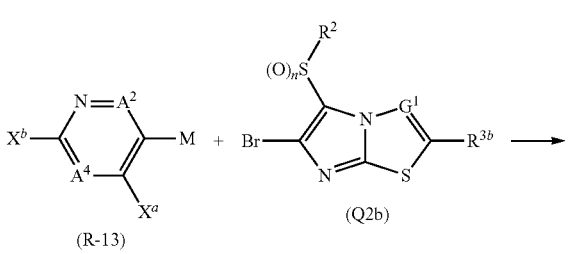

-continued

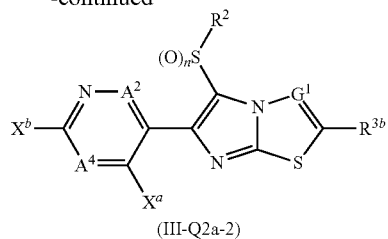

(III-Q2a-2)

wherein the symbols are the same as those defined above.

The reactions can be carried out according to a similar method to that described in the Reference process 5.

Reference Process 12

The compound represented by formula (III-Q3a-2) can be prepared by reacting the compound (R-13) with the compound (Q3b) in the presence of a metal catalyst.

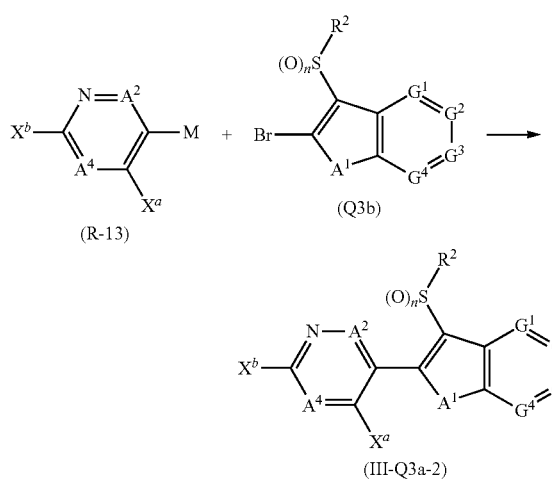

wherein the symbols are the same as those defined above.

The reaction can be carried out according to a similar method to that described in the Reference process 5.

Reference Process 13

The compound (III-M2a) can be prepared according to the following scheme.

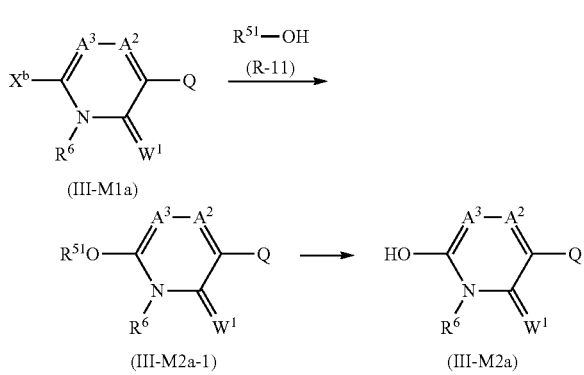

wherein the symbols are the same as those defined above.

The reactions can be carried out according to a similar method to that described in the Reference process 4.

Reference Process 14

The compound (III-M2b) can be prepared according to the following scheme.

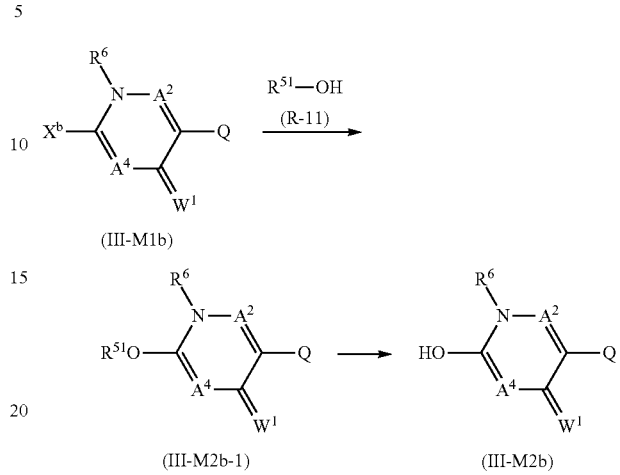

wherein the symbols are the same as those defined above.

The reactions can be carried out according to a similar method to that described in the Reference process 4.

Reference Process 15

The compound (III-M3a) can be prepared by reacting the compound (III-M1a) with a dry ice in the presence of a base.

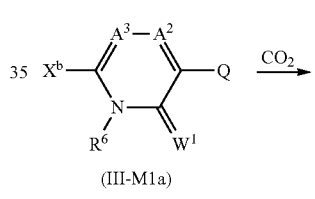

(III-M1a)

(III-M3a)

wherein the symbols are the same as those defined above.

The reaction can be carried out according to a similar method to that described in the Process 10 using a dry ice instead of the compound (R-1d).

Reference Process 16

The compound (III-M3b) can be prepared by reacting the compound (III-M1b) with a dry ice in the presence of a base.

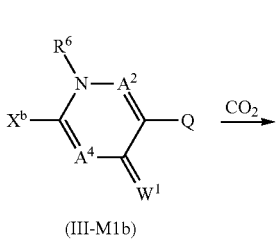

(III-M1b)

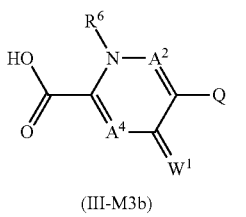

(III-M3b)

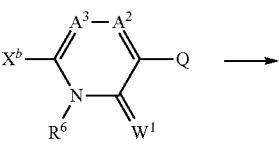

(III-M1a)

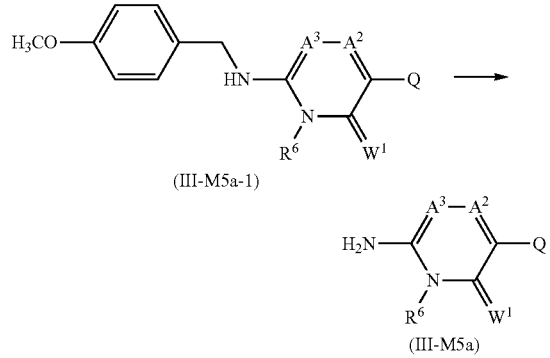

wherein the symbols are the same as those defined above.

The reaction can be carried out according to a similar method to that described in Process 10 using a dry ice instead of the compound (R-1d).

Reference Process 17

The compound (III-M4a) can be prepared by reacting the compound (III-M3a) with a reducing agent.

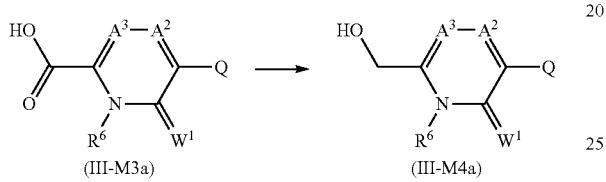

wherein the symbols are the same as those defined above.

The reaction is usually carried out in a solvent. Examples of the solvent to be used in the reaction include ethers, aliphatic hydrocarbons, aromatic hydrocarbons, alcohols, and two or more mixed solvents thereof.

Examples of the reducing agent to be used in the reaction include sodium borohydride, lithium borohydride, lithium aluminium hydride, and diisobutylaluminium hydride.

In the reaction, the reducing agent is used usually within a range of 1 to 5 molar ratio(s) relative to 1 mole of the compound (III-M3a).

A reaction temperature in the reaction is usually within a range of –20 to 120° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-M4a).

Reference Process 18

The compound (III-M4b) can be prepared by reacting the compound (III-M3b) with a reducing agent.

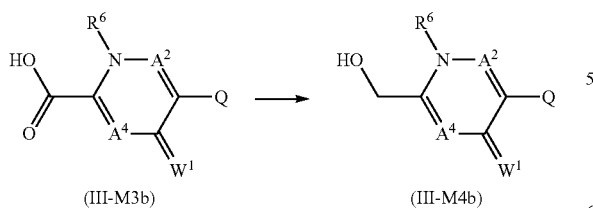

wherein the symbols are the same as those defined above.

The reactions can be carried out according to a similar method to that described in the Reference process 17.

Reference Process 19

The compound (III-M5a) can be prepared according to the following scheme.

wherein the symbols are the same as those defined above.

A compound represented by formula (III-M5a-1) (hereinafter, referred to as "compound (III-M5a-1)") can be prepared according to a similar method to that described in the Reference process 4 using the compound (III-M1a) instead of the compound (III-M1a-3) and using p-methoxybenzylamine instead of the compound (R-11).

The compound (III-M5a) can be prepared according to a similar method to that described in the Reference process 4 using the compound (III-M5a-1) instead of the compound (III-M1a-2).

Reference Process 20

The compound (III-M5b) can be prepared according the following scheme.

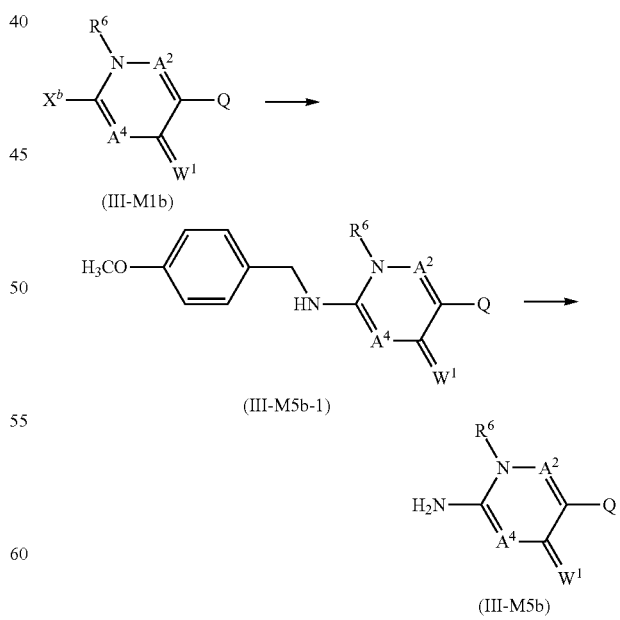

wherein the symbols are the same as those defined above.

The reactions can be carried out according to a similar method to that described in the Reference process 19.

Reference Process 21

The compound (III-M6a) can be prepared by reacting the compound (III-M1a) with a compound represented by formula (R-14) (hereinafter, referred to as "compound (R-14)") in the presence of a palladium catalyst, phenol, and potassium tert-butoxide.

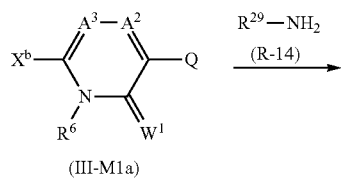

wherein the symbols are the same as those defined above.

The reaction is usually carried out in a solvent. Examples of the solvent to be used in the reaction include ethers, aromatic hydrocarbons, polar aprotic solvents, and two or more mixed solvents thereof.

Examples of the palladium catalyst include allylpalladium (II) chloride.

In the reaction, the compound (R-14) is used usually within a range of 1 to 10 molar ratio(s), the palladium catalyst is used usually within a range of 0.01 to 1 molar ratio(s), phenol is used usually within a range of 1 to 5 molar ratio(s), and potassium tert-butoxide is used usually within a range of 0.1 to 10 molar ratio(s), relative to 1 mole of the compound (III-M1a).

A reaction temperature in the reaction is usually within a range of 40 to 180° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-M6a).

The compound (R-14) is commercially-available and can be prepared according to a known method.

Reference Process 22

The compound (III-M6b) can be prepared by reacting the compound (III-M1b) with the compound (R-14) in the presence of a base.

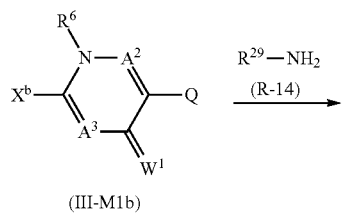

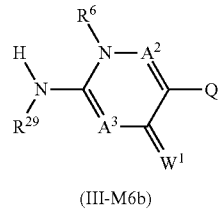

wherein the symbols are the same as those defined above.

The reaction can be carried out according to a similar method to that described in the Reference process 21.

Reference Process 23

The compound (III-M7a) can be prepared according to the following scheme.

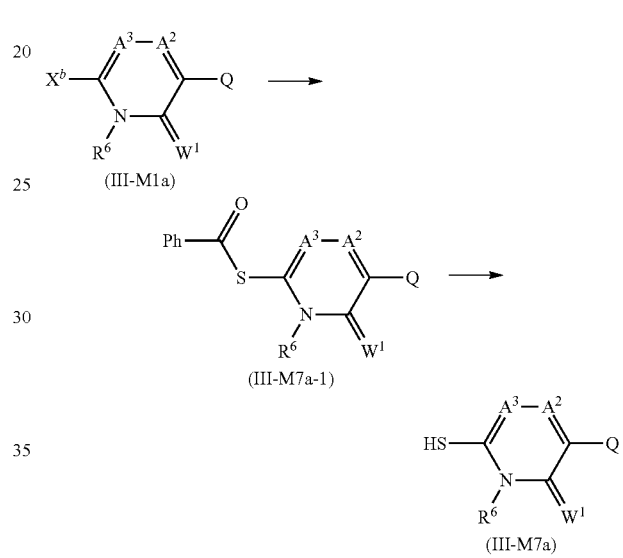

wherein the symbols are the same as those defined above.

Firstly, a process for preparing a compound represented by formula (III-M7a-1) (hereinafter, referred to as "compound (III-M7a-1)") is described.

The compound (III-M7a-1) can be prepared by reacting the compound (III-M1a) with thiobenzoic acid in the presence of a copper catalyst and a base.

The reaction is usually carried out in a solvent. Examples of the solvent to be used in the reaction include ethers, aromatic hydrocarbons, polar aprotic solvents, water, and two or more mixed solvents thereof.

Examples of the copper catalyst to be used in the reaction include copper(I) chloride, copper(I) bromide, and copper(I) iodide.

Examples of the base to be used in the reaction include alkali metal hydrides, alkali metal carbonates, and organic bases.

A ligand may be used in the reaction as needed. Examples of the ligand include 2,2'-bipyridine, 2-aminoethanol, 8-hydroxyquinoline, and 1,10-phenanthroline. When the ligand is used in the reaction, the ligand is used usually within a range of 0.01 to 1 molar ratio(s) relative to 1 mole of the compound (III-M1a).

In the reaction, thiobenzoic acid is used usually within a range of 1 to 10 molar ratio(s), the copper catalyst is used usually within a range of 0.01 to 0.5 molar ratios, and the base is used usually within a range of 0.1 to 5 molar ratios, relative to 1 mole of the compound (III-M1a).

A reaction temperature in the reaction is usually within a range of −20 to 200° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (III-M7a-1).

Next, a process for preparing the compound (III-M7a) is described.

The compound (III-M7a) can be prepared according to, for example, the method described in WO 2011/068171 or Journal of Organic Chemistry, 1978, 43(6), 1190-1192.

Reference Process 24

A compound represented by formula (III-M7b) can be prepared according to the following scheme.

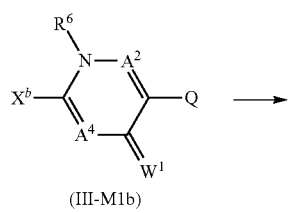
(III-M1b)

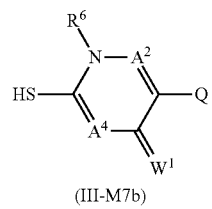
(III-M7b-1)

(III-M7b)

wherein the symbols are the same as those defined above.

The reactions can be carried out according to a similar method to that described in the Reference process 23.

Reference Process 25

A compound represented by formula (Q1e) and a compound represented by formula (Q1f) can be prepared by reacting the compound represented by formula (Q1d) with an oxidizing agent.

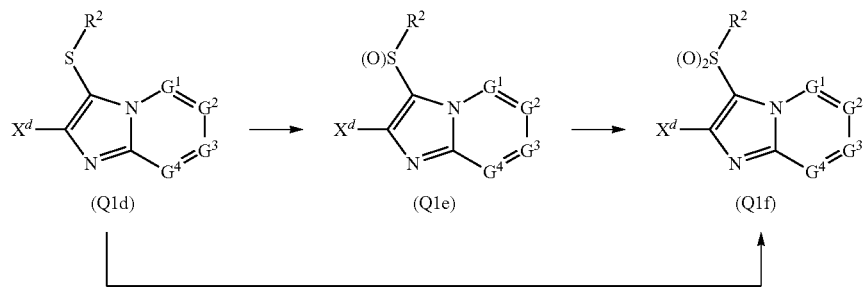
(Q1d)　(Q1e)　(Q1f)

wherein $X^d$ represents a halogen atom, and the other symbols are the same as those defined above.

The reactions can be carried out according to a similar method to that described in the Process 1.

Reference Process 26

A compound represented by formula (Q2e) and a compound represented by formula (Q2f) can be prepared by reacting the compound represented by formula (Q2d) with an oxidizing agent.

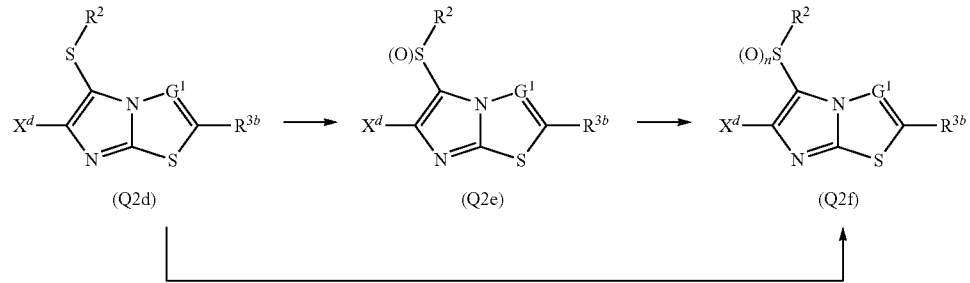
(Q2d)　(Q2e)　(Q2f)

wherein the symbols are the same as those defined above.

The reactions can be carried out according to a similar method to that described in the Process 1.
Reference Process 27

A compound represented by formula (Q3e) and a compound represented by formula (Q3f) can be prepared by reacting the compound represented by formula (Q3d) with an oxidizing agent.

The compound (Q1g-1) can be prepared by reacting a compound represented by formula (R-15) (hereinafter, referred to as "compound (R-15)") and the compound (R-7).

The reaction is usually carried out in a solvent. Examples of the solvent to be used in the reaction include aromatic hydrocarbons, alcohols, nitriles, and two or more mixed solvents thereof.

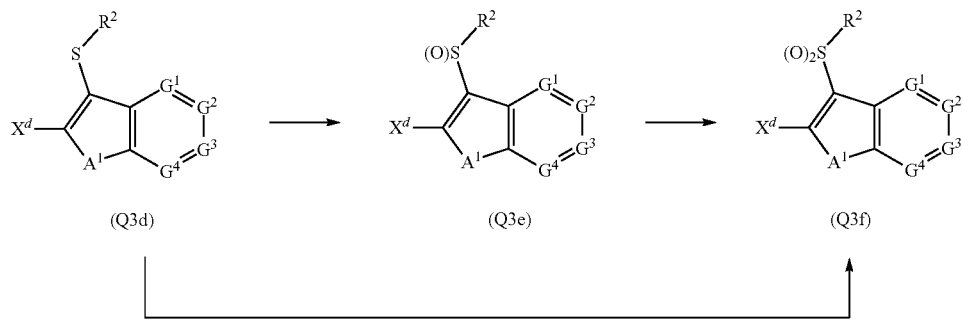

wherein the symbols are the same as those defined above.

The reactions can be carried out according to a similar method to that described in the Process 1.
Reference Process 28

A compound represented by formula (Q1g) (hereinafter, referred to as "compound (Q1g)") can be prepared according to the following scheme.

In the reaction, the compound (R-7) is used usually within a range of 1 to 10 molar ratio(s) relative to 1 mole of the compound (R-15).

A reaction temperature in the reaction is usually within a range of 0 to 200° C. A reaction period in the reaction is usually within a range of 0.1 to 48 hours.

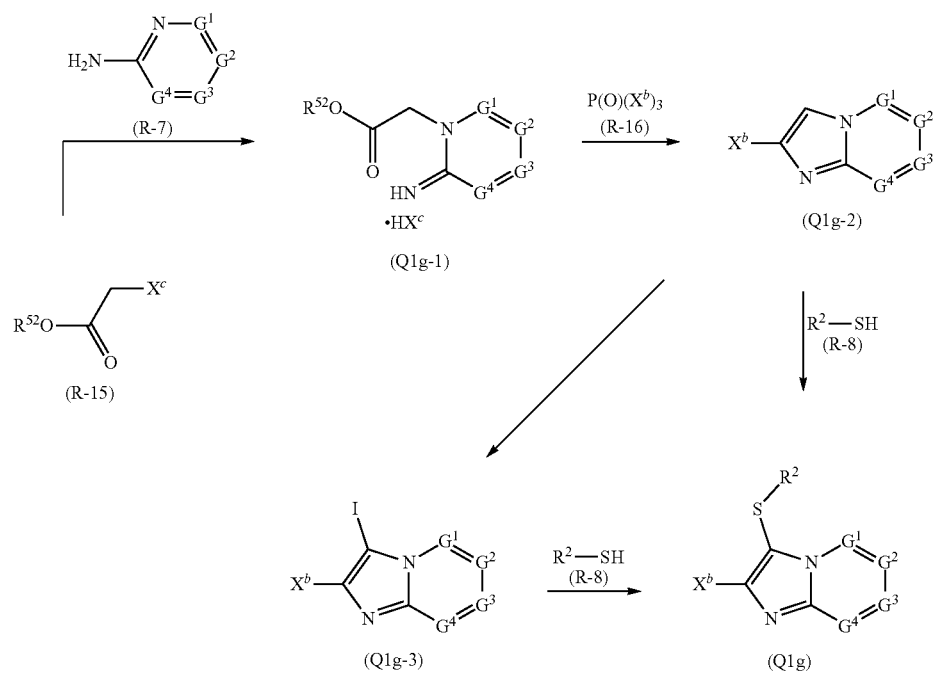

wherein $R^{52}$ represents a methyl group, an ethyl group, or a hydrogen atom, and the other symbols are the same as those defined above.

Firstly, a process for preparing a compound represented by formula (Q1g-1) (hereinafter, referred to as "compound (Q1g-1)") is described.

When the reaction is completed, the reaction mixture can be usually worked up to give the compound (Q1g-1).

The compound (R-15) is commercially available, or can be prepared according to a known method.

Next, a process for preparing a compound represented by formula (Q1g-2) (hereinafter, referred to as "compound (Q1g-2)") is described.

The compound (Q1g-2) can be prepared by reacting the compound (Q1g-1) with a compound represented by formula (R-16) (hereinafter, referred to as "compound (R-16)").

The reaction is usually carried out in a solvent. Examples of the solvent to be used in the reaction include aromatic hydrocarbons, nitriles, and two or more mixed solvents thereof.

In the reaction, the compound (R-16) is used usually within a range of 1 to 10 molar ratio(s) relative to 1 mole of the compound (Q1g-1).

A reaction temperature in the reaction is usually within a range of 60 to 120° C. A reaction period in the reaction is usually within a range of 0.1 to 48 hours.

When the reaction is completed, the reaction mixture can be usually worked up to give the compound (Q1g-2).

The compound (R-16) is commercially available, or can be prepared according to a known method.

Next, a process for preparing a compound represented by formula (Q1g-3) (hereinafter, referred to as "compound (Q1g-3)") is described.

The compound (Q1g-3) can be prepared by reacting the compound (Q1g-2) with N-iodosuccinimide. The reaction can be prepared according to a similar method to that described in the process for preparing the compound (III-M8a-3) from the compound (III-M8a-2) in the Process 24.

Next, a process for preparing the compound (Q1g) is described.

The compound (Q1g) can be prepared by reacting the compound (Q1g-2) or the compound (Q1g-3) with the compound (R-8). The reaction can be carried out according to a similar method to that described in the process for preparing the compound (III-8a) from the compound (III-M8a-2) or the compound (III-M8a-3) in the Process 24.

Reference Process 29

A compound represented by formula (Q2g) (hereinafter, referred to as "compound (Q2g)") can be prepared according the the following scheme.

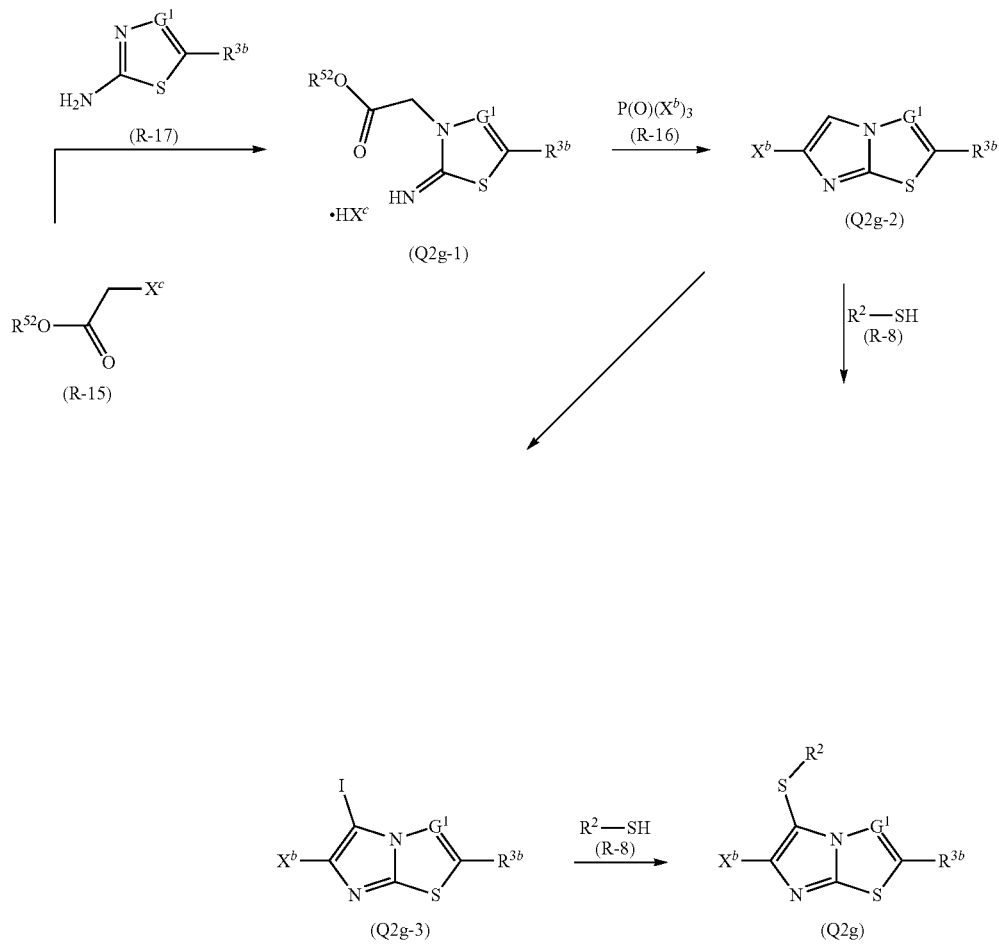

wherein the symbols are the same as those defined above.

The reaction can be carried out according to a similar method to that described in the Process 28.

A compound represented by formula (R-17) is commercially available, or can be prepared according to a known method.

Reference Process 30

A compound represented by formula (Q3g) (hereinafter, referred to as "compound (Q3g)") can be prepared according to the following scheme.

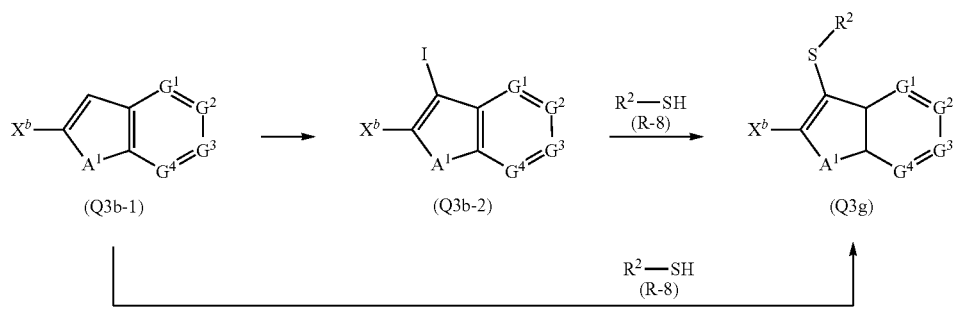

(Q3b-1)   (Q3b-2)   (Q3g)

wherein the symbols are the same as those defined above.

A process for preparing a compound represented by formula (Q3b-2) (hereinafter, referred to as "compound (Q3b-2)") is described.

The compound (Q3b-2) can be prepared by reacting a compound represented by formula (Q3b-1) (hereinafter, referred to as "compound (Q3b-1)") with N-iodosuccinimide. The reaction can be carried out according to a similar method to that described in the process for preparing the compound (III-M8a-3) from the compound (III-M8a-2) in the Process 24.

Next, a process for preparing the compound (Q3g) is described.

The compound (Q3g) can be prepared by reacting the compound (Q3b-1) or the compound (Q3b-2) with the compound (R-8). The reaction can be carried out according to a similar method to that described in the process for preparing the compound (III-8a) from the compound (III-M8a-2) or the compound (III-M8a-3) in the Process 24.

Reference Process 31

A compound represented by formula (IV-M3) (hereinafter, referred to as "compound (IV-M3)") can be prepared by reacting a compound represented by formula (IV-M2) (hereinafter, referred to as "compound (IV-M2)") with the compound (Q1c) in the presence of a metal catalyst and a base.

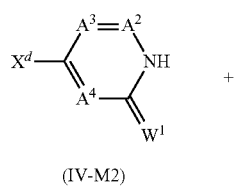

(IV-M2)

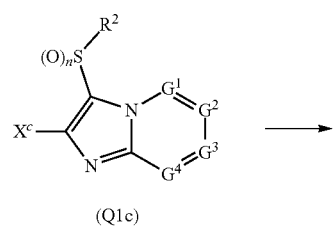

(Q1c)

-continued

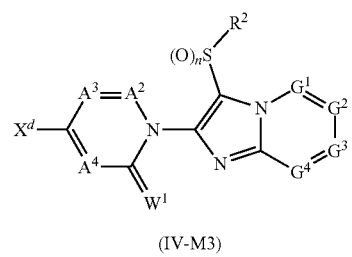

(IV-M3)

wherein the symbols are the same as those defined above.

The reaction can be prepared according to a similar method to that described in the Process 29 using the compound (IV-M2) instead of the compound (IV-M1).

The compound (IV-M2) is known, or can be prepared according to the method described in Synlett, 27(1), 67, 2016.

Reference Process 32

A compound represented by formula (IV-M5-2) (hereinafter, referred to as "compound (IV-M5-2)") can be prepared according to the following scheme.

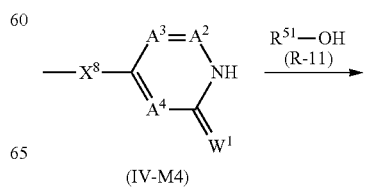

(IV-M4)

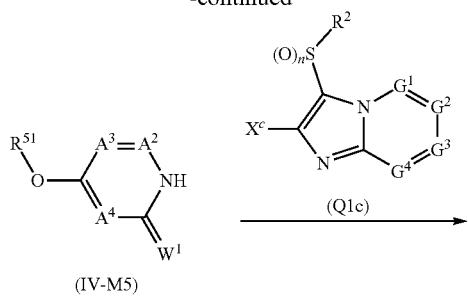

(IV-M5)

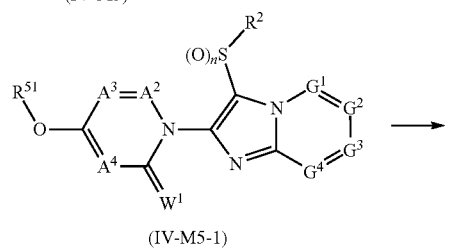

(IV-M5-1)

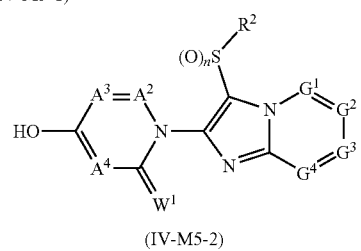

(IV-M5-2)

wherein the symbols are the same as those defined above.

A compound represented by formula (IV-M5) (hereinafter, referred to as "compound (IV-M5)") can be prepared by reacting a compound represented by formula (IV-M4) (hereinafter, referred to as "compound (IV-M4)") with the compound (R-11) in the presence of a base.

The reaction can be carried out according to a similar method to that described in the Reference process 4.

A compound represented by formula (IV-M5-1) (hereinafter, referred to as "compound (IV-M5-1)") can be prepared by reacting the compound (IV-M5) with the compound (Q1c) in the presence of a metal catalyst and a base.

The reaction can be carried out according to a similar method to that described in the Process 29.

The compound (IV-M5-2) can be prepared by reacting the compound (IV-M5-1) with an acid.

The reaction can be carried out according to a similar method to that described in the Reference process 4.

Reference Process 33

A compound represented by formula (IV-M6) (hereinafter, referred to as "compound (IV-M6)") can be prepared by reacting the compound (IV-M2) with the compound (Q2c) in the presence of a metal catalyst and a base.

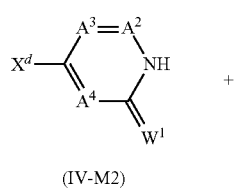

(IV-M2)

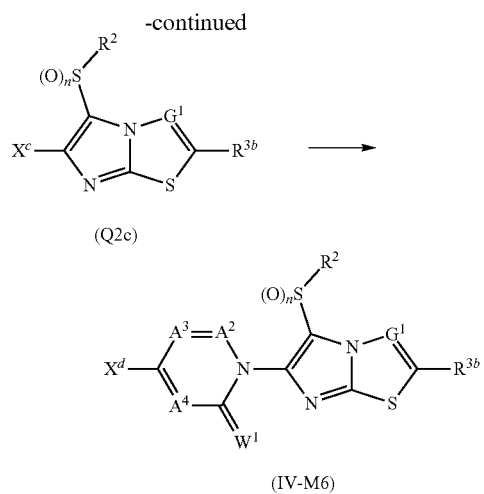

wherein the symbols are the same as those defined above.

The reaction can be carried out according to a similar method to that described in the Process 29.

Reference Process 34

A compound represented by formula (IV-M8-2) (hereinafter, referred to as "compound (IV-M8-2)") can be prepared according to the following scheme.

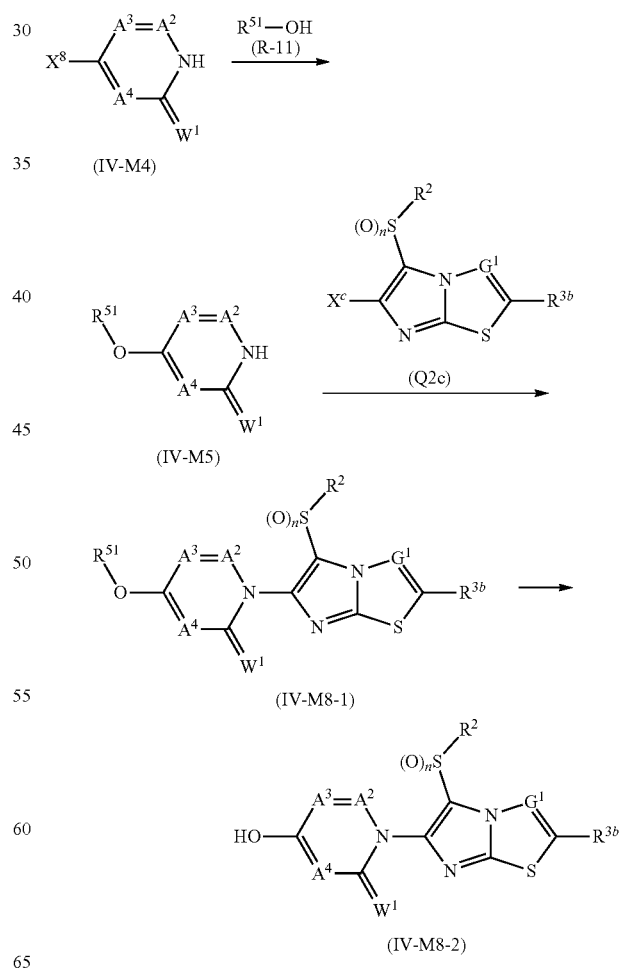

wherein the symbols are the same as those defined above.

The reaction can be carried out according to a similar method to that described in the Reference process 32.

Reference Process 35

A compound represented by formula (IV-M9) (hereinafter, referred to as "compound (IV-M9)") can be prepared by reacting the compound (IV-M2) with the compound (Q1c) in the presence of a metal catalyst and a base.

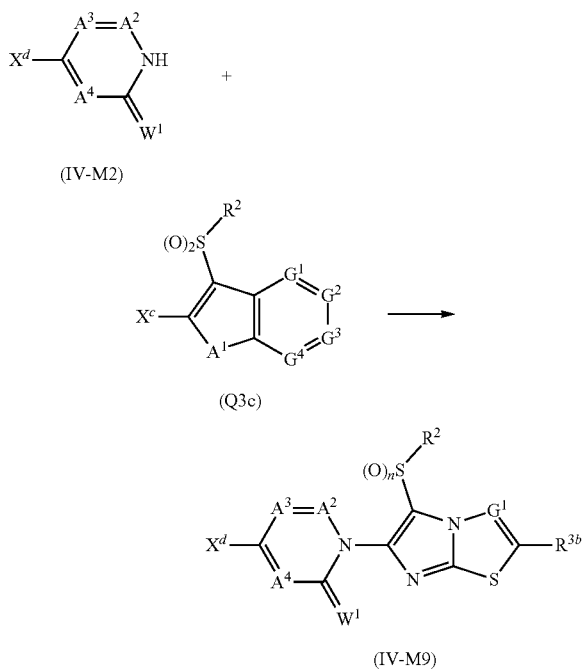

wherein the symbols are the same as those defined above.

The reaction can be carried out according to a similar method to that described in the Process 29.

Reference Process 37

A compound represented by formula (IV-M11-2) (hereinafter, referred to as "compound (IV-M11-2)") can be prepared according to the following scheme.

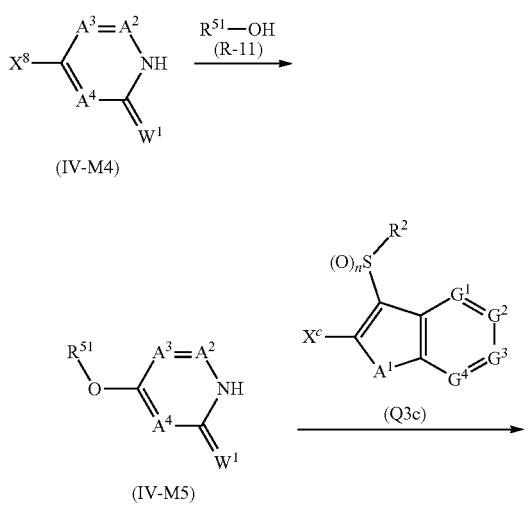

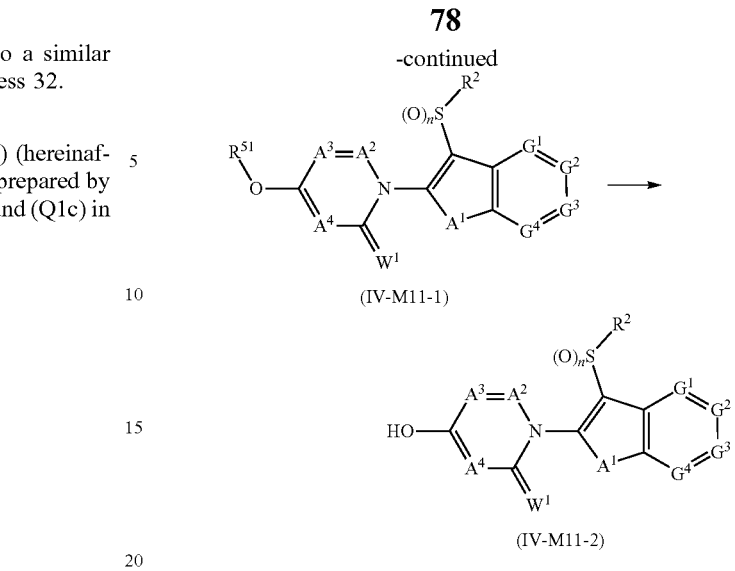

wherein the symbols are the same as those defined above.

The reaction can be carried out according to a similar method to that described in the Reference process 32.

Reference Process 38

A compound represented by formula (III-M1a-c) (hereinafter, referred to as "compound (III-M1a-c)") can be prepared by reacting the compound (III-M1a-a) with a sulfurizing agent.

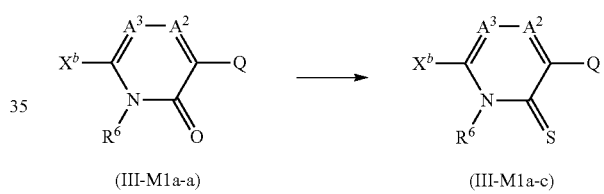

wherein the symbols are the same as those defined above.

The reaction can be carried out according to, for example, the method described in Tetrahedron, 63, 11862 (2007).

Reference Process 39

A compound represented by formula (III-M1b-d) (hereinafter, referred to as "compound (III-M1b-d)") can be prepared by reacting the compound (III-M1b) with a sulfurizing agent.

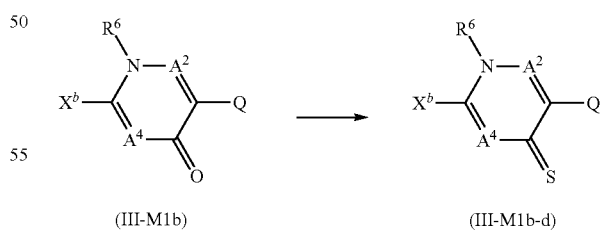

wherein the symbols are the same as those defined above.

The reaction can be carried out according to a similar method to that described in the Reference process 38.

Reference Process 40

A compound represented by formula (Q1i) (hereinafter, referred to as "compound (Q1i)") can be prepared by reacting a compound represented by formula (Q1h) with silver fluoride in the presence of a metal catalyst.

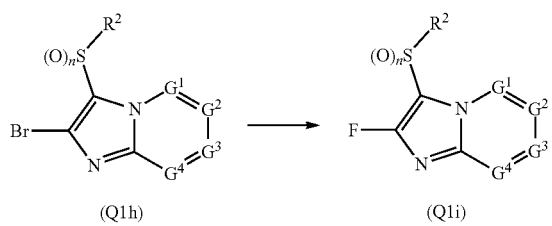

wherein the symbols are the same as those defined above.

The reaction can be carried out according to, for example, the method described in Journal of the American Chemical Society, 2014, 136, 3792.

Reference Process 41

A compound represented by formula (Q1j) (hereinafter, referred to as "compound (Q1j)") can be prepared by reacting the compound (Q1h) with sodium iodide in the presence of a metal catalyst.

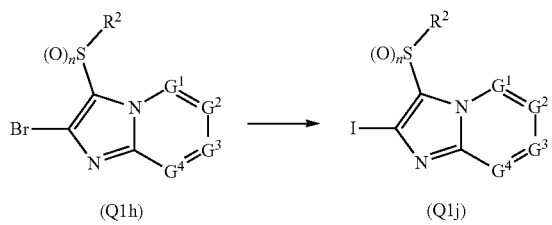

wherein the symbols are the same as those defined above.

The reaction can be carried out according to, for example, the method described in Journal of the American Chemical Society, 2002, 124, 14844.

Reference Process 42

A compound represented by formula (Q2i) (hereinafter, referred to as "compound (Q2i)") can be prepared by reacting a compound represented by formula (Q2h) (hereinafter, referred to as "compound (Q2h)") with silver fluoride in the presence of a metal catalyst.

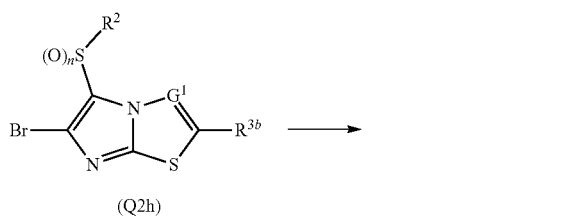

wherein the symbols are the same as those defined above.

The reaction can be carried out according to, for example, the method described in Journal of the American Chemical Society, 2014, 136, 3792.

Reference Process 43

A compound represented by formula (Q2j) (hereinafter, referred to as "compound (Q2j)") can be prepared by reacting the compound (Q2h) with sodium iodide in the presence of a metal catalyst.

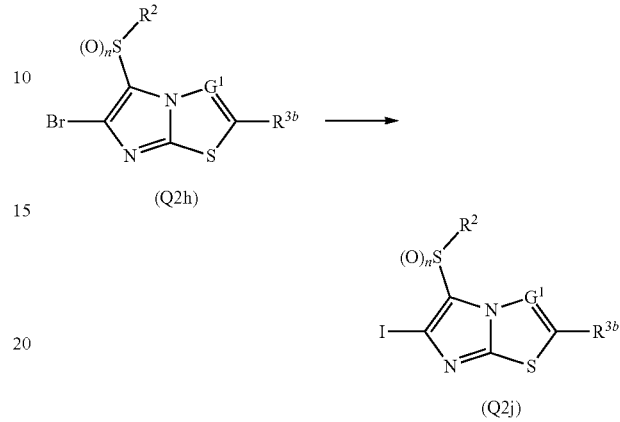

wherein the symbols are the same as those defined above.

The reaction can be carried out according to, for example, the method described in Journal of the American Chemical Society, 2002, 124, 14844.

Reference Process 44

A compound represented by formula (Q3i) (hereinafter, referred to as "compound (Q3i)") can be prepared by reacting a compound represented by formula (Q3h) (hereinafter, referred to as "compound (Q3h)") with silver fluoride in the presence of a metal catalyst.

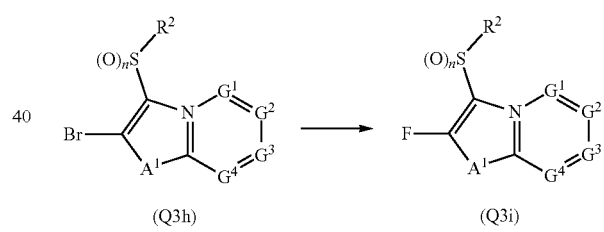

wherein the symbols are the same as those defined above.

The reaction can be carried out according to, for example, the method described in Journal of the American Chemical Society, 2014, 136, 3792.

Reference Process 45

A compound represented by formula (Q3j) (hereinafter, referred to as "compound (Q3j)") can be prepared by reacting the compound (Q3h) with sodium iodide in the presence of a metal catalyst.

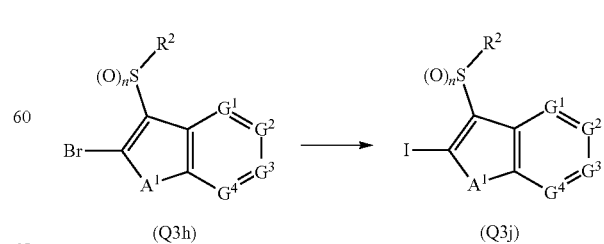

wherein the symbols are the same as those defined above.

The reaction can be carried out according to, for example, the method described in Journal of the American Chemical Society, 2002, 124, 14844.

The present compound or the present compound X can be mixed or combined with one or more ingredients selected from the group consisting of the following Group (a), Group (b), Group (c), Group (d), Group (e), Group (f), Group (g), and Group (h) (hereinafter, referred to as "present ingredient").

The mixing or combining represents that the present compound or the present compound X and the present ingredient are used concurrently, separately, or at an interval.

When the present compound or the present compound X and the present ingredient are concurrently used, the present compound or the present compound X and the present ingredient may be incorporated as a separate formulation or one formulation.

One aspect of the present invention relates to a composition comprising one or more ingredients selected from the group consisting of the Group (a) and the Group (b), and the present compound.

One aspect of the present invention relates to a composition comprising one or more ingredients selected from the group consisting of the Group (a) and the Group (b), and the present compound X (hereinafter, referred to as "composition A").

The Group (a) represents a group consisting of acetylcholinesterase inhibitors (for example, carbamate insecticides and organophosphate insecticides), GABA-gated chloride ion channel antagonists (for example, phenylpyrazole insecticides), sodium channel modulators (for example, pyrethroid insecticides), nicotinic acetylcholine receptor antagonist modulators (for example, neonicotinoid insecticides), nicotinic acetylcholine receptor allosteric modulators, glutamate-gated chloride ion channel allosteric modulators (for example, macrolide insecticides), juvenile hormone mimics, multisite inhibitors, chordotonal organ TRPV channel modulators, mites growth regulators, mitochondrial ATP synthase inhibitors, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, Inhibitors of mitochondrial electron transport chain complex I, II, III, and IV, voltage-dependent sodium channel blockers, Inhibitors of acetyl CoA carboxylase, ryanodine receptor modulators (for example, diamide insecticides), chordotonal organ modulators, each active ingredient of microbial fungicides, and other insecticidal ingredients, miticidal ingredients and nematicidal ingredients. These agents are described in the classification based on the IRAC mode of action.

The Group (b) represents a group consisting of nucleic acid synthesis inhibitors (for example, phenylamide fungicides and acylamino acid fungicides), cytostatic and cytoskeletal inhibitors (for example, MBC fungicides), respiration inhibitors (for example, QoI fungicides and QiI fungicides), amino-acid synthesis and protein synthesis inhibitors (for example, anilinopyridine fungicides), signal-transduction inhibitors, lipid synthesis and membrane synthesis inhibitors, sterol biosynthesis inhibitors (for example, DMI fungicides such as triazoles), cell wall synthesis inhibitors, melanin synthesis inhibitors, plant defense inducer, multisite fungicides, microbial fungicides, and other fungicidal ingredients. These agents are described in the classification based on the FRAC mode of action.

The Group (c) represents a group of plant growth modulating ingredients including mycorrhizal fungus and *rhizobia*.

The Group (d) represents a group of phytotoxicity mitigation ingredients.

The Group (e) represents a group of synergists.

The Group (f) represents a group of repellent ingredients consisting of bird repellent ingredients, insect repellent ingredients, and animal repellent ingredients.

The Group (g) represents a group of molluscicide ingredients.

The Group (h) represents a group of insect pheromones.

Examples of combinations of the present ingredient and the present compound X are recited as follows. For example, the "alanycarb+SX" indicates a combination of alanycarb and SX.

The abbreviation "SX" means to any one of the present compounds X selected from the compound groups SX1 to SX2496 described in Examples. Further, any of the present ingredients as described below are a known ingredient, and can be obtained as a commercially available drug or prepared according to a known method. When the present ingredient represents a microorganism, the present ingredient can be obtained from a microorganism depositary authority. The number in parentheses represents CAS RN (registered trademark).

A combination of the present ingredient in the above-mentioned Group (a) and the present compound X:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, *Celastrus angulatus* (bark of *Celastrus angulatus*)+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, dried leaves of Dryopteris filix-mas+SX, emamectin-benzoate+SX, empenthrin+SX, endosulfan+SX, EPN (O-ethyl 0-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absin-* thium+SX, extract of *Cassia nigricans*+SX, extract of *clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, propylene glycol alginate+SX, prothiofos+SX, pyflubumide)+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *chenopodium ambrosioides* near *ambrosioides*+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide)+SX, 3-bromo-N-[2,4-dichloro-6-(methylcarbamoyl)phenyl]-1-(3,5-dichloropyridin-2-yl)-1H-pyrazol-5-carboxamide (1104384-14-6)+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietane-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus BV-0001+SX, *Anticarsia gemmatalis* mNPV+SX, *Autographa californica* mNPV+SX, *Cydia pomonella* GV V15+SX, *Cydia pomonella* GV V22+SX, Cryptophlebia leucotreta GV+SX, *Dendrolimus* punctatus cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema* locustae+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* I-1582+SX, *Bacillus megaterium*+SX, *Bacillus* sp. AQ175+SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. Aizawai ABTS-1857+SX, *Bacillus thuringiensis* subsp. Aizawai AM65-52+SX, *Bacillus thuringiensis* subsp. Aizawai GC-91+SX, *Bacillus thuringiensis* subsp. Aizawai Serotype H-7+SX, *Bacillus thuringiensis* subsp. Kurstaki ABTS351+SX, *Bacillus thuringiensis* subsp. Kurstaki BMP123+SX, *Bacillus thuringiensis* subsp. Kurstaki EG234+SX, *Bacillus thuringiensis* subsp. Kurstaki EG7841+SX, *Bacillus thuringiensis* subsp. Kurstaki EVB113-19+SX, *Bacillus thuringiensis* subsp. Kurstaki F810+SX, *Bacillus thuringiensis* subsp. Kurstaki HD-1+SX, *Bacillus thuringiensis* subsp. Kurstaki PB54+SX, *Bacillus thuringiensis* subsp. Kurstaki SA-11+SX, *Bacillus thuringiensis* subsp. Kurstaki SA-12+SX, *Bacillus thuringiensis* subsp. Tenebriosis NB176+SX, *Bacillus thuringiensis* subsp. *Thuringiensis* MPPL002+SX, *Bacillus thuringiensis* subsp. morrisoni+SX, *Bacillus thuringiensis* var. colmeri+SX, *Bacillus thuringiensis* var. darmstadiensis 24-91+SX, *Bacillus thuringiensis* var. dendrolimus+SX, *Bacillus thu-*

*ringiensis* var. galleriae+SX, *Bacillus thuringiensis* var. *israelensis* BMP144+SX, *Bacillus thuringiensis* var. *israelensis* serotype H-14+SX, *Bacillus thuringiensis* var. *japonensis* buibui+SX, *Bacillus thuringiensis* var. san diego M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*)+SX, *Hirsutella rhossiliensis*+SX, *Hirsutella thompsonii*+SX, *Lagenidium giganteum*+SX, *Lecanicillium lecanii* KV01+SX, *Lecanicillium lecanii* conidia of strain DAOM198499+SX, *Lecanicillium lecanii* conidia of strain DAOM216596+SX, *Metarhizium anisopliae* F52+SX, *Metarhizium anisopliae* var. acridum+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* NCIM1312+SX, isocycloseram+SX, *Metarhizium anisopliae* var. anisopliae BIPESCO 5/F52+SX, *Lecanicillium muscarium* Ve6+SX, N-ethyl-5-methyl-1-(3-methylbutan-2-yl)-N-(pyridazin-4-yl)-1H-pyrazole-4-carboxamide (1403615-77-9)+SX, and imidaclothiz+SX.

A combination of the present ingredient in the above-mentioned Group (b) and the present compound X:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl)+SX, benzovindiflupyr+SX, binapacryl+SX, biphenyl+SX, bitertanol+SX, bixafen+SX, blasticidin-S+SX, bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole–M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca* alternifolia+SX, extract from *Reynoutria sachalinensis*+SX, extract from the cotyledons of lupine plantlets (“BLAD”)+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, 3-(difluorodifluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluorodifluoromethyl)-N-methoxy-1-methyl-N-[(1S)-1-methyl-2-(2,4,6-trichlorophenyl)ethyl]pyrazole-4-carboxamide (1639015-49-8)+SX, 3-(difluorodifluoromethyl)-1-methyl-N-(1,1,3-trimethylindan-4-yl)pyrazole-4-carboxamide (141573-94-6)+SX, 3-(difluorodifluoromethyl)-N-[(3R)-7-fluoro-1,1,3-trimethylindan-4-yl]-1-methylpyrazole-4-carboxamide (1513466-73-3)+SX, N'-[4-({3-[(4-chlorophenyl)methyl]-1,2,4-thiadiazol-5-yl}oxy)-2,5-dimethylphenyl]-N-ethyl-N-methylmethaneimidamide (1202781-91-6)+SX, 2-{3-[2-(1-{[3,5-bis(difluorodifluoromethyl)-1H-pyrazol-1-yl]

acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo4-fluorophenyl)-N-(2-chloro-6-fluorophenyl)-1,3-dimethyl-1H-pyrazole-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridine-2-amine (1446247-98-8)+SX, α-[3-(4-chloro-2-fluorophenyl)-5-(2,4-difluorophenyl)-4-isoxazolyl]-3-pyridinemethanol (1229605-96-2)+SX, (αS)-[3-(4-chloro-2-fluorophenyl)-5-(2,4-difluorophenyl)-4-isoxazolyl]-3-pyridinemethanol (1229606-46-5)+SX, (αR)-[3-(4-chloro-2-fluorophenyl)-5-(2,4-difluorophenyl)-4-isoxazolyl]-3-pyridinemethanol (1229606-02-3)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanato (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanato(1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanato (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanato (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanato (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5R)-5-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, methyl=3-[(4-chlorophenyl)methyl]-2-hydroxy-1-methyl-2-(1H-1,2,4-triazol-1-ylmethyl)cyclopentanecarboxylate (1791398-02-1)+SX, methyl=(1R,2S,3S)-3-[(4-chlorophenyl)methyl]-2-hydroxy-1-methyl-2-(1H-1,2,4-triazol-1-ylmethyl)cyclopentanecarboxylate (2080743-90-2)+SX, methyl=(1S,2R,3R)-3-[(4-chlorophenyl)methyl]-2-hydroxy-1-methyl-2-(1H-1,2,4-triazol-1-ylmethyl)cyclopentanecarboxylate (2080743-91-3)+SX, methyl=(1R,2R,3R)-3-[(4-chlorophenyl)methyl]-2-hydroxy-1-methyl-2-(1H-1,2,4-triazol-1-ylmethyl)cyclopentanecarboxylate (2080743-92-4)+SX, methyl=(1S,2S,3S)-3-[(4-chlorophenyl)methyl]-2-hydroxy-1-methyl-2-(1H-1,2,4-triazol-1-ylmethyl)cyclopentanecarboxylate (2080743-93-5)+SX, methyl=(1R,2R,3S)-3-[(4-chlorophenyl)methyl]-2-hydroxy-1-methyl-2-(1H-1,2,4-triazol-1-ylmethyl)cyclopentanecarboxylate (2080743-94-6)+SX, methyl=(1S,2S,3R)-3-[(4-chlorophenyl)methyl]-2-hydroxy-1-methyl-2-(1H-1,2,4-triazol-1-ylmethyl)cyclopentanecarboxylate (2080743-95-7)+SX, methyl=(1R,2S,3R)-3-[(4-chlorophenyl)methyl]-2-hydroxy-1-methyl-2-(1H-1,2,4-triazol-1-ylmethyl)cyclopentanecarboxylate (2081061-22-3)+SX, methyl=(1S,2R,3S)-3-[(4-chlorophenyl)methyl]-2-hydroxy-1-methyl-2-(1H-1,2,4-triazol-1-ylmethyl)cyclopentanecarboxylate (2081061-23-4)+SX, 2-chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1801930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4)+SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1)+SX, (1S,2S,5R)-2-chloromethyl-5-(4-fluorobenzyl)-2-methyl-1-(1H-1,2,4-triazol-1-ylmethyl)cyclopentanol (1638898-16-4)+SX, (1R,2S,5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy)phenyl]-1-(1,2,4-triazol-1-yl)pent-3-in-2-ol (1801919-59-4)+SX, (R)-2-[4-(4-chlorophenoxy)-2-(trifluoromethyl)phenyl]-1-(1,2,4-triazol-1-yl)propan-2-ol (1616236-94-2)+SX, (R)-1-[4-(4-chlorophenoxy)-2-(trifluoromethyl)phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butan-2-ol (1801919-61-8)+SX, 3-[5-(4-chlorophenyl)-2,3-dimethyl-1,2-oxazolin-3-yl]pyridine (847749-37-5)+SX, *Agrobacterium* radiobacter K1026+SX, *Agrobacterium* radiobacter K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SB3086)+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX,

*Bacillus subtilis* FZB24+SX, *Bacillus subtilis* GB03+SX, *Bacillus subtilis* HAI0404+SX, *Bacillus subtilis* IAB/BSO3+SX, *Bacillus subtilis* MBI600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* O+SX, *Candida saitoana*+SX, *Chaetomium cupreum*+SX, Clonostachys *rosea*+SX, *Coniothyrium minitans* CGMCC8325+SX, *Coniothyrium minitans* CON/M/91-8+SX, *cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, *Pseudozyma flocculosa* PF-A22UL+SX, *Pseudomonas rhodesiae* HAI-0804+SX, *Pythium oligand Rum* DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* V117b+SX, *Trichoderma asperellum* ICCO12+SX, *Trichoderma asperellum* SKT-1+SX, *Trichoderma asperellum* T34+SX, *Trichoderma atroviride* CNCM 1-1237+SX, *Trichoderma atroviride* LC52+SX, *Trichoderma* atroviride SC1+SX, *Trichoderma* atroviride SKT-1+SX, *Trichoderma gamsii* ICC080+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum* kd+SX, *Trichoderma harzianum* MO1+SX, *Trichoderma harzianum* SF+SX, *Trichoderma harzianum* T22+SX, *Trichoderma harzianum* T39+SX, *Trichoderma harzianum* TEM908+SX, *Trichoderma harzianum* TH35+SX, *Trichoderma polysporum* IMI206039+SX, *trichoderma stromaticum*+SX, *Trichoderma virens* G-41+SX, *Trichoderma virens* GL-21+SX, *Trichoderma viride*)+SX, *Variovorax paradoxus* CGF4526+SX, Harpin protein+SX, *Bacillus amyloliquefaciens* subsp. *plantarum* D747+SX, *Pythium oligand Rum* M1+SX, *Trichoderma asperellum* T25+SX, *Trichoderma asperellum* TV1+SX, *Trichoderma atroviride* IMI 206040+SX, *Trichoderma atroviride* T11+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Pseudomonas chlororaphis* strain AFS009+SX, *Bacillus amyloliquefaciens* (Aveo (registered trademark) EZ Nematicide)+SX.

A combination of the present ingredient in the above-mentioned Group (c) and the present compound X:

1-methylcyclopropene+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butylate+SX, methyl 5-(trifluoromethyl)benzo[b]thiophene-2-carboxylate+SX, 3-[(6-chloro-4-phenylquinazolin-2-yl)amino]-1-propanol+SX, formononetin+SX, *Glomus intraradices*+SX, *Glomus mosseae*+SX, *Glomus aggregatum*+SX, *Glomus etunicatum*+SX, *Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*)+SX, *Rhizobium fredii*+SX, *Rhizobium loti*+SX, *Rhizobium trifolii*+SX, *Rhizobium tropici*+SX, 1,3-diphenylurea+SX, lipochitooligosaccharide SP104+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Claroideoglomus claroideum*+SX, *Delftia acidovorans* RAY209+SX, *Gigaspora margarita*+SX, *Gigaspora rosea*+SX, *Glomus deserticola*+SX, *Glomus monosporum*+SX, *Mesorhizobium ciceri*+SX, *Mesorhizobium huakii*+SX, *Rhizophagus clarus*+SX, *Rhizobium etli*+SX, *Rhizobium galegae*+SX, *Rhizophagus irregularis* DAOM 197198+SX, *Paraglomus brasillianum*+SX, Zucchini Yellow Mosaik Virus weak strain+SX.

A combination of the present ingredient in the above-mentioned Group (d) and the present compound X:

allidochlor+SX, benoxacor+SX, cloquintocet+SX, cloquintocet-mexyl+SX, cyometrinil+SX, cyprosulfamide+SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+SX, 1,8-octamethylene diamine+SX, AD-67 (4-(dichloroacetyl)-1-oxa-4-azaspiro[4.5]decane)+SX, CL-304415 (4-carboxy-3,4-dihydro-2H-1-benzopyran-4- acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, TI-35 (1-(dichloroacetyl)azepane)+SX.

A combination of the present ingredient in the abovementioned Group (e) and the present compound X:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis(4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)SX, TPP (triphenyl phosphate)+SX.

A combination of the present ingredient in the abovementioned Group (f) and the present compound X:

anthraquinone+SX, chloralose+SX, acrep+SX, butopyronoxyl+SX, camphor+SX, d-camphor+SX, carboxide+SX, dibutyl phthalate+SX, deet+SX, dimethyl carbate+SX, dimethyl phthalate+SX, dibutyl succinate+SX, dibutyl adipate+SX, ethohexadiol+SX, hexamide+SX, icaridin+SX, methoquin-butyl+SX, methylneodecanamide+SX, 2-(octylthio)ethanol+SX, butoxypolypropylene glycol+SX, oxamate+SX, quwenzhi+SX, quyingding+SX, zengxiaon+SX, rebemide+SX, copper naphthenate+SX, zinc naphthenate+SX.

A combination of the present ingredient in the abovementioned Group (g) and the present compound X:

bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, trifenmorph+SX.

A combination of the present ingredient in the abovementioned Group (h) and the present compound X:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2,4-dimethyl-5-ethyl-6,8-dioxabicyclo[3,2,1]octane+SX, (−)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyl eugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, (S)-verbenone+SX.

Examples of a ratio of the present compound X to the present ingredient include, but are not particularly limited to 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10 in the weight ratio (the present compound X: the present ingredient).

The present compound or the present compound X has a control effect on harmful arthropods such as harmful insects and harmful mites, harmful nematodes, and harmful mollusks. Examples of the harmful arthropods, harmful nematodes, and harmful mollusks are recited as follows.

Hemiptera Pests:

Delphacidae (for example, *Laodelphax striatellus, Nilaparvata lugens, Sogatella furcifera, Peregrinus maidis, Javesella pellucida, Perkinsiella saccharicida*, and *Tagosodes orizicolus;*

Cicadellidae (for example, *Nephotettix cincticeps, Nephotettix virescens, Nephotettix nigropictus, Recilia dorsalis, Empoasca onukii, Empoasca fabae, Dalbulus maidis*, and Cofana spectra);

Cercopidae (for example, *Mahanarva posticata*, and *Mahanarva fimbriolata*);

Aphididae (for example, *Aphis fabae*, *Aphis glycines*, *Aphis gossypii*, *Aphis pomi*, *Aphis spiraecola*, *Myzus persicae*, *Brachycaudus helichrysi*, *Brevicoryne brassicae*, *Dysaphis plantaginea* (Rosy apple aphid), *Lipaphis erysimi*, *Macrosiphum euphorbiae*, *Aulacorthum solani*, *Nasonovia ribisnigri*, *Rhopalosiphum padi*, *Rhopalosiphum maidis*, *Toxoptera citricida*, *Hyalopterus pruni*, *Melanaphis sacchari*, Tetraneura nigriabdominalis, Ceratovacuna *lanigera*, and *Eriosoma lanigerum*);

Phylloxeridae (for example, *Daktulosphaira vitifoliae*, *Phylloxera devastatrix* (Pecan *phylloxera*), *Phylloxera notabilis* (Pecan leaf *phylloxera*), and *Phylloxera russellae* (Southern pecan leaf *phylloxera*);

Adelgidae (for example, *Adelges tsugae*, *Adelges piceae*, and *Aphrastasia pectinatae*);

Pentatomidae (for example, *Scotinophara lurida*, *Scotinophara coarctata* (Malayan rice black bug), *Nezara antennata*, *Eysarcoris aeneus*, *Eysarcoris lewisi*, *Eysarcoris ventralis*, *Eysarcoris annamita*, *Halyomorpha halys*, *Nezara viridula*, *Euschistus heros* (Brown stink bug), *Piezodorus guildinii* (Red banded stink bug), *Oebalus pugnax*, and *Dichelops melacanthus*);

Cydnidae (for example, *Scaptocoris castanea* (Burrower brown bug);

Alydidae (for example, *Riptortus pedestris*, *Leptocorisa chinensis*, and *Leptocorisa acuta*);

Coreidae (for example, *Cletus punctiger*, and *Leptoglossus australis*);

Lygaeidae (for example, *Caverelius saccharivorus*, *Togo hemipterus*, and *Blissus leucopterus*);

Miridae (for example, *Trigonotylus caelestialium*, *Stenotus rubrovittatus*, *Stenodema calcarata*, and *Lygus lineolaris*);

Aleyrodidae (for example, *Trialeurodes vaporariorum*, *Bemisia tabaci*, *Dialeurodes citri*, *Aleurocanthus spiniferus*, *Aleurocanthus camelliae*, and *Pealius euryae*);

Diaspididae (for example, *Abgrallaspis cyanophylli*, *Aonidiella aurantii*, *Diaspidiotus perniciosus*, *Pseudaulacaspis pentagona*, *Unaspis yanonensis*, and *Unaspis citri*);

Coccidae (for example, *Ceroplastes rubens*);

Margarodidae (for example, *Icerya purchasi*, and *Icerya seychellarum*);

Pseudococcidae (for example, *Phenacoccus solani*, *Phenacoccus solenopsis*, *Planococcus kraunhiae*, *Pseudococcus comstocki*, *Planococcus citri*, *Pseudococcus calceolariae*, *Pseudococcus longispinus*, and *Brevennia rehi*);

Psyllidae (for example, *Diaphorina citri*, *Trioza erytreae*, *Cacopsylla pyrisuga*, *Cacopsylla chinensis*, *Bactericera cockerelli*, and *Cacopsylla pyricola* (Pear *psylla*));

Tingidae (for example, *Corythucha ciliata*, *Corythucha marmorata*, *Stephanitis nashi*, and *Stephanitis pyrioides*);

Cimicidae (for example, *Cimex lectularius*);

Cicadidae (for example, *Quesada gigas* (Giant Cicada);

*Triatoma* spp. such as *Triatoma infestans*; and others.

Lepidoptera Pests:

Crambidae (for example, *Chilo suppressalis*, *Chilo polychrysus* (Darkheaded stem borer), *Scirpophaga innotata* (White stem borer), *Scirpophaga incertulas*, *Rupela albina*, *Cnaphalocrocis medinalis*, *Marasmia patnalis*, *Marasmia exigua*, *Notarcha derogata*, *Ostrinia furnacalis*, *Ostrinia nubilalis* (European corn borer), *Hellula undalis*, *Herpetogramma luctuosale*, *Pediasia teterrellus*, *Nymphula depunctalis*, and *Diatraea saccharalis* (Sugarcane borer);

Pyralidae (for example, *Elasmopalpus lignosellus*, *Plodia interpunctella*, and *Euzophera batangensis*);

Noctuidae (for example, *Spodoptera litura*, *Spodoptera exigua*, *Mythimna separata*, *Mamestra brassicae*, *Sesamia inferens*, *Spodoptera mauritia*, *Naranga aenescens*, *Spodoptera frugiperda*, *Spodoptera exempta*, *Agrotis ipsilon*, *Autographa nigrisigna*, *Plusia festucae*, *Chrysodeixis includens* (Soybean looper), *Trichoplusia* spp., *Heliothis* spp. such as *Heliothis virescens*, *Helicoverpa* spp. such as *Helicoverpa armigera* and *Helicoverpa zea*, *Anticarsia gemmatalis* (Velvetbean caterpillar), *Alabama argillacea* (Cotton leafworm), and *Hydraecia immanis* (Hop vine borer));

Pieridae (for example, *Pieris rapae*);

Tortricidae (for example, *Grapholita molesta*, *Grapholita dimorpha*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*, *Tetramoera schistaceana*, *Epinotia aporema* (Bean Shoot Borer), and *Ecdytolopha aurantiana* (Citrus fruit borer));

Gracillariidae (for example, *Caloptilia theivora*, and *Phyllonorycter ringoniella*);

Carposinidae (for example, *Carposina sasakii*);

Lyonetiidae (for example, *Leucoptera coffeella* (Coffee Leaf miner), *Lyonetia clerkella*, and *Lyonetia* prunifoliella);

Lymantriidae (for example, *Lymantria* spp. such as *Lymantria dispar*, and *Euproctis* spp. such as *Euproctis pseudoconspersa*);

Plutellidae (for example, *Plutella xylostella*);

Gelechiidae (for example, *Anarsia lineatella*, *Helcystogramma triannulella*, *Pectinophora gossypiella*, *Phthorimaea operculella*, and *Tuta absoluta*);

Arctiidae (for example, *Hyphantria cunea*);

Castniidae (for example, *Telchin licus* (Giant Sugarcane borer));

Cossidae (for example, *Cossus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis*, *Synanthedon hector*, and *Synanthedon tenuis*);

Hesperiidae (for example, *Parnara guttata*);

Tinedae (for example, *Tinea translucens*, and *Tineola bisselliella*);

and others.

Thysanoptera Pests:

Thripidae (for example, *Frankliniella occidentalis*, *Thrips palmi*, *Scirtothrips dorsalis*, *Thrips tabaci*, *Frankliniella intonsa*, *Stenchaetothrips biformis*, and *Echinothrips americanus*);

Phlaeothripidae (for example, *Haplothrips aculeatus*);

and others.

Diptera Pests:

Anthomyiidae (for example, *Delia platura*, *Delia antiqua*, and *Pegomya cunicularia*);

Ulidiidae (for example, *Tetanops myopaeformis*);

Agromyzidae (for example, *Agromyza oryzae*, *Liriomyza sativae*, *Liriomyza trifolii*, and *Chromatoryia horticola*);

Chloropidae (for example, *Chlorops oryzae*);

Tephritidae (for example, *Bactrocera cucurbitae*, *Bactrocera dorsalis*, *Bactrocera latifrons*, *Bactrocera oleae*, *Bactrocera tryoni*, *Ceratitis capitata*, *Rhagoletis pomonella*, and *Rhacochlaena japonica*);

Ephydridae (for example, *Hydrellia griseola*, *Hydrellia philippina*, and *Hydrellia sasakii*);

Drosophilidae (for example, *Drosophila suzukii*);

Phoridae (for example, *Megaselia spiracularis*);

Psychodidae (for example, *Clogmia albipunctata*);

Sciaridae (for example, *Bradysia difformis*);

Cecidomyiidae (for example, *Mayetiola destructor*, and *Orseolia oryzae*);

Diopsidae (for example, *Diopsis macrophthalma*);

Tipulidae (for example, *Tipula aino*, *Tipula oleracea* (Common cranefly), and *Tipula paludosa* (European cranefly));

Culicidae (for example, *Culex pipiens pallens*, *Aedes aegypti*, *Aedes albopicutus*, *Anopheles hyracanus sinensis*, *Culex quinquefasciatus*, *Culex pipiens molestus Forskal*, and *Culex quinquefasciatus*);

Simulidae (for example, *Prosimulium yezoensis*, and *Simulium ornatum*);

Tabanidae (for example, *Tabanus trigonus*);

Muscidae (for example, *Musca domestica*, *Muscina stabulans*, *Stomoxys calcitrans*, and *Haematobia irritans*);

Calliphoridae;

Sarcophagidae;

Chironomidae (for example, *Chironomus plumosus*, *Chironomus yoshimatsui*, and *Glyptotendipes tokunagai*);

Fannidae;

and others.

Coleoptera Pests:

Chrysomelidae (for example, *Diabrotica virgifera virgifera*, *Diabrotica undecimpunctata howardi*, *Diabrotica barberi*, *Diabrotica virgifera zeae*, *Diabrotica balteata*, *Diabrotica speciosa* (Cucurbit Beetle), *Cerotoma trifurcata*, *Oulema melanopus*, *Aulacophora femoralis*, *Phyllotreta striolata*, *Phyllotreta cruciferae* (Cabbage flea beetle), *Phyllotreta pusilla* (Western black flea beetle), *Psylliodes chrysocephala* (Cabbage stem flea beetle), *Leptinotarsa decemlineata*, *Oulema oryzae*, *Colaspis brunnea*, *Chaetocnema pulicaria*, *Chaetocnema confinis*, *Epitrix cucumeris*, *Dicladispa armigera*, *Myochrous denticollis* (southern corn leaf beetle), *Laccoptera quadrimaculata*, and *Epitrix hirtipennis*);

Carabidae (for example, *Stenolophus lecontei* (Seedcorn beetle), and *Clivina impressifrons* (Slender seedcorn beetle));

Scarabaeidae (for example, *Anomala cuprea*, *Anomala rufocuprea*, *Anomala albopilosa*, *Popillia japonica*, *Heptophylla picea*, *Rhizotrogus majalis* (European Chafer), *Tomarus gibbosus*, *Holotrichia* spp., *Phyllophaga* spp. such as *Phyllophaga crinita*, and *Diloboderus* spp. such as *Diloboderus abderus*);

Curculionidae (for example, *Araecerus coffeae*, *Cylas formicarius*, *Euscepes postfasciatus*, *Hypera postica*, *Sitophilus zeamais*, *Echinocnemus squameus*, *Lissorhoptrus oryzophilus*, *Rhabdoscelus lineatocollis*, *Anthonomus grandis*, *Sphenophorus venatus*, *Sphenophorus callosus* (Southern Corn Billbug), *Sternechus subsignatus* (Soybean stalk weevil), *Sphenophorus levis* (Sugarcane weevil), *Scepticus griseus*, *Scepticus uniformis*, *Zabrotes subfasciatus*, *Tomicus piniperda*, *HvPothenemus hampei* (Coffee Berry Borer), *Aracanthus* spp. such as *Aracanthus mourei*, and *Eutinobothrus brasiliensis* (cotton root borer));

Tenebrionidae (for example, *Tribolium castaneum*, and *Tribolium confusum*);

Coccinellidae (for example, *Epilachna vigintioctopunctata*);

Bostrychidae (for example, *Lyctus brunneus*);

Ptinidae;

Cerambycidae (for example, *Anoplophora malasiaca*, and *Migdolus fryanus*);

Elateridae (for example, *Melanotus okinawensis*, *Agriotes fuscicollis*, *Melanotus legatus*, *Anchastus* spp., *Conoderus* spp., *Ctenicera* spp., *Limonius* spp., and *Aeolus* spp.);

Staphylinidae (for example, *Paederus fuscipes*);

Dermestidae (for example, *Anthrenus verbasci*, and *Dermestes maculates*);

Anobidae (for example, *Lasioderma serricorne*, and *Stegobium paniceum*);

and others

Orthoptera Pests:

Acrididae (for example, *Locusta migratoria*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Two striped grasshopper), *Melanoplus sanguinipes* (Migratory grasshopper), *Melanoplus femurrubrum* (Red-Legged grasshopper), Camnula pellucida (Clearwinged grasshopper), *Schistocerca gregaria*, Gastrimargus musicus (Yellow-winged locust), Austracris guttulosa (Spur-throated locust), *Oxya yezoensis*, *Oxya japonica*, and Patanga succincta);

Gryllotalpidae (for example, *Gryllotalpa orientalis*);

Gryllidae (for example, *Acheta domestica*, and Teleogryllus emma);

Tettigoniidae (for example, Anabrus simplex (Mormon cricket);

and others.

Hymenoptera Pests:

Tenthredinidae (for example, *Athalia rosae*, and *Athalia japonica*);

Formicidae (for example, *Solenopsis invicta*, *Solenopsis* spp. such as *Solenopsis geminata*, *Atta* spp. such as *Atta capiguara* (Brown leaf-cutting ant), *Acromyrmex* spp., *Paraponera clavata*, *Ochetellus glaber*, *Monomorium pharaonis*, *Linepithema humile*, *Formica fusca japonica*, *Pristomyrmex punctutus*, *Pheidole noda*, *Pheidole megacephala*, *Camponotus japonicus*, *Camponotus* spp. such as *Camponotus obscuripes*, *Pogonomyrmex* spp. such as *Pogonomyrmex occidentalis*, *Wasmania* spp. such as *Wasmania auropunctata*, and *Anoplolepis gracilipes*);

Vespidae (for example, *Vespa mandarinia japonica*, *Vespa simillima*, *Vespa analis Fabriciusi*, *Vespa velutina*, and *Polistes* jokahamae);

Siricidae (for example, *Urocerus gigas*);

Bethylidae;

and others.

Blattodea Pests:

Blattellidae (for example, *Blattella germanica*);

Blattidae (for example, *Periplaneta fuliginosa*, *Periplaneta americana*, *Periplaneta brunnea*, and *Blatta orientalis*);

Termitidae (for example, *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*);

and others.

Siphonaptera Pests:

*Ctenocephalidae felis*, *Ctenocephalides canis*, *Pulex irritans*, *Xenopsylla cheopis*, *Tunga penetrans*, *Echidnophaga gallinacea*, *Nosopsyllus fasciatus* and others.

Anoplura Pests:

*Haematopinus suis*, *Haematopinus eurysternus*, *Dalmalinia ovis*, *Linognathus seypsus*, *Pediculus humanis*, *Pediculuc humanus corporis*, *Pediculus humanus humanus*, *Phthirus pubis*, and others.

Mallophagida Pests:
  Bovicola spp. such as *Dalmalinia bovis* and *Dalmalinia ovis*;
  Menoponidae (for example, *Trichodectes* spp. such as *Trichodectes canis*, *Felocpla* spp. such as *Felicola subrostrata*, *Lipeurus* spp. such as *Lipeurus caponis*, *Trimenopon* spp., and *Menopon* spp.);
  and others.
Acari Pests:
  Tetranychidae (for example, *Tetranychus urticae*, *Tetranychus kanzawai*, *Tetranychus evansi*, *Panonychus citri*, *Panonychus ulmi*, and *Oligonychus* spp.);
  Eriophyidae (for example, *Aculops pelekassi*, *Phyllocoptruta citri*, *Aculops lycopersici*, *Calacarus carinatus*, *Acaphylla theavagrans*, *Eriophyes chibaensis*, *Aculus schlechtendali*, *Aceria diospyri*, *Aceria tosichella*, and *Shevtchenkella* sp.);
  Tarsonemidae (for example, *Polyphagotarsonemus latus*);
  Tenuipalpidae (for example, *Brevipalpus phoenicis*);
  Tuckerellidae;
  Ixodidae (for example, *Haemaphysalis longicornis*, *Haemaphysalis flava*, *Dermacentor taiwanensis*, *Dermacentor variabilis*, *Dermacentor andersoni*, *Ixodes ovatus*, *Ixodes persulcatus*, *Ixodes ricinus*, *Ixodes scapularis*, *Amblyomma americanum*, *Ambryomma maculatum*, *Boophilus microplus*, *Boophilus annulatus*, and *Rhipicephalus sanguineus*);
  Acaridae (for example, *Tyrophagus putrescentiae*, and *Tyrophagus similis*);
  Pyroglyphidae (for example, *Dermatophagoides farinae*, and *Dermatophagoides pteronyssinus*);
  Cheyletidae (for example, *Cheyletus eruditus*, *Cheyletus malaccensis*, *Cheyletus moorei*, and *Cheyletiella yasguri*);
  Sarcoptidae (for example, *Otodectes cynotis*, and *Sarcoptes scabiei*);
  Demodicidae (for example, *Demodex canis*);
  Listrophoridae;
  Haplochthoniidae;
  Macronyssidae (for example, *Ornithonyssus bacoti*, and *Ornithonyssus sylviarum*);
  Dermanyssidae (for example, *Dermanyssus gallinae*);
  Trombiculidae (for example, *Leptotrombidium akamushi*);
  and others.
Araneae Pests:
  Eutichuridae (for example, *Cheiracanthium japonicum*);
  Theridiidae (for example, *Latrodectus hasseltii*);
  and others.
Polydesmida Pests:
  Paradoxosomatidae (for example, *Oxidus gracilis*, and *Nedyopus tambanus*);
  and others.
Isopoda Pests:
  Armadillidiidae (for example, *Armadillidium vulgare*);
  and others.
Chilopoda Pests:
  Scutigeridae (for example, *Thereuonema hilgendorfi*);
  Scolopendridae (for example, *Scolopendra subspinipes*);
  Ethopolidae (for example, *Bothropolys rugosus*); and others.
Gastropoda Pests:
  Limacidae (for example, *Limax marginatus*, and *Limax flavus*);
  Philomycidae (for example, *Meghimatium bilineatum*);
  Ampullariidae (for example, *Pomacea canaliculata*);
  Lymnaeidae (for example, *Austropeplea ollula*); and others.

Nematoda Pests:
  Aphelenchoididae (for example, *Aphelenchoides besseyi*);
  Pratylenchidae (for example, *Pratylenchus coffeae*, *Pratylenchus brachyurus*, *Pratylenchus neglectus*, and *Radopholus similis*);
  Heteroderidae (for example, *Meloidogyne javanica*, *Meloidogyne incognita*, *Meloidogyne hapla*, *Heterodera glycines*, *Globodera rostochiensis*, and *Globodera pallida*);
  Hoplolaimidae (for example, *Rotylenchulus reniformis*);
  Anguinidae (for example, *Nothotylenchus acris*, and *Ditylenchus dipsaci*);
  Tylenchulidae (for example, *Tylenchulus semipenetrans*);
  Longidoridae (for example, *Xiphinema index*);
  Trichodoridae;
  Parasitaphelenchidae (for example, *Bursaphelenchus xylophilus*);
  and others.

The target harmful arthropods such as harmful insects and harmful mites, harmful mollusks, and harmful nematodes may have a reduced agent-sensitivity to or a developed agent-resistance to an insecticide, a miticide, a molluscicide or a nematicide. However, when the agent-sensitivity is greatly reduced or the agent-resistance is greatly developed, a composition comprising an insecticide, a miticide, a molluscicide, and a nematicide other than the intended insecticide, miticide, molluscicide, and nematicide is preferably used.

The present compound X can be also used to protect a plant from a plant disease caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, *Cycas* necrotic stunt, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, *Capsicum* chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, *Chrysanthemum* stem necrosis virus, *Impatiens* necrotic spot virus, Iris yellow spot virus, Lily mottle virus, Lilly symptomless virus, Tulip mosaic virus, and others.

Examples of the insect-borne bacteria are recited as follows.

Candidatus Phytoplasma *oryzae*, Candidatus Phytoplasma asteris, Maize bushy stunt phytoplasma, Candidatus Liberbacter *asiaticus*, Candidatus Liberbacter *africanus*, Candidatus Liberbacter *americanus*, and others.

A composition for controlling harmful arthropods of the present invention comprises the present compound, the present compound X, or the composition A, and an inert carrier (hereinafter, referred to as "present composition"), The present composition is usually prepared by mixing the present compound, the present compound X, or the composition A with an inert carrier such as solid carrier, liquid carrier and gaseous carrier, and if necessary, adding surfactants and other auxiliary agents for formulation to formulate them into emulsifiable concentrates, oil solutions, poweders, granules, wettable powders, flowables, microcapsules, aerosols, smoking agents, poison baits, resin formulations, shampoo formulations, paste-like formulations, foams, carbon dioxide formulations, tablets, and the others. Such formulations may be processed into mosquito repellent coils, electric mosquito repellent mats, liquid mosquito formulations, smoking agents, fumigants, sheet formulations, spot-on formulations or formulations for oral treatment to use. The present composition comprises usually 0.0001 to 95% by weight of the present compound, the present compound X, or the composition A.

Examples of the solid carrier to be used in the formulation include fine powders or granules such as clays (for example, kaolin clay, diatomaceous earth, bentonite, Fubasami clay, or acid white clay), dry process silica, wet process silica, talcs, ceramics, other inorganic minerals (for example, sericite, quartz, sulfur, active carbon, or calcium carbonate) and chemical fertilizers (for example, ammonium sulfate, ammonium phosphate, ammonium nitrate, urea, or ammonium chloride); as well as synthetic resins (for example, polyester resins such as polypropylene, polyacrylonitrile, polymethyl methacrylate and polyethylene terephthalate; nylon resins such as nylon-6, nylon-11 and nylon-66; polyamide resins; polyvinyl chloride, polyvinylidene chloride, vinyl chloride-propylene copolymers, and the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, 1,2-dimethoxyethane, diethylene glycol dimethyl ether, diethylene glycol monomethyl ether, dipropylene glycol monomethyl ether, or 3-methoxy-3-methyl-1-butanol); amides (for example, DMF, or N,N-dimethylacetamide); sulfoxides (for example, DMSO); propylene carbonate; and vegetable oils (for example, soybean oil, or cottonseed oil).

Examples of the gaseous carrier include fluorocarbon, butane gas, LPG (liquefied petroleum gas), dimethyl ether, and carbon dioxide gas.

Examples of the surfactant include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of other auxiliary agent for formulation include a binder, a dispersant, a colorant, and a stabilizer. Specific examples include casein, gelatin, polysaccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of a base material of the resin formulation include polyvinyl chloride polymers, polyurethane, and the others, and a plasticizer such as phthalate esters (for example, dimethyl phthalate, and dioctyl phthalate), adipic acid esters and stearic acid may be added to the base material, if necessary. The resin formulation can be prepared by kneading the present compound in the base material with a conventional kneading machine, and then molding it by injection molding, extrusion molding, or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the present composition to a harmful arthropod directly and/or a habitat where the harmful arthropod lives (for example, plant bodies, soil, an interior of a house, and animal bodies). Further, the effective amount of the present composition can be applied to seeds. Examples of a method for applying the present composition include foliar application, soil application, root application, shower application, smoking application, water-surface application, and seed application.

As used herein, examples of the plant include whole plant, stem and leaf, flower, ear, fruit, tree stem, branch, crown, seed, vegetative reproductive organ, and seedling.

The vegetative reproductive organ represents a part of plant such as root, stem and leaf, which has a growth capacity if the part is cut off from its plant and then placed in the soil. Examples of the vegetative reproductive organ include tuberous root, creeping root, bulb, corm or solid bulb, tuber, rhizome, stolon, rhizophore, cane cuttings, propagule, and vine cutting. The "stolon" is often referred to as "runner", and the "propagule" is often referred to as "brood bud", which is divided into broad bud and bulbil. The vine cutting represents a shoot (which is a generic name of leaf and stem) of sweet potato (*Ipomoea batatas*) and Japanese yam (*Dioscorea japonica*), etc. The bulb, corm or solid bulb, tuber, rhizome, cane cuttings, rhizophore, and tuberous root are also collectively referred to as "bulb". For example, when the cultivation of potato starts with planting tubers in the soil, the used tuber is generally referred to as "seed potato".

Examples of applying an effective amount of the present composition to plants or soils for cultivating the plant include a method of applying an effective amount of the present compound X or the present composition to the plant; a method of applying an effective amount of the present compound X or the present composition to a seed or a vegetative reproductive organ (for example, a seed disinfection, a seed soaking, or a seed coating), or a method of applying an effective amount of the present compound X or the present composition to soils before planting plants or solils after planting the plants.

Examples of the method of applying an effective amount of the present composition to soils before planting plants or after planting plants include a method of applying an effective amount of the present composition to a root part of a crop to be protected from damage such as ingestion by harmful arthropods, and a method of controlling harmful arthropods that ingest a plant by permeating and transfering an effective amount of the present composition from a root into the interior of the plant body. Specifically, examples of the application method include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering with soils), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

When the present composition is used for controlling harmful arthropods in an agricultural field, an applied dose as an amount of the present compound or the present compound X is usually within a range from 1 to 10,000 g per 10,000 $m^2$. When the present composition is applied to seeds or vegetative reproductive organs, an applied dose as an amount of the present compound or the present compound X is usually within a range from 0.001 to 100 g relative to 1 kg of the seeds or vegetative reproductive organs. An applied dose of the composition A is usually within a range from 0.001 to 100 g relative to 1 kg of the seeds or vegetative reproductive organs. The emulsifiable concentrate, the wettable powder, or the flowable formulation etc. of the present composition is usually applied by diluting it with water in such a way that a concentration of the active ingredient of the present composition is within a range from 0.01 to 10,000 ppm. The granular formulation, or the powder formulation etc., is usually applied as itself without diluting it.

These formulations and diluents of the formulations with water may be directly sprayed to a harmful arthropod or a plant such as a crop to be protected from the harmful arthropod, or applied to a soil in a cultivated area to control the harmful arthropod that inhabits the soil.

Also, the resin formulation processed into a sheet shape or string shape may be wrapped around a crop, stretched near a crop, spread on a foot soil of a plant, or the like.

When the present composition is used to control harmful arthropods that live inside a house, an applied dose as an amount of the present compound or the present compound X is usually within a range from 0.01 to 1,000 mg per 1 $m^2$ of an area to be treated, in the case of using it on a planar area. In the case of using it spatially, the applied dose as an amount of the present compound or the present compound X is usually within a range from 0.01 to 500 mg per 1 $m^3$ of the space to be treated. When the present composition is formulated into emulsifiable concentrates, wettable powders, flowables or the others, the formulation is usually applied after diluting it with water in such a way that a concentration of the active ingredient is within a range from 0.1 to 10,000 ppm, and then sparging it. In the case of being formulated into oil solutions, aerosols, smoking agents, poison baits and the others, the formulation is used as itself without diluting it.

When the present composition is used for controlling external parasites of livestock such as cows, horses, pigs, sheep, goats and chickens, and small animals such as dogs, cats, rats and mice, the present composition can be applied to the animal by a known method in the veterinary field. Specifically, when systemic control is intended, the present composition is administered to the animal as a tablet, a mixture with feed or a suppository, or by injection (including intramuscular, subcutaneous, intravenous and intraperitoneal injections). On the other hand, when non-systemic control is intended, the present composition is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound or the present compound X is usually within a range from 0.1 to 1,000 mg per 1 kg of a body weight of the animal.

Further, the present composition can be used as an agent for controlling harmful arthropods in the agricultural land such as field, paddy, lawn and orchard. The present composition can control harmful arthropods in the agricultural land for cultivating the following plants, etc.

Crops:

corn, rice, wheat, barley, rye, oat, sorghum, cotton, soybean, peanut, buckwheat, beet, rapeseed, sunflower, sugarcane, tobacco, and the others;

Vegetables:

solanaceous vegetables (for example, eggplant, tomato, green pepper, hot pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), ammiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, flowering plants, foliage plants, and the others;

Fruits:

pomaceous fruits (for example, apple, pear, Japanese pear, Chinese quince, and quince), stone fleshy fruits (for example, peach, plum, nectarine, *Prunus* mume, cherry fruit, apricot, and prune), citrus fruits (for example, citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese plum, banana, coffee, date palm, coconuts, and the others;

Trees Other than Fruits tea, mulberry, flowering plants, roadside trees (for example, ash, birch, dogwood, *eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate), The above plants also include a plant that can be generated by a natural crossbreeding, a plant that can be generated by mutations, an F1 hybrid plant, and a genetically modified crop. Examples of the genetically modified crop include a plant modified to have the resistance to HPPD (4-hydroxyphenylpyruvate dioxygenase) inhibitors such as isoxaflutole, ALS (acetolactate synthase) inhibitors such as imazethapyr and thifensulfuron-methyl, EPSP (5-enolpyruvoylshikimate-3-phosphate synthase) inhibitors, glutamine synthetase inhibitors, PPO (protoporphyrinogen oxidase) inhibitors, or herbicides such as bromoxynil and dicamba; a plant modified to synthesize a selective toxin known to be produced in *Bacillus* such as *Bacillus thuringiensis*; and a plant modified to have a specific insecticidal activity by synthesizing a gene fragment partially corresponding to an endogenous gene derived from a harmful insect to induce the gene silencing (RNAi; RNA interference) in the target harmful insect.

The above-mentioned plants are not limited specifically, as long as they are breeds that are usually cultivated.

EXAMPLES

Hereinafter, the present invention is explained in more detail by using Preparation exmaple, Formulation example, and Test example, however, the present invention should not be limited to these examples.

As used herein, "Me" represents a methyl group, "Et" represents an ethyl group, "Pr" represents a propyl group, "i-Pr" represents an isopropyl group, "Bu" represents a butyl group, "c-Pr" represents a cyclopropyl group, "Ph" represents a phenyl group, "Py2" represents a 2-pyridyl group, "Py3" represents a 3-pyridyl group, "Py4" represents a 4-pyridyl group. When c-Pr, Ph, Py2, Py3, and Py4 have a substituent, the subtituent is written with its substituted position before the symbol. For example, "1-CN-c-Pr" represents a 1-cyanocyclopropyl group, "4-CF$_3$—Py2" represents a 4-(trifluoromethyl)-2-pyridyl, and "3,5-(CF$_3$)$_2$-Ph" represents a 3,5-bis(trifluoromethyl)phenyl group.

Firstly, the preparation examples of the present compound X are described.

When a physical property of a compound is determined using a lipid chromatography/mass spectrography (hereinafter, referred to as "LCMS"), a determined molecular ion value [M+H]$^+$ and retention time (hereinafter, referred to as "RT") are recorded. A condition for the lipid chromatography (hereinafter, referred to as "LC") is recited as follows.

[LC Condition]

Column: L-column2 ODS, inner diameter 4.6 mm, length 30 mm, particle size 3 μm (manufactured by Chemicals Evaluation and Research Institute, Japan)

UV measurement wavelength: 254 nm

Mobile phase: A solution: 0.1% formic acid solution, B solution: 0.1% formic acid-acetonitrile Rate: 2.0 mL/min Gradient condition: the solutions are run with the concentrataion gradients shown in [Table LC1].

TABLE LC1

| Time (min) | A solution (%) | B solution (%) |
|---|---|---|
| 0 | 90 | 10 |
| 2.00 | 0 | 100 |
| 4.00 | 0 | 100 |
| 4.01 | 90 | 10 |

Reference Preparation Example 1

A mixture of 2,2,3,3,3-pentafluoro-1-propanol 950 mg, 3-bromo-6-chloro-1-methylpyridin-2(1H)-one 700 mg, cesium carbonate 2.1 g, and DMF 15 mL was stirred at room temperature for 2 hours. To the obtained mixture was added water, and the mixture was extracted with ethyl acetate. The resulting organic layer was dried over anhydrous sodium sulfate and concentrated under reduced pressure. The resulting residue was subjected to a silica gel column chromatography to give the intermediate compound 1 represented by the following formula 1.06 g.

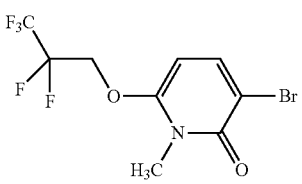

The intermediate compound 1: $^1$H-NMR (CDCl$_3$) δ: 3.53 (3H, s), 4.44 (2H, t), 5.45 (1H, d), 7.66 (1H, d).

Reference Preparation Example 1-1

The intermediate compound 2 represented by the following formula was prepared according to a similar method to that described in the Reference preparation example 1 using 5-bromo-2-chloro-3-methylpyrimidin-4(3H)-one instead of 3-bromo-6-chloro-1-methylpyridin-2(1H)-one.

The intermediate compound 2: $^1$H-NMR (CDCl$_3$) δ: 3.50 (3H, s), 4.84 (2H, t), 7.91 (1H, s).

Reference Preparation Example 1-2

To a mixture of 1-(6-chloro-4-hydroxypyridin-3-yl)ethanone 20.3 g and dioxane 150 mL were sequentially added methyl iodide 8.8 mL and cesium carbonate 46.5 g, and the mixture was stirred at room temperature for one hour. To the obtained mixture was added water, and the mixture was extracted with ethyl acetate. The resulting organic layer was dried over anhydrous sodium sulfate and concentrated under reduced pressure to give a residue 26.2 g. To a mixture of the residue 13.1 g, 2,2,3,3,3-pentafluoro-1-propanol 9.1 mL, and DMF 50 mL was added cesium carbonate 30.0 g, and the mixture was stirred at room temperature for one hour. To the resulting mixture was added water, and the precipitated solid was filtrated. The obtained solid was subjected to a silica gel column chromatography to give the intermediate compound 20 represented by the following formula 6.25 g.

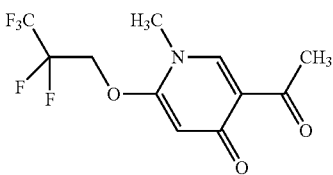 [SMILES: CC(=O)c1cn(C)c(OCC(F)(F)C(F)(F)F)cc1=O]

The intermediate compound 20: $^1$H-NMR (CDCl$_3$) δ: 8.01 (1H, s), 5.89 (1H, s), 4.45 (2H, t), 3.59 (3H, s), 2.69 (3H, s).

Reference Preparation Example 2

To a mixture of the intermediate 1 (6.21 g), bis(triphenylphosphine)palladium(II) dichloride 1.3 g, and toluene 30 mL was added tributyl(1-ethoxyvinyl)stannane 10.0 g, and the mixture was stirred while heating under reflux for one hour. The resulting mixture was cooled to room temperature, and 10% potassium fluoride solution 10 mL was added thereto, and then the mixture was stirred for one hour. The obtained mixture was extracted with MTBE. The resulting organic layer was dried over anhydrous sodium sulfate and concentrated under reduced pressure. To the resulting residue were added THF 4 mL and 2N hydrochloric acid 40 mL, and the mixture was stirred at room temperature for 3 hours. The resulting mixture was extracted with MTBE. The resulting organic layer was dried over anhydrous sodium sulfate and concentrated under reduced pressure. The obtained residue was subjected to a silica gel column chromatography to give the intermediate compound 3 represented by the following formula 4.84 g.

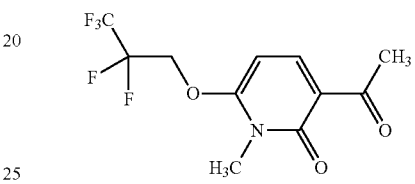

The intermediate compound 3: $^1$H-NMR (CDCl$_3$) δ: 2.66 (3H, s), 3.51 (3H, s), 4.54 (2H, t), 5.67 (1H, d), 8.22 (1H, d).

Reference Preparation Example 3-1

To a mixture of the intermediate compound 3 (4.84 g) and THF 100 mL was added trimethylphenylammonium tribromide 6.69 g, and the mixture was stirred at room temperature for 3 hours. To the obtained mixture was added water, and the mixture was extracted with MTBE. The resulting organic layer was dried over anhydrous sodium sulfate and concentrated under reduced pressure. The resulting residue was subjected to a silica gel column chromatography to give the intermediate compound 4 represented by the following formula 4.58 g.

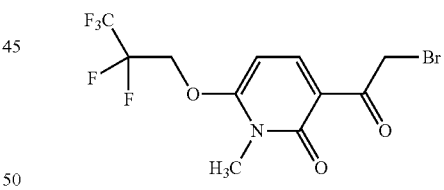

The intermediate compound 4: $^1$H-NMR (CDCl$_3$) δ: 3.53 (3H, s), 4.57 (2H, t), 4.76 (2H, s), 5.75 (1H, d), 8.33 (1H, d).

Reference Preparation Example 3-2

To a mixture of the intermediate compound 20 (10.0 g) and THF 200 mL was added trimethylphenylammonium tribromide 26.2 g, and the mixture was stirred at room temperature for one hour. To the obtained mixture was added water, and the mixture was extracted with ethyl acetate. The resulting organic layer was dried over anhydrous sodium sulfate and concentrated under reduced pressure. To a mixture of the obtained residue, diisopropylethylamine 14.0 mL, and THF 200 mL was added diethyl phosphite 10.3 mL under ice-cooling, and the mixture was stirred under ice-cooling for 2 hours. To the resulting mixture was added water, and the mixture was extracted with ethyl acetate. The resulting organic layer was dried over anhydrous sodium sulfate and concentrated under reduced pressure. The obtained residue was subjected to a silica gel column chromatography to give the intermediate compound 21 represented by the following formula 12.0 g.

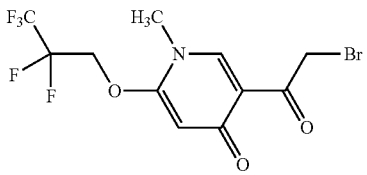 [SMILES: Cn1cc(C(=O)CBr)c(=O)cc1OCC(F)(F)C(F)(F)F]

The intermediate compound 21: $^1$H-NMR (CDCl$_3$) δ: 8.13 (1H, s), 6.01 (1H, s), 4.80 (2H, s), 4.50 (2H, t), 3.64 (3H, s).

Reference Preparation Example 4

To a mixture of the intermediate compound 2 (21 g), bis(triphenylphosphine)palladium(II) dichloride 3.3 g, and toluene 100 mL was added tributyl(1-ethoxyvinyl)stannane 24.7 g, and the mixture was stirred while heating under reflux for 16 hours. The obtained mixture was cooled to room temperature and filtrated. The resulting filtrate was concentrated under reduced pressure. To the resulting residue were added dioxane 30 mL and water 20 mL. To the resulting mixture was added N-bromosuccinimide 17.7 g under ice-cooling, and the mixture was stirred at room temperature for 30 minutes. To the resulting mixture was added water, and the mixture was extracted with ethyl acetate. The resulting organic layer was dried over anhydrous sodium sulfate and concentrated under reduced pressure. The resulting residue was subjected to a silica gel column chromatography to give the intermediate compound 5 represented by the following formula 11 g.

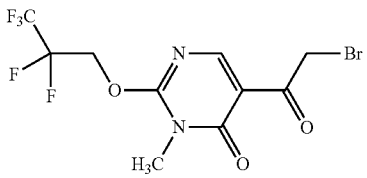

The intermediate compound 5: $^1$H-NMR (CDCl$_3$) δ: 3.50 (3H, s), 4.65 (2H, s), 4.96 (2H, t), 8.55 (1H, s).

Reference Preparation Example 5

To a mixture of the intermediate compound 4 (2.2 g) and ethanol 30 mL was added 5-(trifluoromethyl)-2-aminopyridine 1.04 g at room temperature, and the mixture was stirred while heating under reflux for 9 hours. The obtained mixture was cooled to room temperature and concentrated under reduced pressure. To the resulting residue was added water, and the mixture was extracted with ethyl acetate. The resulting organic layer was dried over anhydrous sodium sulfate and concentrated under reduced pressure. The obtained residue was subjected to a silica gel column chromatography to give the intermediate compound 6 represented by the following formula 2.10 g.

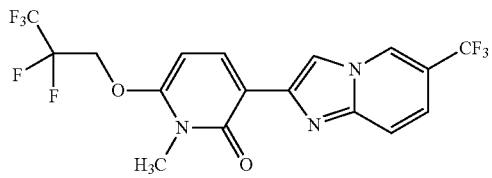

The intermediate compound 6: $^1$H-NMR (CDCl$_3$) δ: 8.70 (1H, s), 8.50 (2H, dt), 7.64 (1H, d), 7.31 (1H, dd), 5.78 (1H, d), 4.55 (2H, t), 3.62 (3H, s).

Reference Preparation Example 6

The compounds prepared according to a similar method to that described in the Reference preparation example 5 and their physical properties are shown as follows.

A compound represented by formula (A-1):

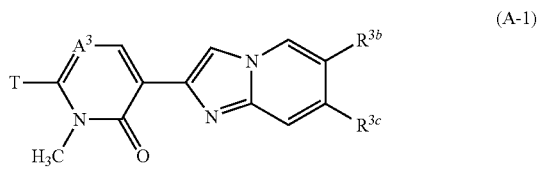

wherein a combination of T, A$^3$, R$^{3b}$, and R$^{3c}$ represents any of the combinations indicated in [Table A1].

TABLE A1

| Intermediate compound | T | A$^3$ | R$^{3b}$ | R$^{3c}$ |
|---|---|---|---|---|
| 7 | OCH$_2$CF$_2$CF$_3$ | CH | H | H |
| 8 | OCH$_2$CF$_2$CF$_3$ | CH | Br | H |
| 9 | OCH$_2$CF$_2$CF$_3$ | N | CF$_3$ | H |
| 10 | OCH$_2$CF$_2$CF$_3$ | N | H | H |
| 11 | OCH$_2$CF$_2$CF$_3$ | N | Br | H |

The intermediate compound 7: $^1$H-NMR (CDCl$_3$) δ: 3.46 (3H, s), 5.10 (2H, t), 6.19 (1H, d), 6.83 (1H, t), 7.21 (1H, t), 7.49 (1H, d), 8.39 (1H, d), 8.58-8.60 (2H, m).

The intermediate compound 8: $^1$H-NMR (CDCl$_3$) δ: 3.47 (3H, s), 5.12 (2H, t), 6.24 (1H, d), 7.50 (1H, d), 7.58 (1H, d), 8.39 (1H, d), 8.66 (1H, s), 9.04 (1H, s).

The intermediate compound 9: $^1$H-NMR (CDCl$_3$) δ: 8.76 (1H, s), 8.59 (1H, s), 8.50 (1H, s), 7.67 (1H, d), 7.33 (1H, dd), 4.99-4.92 (2H, m), 3.58 (3H, s).

The intermediate compound 10: $^1$H-NMR (CDCl$_3$) δ: 3.56 (3H, s), 4.92 (2H, t), 6.75 (1H, t), 7.15-7.19 (1H, m), 7.56 (1H, d), 8.11 (1H, d), 8.47 (1H, s), 8.74 (1H, s).

The intermediate compound 11: $^1$H-NMR (CDCl$_3$) δ: 3.55 (3H, s), 4.93 (2H, t), 7.21 (1H, d), 7.45 (1H, d), 8.25 (1H, s), 8.44 (1H, s), 8.71 (1H, s).

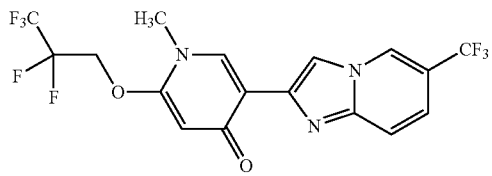

The intermediate compound 22: $^1$H-NMR (CDCl$_3$) δ: 8.86 (1H, s), 8.49 (1H, s), 8.36 (1H, s), 7.61 (1H, d), 7.31 (1H, d), 5.95 (1H, s), 4.50 (2H, t), 3.67 (3H, s).

Reference Preparation Example 7

A mixture of the intermediate compound 8 (3.6 g), tetrakis(triphenylphosphine)palladium(0) 920 mg, sodium carbonate 2.53 g, 4-fluorophenylboronic acid 1.67 mg, water 10 mL, and 1,4-dioxane 40 mL was stirred under nitrogen atmosphere at 80° C. for 4 hours. The resulting mixture was cooled to room temperature and filtrated. The filtrate was concentrated under reduced pressure. The obtained residue was subjected to a silica gel column chromatography to give the intermediate compound 12 represented by the following formula 3.0 g.

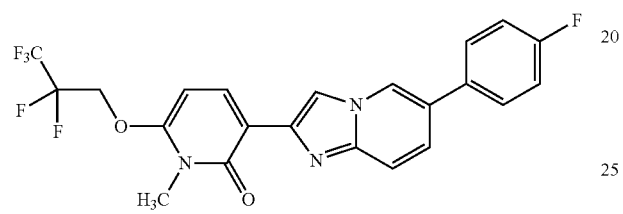

The intermediate compound 12: $^1$H-NMR (CDCl$_3$) δ: 3.61 (3H, s), 4.53 (2H, t), 5.75 (1H, d), 7.15 (2H, t), 7.45-7.51 (3H, m), 7.63-7.68 (2H, m), 8.40 (1H, d), 8.63 (1H, s).

Reference Preparation Example 8

The compound prepared according to a similar method to that described in the Reference preparation example 7 and its physical properties are shown as follows.
A compound represented by formula (A-1):

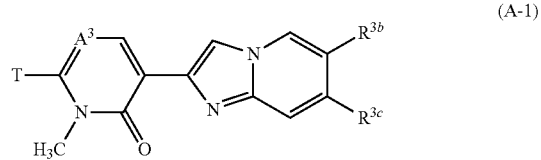

(A-1)

wherein a combination of T, A$^3$, R$^{3b}$, and R$^{3c}$ represents any of the combinations indicated in [Table A2].

TABLE A2

| Intermediate compound | T | A$^3$ | R$^{3b}$ | R$^{3c}$ |
| --- | --- | --- | --- | --- |
| 13 | OCH$_2$CF$_2$CF$_3$ | N | 4-F—Ph | H |

The intermediate compound 13: LCMS: 469 [M+H]$^+$

Reference Preparation Example 9

To a mixture of the intermediate compound 6 (2.10 g) and DMF 20 mL was added N-iodesuccinimide 1.2 g under ice-cooling, and the mixture was stirred at room temperature for 9 hours. To the mixture was added sodium thiosulfate solution. The precipitated solid was sequentially washed with water and MTBE and dried to give the intermediate compound 14 represented by the following formula 2.81 g.

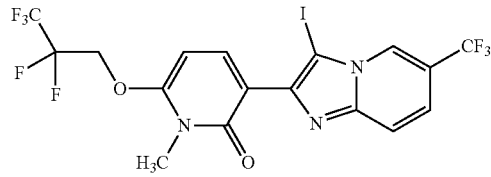 [SMILES: Cn1c(OCC(F)(F)C(F)(F)F)ccc(-c2nc3ccc(C(F)(F)F)cn3c2I)c1=O]

The intermediate compound 14: $^1$H-NMR (CDCl$_3$) δ: 8.56 (1H, s), 7.77 (1H, d), 7.69 (1H, d), 7.38 (1H, dd), 5.69 (1H, d), 4.55 (2H, t), 3.60 (3H, s).

Reference Preparation Example 10

The compounds prepared according to a similar method to that described in the Reference preparation example 9 and their physical properties are shown as follows.
A compound represented by formula (A-2):

(A-2)

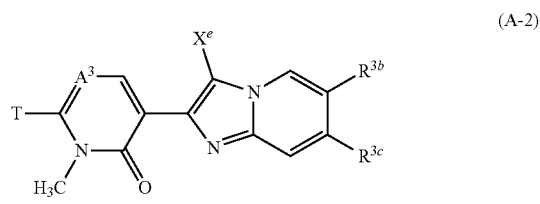

wherein a combination of T, X$^e$, A$^3$, R$^{3b}$, and R$^{3c}$ represents any of the combinations indicated in [Table A3].

TABLE A3

| Intermediate compound | T | X$^e$ | A$^3$ | R$^{3b}$ | R$^{3c}$ |
| --- | --- | --- | --- | --- | --- |
| 15 | OCH$_2$CF$_2$CF$_3$ | I | CH | H | H |
| 16 | OCH$_2$CF$_2$CF$_3$ | I | CH | 4-F—Ph | H |
| 17 | OCH$_2$CF$_2$CF$_3$ | I | N | CF$_3$ | H |
| 18 | OCH$_2$CF$_2$CF$_3$ | I | N | H | H |
| 19 | OCH$_2$CF$_2$CF$_3$ | I | N | 4-F—Ph | H |

The intermediate compound 15: $^1$H-NMR (CDCl$_3$) δ: 3.58 (3H, s), 4.53 (2H, t), 5.67 (1H, d), 6.94 (1H, d), 7.16 (1H, d), 7.64 (1H, d), 7.73 (1H, d), 8.18 (1H, d).

The intermediate compound 16: $^1$H-NMR (CDCl$_3$) δ: 3.59 (3H, s), 4.53 (2H, t), 5.67 (1H, d), 7.18 (2H, t), 7.54 (3H, t), 7.63-7.68 (2H, m), 8.29 (1H, s).

The intermediate compound 17: $^1$H-NMR (CDCl$_3$) δ: 8.55 (1H, s), 8.06 (1H, s), 7.72 (1H, d), 7.42-7.40 (1H, m), 4.98-4.92 (2H, m), 3.57 (3H, s).

The intermediate compound 18: $^1$H-NMR (CDCl$_3$) δ: 3.55 (3H, s), 4.92 (2H, t), 6.94 (1H, t), 7.25-7.28 (1H, m), 7.62 (1H, d), 8.02 (1H, s), 8.17 (1H, d).

The intermediate compound 19: $^1$H-NMR (CDCl$_3$) δ: 3.55 (3H, s), 4.93 (2H, t), 7.19 (2H, t), 7.45 (1H, d), 7.54-7.58 (2H, m), 7.65 (1H, d), 8.04 (1H, s), 8.28 (1H, s).

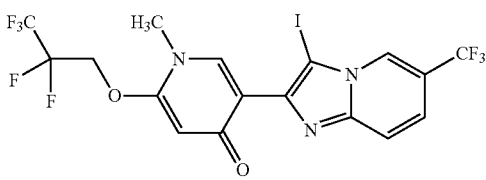 [SMILES: Cn1cc(-c2nc3ccc(C(F)(F)F)cn3c2I)c(=O)cc1OCC(F)(F)C(F)(F)F]

The intermediate compound 23: ¹H-NMR (DMSO-D₆) δ: 8.66 (1H, s), 7.89 (1H, s), 7.80 (1H, d), 7.59 (1H, d), 6.04 (1H, s), 5.06 (2H, t), 3.54 (3H, s).

Reference Preparation Example 11

To a mixture of the intermediate compound 4 (10.3 g), potassium carbonate 11.3 g, THF 80 mL, and NMP 40 mL was added ethanethiol 2.0 mL under ice-cooling, and the mixture was stirred at room temperature for one hour. To the resulting mixture was added water, and the mixture was extracted with MTBE. The resulting organic layer was washed with saturated sodium hydrogen carbonate solution, dried over anhydrous sodium sulfate, and concentrated under reduced pressure. The resulting residue was subjected to a silica gel column chromatography to give the intermediate compound 24 represented by the following formula 7.5 g.

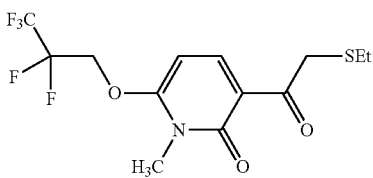

The intermediate compound 24: ¹H-NMR (CDCl₃) δ: 1.24 (3H, t), 2.52 (2H, q), 3.53 (3H, s), 4.03 (2H, s), 4.57 (2H, t), 5.73 (1H, d), 8.34 (1H, d).

Reference Preparation Example 12

The compound prepared according to a similar method to that described in the Reference preparation example 11 and its physical properties are shown as follows.

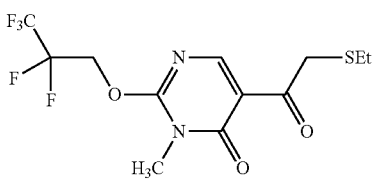

The intermediate compound 25: ¹H-NMR (CDCl₃) δ: 8.54 (1H, s), 4.96 (2H, t), 3.92 (2H, s), 3.50 (3H, s), 2.50 (2H, q), 1.24 (3H, t).

Preparation Example 1

A mixture of the intermediate compound 14 (2.52 g), 1,4-dioxane 18 mL, tris(dibenzylideneacetone)dipalladium (0) 0.21 g, 4,5-bis(diphenylphosphino)-9,9-dimethylxanthene (hereinafter, referred to as "Xantphos") 0.27 g, diisopropylethylamine 2.4 mL, and ethanethiol 0.49 mL was stirred while heating under reflux for 120 minutes. To the resulting mixture was added water, and the mixture was extracted with MTBE. The resulting organic layer was dried over anhydrous sodium sulfate and concentrated under reduced pressure. The obtained residue was subjected to a silica gel column chromatography to give the present compound 1 represented by the following formula 1.22 g.

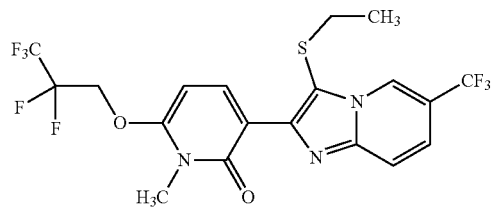 [SMILES: CCSc1c(-c2ccc(OCC(F)(F)C(F)(F)F)n(C)c2=O)nc2ccc(C(F)(F)F)cn12]

The present compound 1: ¹H-NMR (CDCl₃) δ: 8.82 (1H, dd), 7.73 (2H, dd), 7.40 (1H, dd), 5.66 (1H, d), 4.54 (2H, dd), 3.59 (3H, s), 2.75 (2H, q), 1.14 (3H, t).

Preparation Example 2

The compounds prepared according to a similar method to that described in the Preparation example 1 and their physical properties are shown as follows.

A compound represented by formula (A-3):

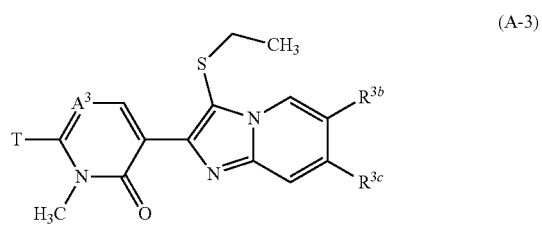

(A-3)

wherein a combination of T, $A^3$, $R^{3b}$, and $R^{3c}$ represents any of the combinations indicated in [Table A4].

TABLE A4

| Present compound | T | $A^3$ | $R^{3b}$ | $R^{3c}$ |
|---|---|---|---|---|
| 2 | OCH₂CF₂CF₃ | CH | H | H |
| 3 | OCH₂CF₂CF₃ | CH | 4-F—Ph | H |
| 4 | OCH₂CF₂CF₃ | N | CF₃ | H |
| 5 | OCH₂CF₂CF₃ | N | H | H |
| 6 | OCH₂CF₂CF₃ | N | 4-F—Ph | H |

The present compound 2: ¹H-NMR (CDCl₃) δ: 1.11 (3H, t), 2.70 (2H, q), 3.56 (3H, s), 4.50 (2H, t), 5.62 (1H, d), 6.89 (1H, t), 7.23-7.25 (1H, m), 7.61-7.68 (2H, m), 8.44 (1H, d).

The present compound 3: ¹H-NMR (CDCl₃) δ: 1.13 (3H, t), 2.73 (2H, q), 3.57 (3H, s), 4.51 (2H, t), 5.63 (1H, d), 7.18 (2H, t), 7.45 (1H, d), 7.56-7.58 (2H, m), 7.69 (2H, t), 8.54 (1H, s).

The present compound 4: ¹H-NMR (CDCl₃) δ: 8.82-8.81 (1H, m), 8.02 (1H, s), 7.77 (1H, t), 7.44 (1H, dd), 4.94 (2H, td), 3.56 (3H, s), 2.75 (2H, q), 1.17 (3H, t).

The present compound 5: ¹H-NMR (CDCl₃) δ: 1.13 (3H, t), 2.70 (2H, q), 3.53 (3H, s), 4.91 (2H, t), 6.92 (1H, t), 7.25-7.29 (1H, m), 7.67 (1H, d), 7.98 (1H, s), 8.45 (1H, d).

The present compound 6: ¹H-NMR (CDCl₃) δ: 1.15 (3H, t), 2.72-2.73 (2H, m), 3.54 (3H, s), 4.92 (2H, t), 7.18 (2H, t), 7.47-7.50 (1H, m), 7.56 (2H, m), 7.71 (1H, d), 8.01 (1H, s), 8.57 (1H, s).

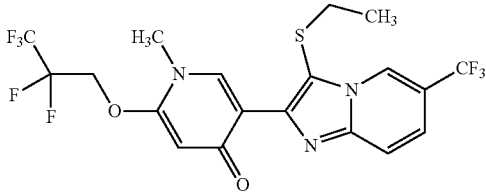 [SMILES: CCSc1c(-c2cn(C)c(OCC(F)(F)C(F)(F)F)cc2=O)nc2ccc(C(F)(F)F)cn12]

The present compound 13: ¹H-NMR (CDCl₃) δ: 8.82 (1H, s), 7.72 (1H, d), 7.55 (1H, s), 7.41 (1H, d), 5.95 (1H, s), 4.49 (2H, t), 3.59 (3H, s), 2.84 (2H, q), 1.18 (3H, t).

Preparation Example 3

To a mixture of the intermediate compound 24 (1.50 g), triethylamine 0.6 mL, and chloroform 8 mL, trimethylsilyl triflate 0.8 mL was added dropwise at −78° C., and then the mixture was stirred at room temperature for 30 minutes. After the resulting mixture was cooled to −78° C., trimethylphenylammonium tribromide 1.60 g was added thereto, and the mixture was stirred at room temperature for one hour. To the resulting mixture was added water, and the mixture was extracted with chloroform. The resulting organic layer was dried over sodium sulfate and filtrated. To the filtrate was added 5-chloro-2-aminopyridine 0.54 g at room temperature, and the mixture was stirred while heating under reflux for one hour. After the resulting mixture was cooled to room temperature, saturated sodium hydrogen carbonate solution was added thereto, and the mixture was extracted with chloroform. The resulting organic layer was dried over anhydrous sodium sulfate and concentrated under reduced pressure. The obtained residue was subjected to a silica gel column chromatography (hexane:ethyl acetate=1: 1) to give the present compound 14 represented by the following formula 0.31 g.

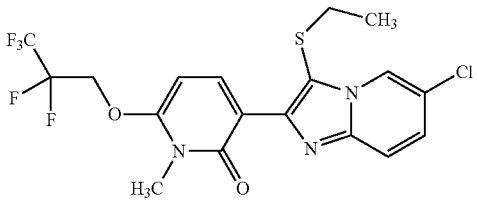 [SMILES: CCSc1c(-c2ccc(OCC(F)(F)C(F)(F)F)n(C)c2=O)nc2ccc(Cl)cn12]

The present compound 14: ¹H-NMR (CDCl₃) δ: 1.14 (3H, t), 2.72 (2H, q), 3.58 (3H, s), 4.53 (2H, t), 5.64 (1H, d), 7.22 (1H, dd), 7.58 (1H, d), 7.69 (1H, d), 8.48-8.49 (1H, m).

Preparation Example 4-1

The compounds prepared according to a similar method to that described in the Preparation example 3 and their physical properties are shown as follows.

A compound represented by formula (A-5):

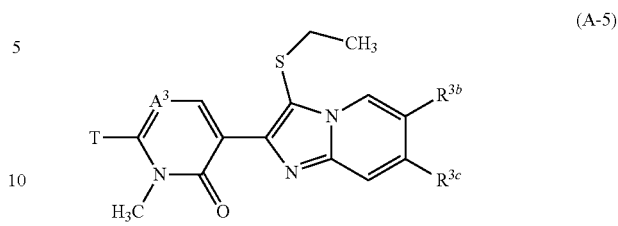

wherein a combination of $A^3$, $R^{3b}$, $R^{3c}$, and $R^{3d}$ represents any of the combinations indicated in [Table A5].

TABLE A5

| Present compound | T | $A^3$ | $R^{3b}$ | $R^{3c}$ | $R^{3d}$ |
|---|---|---|---|---|---|
| 86 | OCH₂CF₂CHF₂ | CH | Br | H | H |
| 87 | OCH₂CF₂CHF₂ | CH | I | H | H |
| 15 | OCH₂CF₂CF₃ | CH | Br | H | H |
| 16 | OCH₂CF₂CF₃ | CH | I | H | H |
| 17 | OCH₂CF₂CF₃ | N | H | H | H |
| 18 | OCH₂CF₂CF₃ | N | F | H | H |
| 19 | OCH₂CF₂CF₃ | N | Cl | H | H |
| 20 | OCH₂CF₂CF₃ | N | Br | H | H |
| 21 | OCH₂CF₂CF₃ | N | I | H | H |
| 50 | OCH₂CF₂CF₃ | N | NO₂ | H | H |
| 51 | OCH₂CF₂CF₃ | N | H | Br | H |
| 52 | OCH₂CF₂CF₃ | N | H | Cl | H |
| 53 | OCH₂CF₂CF₃ | N | H | H | Cl |
| 54 | OCH₂CF₂CF₃ | N | Me | H | H |
| 55 | OCH₂CF₂CF₃ | N | CN | H | H |
| 56 | OCH₂CF₂CF₃ | N | C(O)Me | H | H |
| 57 | OCH₂CF₂CF₃ | N | C(O)Me | H | H |
| 58 | OCH₂CF7CF₃ | N | Br | Br | H |
| 88 | OCH₂CF₂CF₃ | N | Cl | Br | H |
| 89 | OCH₂CF₂CF₃ | N | I | Br | H |

The present compound 86: ¹H-NMR (CDCl₃) δ: 8.58 (1H, d), 7.69 (1H, d), 7.53 (1H, d), 7.31 (1H, dd), 6.17-5.88 (1H, m), 5.66 (1H, d), 4.49 (2H, t), 3.58 (3H, s), 2.72 (2H, q), 1.13 (3H, t).

The present compound 87: ¹H-NMR (CDCl₃) δ: 8.69 (1H, s), 7.68 (1H, d), 7.42 (1H, s), 6.16-5.89 (1H, m), 5.66 (1H, d), 4.48 (2H, t), 3.58 (3H, s), 2.72 (2H, q), 1.13 (3H, t).

The present compound 15: ¹H-NMR (CDCl₃) δ: 1.13 (3H, t), 2.72 (2H, q), 3.58 (3H, s), 4.52 (2H, t), 5.63 (1H, d), 7.32 (1H, dd), 7.53 (1H, d), 7.69 (1H, d), 8.58 (1H, d).

The present compound 16: ¹H-NMR (CDCl₃) δ: 1.13 (3H, t), 2.72 (2H, q), 3.57 (3H, s), 4.53 (2H, t), 5.64-5.66 (1H, m), 7.42 (2H, m), 7.66-7.69 (1H, m), 8.69 (1H, d).

The present compound 17: ¹H-NMR (CDCl₃) δ: 8.48-8.46 (1H, m), 8.00 (1H, s), 7.68-7.65 (1H, m), 7.31-7.29 (1H, m), 6.94-6.93 (1H, m), 4.93 (2H, t), 3.55 (3H, s), 2.72 (2H, q), 1.15 (3H, t).

The present compound 18: ¹H-NMR (CDCl₃) δ: 8.40-8.39 (1H, m), 7.99 (1H, s), 7.65-7.63 (1H, m), 7.23-7.19 (1H, m), 4.93 (2H, t), 3.55 (3H, s), 2.72 (2H, q), 1.16 (3H, t).

The present compound 19: ¹H-NMR (CDCl₃) δ: 8.49 (1H, d), 8.00 (1H, s), 7.61 (1H, d), 7.27-7.24 (1H, m), 4.93 (2H, t), 3.55 (3H, s), 2.73 (2H, q), 1.16 (3H, t).

The present compound 20: ¹H-NMR (CDCl₃) δ: 8.58 (1H, s), 7.99 (1H, d), 7.55 (1H, d), 7.34 (1H, dd), 4.92 (2H, t), 3.54 (3H, s), 2.72 (2H, q), 1.15 (3H, t).

The present compound 21: ¹H-NMR (CDCl₃) δ: 8.70-8.69 (1H, m), 7.99 (1H, s), 7.46-7.45 (2H, m), 4.93 (2H, t), 3.55 (3H, s), 2.72 (2H, q), 1.15 (3H, t).

The present compound 50: $^1$H-NMR (CDCl$_3$) δ: 9.54 (1H, dd), 8.05-8.05 (2H, m), 7.73 (1H, dd), 4.95 (2H, dd), 3.56 (3H, s), 2.79 (2H, q), 1.19 (3H, t).

The present compound 51: $^1$H-NMR (CDCl$_3$) δ: 8.32 (1H, dd), 7.98 (1H, s), 7.83 (1H, dd), 7.03 (1H, dd), 4.93 (2H, dd), 3.54 (3H, s), 2.71 (2H, q), 1.14 (3H, t).

The present compound 52: $^1$H-NMR (CDCl$_3$) δ: 8.38 (1H, dd), 7.98 (1H, s), 7.65 (1H, dd), 6.92 (1H, dd), 4.93 (2H, dd), 3.54 (3H, s), 2.71 (2H, q), 1.14 (3H, t).

The present compound 53: $^1$H-NMR (CDCl$_3$) δ: 8.41 (1H, dd), 7.99 (1H, s), 7.37 (1H, dd), 6.89 (1H, dd), 4.93 (2H, dd), 3.53 (3H, s), 2.74 (2H, q), 1.15 (3H, t).

The present compound 54: $^1$H-NMR (CDCl$_3$) δ: 8.24-8.23 (1H, m), 7.98 (1H, s), 7.56 (1H, dd), 7.13 (1H, dd), 4.92 (2H, dd), 3.54 (3H, s), 2.70 (2H, q), 2.40 (3H, d), 1.14 (3H, t).

The present compound 55: $^1$H-NMR (CDCl$_3$) δ: 8.89 (1H, dd), 8.03 (1H, s), 7.74 (1H, dd), 7.41-7.38 (1H, m), 4.94 (2H, dd), 3.55 (3H, s), 2.76 (2H, q), 1.17 (3H, t).

The present compound 56: $^1$H-NMR (CDCl$_3$) δ: 9.12 (1H, dd), 8.03 (1H, s), 7.83 (1H, m), 7.68 (1H, d), 4.94 (2H, dd), 3.56 (3H, s), 2.76 (2H, q), 2.69 (3H, d), 1.18 (3H, t).

The present compound 57: $^1$H-NMR (CDCl$_3$) δ: 9.20 (1H, dd), 8.02 (1H, s), 7.84 (1H, dd), 7.66 (1H, dd), 4.94 (2H, dd), 3.99 (3H, s), 3.55 (3H, s), 2.75 (2H, q), 1.16 (3H, t).

The present compound 58: $^1$H-NMR (CDCl$_3$) δ: 8.67 (1H, s), 7.99 (1H, s), 7.97 (1H, s), 4.93 (2H, dd), 3.54 (3H, s), 2.73 (2H, q), 1.15 (3H, t).

The present compound 88: $^1$H-NMR (CDCl$_3$) δ: 8.57 (1H, s), 7.98 (2H, m), 4.93 (2H, t), 3.54 (3H, s), 2.73 (2H, q), 1.15 (3H, t).

The present compound 89: $^1$H-NMR (CDCl$_3$) δ: 8.81 (1H, s), 7.99 (2H, m), 4.93 (2H, t), 3.54 (3H, s), 2.72 (2H, q), 1.15 (3H, t).

Preparation Example 4-2

The compounds prepared according to a similar method to that described in the Preparation example 3 and their physical properties are shown as follows.

A compound represented by formula (A-5-1):

(A-5-1)

wherein Qa represents any of the formulae shown in [Table A5-1].

TABLE A5-1

| Present compound | Qa |
|---|---|
| 63 | 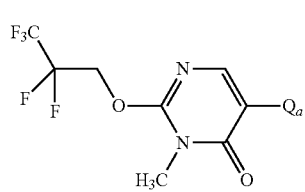 |

TABLE A5-1-continued

| Present compound | Qa |
|---|---|
| 64 | (structure: S-CH$_3$ linked imidazo[1,2-b]pyridazine with Cl) |
| 65 | (structure: S-CH$_3$ linked imidazo[1,2-a]pyrimidine) |
| 66 | (structure: S-CH$_3$ linked imidazo[2,1-b]thiazole) |
| 67 | (structure: S-CH$_3$ linked imidazo[1,2-a]pyrimidine with CF$_3$) |
| 84 | (structure: S-CH$_3$ linked imidazo[1,2-a]pyrimidine with I) |
| 85 | (structure: S-CH$_3$ linked imidazo[1,2-a]pyrimidine with CF$_3$) |
| 112 | (structure: S-CH$_3$ linked imidazo[1,2-b]pyridazine with I) |

The present compound 63: $^1$H-NMR (CDCl$_3$) δ: 8.84 (1H, dd), 8.60 (1H, dd), 8.09 (1H, s), 4.94 (2H, t), 3.55 (3H, s), 2.79 (2H, q), 1.17 (3H, t).

The present compound 64: $^1$H-NMR (CDCl$_3$) δ: 8.00 (1H, s), 7.94 (1H, d), 7.14 (1H, d), 4.94 (2H, t), 3.55 (3H, s), 2.94 (2H, q), 1.18 (3H, t).

The present compound 65: $^1$H-NMR (CDCl$_3$) δ: 9.13 (1H, s), 8.37 (1H, d), 8.05 (1H, s), 8.03 (1H, d), 4.95 (2H, t), 3.56 (3H, s), 2.77 (2H, q), 1.17 (3H, t).

The present compound 66: $^1$H-NMR (CDCl$_3$) δ: 7.94 (1H, s), 7.57 (1H, d), 6.90 (1H, d), 4.91 (2H, t), 3.53 (3H, s), 2.73 (2H, q), 1.18 (3H, t).

The present compound 67: ¹H-NMR (CDCl₃) δ: 9.35 (1H, s), 8.05 (1H, s), 7.93 (1H, s), 4.98-4.92 (2H, m), 3.56 (3H, s), 2.82 (2H, q), 1.20 (3H, t).

The present compound 84: ¹H-NMR (CDCl₃) δ: 8.94 (1H, d), 8.67 (1H, d), 8.09 (1H, s), 4.94 (2H, dd), 3.55 (3H, s), 2.78 (2H, q), 1.17 (3H, t).

The present compound 85: ¹H-NMR (CDCl₃) δ: 8.92 (1H, d), 8.15 (1H, s), 7.33 (1H, d), 4.95 (2H, dd), 3.57 (3H, s), 2.82 (2H, q), 1.18 (3H, t).

The present compound 112: ¹H-NMR (CDCl₃) δ: 8.00 (1H, s), 7.65 (1H, d), 7.40 (1H, d), 4.94 (2H, t), 3.55 (3H, s), 2.93 (2H, q), 1.17 (3H, t).

Preparation Example 5

To a mixture of the present compound 1 (1.22 g) and chloroform 15 mL was added mCPBA (purity 70%, containing 30% water) 1.30 g under ice-cooling, and the mixture was stirred at room temperature for 6 hours. To the resulting mixture were sequentially added saturated sodium hydrogen carbonate solution and sodium thiosulfate solution, and the mixture was extracted with chloroform. The resulting organic layer was dried over anhydrous sodium sulfate and concentrated under reduced pressure. The obtained residue was subjected to a silica gel column chromatography (hexane:ethyl acetate=1:1) to give the present compound 7 represented by the following formula 0.61 g.

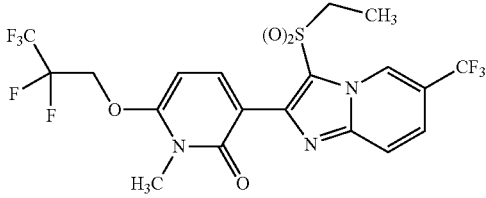

The present compound 7: ¹H-NMR (CDCl₃) δ: 9.27 (1H, s), 7.82 (1H, d), 7.74 (1H, d), 7.59 (1H, dd), 5.70 (1H, d), 4.53 (2H, t), 3.78 (2H, q), 3.56 (3H, s), 1.45 (3H, t).

Preparation Example 6-1

The compounds prepared according to a similar method to that described in the Preparation example 5 and their physical properties are shown as follows.

A combination represented by formula (A-4):

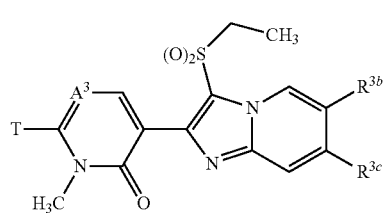

wherein a combination of T, A³, R³ᵇ, R³ᶜ, R³ᵈ, and n represents any of the combinations indicated in [Table A6].

TABLE A6

| Present compound | T | A³ | R³ᵇ | R³ᶜ | R³ᵈ | n |
|---|---|---|---|---|---|---|
| 101 | OCH₂CF₂CHF₂ | CH | Br | H | H | 2 |
| 102 | OCH₂CF₂CHF₂ | CH | I | H | H | 2 |
| 8 | OCH₂CF₂CF₃ | CH | H | H | H | 2 |
| 9 | OCH₂CF₂CF₃ | CH | 4-F—Ph | H | H | 2 |
| 22 | OCH₂CF₂CF₃ | CH | Cl | H | H | 2 |
| 23 | OCH₂CF₂CF₃ | CH | Br | H | H | 2 |
| 24 | OCH₂CF₂CF₃ | CH | I | H | H | 2 |
| 10 | OCH₂CF₂CF₃ | N | CF₃ | H | H | 2 |
| 11 | OCH₂CF₂CF₃ | N | H | H | H | 2 |
| 12 | OCH₂CF₂CF₃ | N | 4-F—Ph | H | H | 2 |
| 25 | OCH₂CF₂CF₃ | N | F | H | H | 2 |
| 26 | OCH₂CF₂CF₃ | N | Cl | H | H | 2 |
| 27 | OCH₂CF₂CF₃ | N | Br | H | H | 2 |
| 28 | OCH₂CF₂CF₃ | N | I | H | H | 2 |
| 32 | OCH₂CF₂CF₃ | N | c-Pr | H | H | 2 |
| 33 | OCH₂CF₂CF₃ | N | (5-methyl-2-CF₃-pyridinyl) | H | H | 2 |
| 34 | OCH₂CF₂CF₃ | N | NO₂ | H | H | 2 |
| 35 | OCH₂CF₂CF₃ | N | H | Br | H | 2 |
| 36 | OCH₂CF₂CF₃ | N | H | OMe | H | 2 |
| 37 | OCH₂CF₂CF₃ | N | H | OEt | H | 2 |
| 38 | OCH₂CF₂CF₃ | N | H | Cl | H | 2 |
| 39 | OCH₂CF₂CF₃ | N | H | H | Cl | 2 |
| 40 | OCH₂CF₂CF₃ | N | Me | H | H | 2 |
| 41 | OCH₂CF₂CF₃ | N | (4-Cl-pyrazol-1-yl) | H | H | 2 |
| 42 | OCH₂CF₂CF₃ | N | CH=CH₂ | H | H | 2 |
| 43 | OCH₂CF₂CF₃ | N | C(Me)=CH₂ | H | H | 2 |
| 44 | OCH₂CF₂CF₃ | N | CN | H | H | 2 |
| 45 | OCH₂CF₂CF₃ | N | C(O)Me | H | H | 2 |
| 46 | OCH₂CF₂CF₃ | N | C(O)OMe | H | H | 2 |
| 47 | OCH₂CF₂CF₃ | N | Br | Br | H | 2 |
| 48 | OCH₂CF₂CF₃ | N | Br | H | H | 1 |
| 49 | OCH₂CF₂CF₃ | N | Br | Me | H | 2 |
| 90 | OCH₂CF₂CF₃ | N | Cl | Br | H | 2 |
| 100 | OCH₂CF₂CF₃ | N | I | Br | H | 2 |
| 107 | OCH₂CF₂CF₃ | N | S(O)₂Et | H | H | 2 |

The present compound 101: ¹H-NMR (CDCl₃) δ: 9.05 (1H, t), 7.71 (1H, d), 7.61 (1H, d), 7.50 (1H, dd), 6.14-5.86 (1H, in), 5.70 (1H, d), 4.48 (2H, t), 3.73 (2H, q), 3.55 (3H, s), 1.44 (3H, t).

The present compound 102: ¹H-NMR (CDCl₃) δ: 9.13 (1H, d), 7.70 (1H, d), 7.61 (1H, d), 7.49 (1H, d), 6.14-5.87 (1H, m), 5.70 (1H, d), 4.48 (2H, t), 3.73 (2H, q), 3.55 (3H, s), 1.43 (3H, t).

The present compound 8: ¹H-NMR (CDCl₃) δ: 1.41 (3H, t), 3.53 (3H, s), 3.70 (2H, q), 4.49 (2H, t), 5.66 (1H, d), 7.01 (1H, t), 7.43 (1H, t), 7.70 (2H, d), 8.89 (1H, d).

The present compound 9: ¹H-NMR (CDCl₃) δ: 1.43 (3H, t), 3.54 (3H, s), 3.73 (2H, q), 4.48-4.59 (2H, m), 5.67 (1H, d), 7.16-7.21 (2H, m), 7.52-7.54 (2H, m), 7.61-7.63 (1H, m), 7.71-7.77 (2H, m), 9.01 (1H, s).

The present compound 22: ¹H-NMR (CDCl₃) δ: 8.95-8.96 (1H, m), 7.71 (1H, d), 7.66 (1H, m), 7.41 (1H, dd), 5.68 (1H, d), 4.52 (2H, t), 3.73 (2H, q), 3.55 (3H, s), 1.44 (3H, t).

The present compound 23: ¹H-NMR (CDCl₃) δ: 9.04 (1H, d), 7.70 (1H, d), 7.61 (1H, d), 7.50 (1H, dd), 5.68 (1H, d), 4.52 (2H, t), 3.73 (2H, q), 3.55 (3H, s), 1.44 (3H, t).

The present compound 24: ¹H-NMR (CDCl₃) δ: 9.13 (1H, d), 7.70 (1H, d), 7.62 (1H, m), 7.50 (1H, m), 5.68 (1H, d), 4.51 (2H, t), 3.72 (2H, q), 3.55 (3H, s), 1.43 (3H, t).

The present compound 10: ¹H-NMR (CDCl₃) δ: 9.27-9.26 (1H, m), 8.04 (1H, s), 7.86 (1H, d), 7.62 (1H, dd), 4.93 (2H, td), 3.71 (2H, q), 3.53 (3H, s), 1.45 (3H, t).

The present compound 11: ¹H-NMR (CDCl₃) δ: 1.41 (3H, t), 3.53 (3H, s), 3.63 (2H, q), 4.90 (2H, t), 7.05 (1H, t), 7.46 (1H, t), 7.75 (1H, d), 7.99 (1H, s), 8.88 (1H, d).

The present compound 12: ¹H-NMR (CDCl₃) δ: 1.43 (3H, t), 3.51 (3H, s), 3.66 (2H, q), 4.88-4.96 (2H, m), 7.17 (2H, t), 7.53-7.54 (2H, m), 7.65 (1H, d), 7.79 (1H, d), 8.01 (1H, s), 9.00 (1H, s).

The present compound 25: ¹H-NMR (CDCl₃) δ: 8.88-8.87 (1H, m), 8.00 (1H, s), 7.75-7.71 (1H, m), 7.42-7.38 (1H, m), 4.92 (2H, t), 3.66 (2H, q), 3.52 (3H, s), 1.43 (3H, t).

The present compound 26: ¹H-NMR (CDCl₃) δ: 8.95 (1H, d), 8.00 (1H, s), 7.69 (1H, d), 7.44 (1H, dd), 4.92 (2H, t), 3.66 (2H, q), 3.52 (3H, s), 1.44 (3H, t).

The present compound 27: ¹H-NMR (CDCl₃) δ: 9.03 (1H, d), 8.00 (1H, s), 7.64 (1H, d), 7.54 (1H, dd), 4.92 (2H, t), 3.66 (2H, q), 3.52 (3H, s), 1.44 (3H, t).

The present compound 28: ¹H-NMR (CDCl₃) δ: 9.12 (1H, s), 8.00 (1H, s), 7.65 (1H, d), 7.52 (1H, d), 4.92 (2H, t), 3.66 (2H, q), 3.52 (3H, s), 1.44 (3H, t).

The present compound 32: ¹H-NMR (CDCl₃) δ: 8.67 (1H, s), 7.98 (1H, s), 7.63 (1H, d), 7.16 (1H, d), 4.90 (2H, dd), 3.62 (2H, q), 3.51 (3H, s), 2.01-1.97 (1H, m), 1.42 (3H, t), 1.08-1.03 (2H, m), 0.75 (2H, m).

The present compound 33: ¹H-NMR (CDCl₃) δ: 9.17 (1H, dd), 9.00 (1H, d), 8.13 (1H, dd), 8.07 (1H, s), 7.93 (1H, d), 7.88 (1H, d), 7.72 (1H, dd), 4.95 (2H, dd), 3.74 (2H, q), 3.56 (3H, s), 1.48 (3H, t).

The present compound 34: ¹H-NMR (CDCl₃) δ: 9.95 (1H, dd), 8.24 (1H, dd), 8.08 (1H, s), 7.83 (1H, dd), 4.94 (2H, dd), 3.77 (2H, q), 3.53 (3H, s), 1.49 (3H, t).

The present compound 35: ¹H-NMR (CDCl₃) δ: 8.76 (1H, dd), 8.00 (1H, s), 7.92 (1H, dd), 7.15 (1H, dd), 4.91 (2H, dd), 3.66 (2H, q), 3.51 (3H, s), 1.42 (3H, t).

The present compound 36: ¹H-NMR (CDCl₃) δ: 8.69 (1H, d), 7.99 (1H, s), 6.98 (1H, d), 6.74 (1H, dd), 4.90 (2H, dd), 3.91 (3H, s), 3.60 (2H, q), 3.51 (3H, s), 1.40 (3H, t).

The present compound 37: ¹H-NMR (CDCl₃) δ: 8.67 (1H, d), 7.99 (1H, s), 6.94 (1H, d), 6.72 (1H, dd), 4.90 (2H, dd), 4.11 (2H, t), 3.58 (2H, q), 3.51 (3H, s), 1.49 (3H, t), 1.40 (3H, t).

The present compound 38: ¹H-NMR (CDCl₃) δ: 8.83 (1H, dd), 8.00 (1H, s), 7.73 (1H, dd), 7.04 (1H, dd), 4.91 (2H, dd), 3.66 (2H, q), 3.52 (3H, s), 1.42 (3H, t).

The present compound 39: ¹H-NMR (CDCl₃) δ: 8.85 (1H, dd), 8.05 (1H, s), 7.54 (1H, dd), 7.01 (1H, dd), 4.92 (2H, dd), 3.68 (2H, q), 3.51 (3H, s), 1.43 (3H, t).

The present compound 40: ¹H-NMR (CDCl₃) δ: 8.65 (1H, s), 7.99 (1H, s), 7.64 (1H, d), 7.32 (1H, dd), 4.91 (2H, dd), 3.63 (2H, q), 3.51 (3H, s), 2.42 (3H, s), 1.42 (3H, t).

The present compound 41: ¹H-NMR (CDCl₃) δ: 9.25 (1H, dd), 8.03 (1H, s), 7.93 (1H, d), 7.84-7.84 (2H, m), 7.72 (1H, s), 4.92 (2H, dd), 3.70 (2H, q), 3.53 (3H, s), 1.46 (3H, t).

The present compound 42: ¹H-NMR (CDCl₃) δ: 8.78 (1H, s), 8.00 (1H, s), 7.68-7.68 (2H, m), 6.73 (1H, dd), 5.84 (1H, d), 5.45 (1H, d), 4.91 (2H, dd), 3.64 (2H, q), 3.52 (3H, s), 1.43 (3H, t).

The present compound 43: ¹H-NMR (CDCl₃) δ: 8.89 (1H, s), 8.00 (1H, s), 7.67-7.67 (2H, m), 5.49 (1H, s), 5.26 (1H, s), 4.91 (2H, dd), 3.64 (2H, q), 3.52 (3H, s), 2.21 (3H, s), 1.43 (3H, t).

The present compound 44: ¹H-NMR (CDCl₃) δ: 9.34 (1H, dd), 8.05 (1H, s), 7.83 (1H, dd), 7.57 (1H, dd), 4.93 (2H, dd), 3.73 (2H, q), 3.53 (3H, s), 1.46 (3H, t).

The present compound 45: ¹H-NMR (CDCl₃) δ: 9.55 (1H, s), 8.05 (1H, s), 8.02 (1H, dd), 7.77 (1H, d), 4.93 (2H, dd), 3.72 (2H, q), 3.53 (3H, s), 2.68 (3H, s), 1.46 (3H, t)

The present compound 46: ¹H-NMR (CDCl₃) δ: 9.57 (1H, s), 8.03-8.02 (2H, m), 7.75 (1H, d), 4.92 (2H, dd), 4.00 (3H, s), 3.70 (2H, q), 3.53 (3H, s), 1.46 (3H, t).

The present compound 47: ¹H-NMR (CDCl₃) 9.12 (1H, s), 8.06 (1H, s), 8.00 (1H, s), 4.92 (2H, dd), 3.67 (2H, q), 3.52 (3H, s), 1.44 (3H, t).

The present compound 48: ¹H-NMR (CDCl₃) δ: 9.20 (1H, dd), 8.26 (1H, s), 7.58 (1H, dd), 7.43 (1H, dd), 4.98-4.90 (2H, m), 3.68-3.54 (2H, m), 3.52 (3H, s), 1.56 (3H, t).

The present compound 49: ¹H-NMR (CDCl₃) δ: 9.04 (1H, s), 7.99 (1H, s), 7.58 (1H, s), 4.91 (2H, dd), 3.64 (2H, q), 3.51 (3H, s), 2.52 (3H, s), 1.43 (3H, t).

The present compound 90: ¹H-NMR (CDCl₃) δ: 9.03 (1H, d), 8.03 (2H, m), 4.92 (2H, t), 3.68 (2H, q), 3.52 (3H, s), 1.43 (3H, t).

The present compound 100: ¹H-NMR (CDCl₃) δ: 9.24 (1H, d), 8.08 (1H, s), 7.99 (1H, s), 4.90 (2H, t), 3.67 (2H, q), 3.51 (3H, s), 1.43 (3H, t).

The present compound 107: ¹H-NMR (CDCl₃) δ: 9.48 (1H, s), 8.06 (1H, s), 7.88 (1H, d), 7.81 (1H, d), 4.94 (2H, t), 3.74 (2H, q), 3.54 (3H, s), 3.24 (2H, q), 1.47 (3H, t), 1.37 (3H, t).

The present compound 29: ¹H-NMR (CDCl₃) δ: 9.27 (1H, s), 7.81 (1H, d), 7.60-7.59 (2H, m), 5.90 (1H, s), 4.49 (2H, t), 3.87 (2H, q), 3.59 (3H, s), 1.47 (3H, t).

Preparation Example 6-2

The compounds prepared according to a similar method to that described in the Preparation example 5 and their physical properties are shown as follows.

A compound represented by formula (A-4-1):

(A-4-1)

wherein Qa represents any of the formulae shown in [Table A6-1].

TABLE A6-1

| Present compound | Qa |
|---|---|
| 68 | 3-(ethylsulfonyl)-2-methyl-6-bromoimidazo[1,2-a]pyrimidine |
| 69 | 3-(ethylsulfonyl)-2-methyl-6-chloroimidazo[1,2-b]pyridazine |
| 70 | 3-(ethylsulfonyl)-2-methylimidazo[1,2-a]pyrazine |
| 71 | 6-(ethylsulfonyl)-5-methylimidazo[2,1-b]thiazole |
| 113 | 3-(ethylsulfonyl)-6-iodoimidazo[1,2-b]pyridazine |
| 72 | 6-(ethylsulfonyl)-5-methylimidazo[2,1-b]thiazole variant |
| 73 | 3-(ethylsulfonyl)-2-methyl-7-(trifluoromethyl)imidazo[1,2-c]pyrimidine |
| 74 | 3-(ethylsulfonyl)-2-methyl-7-(trifluoromethyl)imidazo[1,2-a]pyrimidine |

TABLE A6-1-continued

| Present compound | Qa |
|---|---|
| 99 | 3-(ethylsulfonyl)-2-methyl-6-iodoimidazo[1,2-a]pyrimidine |
| 91 | 3-(ethylsulfonyl)-2-methyl-6-(trifluoromethyl)imidazo[1,2-a]pyrimidine |

The present compound 68: $^1$H-NMR (CDCl$_3$) δ: 9.30 (1H, d), 8.75 (1H, d), 8.13 (1H, s), 4.93 (2H, t), 3.79 (2H, q), 3.53 (3H, s), 1.47 (3H, t).

The present compound 69: $^1$H-NMR (CDCl$_3$) δ: 8.02 (1H, d), 7.98 (1H, s), 7.33 (1H, d), 4.92 (2H, t), 3.68 (2H, q), 3.52 (3H, s), 1.47 (3H, t).

The present compound 70: $^1$H-NMR (CDCl$_3$) δ: 9.25 (1H, s), 8.80 (1H, d), 8.15 (1H, d), 8.06 (1H, s), 4.93 (2H, t), 3.74 (2H, q), 3.54 (3H, s), 1.45 (3H, t).

The present compound 71: $^1$H-NMR (CDCl$_3$) δ: 8.28 (1H, s), 8.18 (1H, d), 6.94 (1H, d), 4.92 (2H, t), 3.51 (3H, s), 3.49-3.38 (2H, m), 1.50 (3H, t).

The present compound 113: $^1$H-NMR (CDCl$_3$) δ: 7.97 (1H, s), 7.75 (1H, d), 7.59 (1H, d), 4.95-4.88 (2H, m), 3.67 (2H, q), 3.52 (3H, s), 1.47 (3H, t).

The present compound 72: $^1$H-NMR (CDCl$_3$) δ: 8.02 (1H, s), 7.95 (1H, d), 7.04 (1H, d), 4.91 (2H, t), 3.64 (2H, q), 3.52 (3H, s), 1.39 (3H, t).

The present compound 73: $^1$H-NMR (CDCl$_3$) δ: 10.04 (1H, s), 8.41 (1H, s), 7.96 (1H, s), 5.00-4.93 (2H, m), 3.70-3.62 (2H, m), 3.53 (3H, s), 1.61 (3H, t).

The present compound 74: $^1$H-NMR (CDCl$_3$) δ: 9.77 (1H, s), 8.09 (1H, s), 8.03 (1H, s), 4.94 (2H, t), 3.80 (2H, q), 3.54 (3H, s), 1.49 (3H, t).

The present compound 99: $^1$H-NMR (CDCl$_3$) δ: 9.38 (1H, d), 8.83 (1H, d), 8.13 (1H, s), 4.93 (2H, t), 3.79 (2H, q), 3.53 (3H, s), 1.47 (3H, t).

The present compound 91: $^1$H-NMR (CDCl$_3$) δ: 9.40 (1H, d), 8.16 (1H, s), 7.45 (1H, d), 4.94 (2H, t), 3.83 (2H, q), 3.54 (3H, s), 1.46 (3H, t).

Preparation Example 7

To a mixture of the present compound 28 (181 mg), (1-cyanocyclopropyl)methanol 45 mg, and DMF 1 mL was added cesium carbonate 150 mg, and the mixture was stirred at room temperature for one hour. To the mixture was added water, and the mixture was extracted with ethyl acetate. The resulting organic layer was dried over anhydrous sodium sulfate and concentrated under reduced pressure. The obtained residue was subjected to a silica gel column chromatography to give the present compound 30 represented by the following formula 139 mg.

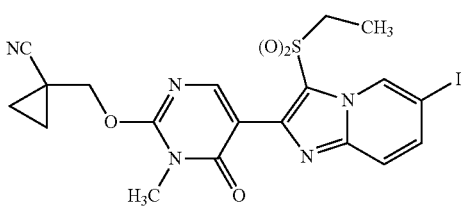

The present compound 30: ¹H-NMR (CDCl₃) δ: 9.12-9.12 (1H, m), 7.96 (1H, s), 7.65-7.63 (1H, m), 7.53-7.50 (1H, m), 4.46 (2H, s), 3.67 (2H, q), 3.57 (3H, s), 1.47-1.44 (5H, m), 1.25-1.20 (2H, m).

Preparation Example 8

The compounds prepared according to a similar method to that described in the Preparation example 7 and their physical properties are shown as follows.

A compound represented by formula (A-8):

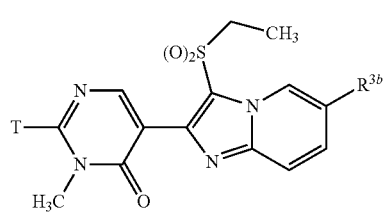

(A-8)

wherein a combination of T and $R^{3b}$ represents any of the combinations indicated in [Table A8].

TABLE A8

| Present compound | T | $R^{3b}$ |
|---|---|---|
| 31 | OCH₂C(CH₃)₂CN | I |
| 78 | OCH₂CF₂CHF₂ | I |
| 79 | OCH₂CF₂CHFCF₃ | I |
| 80 | OCH₂CF₂CF₂CF₂CF₃ | I |
| 81 | OCH₂CH₂CF₂CF₂CF₃ | I |
| 82 | OCH₂CF₂CHF₂ | Br |
| 83 | OCH₂CF₂CF₂CF₃ | Br |
| 59 | OCH₂CF₂CF₂CF₃ | I |
| 60 | OCH₂CF₂CHFCF₃ | Br |
| 103 | OCH₂CF₃ | Br |
| 104 | OCH₂CF₃ | I |
| 105 | OCH₂CF₂CF₃ | Br |
| 106 | OCH₂CF₂CF₃ | I |

The present compound 31: ¹H-NMR (CDCl₃) δ: 9.13-9.12 (1H, m), 7.99 (1H, s), 7.65-7.63 (1H, m), 7.53-7.51 (1H, m), 4.39 (2H, s), 3.67 (2H, q), 3.56 (3H, s), 1.52 (6H, s), 1.44 (3H, t).

The present compound 78: ¹H-NMR (CDCl₃) δ: 9.12 (1H, d), 8.01 (1H, s), 7.65 (1H, dd), 7.53 (1H, d), 5.96 (1H, tt), 4.87 (2H, t), 3.66 (2H, q), 3.52 (3H, s), 1.44 (3H, t).

The present compound 79: ¹H-NMR (CDCl₃) δ: 9.13 (1H, d), 8.03 (1H, s), 7.68 (1H, dd), 7.57 (1H, d), 5.10-4.93 (1H, m), 4.90-4.84 (2H, m), 3.67 (2H, q), 3.53 (3H, s), 1.44 (3H, t).

The present compound 80: ¹H-NMR (CDCl₃) δ: 9.13 (1H, s), 8.01 (1H, s), 7.66 (1H, d), 7.53 (1H, d), 4.97 (2H, t), 3.66 (2H, q), 3.53 (3H, s), 1.44 (3H, t).

The present compound 81: ¹H-NMR (CDCl₃) δ: 9.13 (1H, s), 8.01 (1H, s), 7.64 (1H, d), 7.52 (1H, d), 4.55 (2H, t), 3.67 (2H, q), 3.49 (3H, s), 2.26-2.21 (2H, m), 1.43 (3H, t).

The present compound 82: ¹H-NMR (CDCl₃) δ: 9.04 (1H, d), 8.01 (1H, s), 7.64 (1H, d), 7.53 (1H, dd), 5.96 (1H, tt), 4.87 (2H, t), 3.67 (2H, q), 3.52 (3H, s), 1.44 (3H, t).

The present compound 83: ¹H-NMR (CDCl₃) δ: 9.03 (1H, d), 8.01 (1H, s), 7.65 (1H, d), 7.54 (1H, dd), 4.96 (2H, t), 3.67 (2H, q), 3.52 (3H, s), 1.44 (3H, t).

The present compound 59: 9.12 (1H, s), 8.00 (1H, s), 7.65 (1H, d), 7.53 (1H, d), 4.96 (2H, t), 3.66 (2H, q), 3.52 (3H, s), 1.44 (3H, t).

The present compound 60: ¹H-NMR (CDCl₃) δ: 9.04 (1H, d), 8.01 (1H, s), 7.65 (1H, d), 7.54 (1H, dd), 5.06-4.96 (1H, m), 4.90-4.84 (2H, m), 3.67 (2H, q), 3.53 (3H, s), 1.44 (3H, t).

The present compound 103: ¹H-NMR (CDCl₃) δ: 9.03 (1H, dd), 8.00 (1H, s), 7.64 (1H, dd), 7.54 (1H, dd), 4.85 (2H, q), 3.66 (2H, q), 3.54 (3H, s), 1.44 (3H, t).

The present compound 104: ¹H-NMR (CDCl₃) δ: 9.12 (1H, dd), 8.00 (1H, s), 7.65 (1H, dd), 7.52 (1H, dd), 4.85 (2H, q), 3.66 (2H, q), 3.54 (3H, s), 1.44 (3H, t).

The present compound 105: ¹H-NMR (CDCl₃) δ: 9.04 (1H, dd), 8.01 (1H, s), 7.63 (1H, dd), 7.53 (1H, dd), 4.71 (2H, t), 3.67 (2H, q), 3.48 (3H, s), 2.73-2.62 (2H, m), 1.44 (3H, t).

The present compound 106: ¹H-NMR (CDCl₃) δ: 9.12 (1H, s), 8.00 (1H, s), 7.64 (1H, d), 7.52 (1H, d), 4.70 (2H, t), 3.66 (2H, q), 3.48 (3H, s), 2.67 (2H, tt), 1.43 (3H, t).

Preparation Example 8-1

A mixture of the present compound 27 (0.50 g), 2,4-bis(4-methoxyphenyl)-1,3,2,4-dithiadiphosphetane-2,4-disulfide 1.1 g, and xylene 2 mL was stirred while heating under reflux for 5 hours. The resulting mixture was filtrated through Celite (registered trademark) and washed with sodium thiosulfate solution. The resulting organic layer was dried over anhydrous sodium sulfate and concentrated under reduced pressure. The obtained residue was subjected to a silica gel column chromatography to give the present compound 75 represented by the following formula 0.3 g.

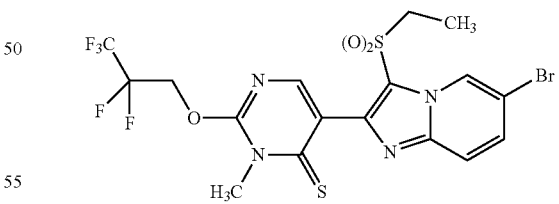

The present compound 75: ¹H-NMR (CDCl₃) δ: 9.08 (1H, dd), 7.77 (1H, s), 7.67 (1H, dd), 7.56 (1H, dd), 5.00-4.90 (2H, m), 3.94 (3H, s), 3.41 (2H, q), 1.35 (3H, t).

Preparation Example 8-2

The compounds prepared according to a similar method to that described in the Preparation example 8-1 and their physical properties are shown as follows.

A compound represented by formula (A-8-1):

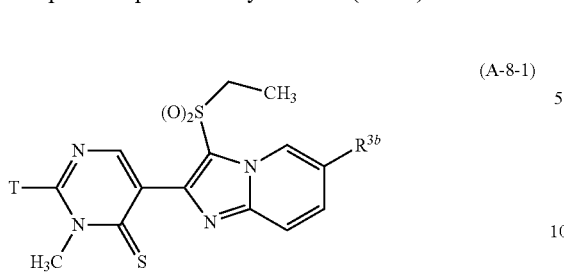

(A-8-1)

wherein a combination of T and $R^{3b}$ represents any of the combinations indicated in [Table A8-1].

TABLE A8-1

| Present compound | T | $R^{3b}$ |
|---|---|---|
| 76 | $OCH_2CF_2CF_3$ | Cl |
| 77 | $OCH_2CF_2CF_3$ | I |
| 92 | $OCH_2CF_2CHF_2$ | Br |
| 93 | $OCH_2CF_2CHF_2$ | I |

The present compound 76: $^1$H-NMR (CDCl$_3$) δ: 8.99 (1H, dd), 7.77 (1H, s), 7.72 (1H, dd), 7.46 (1H, dd), 5.00-4.90 (2H, m), 3.94 (3H, s), 3.42 (2H, q), 1.34 (3H, t).
The present compound 77: $^1$H-NMR (CDCl$_3$) δ: 9.16 (1H, d), 7.77 (1H, s), 7.67 (1H, dd), 7.55 (1H, d), 5.00-4.90 (2H, m), 3.94 (3H, s), 3.41 (2H, q), 1.34 (3H, t).
The present compound 92: $^1$H-NMR (CDCl$_3$) δ: 9.08 (1H, s), 7.78 (1H, s), 7.66 (1H, d), 7.55 (1H, d), 5.97 (1H, t), 4.95-4.86 (2H, m), 3.94 (3H, s), 3.42 (2H, d), 1.34 (3H, t).
The present compound 93: $^1$H-NMR (CDCl$_3$) δ: 9.09 (1H, dd), 7.70 (1H, s), 7.60 (1H, dd), 7.48 (1H, dd), 6.04-5.76 (1H, m), 4.88-4.79 (2H, m), 3.87 (3H, s), 3.34 (2H, q), 1.27 (3H, t).

Reference Preparation Example 13

To a mixture of chloroacetic acid 9.49 g and water 15 mL was added triethylamine 16.7 mL at 0° C. over 30 minute. To the resulting mixture was added 2-amino-5-(trifluoromethyl)pyridine 16.1 g, and the mixture was stirred while heating under reflux for 2 hours. The resulting mixture was filtrated and the filtrate was washed with water. The obtained solid was dried to give a crude product of the intermediate compound 26 represented by the following formula 11.0 g.

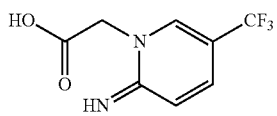

The intermediate compound 26: LC-MS: 219(−)

Reference Preparation Example 14

A mixture of the crude product of the intermediate compound 26 obtained in the Reference preparation example 13 (4.40 g), phosphorus oxybromide 22.37 g, and toluene 50 mL was stirred while heating under reflux for 5 hours. The resulting mixture was added dropwise to sodium hydroxide solution, and the mixture was extracted with toluene. The resulting organic layer was dried over anhydrous sodium sulfate and concentrated under reduced pressure to give the intermediate compound 27 represented by the following formula 4.7 g.

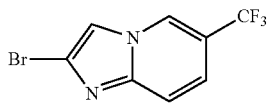

The intermediate compound 27: $^1$H-NMR (CDCl$_3$) δ: 8.45 (1H, d), 7.69 (1H, s), 7.67 (1H, dd), 7.36 (1H, dd).

Reference Preparation Example 15

A mixture of the intermediate compound 27 (500 mg), 4-(2,2,3,3,3-pentafluoropropoxy)-2-pyridinone 453 mg, trans-N,N-dimethylcyclohexane-1,2-diamine 97 mg, copper (I) iodide 130 mg, lithium tert-butoxide 328 mg, and NMP 5 mL was stirred at 120° C. for 5 hours. To the resulting mixture was added water, and the mixture was extracted with chloroform. The resulting organic layer was dried over anhydrous sodium sulfate and concentrated under reduced pressure. The resulting residue was subjected to a silica gel column chromatography to give the intermediate compound 28 represented by the following formula 80 mg.

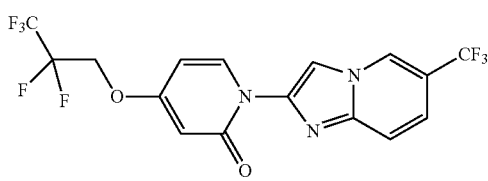

The intermediate compound 28: $^1$H-NMR (CDCl$_3$) δ: 8.68 (2H, m), 8.52 (1H, s), 7.65 (1H, d), 7.40 (1H, dd), 6.22 (1H, dd), 5.98 (1H, d), 4.41 (2H, dd).

Reference Preparation Example 15-1

The compound prepared according to a similar method to that described in the Reference preparation example 15 and its physical properties are shown as follows.

A compound represented by formula (A-15):

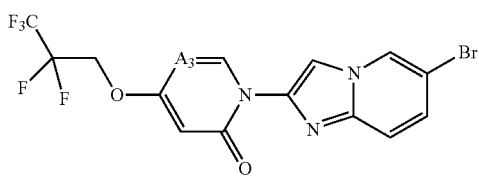

(A-15)

wherein $A^3$ represents any of the substituent indicated in [Table A15].

TABLE 15

| Intermediate compound | $A^3$ |
|---|---|
| 31 | CH |
| 40 | N |

The intermediate compound 31: $^1$H-NMR (CDCl$_3$) δ: 8.66 (1H, d), 8.54 (1H, s), 8.29 (1H, d), 7.45 (1H, d), 7.31 (1H, dd), 6.20 (1H, dd), 5.97 (1H, d), 4.41 (2H, t).
The intermediate compound 40: LC-MS: 439,441(+)

Reference Preparation Example 15-2

A mixture of 6-bromo-2-trifluoromethylimidazo[1,2-a]pyridine 2120 mg, 4-(2,2,3,3,3-pentafluoropropoxy)pyrimidin-6(1H)-one 3730 mg, pyridine-2-carboxylic acid 394 mg, copper(I) iodide 609 mg, cesium carbonate 5210 mg, and NMP 20 mL was stirred at 120° C. for 8 hours. To the resulting mixture was added water, and the mixture was extracted with chloroform. The resulting organic layer was dried over anhydrous sodium sulfate and concentrated under reduced pressure. The resulting residue was subjected to a silica gel column chromatography to give the intermediate compound 32 represented by the following formula 100 mg.

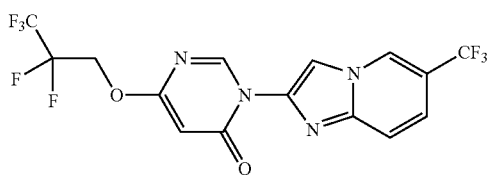 [SMILES: O=c1cc(OCC(F)(F)C(F)(F)F)ncn1-c1cn2cc(C(F)(F)F)ccc2n1]

The intermediate compound 32: $^1$H-NMR (CDCl$_3$) δ: 9.37 (1H, d), 8.65 (1H, d), 8.55 (1H, s), 7.70 (1H, d), 7.45 (1H, d), 6.00 (1H, d), 4.89 (2H, t).

Reference Preparation Example 16

To a mixture of the intermediate compound 28 (110 mg) and acetonitrile 10 mL was N-iodosuccinimide 64 mg under ice-cooling, and the mixture was stirred at room temperature for 5 hours. To the resulting mixture was added sodium thiosulfate solution, and the mixture was extracted with chloroform. The resulting organic layer was dried over anhydrous sodium sulfate and concentrated under reduced pressure to give the intermediate compound 29 represented by the following formula 130 mg.

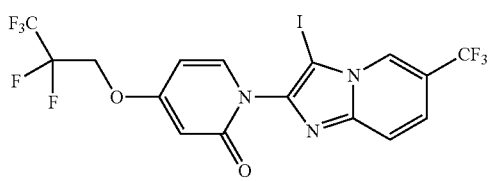

The intermediate compound 29: $^1$H-NMR (CDCl$_3$) δ: 8.54 (1H, s), 7.73 (1H, d), 7.52-7.47 (1H, m), 7.40 (1H, d), 6.15 (1H, dd), 5.97 (1H, d), 4.42 (2H, dd).

Reference Preparation Example 16-1

The compounds prepared according to a similar method to that described in the Reference preparation example 16 and their physical properties are shown as follows.

A compound represented by formula (A-16):

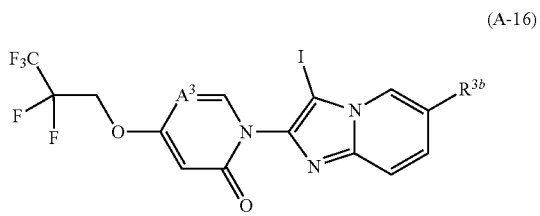

(A-16)

wherein a combination of A$^3$ and R$^{3b}$ represents any of the combinations indicated in [Table A16].

TABLE A16

| Intermediate compound | A$^3$ | R$^{3b}$ |
|---|---|---|
| 33 | CH | Br |
| 34 | N | CF$_3$ |
| 31 | N | Br |

The intermediate compound 33: $^1$H-NMR (CDCl$_3$) δ: 8.32 (1H, d), 7.51 (1H, d), 7.42-7.39 (2H, m), 6.13 (1H, dd), 5.96 (1H, d), 4.41 (2H, t).

The intermediate compound 34: $^1$H-NMR (CDCl$_3$) δ: 8.55 (1H, d), 8.19 (1H, d), 7.77 (1H, d), 7.53 (1H, dd), 5.98 (1H, d), 4.87 (2H, t).

The intermediate compound 41: $^1$H-NMR (CDCl$_3$) δ: 8.34 (1H, t), 8.17 (1H, s), 7.54 (1H, d), 7.45 (1H, dd), 5.97 (1H, s), 4.86 (2H, t).

Preparation Example 11

A mixture of the intermediate compound 29 (130 mg), 1,4-dioxane 2 mL, tris(dibenzylideneacetone)dipalladium (0) 22 mg, Xantphos 29 mg, diisopropylethylamine 0.040 mL, and ethanethiol 0.12 mL was stirred while heating under reflux for 270 minutes. To the resulting mixture was added water, and the mixture was extracted with chloroform. The resulting organic layer was dried over anhydrous sodium sulfate and concentrated under reduced pressure to give a crude product of the present compound 61 represented by the following formula 140 mg.

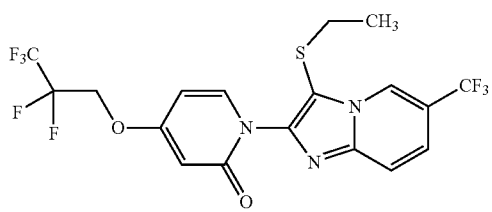 [SMILES: CCSc1c(-n2ccc(OCC(F)(F)C(F)(F)F)cc2=O)nc2ccc(C(F)(F)F)cn12]

The present compound 61: LC-MS: 488 (+)

Preparation Example 11-1

The compounds prepared according to a similar method to that described in the Preparation example 11 and their physical properties are shown as follows.

A compound represented by formula (A-11):

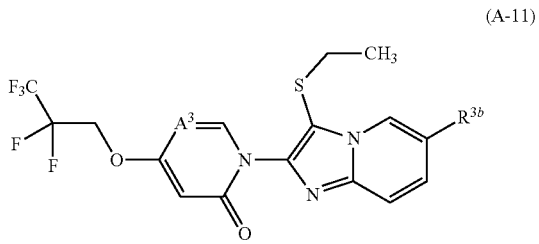

(A-11)

wherein a combination of $A^3$ and $R^{3b}$ represents any of the combinations indicated in [Table A11].

TABLE A11

| Present compound | $A^3$ | $R^{3b}$ |
|---|---|---|
| 94 | CH | Br |
| 95 | N | $CF_3$ |
| 108 | N | Br |

The present compound 94: $^1$H-NMR (CDCl$_3$) δ: 8.60 (1H, d), 7.57-7.31 (3H, m), 6.14-6.09 (1H, m), 5.96 (1H, d), 4.41 (2H, t), 2.77 (2H, q), 1.19 (3H, t).

The present compound 95: $^1$H-NMR (CDCl$_3$) δ: 8.85 (1H, s), 8.10 (1H, s), 7.80 (1H, d), 7.56 (1H, dd), 5.98 (1H, s), 4.87 (2H, t), 2.81 (2H, q), 1.21 (3H, t).

The present compound 108: $^1$H-NMR (CDCl$_3$) δ: 8.62 (1H, d), 8.09 (1H, d), 7.58 (1H, d), 7.48 (1H, dd), 5.97 (1H, s), 4.86 (3H, t), 2.78 (2H, q), 1.20 (3H, t).

Preparation Example 12

To a mixture of the crude product of the present compound 61 obtained in the Preparation example 11 (140 mg) and chloroform 3 mL was added mCPBA (purity 70%, containing 30% water) 260 mg under ice-cooling, and the mixture was stirred at room temperature for 4 hours. To the resulting mixture were sequentially added saturated sodium hydrogen carbonate solution and sodium thiosulfate solution, and the mixture was extracted with chloroform. The resulting organic layer was dried over anhydrous sodium sulfate and concentrated under reduced pressure. The obtained residue was subjected to a silica gel column chromatography to give the present compound 62 represented by the following formula 76 mg.

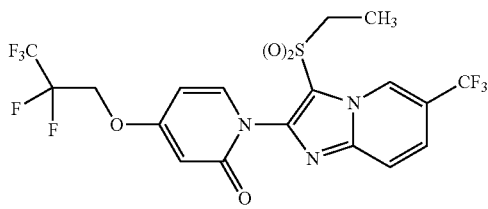

The present compound 62: $^1$H-NMR (CDCl$_3$) δ: 9.25 (1H, s), 7.88 (1H, d), 7.69 (1H, dd), 7.42 (1H, d), 6.17 (1H, dd), 5.91 (1H, d), 4.41 (2H, dd), 3.66 (2H, q), 1.46 (3H, t).

Preparation Example 12-1

The compounds prepared according to a similar method to that described in the Preparation example 12 and their physical properties are shown as follows.

A compound represented by formula (A-12):

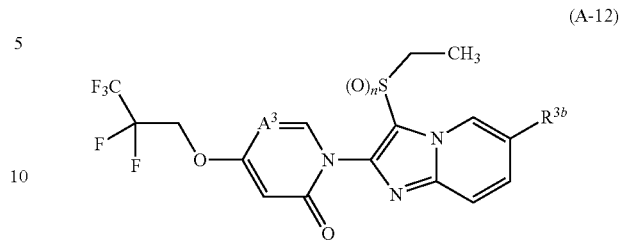

(A-12)

wherein a combination of $A^3$, $R^{3b}$, and n represents any of the combinations indicated in [Table A12].

TABLE A12

| Present compound | $A^3$ | $R^{3b}$ | n |
|---|---|---|---|
| 96 | CH | Br | 2 |
| 109 | CH | I | 2 |
| 97 | N | $CF_3$ | 2 |
| 110 | N | Br | 1 |
| 111 | N | Br | 2 |

The present compound 96: $^1$H-NMR (CDCl$_3$) δ: 9.03 (1H, d), 7.66-7.62 (2H, m), 7.40 (1H, d), 6.15 (1H, dd), 5.90 (1H, d), 4.41 (2H, t), 3.61 (2H, q), 1.45 (3H, t).

The present compound 109: LC-MS: 578 [M+H]$^+$ RT=1.92 min

The present compound 97: $^1$H-NMR (CDCl$_3$) δ: 9.26 (1H, s), 8.18 (1H, s), 7.93 (1H, d), 7.74 (1H, dd), 5.94 (1H, s), 4.87 (2H, m), 3.59 (2H, q), 1.44 (3H, t).

The present compound 110: LC-MS: 515 [M+H]$^+$ RT=2.00 min

The present compound 111: LC-MS: 531 [M+H]+

Reference Preparation Example 17

A mixture of the crude product of the present compound 28 (100 mg), 2N sodium hydroxide solution 1 mL, and DMF 1 mL is stirred at 60° C. for one hour. To the resulting mixture is added water, and the mixture is extracted with ethyl acetate. The resulting organic layer is dried over anhydrous sodium sulfate and concentrated under reduced pressure. The resulting residue is subjected to a silica gel column chromatography to give the intermediate compound 30 represented by the following formula.

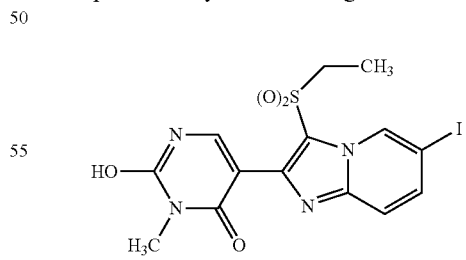

Intermediate Compound 30

Preparation Example 13

A mixture of the intermediate compound 30 obtained in the Reference preparation example 17 (100 mg), 2,2,3,3- tetrafluoropropyl triflate 282 mg, cesium carbonate 360 mg, and DMF 1 mL is stirred at 60° C. for one hour. To the resulting mixture is added water, and the mixture is extracted with ethyl acetate. The resulting organic layer is dried over anhydrous sodium sulfate and concentrated under reduced pressure. The resulting residue is subjected to a silica gel column chromatography to give the present compound 78.

Reference Preparation Example 18

The compound prepared according to a similar method to that described in the Reference preparation example 16 using the intermediate compound 27 instead of the intermediate compound 28, and its physical properties are shown as follows.

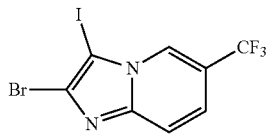

The intermediate compound 35: $^1$H-NMR (CDCl$_3$) δ: 8.42-8.41 (1H, m), 7.66 (1H, d), 7.41 (1H, dd).

Reference Preparation Example 19

The compound prepared according to a similar method to that described in the Preparation example 11 using the intermediate compound 35 instead of the intermediate compound 29, and its physical properties are shown as follows.

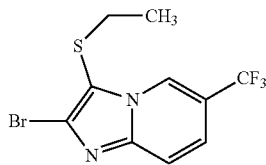

The intermediate compound 36: $^1$H-NMR (CDCl$_3$) δ: 8.75 (1H, d), 7.69 (1H, d), 7.44 (1H, dd), 2.79 (2H, q), 1.23 (3H, t).

Reference Preparation Example 20

The compound prepared according to a similar method to that described in the Preparation example 12 using the intermediate compound 36 instead of the present compound 61, and its physical properties are shown as follows.

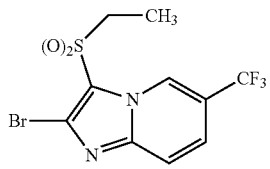

The intermediate compound 37: $^1$H-NMR (CDCl$_3$) δ: 9.42 (1H, s), 7.82 (1H, d), 7.65 (1H, dd), 3.41 (2H, q), 1.37 (3H, t).

Reference Preparation Example 21

A mixture of the intermediate compound 37 (1.79 g), di-tert-butyl 1,2-hydrazinecarboxylate 1.16 g, tripotassium phosphate 3.18 g, copper(I) iodide 0.19 g, pyridine-2-carboxylic acid 0.12 g, and NMP 20 mL was stirred at 100° C. for 12 hours. To the resulting mixture was added water, and the mixture was extracted with chloroform. The resulting organic layer was dried over anhydrous magnesium sulfate and concentrated under reduced pressure. To a mixture of the resulting residue and THF 10 mL was added trifluoroacetic acid 10 mL under ice-cooling, and the mixture was stirred at room temperature for 6 hours. To the resulting mixture was added water, and the mixture was extracted with chloroform. The resulting organic layer was dried over anhydrous magnesium sulfate and concentrated under reduced pressure. The resulting residue was subjected to a silica gel column chromatography to give the intermediate compound 38 represented by the following formula 0.45 g.

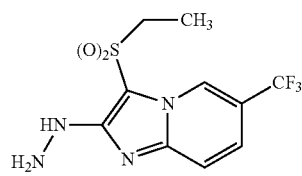

The intermediate compound 38: $^1$H-NMR (CDCl$_3$) δ: 9.23 (1H, s), 8.37 (1H, s), 8.12 (1H, d), 7.76 (1H, d), 5.92 (2H, br s), 3.32 (2H, q), 1.39 (3H, t).

Reference Preparation Example 22

A mixture of the intermediate compound 38 (93 mg), mucochloric acid 51 mg, and 10% hydrochloric acid 0.9 mL was stirred at 100° C. for 8 hours. To the resulting mixture is added water, and the mixture was extracted with chloroform. The resulting organic layer was dried over anhydrous magnesium sulfate and concentrated under reduced pressure. The resulting residue was subjected to a silica gel column chromatography to give the intermediate compound 39 represented by the following formula 30 mg.

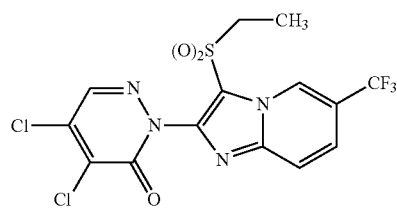

The intermediate compound 39: $^1$H-NMR (CDCl$_3$) δ: 9.23 (1H, s), 7.98 (1H, s), 7.94 (1H, d), 7.72 (1H, d), 3.56 (2H, q), 1.45 (3H, t).

Preparation Example 14

To a mixture of the intermediate compound 39 (30 mg), 2,2,3,3,3-pentafluoro-1-propanol 30 mg, and DMF 2 mL was added cesium carbonate 195 mg, and the mixture was stirred at room temperature for one hour. To the resulting mixture was added water, and the mixture was extracted with ethyl acetate. The resulting organic layer was dried over anhydrous magnesium sulfate and concentrated under reduced pressure. The resulting residue was subjected to a silica gel column chromatography to give the present compound 98 represented by the following formula 20 mg.

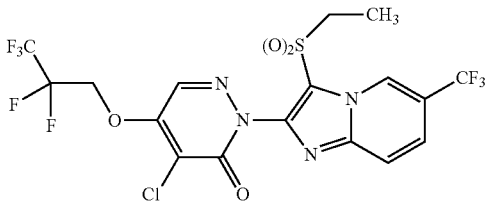

The present compound 98: $^1$H-NMR (CDCl$_3$) δ: 10.24 (1H, s), 9.47 (1H, s), 7.76 (1H, d), 7.68 (1H, d), 5.38 (2H, t), 3.47 (2H, q), 1.36 (3H, t).

Next, examples of the present compounds X prepared according to any of the preparation examples described in Examples and the preparation methods as described herein are recited as follows.

A compound represented by formula (L-1):

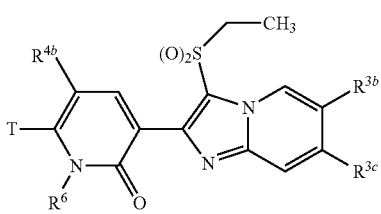

(L-1)

(hereinafter, referred to as "compound (L-1)"),
wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX1").

TABLE 1A

CF$_3$
CHF$_2$
CH$_2$CF$_3$
CH$_2$CF$_3$
CH$_2$CF$_2$CF$_3$
CF$_2$CF$_2$CF$_3$
CF$_2$CF$_2$CF$_2$CF$_3$
CF$_2$CF$_2$CF$_2$CF$_2$CF$_3$
OCF$_3$
OCHF$_2$
OCH$_2$CF$_3$
OCH$_2$CHF$_2$
OCF$_2$CF$_3$
OCH(CH$_3$)CF$_3$
OCH$_2$CF$_2$CHF$_2$
OCH$_2$CF$_2$CF$_3$
OCF$_2$CF$_2$CF$_3$
OCH$_2$CF$_2$CHFCF$_3$
OCH$_2$CF$_2$CF$_2$CF$_3$
OCF$_2$CF$_2$CF$_2$CF$_3$
OCH$_2$CF$_2$CF$_2$CF$_2$CF$_3$
OCH$_2$CMe$_2$CN
OCH$_2$-1-CN-c-Pr
OH

TABLE 2A

SCF$_3$
SCH$_2$CF$_3$
SCF$_2$CF$_3$

TABLE 2A-continued

SCH$_2$CF$_2$CF$_3$
SCF$_2$CF$_2$CF$_3$
SCH$_2$CF$_2$CF$_2$CF$_3$
SCF$_2$CF$_2$CF$_2$CF$_3$
S(O)CF$_3$
S(O)CH$_2$CF$_3$
S(O)CF$_2$CF$_3$
S(O)CH$_2$CF$_2$CF$_3$
S(O)CF$_2$CF$_2$CF$_3$
S(O)CH$_2$CF$_2$CF$_2$CF$_3$
S(O)CF$_2$CF$_2$CF$_2$CF$_3$
S(O)$_2$CF$_3$
S(O)$_2$CH$_2$CF$_3$
S(O)$_2$CF$_2$CF$_3$
S(O)$_2$CH$_2$CF$_2$CF$_3$
S(O)$_2$CF$_2$CF$_2$CF$_3$
S(O)$_2$CH$_2$CF$_2$CF$_2$CF$_3$
S(O)$_2$CH$_2$CF$_2$CF$_2$CF$_3$
SCH$_2$CMe$_2$CN
SCH$_2$-1-CN-c-Pr
Cl

TABLE 3A

NHCH$_2$CF$_3$
NHCH$_2$CF$_2$CF$_3$
NHCH$_2$CF$_2$CF$_2$CF$_3$
NMeCH$_2$CF$_3$
NMeCH$_2$CF$_2$CF$_3$
NMeCH$_2$CF$_2$CF$_2$CF$_3$
NEtCH$_2$CF$_3$
NEtCH$_2$CF$_2$CF$_3$
NEtCH$_2$CF$_2$CF$_2$CF$_3$
OS(O)$_2$CF$_3$
OS(O)$_2$CF$_2$CF$_3$
OS(O)$_2$CF$_2$CF$_2$CF$_3$
CH$_2$OCF$_3$
CH$_2$OCH$_2$CF$_3$
CH$_2$OCF$_2$CF$_3$
C(O)CF$_3$
C(O)CF$_2$CF$_3$
C(O)CF$_2$CF$_2$CF$_3$
C(O)NMeCH$_2$CF$_3$
NMeC(O)CF$_3$
N=CEtCH$_2$CF$_3$
CH$_2$CH$_2$CMe$_2$CN
CH$_2$CH$_2$-1-CN-c-Pr

TABLE 4A

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph

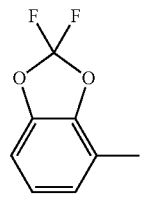

TABLE 4A-continued

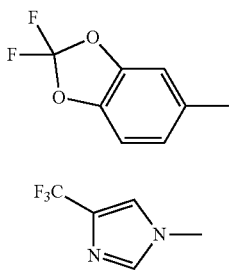

TABLE 5A

4-CF$_3$—Py2
5-CF$_3$—Py2
4-SCF$_3$—Py2
4-S(O)CF$_3$—Py2
4-S(O)$_2$CF$_3$—Py2
5-SCF$_3$—Py2
5-S(O)CF$_3$—Py2
5-S(O)$_2$CF$_3$—Py2
5-NMeCH$_2$CF$_3$—Py2

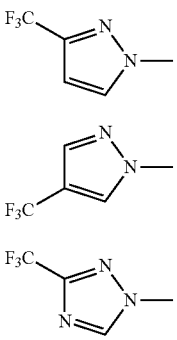

TABLE 6A

5-CF$_3$—Py3
6-CF$_3$—Py3
5-SCF$_3$—Py3
5-S(O)CF$_3$—Py3
5-S(O)$_2$CF$_3$—Py3
6-SCF$_3$—Py3
6-S(O)CF$_3$—Py3
6-S(O)$_2$CF$_3$—Py3
6-NMeCH$_2$CF$_3$—Py3

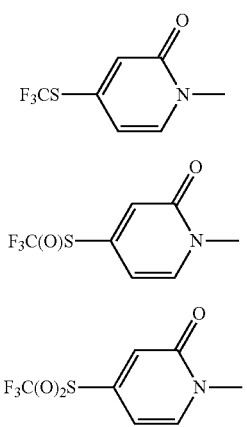

The compound (L-1), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX2").

The compound (L-1), wherein $R^{3b}$, $R^{3a}$, and $R^{4b}$ represent a hydrogen atom, $R^6$ represents a propyl group, T represents a substituent indicated in any of [Table 1A] to [Table 6A] (hereinafter, referred to as "compound group SX3").

The compound (L-1), wherein $R^{3b}$, $R^{3c}$, and $R^{4d}$ represent a hydrogen atom, $R^6$ represents an isopropyl group, T represents a substituent indicated in any of [Table 1A] to [Table 6A] (hereinafter, referred to as "compound group SX4").

The compound (L-1), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX5").

The compound (L-1), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX6").

The compound (L-1), wherein $R^{2b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX7").

The compound (L-1), wherein $R^{2b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX8").

The compound (L-1), wherein $R^{2b}$ represents a trifluoromethyl group, $R^{3c}$ and $R^{4b}$ represents a hydrogen atom, $R^6$ represents an isopropyl group, T represents a substituent indicated in any of [Table 1A] to [Table 6A](hereinafter, referred to as "compound group SX9").

The compound (L-1), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX10").

The compound (L-1), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX11").

The compound (L-1), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX12").

The compound (L-1), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX13").

The compound (L-1), $R^{3b}$ and $R^{4b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX14").

The compound (L-1), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX15").

The compound (L-1), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX16").

The compound (L-1), $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX17").

The compound (L-1), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX18").

The compound (L-1), wherein $R^{2b}$ represents a chlorine atom, $R^{3c}$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2291").

The compound (L-1), wherein $R^{3b}$ represents a chlorine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2292").

The compound (L-1), wherein $R^{3b}$ represents a chlorine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2293").

The compound (L-1), wherein $R^{3b}$ represents a chlorine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2294").

The compound (L-1), wherein $R^{3b}$ represents a chlorine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2295").

The compound (L-1), wherein $R^{2b}$ represents a chlorine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2296").

The compound (L-1), wherein $R^{3b}$ represents a chlorine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2297").

The compound (L-1), wherein $R^{3b}$ represents a bromine atom, $R^{3c}$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2298").

The compound (L-1), wherein $R^{3b}$ represents a bromine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2299").

The compound (L-1), wherein $R^{3b}$ represents a bromine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2300").

The compound (L-1), wherein $R^{3b}$ represents a bromine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2301").

The compound (L-1), wherein $R^{3b}$ represents a bromine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2302").

The compound (L-1), wherein $R^{3b}$ represents a bromine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2303").

The compound (L-1), wherein $R^{3b}$ represents a bromine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2304").

The compound (L-1), wherein $R^{3b}$ represents an iodine atom, $R^{3c}$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2305").

The compound (L-1), wherein $R^3$ represents an iodine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2306").

The compound (L-1), wherein $R^{3b}$ represents an iodine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2307").

The compound (L-1), wherein $R^{3b}$ represents an iodine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2308").

The compound (L-1), wherein $R^{3b}$ represents an iodine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2309").

The compound (L-1), wherein $R^{3b}$ represents an iodine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2310").

The compound (L-1), wherein $R^{3b}$ represents an iodine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2311").

A compound represented by formula (L-2):

(L-2)

(hereinafter, referred to as "compound (L-2)"), wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX19").

The compound (L-2), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX20").

The compound (L-2), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX21").

The compound (L-2), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX22").

The compound (L-2), wherein $R^{4b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX23").

The compound (L-2), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX24").

The compound (L-2), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX25").

The compound (L-2), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX26").

The compound (L-2), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX27").

The compound (L-2), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX28").

The compound (L-2), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX29").

The compound (L-2), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX30").

The compound (L-2), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX31").

The compound (L-2), wherein $R^{3b}$ and $R^{4b}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX32").

The compound (L-2), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX33").

The compound (L-2), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX34").

The compound (L-2), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX35").

The compound (L-2), wherein $R^{2b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX36").

A compound represented by formula (L-3):

(L-3)

(hereinafter, referred to as "compound (L-3)"), wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX37").

The compound (L-3), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX38").

The compound (L-3), wherein $R^{3b}$, $R^{3c}$ and $R^{4b}$ represent a hydrogen atom, $R^6$ represents a propyl group, T represents a substituent indicated in any of [Table 1A] to [Table 6A] (hereinafter, referred to as "compound group SX39").

The compound (L-3), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX40").

The compound (L-3), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX41").

The compound (L-3), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX42").

The compound (L-3), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX43").

The compound (L-3), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX44").

The compound (L-3), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX45").

The compound (L-3), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX46").

The compound (L-3), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX47").

The compound (L-3), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX48").

The compound (L-3), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX49").

The compound (L-3), wherein $R^{3b}$ and $R^{4b}$ represent a hydrogen atom, $R^{3c}$ represents a trifluoromethyl group, R represents an isopropyl group, T represents a substituent indicated in any of [Table 1A] to [Table 6A] (hereinafter, referred to as "compound group SX50").

The compound (L-3), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX51").

The compound (L-3), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX52").

The compound (L-3), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX53").

The compound (L-3), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX54").

A compound represented by formula (L-4):

(hereinafter, referred to as "compound (L-4)"), wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX 55").

The compound (L-4), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX56").

The compound (L-4), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX57").

The compound (L-4), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX58").

The compound (L-4), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX59").

The compound (L-4), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX60").

The compound (L-4), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX61").

The compound (L-4), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX62").

The compound (L-4), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX63").

The compound (L-4), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX64").

The compound (L-4), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX65").

The compound (L-4), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX66").

The compound (L-4), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX67").

The compound (L-4), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX68").

The compound (L-4), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX69").

The compound (L-4), wherein $R^{3b}$ represents a chlorine atom, $R^{3c}$ represents a hydrogen atom, $R^6$ represents a hydrogen atom, T represents a substituent indicated in any of [Table 1A] to [Table 6A] (hereinafter, referred to as "compound group SX2270").

The compound (L-4), wherein $R^{3b}$ represents a chlorine atom, $R^{3c}$ represents a hydrogen atom, $R^6$ represents a methyl group, T represents a substituent indicated in any of [Table 1A] to [Table 6A] (hereinafter, referred to as "compound group SX2271").

The compound (L-4), wherein $R^{3b}$ represents a chlorine atom, $R^{3c}$ represents a hydroxy group, $R^6$ represents a methyl group, T represents a substituent indicated in any of [Table 1A] to [Table 6A] (hereinafter, referred to as "compound group SX2272").

The compound (L-4), wherein $R^{3b}$ represents a chlorine atom, $R^{3c}$ represents a hydrogen atom, $R^6$ represents an ethyl group, T represents a substituent indicated in any of [Table 1A] to [Table 6A] (hereinafter, referred to as "compound group SX2273").

The compound (L-4), wherein $R^{3b}$ represents a chlorine atom, $R^{3c}$ represents a hydrogen atom, $R^6$ represents a propyl group, T represents a substituent indicated in any of [Table 1A] to [Table 6A] (hereinafter, referred to as "compound group SX2274").

The compound (L-4), wherein $R^{3b}$ represents a chlorine atom, $R^{3c}$ represents a hydrogen atom, $R^6$ represents an isopropyl group, T represents a substituent indicated in any of [Table 1A] to [Table 6A] (hereinafter, referred to as "compound group SX2275").

The compound (L-4), wherein $R^{3b}$ represents a chlorine atom, $R^{3c}$ represents a hydrogen atom, $R^6$ represents a cyclopropyl group, T represents a substituent indicated in any of [Table 1A] to [Table 6A] (hereinafter, referred to as "compound group SX2276").

The compound (L-4), wherein $R^{3b}$ represents a bromine atom, $R^{3c}$ represents a hydrogen atom, $R^6$ represents a hydrogen atom, T represents a substituent indicated in any of [Table 1A] to [Table 6A] (hereinafter, referred to as "compound group SX2277").

The compound (L-4), wherein $R^{3b}$ represents a bromine atom, $R^{3c}$ represents a hydrogen atom, $R^6$ represents a methyl group, T represents a substituent indicated in any of [Table 1A] to [Table 6A] (hereinafter, referred to as "compound group SX2278").

The compound (L-4), wherein $R^{3b}$ represents a bromine atom, $R^{3c}$ represents a hydroxy group, $R^6$ represents a methyl group, T represents a substituent indicated in any of [Table 1A] to [Table 6A] (hereinafter, referred to as "compound group SX2279").

The compound (L-4), wherein $R^{3b}$ represents a bromine atom, $R^{3c}$ represents a hydrogen atom, $R^6$ represents an ethyl group, T represents a substituent indicated in any of [Table 1A] to [Table 6A] (hereinafter, referred to as "compound group SX2280").

The compound (L-4), wherein $R^{3b}$ represents a bromine atom, $R^{3c}$ represents a hydrogen atom, $R^6$ represents a propyl group, T represents a substituent indicated in any of [Table 1A] to [Table 6A] (hereinafter, referred to as "compound group SX2281").

The compound (L-4), wherein $R^{3b}$ represents a bromine atom, $R^{3c}$ represents a hydrogen atom, $R^6$ represents an isopropyl group, T represents a substituent indicated in any of [Table 1A] to [Table 6A] (hereinafter, referred to as "compound group SX2282").

The compound (L-4), wherein $R^{3b}$ represents a bromine atom, $R^{3c}$ represents a hydrogen atom, $R^6$ represents a cyclopropyl group, T represents a substituent indicated in any of [Table 1A] to [Table 6A] (hereinafter, referred to as "compound group SX2283").

The compound (L-4), wherein $R^{3b}$ represents an iodine atom, $R^{3c}$ represents a hydrogen atom, $R^6$ represents a hydrogen atom, T represents a substituent indicated in any of [Table 1A] to [Table 6A] (hereinafter, referred to as "compound group SX2284").

The compound (L-4), wherein $R^{3b}$ represents an iodine atom, $R^{3c}$ represents a hydrogen atom, $R^6$ represents a methyl group, T represents a substituent indicated in any of [Table 1A] to [Table 6A] (hereinafter, referred to as "compound group SX2285").

The compound (L-4), wherein $R^{3b}$ represents an iodine atom, $R^{3c}$ represents a hydroxy group, $R^6$ represents a methyl group, T represents a substituent indicated in any of [Table 1A] to [Table 6A] (hereinafter, referred to as "compound group SX2286").

The compound (L-4), wherein $R^{3b}$ represents an iodine atom, $R^{3c}$ represents a hydrogen atom, $R^6$ represents an ethyl group, T represents a substituent indicated in any of [Table 1A] to [Table 6A] (hereinafter, referred to as "compound group SX2287").

The compound (L-4), wherein $R^{3b}$ represents an iodine atom, $R^{3c}$ represents a hydrogen atom, $R^6$ represents a propyl group, T represents a substituent indicated in any of [Table 1A] to [Table 6A] (hereinafter, referred to as "compound group SX2288").

The compound (L-4), wherein $R^{3b}$ represents an iodine atom, $R^{3c}$ represents a hydrogen atom, $R^6$ represents an isopropyl group, T represents a substituent indicated in any of [Table 1A] to [Table 6A] (hereinafter, referred to as "compound group SX2289").

The compound (L-4), wherein $R^{3b}$ represents an iodine atom, $R^{3c}$ represents a hydrogen atom, $R^6$ represents a cyclopropyl group, T represents a substituent indicated in any of [Table 1A] to [Table 6A] (hereinafter, referred to as "compound group SX2290").

A compound represented by formula (L-5):

(L-5)

(hereinafter, referred to as "compound (L-5)"), wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX70").

The compound (L-5), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX71").

The compound (L-5), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX72").

The compound (L-5), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX73").

The compound (L-5), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX74").

The compound (L-5), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX75").

The compound (L-5), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX76").

The compound (L-5), wherein $R^{3b}$ represents a trifluoromethyl group, $R^{3c}$ represents a hydrogen atom, R represents a propyl group, T represents a substituent indicated in any of [Table 1A] to [Table 6A] (hereinafter, referred to as "compound group SX77").

The compound (L-5), wherein $R^{3b}$ represents a trifluoromethyl group, $R^{3a}$ represents a hydrogen atom, $R^6$ represents an isopropyl group, T represents a substituent indicated in any of [Table 1A] to [Table 6A] (hereinafter, referred to as "compound group SX78").

The compound (L-5), wherein $R^{3b}$ represents a trifluoromethyl group, $R^{3a}$ represents a hydrogen atom, $R^6$ represents a cyclopropyl group, T represents a substituent indicated in any of [Table 1A] to [Table 6A] (hereinafter, referred to as "compound group SX79").

The compound (L-5), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX80").

The compound (L-5), wherein $R^{3b}$ represents a hydrogen atom, $R^{3c}$ represents a trifluoromethyl group, RE represents an ethyl group, T represents a substituent indicated in any of [Table 1A] to [Table 6A] (hereinafter, referred to as "compound group SX81").

The compound (L-5), wherein $R^{3b}$ represents a hydrogen atom, $R^{3c}$ represents a trifluoromethyl group, RE represents a propyl group, T represents a substituent indicated in any of [Table 1A] to [Table 6A] (hereinafter, referred to as "compound group SX82").

The compound (L-5), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX83").

The compound (L-5), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX84").

A compound represented by formula (L-6):

$$ (L-6) $$

(hereinafter, referred to as "compound (L-6)"), wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX85").

The compound (L-6), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX86").

The compound (L-6), wherein $R^{3b}$ and $R^{3c}$ represents a hydrogen atom, $R^6$ represents a propyl group, T represents a substituent indicated in any of [Table 1A] to [Table 6A] (hereinafter, referred to as "compound group SX87").

The compound (L-6), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX88").

The compound (L-6), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX89").

The compound (L-6), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX90").

The compound (L-6), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX91").

The compound (L-6), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX92").

The compound (L-6), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX93").

The compound (L-6), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX94").

The compound (L-6), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX95").

The compound (L-6), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX96").

The compound (L-6), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX97").

The compound (L-6), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX98").

The compound (L-6), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX99").

A compound represented by formula (L-7):

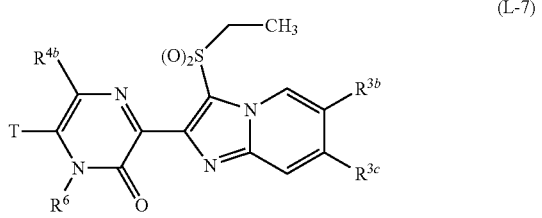

(hereinafter, referred to as "compound (L-7)"), wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX100").

The compound (L-7), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX101").

The compound (L-7), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX102").

The compound (L-7), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX103").

The compound (L-7), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX104").

The compound (L-7), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX105").

The compound (L-7), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX106").

The compound (L-7), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX107").

The compound (L-7), wherein $R^{3b}$ represents a trifluoromethyl group, $R^{3c}$ and $R^{4b}$ represents a hydrogen atom, $R^6$ represents an isopropyl group, T represents a substituent indicated in any of [Table 1A] to [Table 6A](hereinafter, referred to as "compound group SX108").

The compound (L-7), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX109").

The compound (L-7), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX110").

The compound (L-7), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX111").

The compound (L-7), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX112").

The compound (L-7), wherein $R^{3b}$ and $R^{4b}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX113").

The compound (L-7), wherein $R^{3b}$ and $R^{4b}$ represent a hydrogen atom, $R^{3c}$ represents a trifluoromethyl group, $R^5$ represents a cyclopropyl group, T represents a substituent indicated in any of [Table 1A] to [Table 6A] (hereinafter, referred to as "compound group SX114").

The compound (L-7), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX115").

The compound (L-7), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX116").

The compound (L-7), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX117").

A compound represented by formula (L-8):

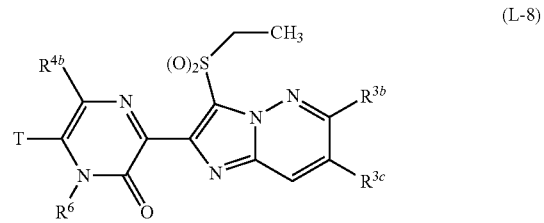

(hereinafter, referred to as "compound (L-8)"), wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX118").

The compound (L-8), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX119").

The compound (L-8), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX120").

The compound (L-8), wherein $R^{3b}$, $R^{3c}$, and $R^{41}$ represent a hydrogen atom, $R^6$ represents an isopropyl group, T represents a substituent indicated in any of [Table 1A] to [Table 6A] (hereinafter, referred to as "compound group SX121").

The compound (L-8), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX122").

The compound (L-8), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX123").

The compound (L-8), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX124").

The compound (L-8), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX125").

The compound (L-8), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX126").

The compound (L-8), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX127").

The compound (L-8), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX128").

The compound (L-8), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX129").

The compound (L-8), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX130").

The compound (L-8), wherein $R^{3b}$ and $R^{4b}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX131").

The compound (L-8), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX132").

The compound (L-8), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX133").

The compound (L-8), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX134").

The compound (L-8), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX135").

A compound represented by formula (L-9):

(L-9)

[Chemical structure: pyrimidinone ring fused/linked with imidazopyrimidine bearing $R^{3b}$, $R^{3c}$, $R^{4b}$, $R^6$, T, and $-S(O)_2-CH_3$ substituents]

(hereinafter, referred to as "compound (L-9)"), wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX136").

The compound (L-9), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX137").

The compound (L-9), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX138").

The compound (L-9), wherein $R^{3b}$, $R^{3c}$, and $R^{41}$ represent a hydrogen atom, $R^6$ represents an isopropyl group, T represents a substituent indicated in any of [Table 1A] to [Table 6A] (hereinafter, referred to as "compound group SX139").

The compound (L-9), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX140").

The compound (L-9), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX141").

The compound (L-9), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX142").

The compound (L-9), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX143").

The compound (L-9), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX144").

The compound (L-9), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX145").

The compound (L-9), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX146").

The compound (L-9), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX147").

The compound (L-9), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX148").

The compound (L-9), wherein $R^{3b}$ and $R^{4b}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX149").

The compound (L-9), wherein $R^{3b}$ and $R^{4b}$ represent a hydrogen atom, $R^{3c}$ represents a trifluoromethyl group, $R^5$ represents a cyclopropyl group, T represents a substituent indicated in any of [Table 1A] to [Table 6A] (hereinafter, referred to as "compound group SX150").

The compound (L-9), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX151").

The compound (L-9), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX152").

The compound (L-9), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX153").

A compound represented by formula (L-10):

(L-10)

(hereinafter, referred to as "compound (L-10)"), wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX154").

The compound (L-10), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX155").

The compound (L-10), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX156").

The compound (L-10), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX157").

The compound (L-10), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX158").

The compound (L-10), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX159").

The compound (L-10), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX160").

The compound (L-10), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX161").

The compound (L-10), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX162").

The compound (L-10), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX163").

The compound (L-10), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX164").

The compound (L-10), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX165").

The compound (L-10), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX166").

The compound (L-10), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX167").

The compound (L-10), wherein $R^{3b}$ and $R^{4c}$ represent a hydrogen atom, $R^{3c}$ represents a trifluoromethyl group, $R^5$ represents a cyclopropyl group, T represents a substituent indicated in any of [Table 1A] to [Table 6A] (hereinafter, referred to as "compound group SX168").

The compound (L-10), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX169").

The compound (L-10), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX170").

The compound (L-10), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX171").

A compound represented by formula (L-11):

(L-11)

(hereinafter, referred to as "compound (L-11)"), wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX172").

The compound (L-11), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX173").

The compound (L-11), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX174").

The compound (L-11), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX175").

The compound (L-11), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX176").

The compound (L-11), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A] (hereinafter, referred to as "compound group SX177").

The compound (L-11), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A] (hereinafter, referred to as "compound group SX178").

The compound (L-11), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A] (hereinafter, referred to as "compound group SX179").

The compound (L-11), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A] (hereinafter, referred to as "compound group SX180").

The compound (L-11), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A] (hereinafter, referred to as "compound group SX181").

The compound (L-11), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX182").

The compound (L-11), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX183").

The compound (L-11), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX184").

The compound (L-11), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX185").

The compound (L-11), wherein $R^{3b}$ and $R^{4c}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX186").

The compound (L-11), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX187").

The compound (L-11), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX188").

The compound (L-11), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX189").

A compound represented by formula (L-12):

<chemical structure> (L-12)

(hereinafter, referred to as "compound (L-12)"), wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX190").

The compound (L-12), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX191").

The compound (L-12), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX192").

The compound (L-12), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX193").

The compound (L-12), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX194").

The compound (L-12), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX195").

The compound (L-12), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX196").

The compound (L-12), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX197").

The compound (L-12), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX198").

The compound (L-12), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX199").

The compound (L-12), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX200").

The compound (L-12), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX201").

The compound (L-12), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX202").

The compound (L-12), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX203").

The compound (L-12), wherein $R^{3b}$ and $R^{4c}$ represent a hydrogen atom, $R^{3c}$ represents a trifluoromethyl group, $R^5$ represents a cyclopropyl group, T represents a substituent indicated in any of [Table 1A] to [Table 6A] (hereinafter, referred to as "compound group SX204").

The compound (L-12), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX205").

The compound (L-12), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX206").

The compound (L-12), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX207").

A compound represented by formula (L-13):

<chemical structure> (L-13)

(hereinafter, referred to as "compound (L-13)"), wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX208").

The compound (L-13), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX209").

The compound (L-13), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX210").

The compound (L-13), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX211").

The compound (L-13), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX212").

The compound (L-13), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX213").

The compound (L-13), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX214").

The compound (L-13), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX215").

The compound (L-13), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX216").

The compound (L-13), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX217").

The compound (L-13), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX218").

The compound (L-13), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX219").

The compound (L-13), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX220").

The compound (L-13), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX221").

The compound (L-13), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX222").

A compound represented by formula (L-14):

(L-14)

(hereinafter, referred to as "compound (L-14)"),
wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX223").

The compound (L-14), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX224").

The compound (L-14), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX225").

The compound (L-14), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX226").

The compound (L-14), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX227").

The compound (L-14), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX228").

The compound (L-14), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX229").

The compound (L-14), wherein $R^{3b}$ represents a trifluoromethyl group, $R^{3c}$ represents a hydrogen atom, $R^5$ represents a propyl group, T represents a substituent indicated in any of [Table 1A] to [Table 6A] (hereinafter, referred to as "compound group SX230").

The compound (L-14), wherein $R^{3b}$ represents a trifluoromethyl group, $R^{3c}$ represents a hydrogen atom, $R^5$ represents an isopropyl group, T represents a substituent indicated in any of [Table 1A] to [Table 6A] (hereinafter, referred to as "compound group SX231").

The compound (L-14), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX232").

The compound (L-14), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX233").

The compound (L-14), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX234").

The compound (L-14), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX235").

The compound (L-14), wherein $R^{3b}$ represents a hydrogen atom, $R^{3c}$ represents a trifluoromethyl group, RE represents an isopropyl group, T represents a substituent indicated in any of [Table 1A] to [Table 6A] (hereinafter, referred to as "compound group SX236").

The compound (L-14), wherein $R^{3b}$ represents a hydrogen atom, $R^{3c}$ represents a trifluoromethyl group, $R^b$ represents a cyclopropyl group, T represents a substituent indicated in any of [Table 1A] to [Table 6A] (hereinafter, referred to as "compound group SX237").

A compound represented by formula (L-15):

(L-15)

(hereinafter, referred to as "compound (L-15)"), wherein $R^{3b}$ and $R^{3c}$ represent a hydrogen atom, Re represents a methyl group, T represents a substituent indicated in any of [Table 1A] to [Table 6A] (hereinafter, referred to as "compound group SX238").

The compound (L-15), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX239").

The compound (L-15), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX240").

The compound (L-15), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX241").

The compound (L-15), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX242").

The compound (L-15), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX243").

The compound (L-15), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX244").

The compound (L-15), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX245").

The compound (L-15), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX246").

The compound (L-15), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX247").

The compound (L-15), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX248").

The compound (L-15), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX249").

The compound (L-15), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX250").

The compound (L-15), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX251").

The compound (L-15), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX252").

A compound represented by formula (L-16):

(L-16)

(hereinafter, referred to as "compound (L-16)"), wherein $R^{3b}$, $R^{3c}$ and $R^{4c}$ represent a hydrogen atom, $R^6$ represents a methyl group, T represents a substituent indicated in any of [Table 1A] to [Table 6A] (hereinafter, referred to as "compound group SX253").

The compound (L-16), wherein $R^{3b}$, $R^{3c}$ and $R^{4c}$ represent a hydrogen atom, $R^6$ represents an ethyl group, T represents a substituent indicated in any of [Table 1A] to [Table 6A] (hereinafter, referred to as "compound group SX254").

The compound (L-16), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX255").

The compound (L-16), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX256").

The compound (L-16), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX257").

The compound (L-16), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX258").

The compound (L-16), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX259").

The compound (L-16), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX260").

The compound (L-16), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX261").

The compound (L-16), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX262").

The compound (L-16), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX263").

The compound (L-16), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX264").

The compound (L-16), wherein $R^{3b}$ and $R^{4c}$ represent a hydrogen atom, $R^{3'}$ represents a trifluoromethyl group, $R^6$ represents a propyl group, T represents a substituent indicated in any of [Table 1A] to [Table 6A] (hereinafter, referred to as "compound group SX265").

The compound (L-16), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX266").

The compound (L-16), wherein $R^{3b}$ and $R^{4c}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX267").

The compound (L-16), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX268").

The compound (L-16), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX269").

The compound (L-16), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX270").

A compound represented by formula (L-17):

(L-17)

(hereinafter, referred to as "compound (L-17)"),
wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX271").

The compound (L-17), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX272").

The compound (L-17), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX273").

The compound (L-17), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX274").

The compound (L-17), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX275").

The compound (L-17), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX276").

The compound (L-17), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX277").

The compound (L-17), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX278").

The compound (L-17), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX279").

The compound (L-17), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX280").

The compound (L-17), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX281").

The compound (L-17), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX282").

The compound (L-17), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX283").

The compound (L-17), wherein $R^{3b}$ and $R^{4c}$ represent a hydrogen atom, $R^{3c}$ represents a trifluoromethyl group, R represents an isopropyl group, T represents a substituent indicated in any of [Table 1A] to [Table 6A] (hereinafter, referred to as "compound group SX284").

The compound (L-17), wherein $R^{3b}$ and $R^{4c}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX285").

The compound (L-17), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX286").

The compound (L-17), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX287").

The compound (L-17), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX288").

A compound represented by formula (L-18):

(L-18)

(hereinafter, referred to as "compound (L-18)"), wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX289").

The compound (L-18), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX290").

The compound (L-18), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX291").

The compound (L-18), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX292").

The compound (L-18), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX293").

The compound (L-18), wherein $R^{3b}$ represent a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX294").

The compound (L-18), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX295").

The compound (L-18), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX296").

The compound (L-18), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX297").

The compound (L-18), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX298").

The compound (L-18), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX299").

The compound (L-18), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX300").

The compound (L-18), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX301").

The compound (L-18), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX302").

The compound (L-18), wherein $R^{3b}$ and $R^{4c}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX303").

The compound (L-18), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX304").

The compound (L-18), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX305").

The compound (L-18), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX306").

A compound represented by formula (L-19):

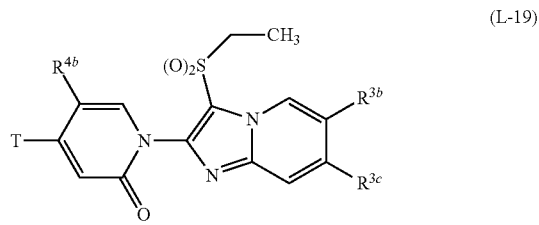

(L-19)

(hereinafter, referred to as "compound (L-19)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX307").

The compound (L-19), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX308").

The compound (L-19), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX2").

The compound (L-19), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX309").

The compound (L-19), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX310").

The compound (L-19), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX311").

A compound represented by formula (L-20):

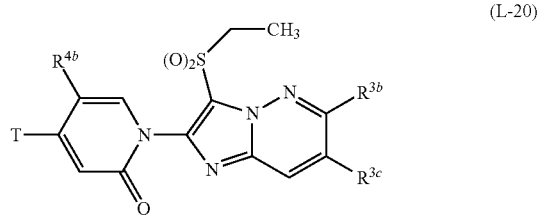

(L-20)

(hereinafter, referred to as "compound (L-20)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX312").

The compound (L-20), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX313").

The compound (L-20), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX314").

The compound (L-20), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX315").

The compound (L-20), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX316").

The compound (L-20), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX317").

A compound represented by formula (L-21):

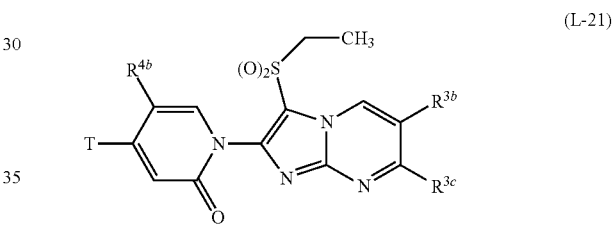

(L-21)

(hereinafter, referred to as "compound (L-21)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX318").

The compound (L-21), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX319").

The compound (L-21), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX320").

The compound (L-21), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX321").

The compound (L-21), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX322").

The compound (L-21), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX323").

A compound represented by formula (L-22):

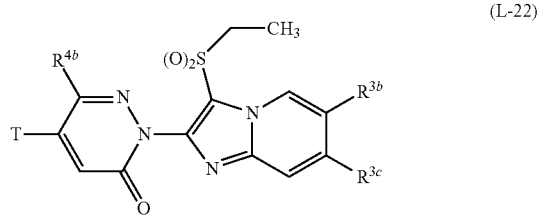

(L-22)

(hereinafter, referred to as "compound (L-22)"),
wherein $R^{3b}$, $R^{3c}$, and $R^{4b}$ represent a hydrogen atom, T represents a substituent indicated in any of [Table 1A] to [Table 6A] (hereinafter, referred to as "compound group SX324").

The compound (L-22), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX325").

The compound (L-22), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX326").

The compound (L-22), wherein $R^{3b}$ and $R^{3c}$ represent a hydrogen atom, $R^{4b}$ represents a chlorine atom, T represents a substituent indicated in any of [Table 1A] to [Table 6A] (hereinafter, referred to as "compound group SX327").

The compound (L-22), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX328").

The compound (L-22), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX329").

A compound represented by formula (L-23):

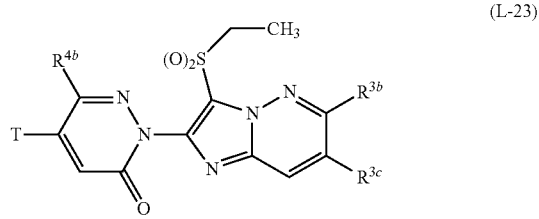

(L-23)

(hereinafter, referred to as "compound (L-23)"),
wherein $R^{3b}$, $R^{3c}$, and $R^{4b}$ represent a hydrogen atom, T represents a substituent indicated in any of [Table 1A] to [Table 6A] (hereinafter, referred to as "compound group SX330").

The compound (L-23), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX331").

The compound (L-23), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX332").

The compound (L-23), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX333").

The compound (L-23), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX334").

The compound (L-23), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX335").

A compound represented by formula (L-24):

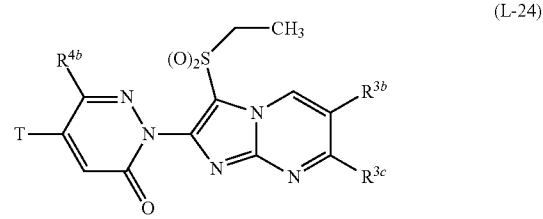

(L-24)

(hereinafter, referred to as "compound (L-24)"),
wherein $R^{4b}$, $R^{3c}$, and $R^{4b}$ represent a hydrogen atom, T represents a substituent indicated in any of [Table 1A] to [Table 6A] (hereinafter, referred to as "compound group SX336").

The compound (L-24), wherein $R^{4b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX337").

The compound (L-24), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX338").

The compound (L-24), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX339").

The compound (L-24), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX340").

The compound (L-24), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX341").

A compound represented by formula (L-25):

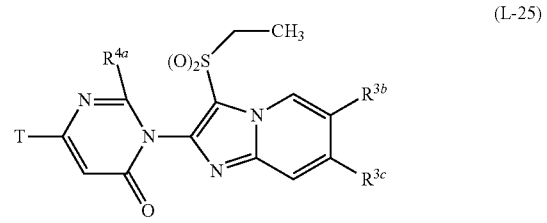

(L-25)

(hereinafter, referred to as "compound (L-25)"), wherein $R^{3b}$, $R^{3c}$, and $R^{4a}$ represent a hydrogen atom, T represents a substituent indicated in any of [Table 1A] to [Table 6A] (hereinafter, referred to as "compound group SX342").

The compound (L-25), wherein $R^{3b}$ represents a trifluoromethyl group, $R^{3c}$ and $R^{4a}$ represent a hydrogen atom, T represents a substituent indicated in any of [Table 1A] to [Table 6A] (hereinafter, referred to as "compound group SX343").

The compound (L-25), wherein $R^{3b}$ and $R^{4a}$ represent a hydrogen atom, $R^{3c}$ represents a trifluoromethyl group, T represents a substituent indicated in any of [Table 1A] to [Table 6A] (hereinafter, referred to as "compound group SX344").

The compound (L-25), wherein $R^{3b}$ and $R^{3c}$ represent a hydrogen atom, $R^{4a}$ represents a chlorine atom, T represents a substituent indicated in any of [Table 1A] to [Table 6A](hereinafter, referred to as "compound group SX345").

The compound (L-25), wherein $R^{3b}$ represents a trifluoromethyl group, $R^{3c}$ represents a hydrogen atom, $R^{4a}$ represents a chlorine atom, T represents a substituent indicated in any of [Table 1A] to [Table 6A] (hereinafter, referred to as "compound group SX346").

The compound (L-25), wherein $R^{3b}$ represents a hydrogen atom, $R^{3c}$ represents a trifluoromethyl group, $R^{4a}$ represents a chlorine atom, T represents a substituent indicated in any of [Table 1A] to [Table 6A] (hereinafter, referred to as "compound group SX347").

A compound represented by formula (L-26):

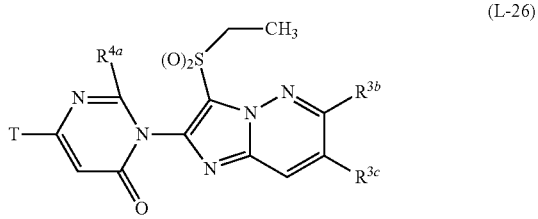

(L-26)

(hereinafter, referred to as "compound (L-26)"), wherein $R^{3b}$, $R^{3c}$, and $R^{4a}$ represent a hydrogen atom, T represents a substituent indicated in any of [Table 1A] to [Table 6A] (hereinafter, referred to as "compound group SX348").

The compound (L-26), wherein $R^{3b}$ represents a trifluoromethyl group, $R^{3c}$ and $R^{4a}$ represent a hydrogen atom, T represents a substituent indicated in any of [Table 1A] to [Table 6A] (hereinafter, referred to as "compound group SX349").

The compound (L-26), wherein $R^{3b}$ and $R^{4a}$ represent a hydrogen atom, $R^{3c}$ represents a trifluoromethyl group, T represents a substituent indicated in any of [Table 1A] to [Table 6A] (hereinafter, referred to as "compound group SX350").

The compound (L-26), wherein $R^{3b}$ and $R^{3c}$ represent a hydrogen atom, $R^{4a}$ represents a chlorine atom, T represents a substituent indicated in any of [Table 1A] to [Table 6A](hereinafter, referred to as "compound group SX351").

The compound (L-26), wherein $R^{3b}$ represents a trifluoromethyl group, $R^{3c}$ represents a hydrogen atom, $R^{4a}$ represents a chlorine atom, T represents a substituent indicated in any of [Table 1A] to [Table 6A] (hereinafter, referred to as "compound group SX352").

The compound (L-26), wherein $R^{3b}$ represents a hydrogen atom, $R^{3c}$ represents a trifluoromethyl group, $R^{4a}$ represents a chlorine atom, T represents a substituent indicated in any of [Table 1A] to [Table 6A] (hereinafter, referred to as "compound group SX353").

A compound represented by formula (L-27):

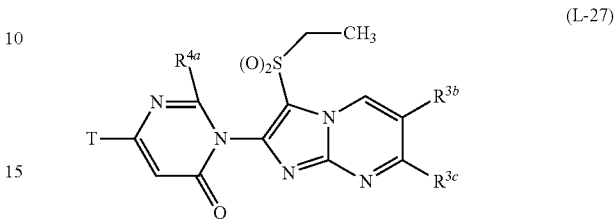

(L-27)

(hereinafter, referred to as "compound (L-27)"), wherein $R^{3b}$, $R^{3c}$, and $R^{4a}$ represent a hydrogen atom, T represents a substituent indicated in any of [Table 1A] to [Table 6A] (hereinafter, referred to as "compound group SX354").

The compound (L-27), wherein $R^{3b}$ represents a trifluoromethyl group, $R^{3c}$ and $R^{4a}$ represent a hydrogen atom, T represents a substituent indicated in any of [Table 1A] to [Table 6A] (hereinafter, referred to as "compound group SX355").

The compound (L-27), wherein $R^{3b}$ and $R^{4a}$ represent a hydrogen atom, $R^{3c}$ represents a trifluoromethyl group, T represents a substituent indicated in any of [Table 1A] to [Table 6A] (hereinafter, referred to as "compound group SX356").

The compound (L-27), wherein $R^{3b}$ and $R^{3c}$ represent a hydrogen atom, $R^{4a}$ represents a chlorine atom, T represents a substituent indicated in any of [Table 1A] to [Table 6A](hereinafter, referred to as "compound group SX357").

The compound (L-27), wherein $R^{3b}$ represents a trifluoromethyl group, $R^{3c}$ represents a hydrogen atom, $R^{4a}$ represents a chlorine atom, T represents a substituent indicated in any of [Table 1A] to [Table 6A] (hereinafter, referred to as "compound group SX358").

The compound (L-27), wherein $R^{3b}$ represents a hydrogen atom, $R^{3c}$ represents a trifluoromethyl group, $R^{4a}$ represents a chlorine atom, T represents a substituent indicated in any of [Table 1A] to [Table 6A] (hereinafter, referred to as "compound group SX359").

A compound represented by formula (L-28):

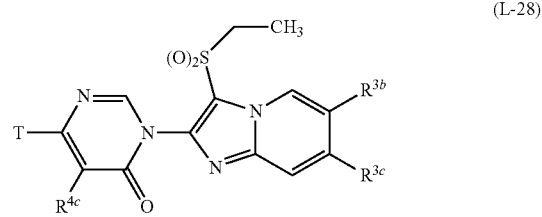

(L-28)

(hereinafter, referred to as "compound (L-28)"), wherein $R^{3b}$, $R^{3c}$, and $R^{4c}$ represent a hydrogen atom, T represents a substituent indicated in any of [Table 1A] to [Table 6A] (hereinafter, referred to as "compound group SX360").

The compound (L-28), wherein $R^{3b}$ represents a trifluoromethyl group, $R^{3c}$ and $R^{4c}$ represent a hydrogen atom, T represents a substituent indicated in any of [Table 1A] to [Table 6A] (hereinafter, referred to as "compound group SX361").

The compound (L-28), wherein $R^{3b}$ and $R^{4c}$ represent a hydrogen atom, $R^{3c}$ represents a trifluoromethyl group, T represents a substituent indicated in any of [Table 1A] to [Table 6A] (hereinafter, referred to as "compound group SX362").

The compound (L-28), wherein $R^{3b}$ and $R^{3c}$ represent a hydrogen atom, $R^{4c}$ represents a chlorine atom, T represents a substituent indicated in any of [Table 1A] to [Table 6A](hereinafter, referred to as "compound group SX363").

The compound (L-28), wherein $R^{3b}$ represents a trifluoromethyl group, $R^{3c}$ represents a hydrogen atom, $R^4$, represents a chlorine atom, T represents a substituent indicated in any of [Table 1A] to [Table 6A] (hereinafter, referred to as "compound group SX364").

The compound (L-28), wherein $R^{3b}$ represents a hydrogen atom, $R^{3c}$ represents a trifluoromethyl group, $R^{4c}$ represents a chlorine atom, T represents a substituent indicated in any of [Table 1A] to [Table 6A] (hereinafter, referred to as "compound group SX365").

A compound represented by formula (L-29):

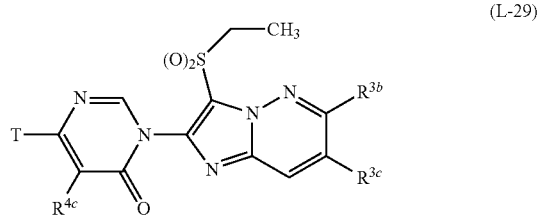

(hereinafter, referred to as "compound (L-29)"), wherein $R^{3b}$, $R^{3c}$, and $R^{4c}$ represent a hydrogen atom, T represents a substituent indicated in any of [Table 1A] to [Table 6A] (hereinafter, referred to as "compound group SX366").

The compound (L-29), wherein $R^{3b}$ represents a trifluoromethyl group, $R^{3c}$ and $R^{4c}$ represent a hydrogen atom, T represents a substituent indicated in any of [Table 1A] to [Table 6A] (hereinafter, referred to as "compound group SX367").

The compound (L-29), wherein $R^{3b}$ and $R^{4c}$ represent a hydrogen atom, $R^{3c}$ represents a trifluoromethyl group, T represents a substituent indicated in any of [Table 1A] to [Table 6A] (hereinafter, referred to as "compound group SX368").

The compound (L-29), wherein $R^{3b}$ and $R^{3c}$ represent a hydrogen atom, $R^{4c}$ represents a chlorine atom, T represents a substituent indicated in any of [Table 1A] to [Table 6A](hereinafter, referred to as "compound group SX369").

The compound (L-29), wherein $R^{3b}$ represents a trifluoromethyl group, $R^{3c}$ represents a hydrogen atom, $R^{4c}$ represents a chlorine atom, T represents a substituent indicated in any of [Table 1A] to [Table 6A] (hereinafter, referred to as "compound group SX370").

The compound (L-29), wherein $R^{3b}$ represents a hydrogen atom, $R^{3c}$ represents a trifluoromethyl group, $R^{4c}$ represents a chlorine atom, T represents a substituent indicated in any of [Table 1A] to [Table 6A] (hereinafter, referred to as "compound group SX371").

A compound represented by formula (L-30):

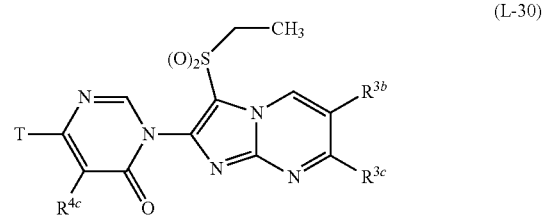

(hereinafter, referred to as "compound (L-30)"), wherein $R^{3b}$, $R^{3c}$, and $R^{4c}$ represent a hydrogen atom, T represents a substituent indicated in any of [Table 1A] to [Table 6A] (hereinafter, referred to as "compound group SX372").

The compound (L-30), wherein $R^{3b}$ represents a trifluoromethyl group, $R^{3c}$ and $R^{4c}$ represent a hydrogen atom, T represents a substituent indicated in any of [Table 1A] to [Table 6A] (hereinafter, referred to as "compound group SX373").

The compound (L-30), wherein $R^{3b}$ and $R^{4c}$ represent a hydrogen atom, $R^{3c}$ represents a trifluoromethyl group, T represents a substituent indicated in any of [Table 1A] to [Table 6A] (hereinafter, referred to as "compound group SX374").

The compound (L-30), wherein $R^{3b}$ and $R^{3c}$ represent a hydrogen atom, $R^{4c}$ represents a chlorine atom, T represents a substituent indicated in any of [Table 1A] to [Table 6A](hereinafter, referred to as "compound group SX375").

The compound (L-30), wherein $R^{3b}$ represents a trifluoromethyl group, $R^{3c}$ represents a hydrogen atom, $R^{4c}$ represents a chlorine atom, T represents a substituent indicated in any of [Table 1A] to [Table 6A] (hereinafter, referred to as "compound group SX376").

The compound (L-30), wherein $R^{3b}$ represents a hydrogen atom, $R^{3c}$ represents a trifluoromethyl group, $R^{4c}$ represents a chlorine atom, T represents a substituent indicated in any of [Table 1A] to [Table 6A] (hereinafter, referred to as "compound group SX377").

A compound represented by formula (L-31):

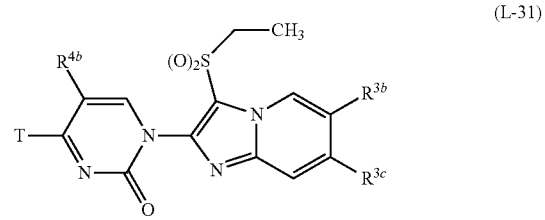

(hereinafter, referred to as "compound (L-31)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX378").

The compound (L-31), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX379").

The compound (L-31), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX380").

The compound (L-31), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX381").

The compound (L-31), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX382").

The compound (L-31), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX383").

A compound represented by formula (L-32):

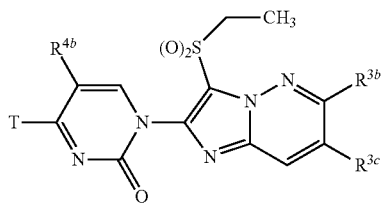

(hereinafter, referred to as "compound (L-32)"),
wherein $R^{4b}$, $R^{3c}$, and $R^{4b}$ represent a hydrogen atom, T represents a substituent indicated in any of [Table 1A] to [Table 6A] (hereinafter, referred to as "compound group SX384").

The compound (L-32), wherein $R^{4b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX385").

The compound (L-32), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX386").

The compound (L-32), wherein $R^{3b}$ and $R^{3c}$ represent a hydrogen atom, $R^4$ represents a chlorine atom, T represents a substituent indicated in any of [Table 1A] to [Table 6A](hereinafter, referred to as "compound group SX387").

The compound (L-32), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX388").

The compound (L-32), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX389").

A compound represented by formula (L-33):

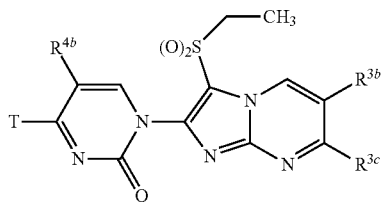

(hereinafter, referred to as "compound (L-33)"),
wherein $R^{3b}$, $R^{3c}$, and $R^{4b}$ represent a hydrogen atom, T represents a substituent indicated in any of [Table 1A] to [Table 6A] (hereinafter, referred to as "compound group SX390").

The compound (L-33), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX391").

The compound (L-33), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX392").

The compound (L-33), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX393").

The compound (L-33), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX394").

The compound (L-33), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX395").

A compound represented by formula (L-34):

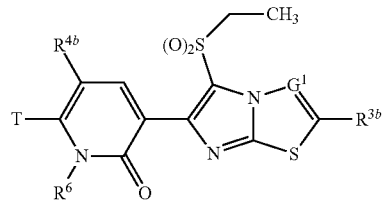

(hereinafter, referred to as "compound (L-34)"),
wherein $G^1$ represents CH, $R^{3b}$ and $R^{4b}$ represent a hydrogen atom, $R^6$ represents a methyl group, T represents a substituent indicated in any of [Table 1A] to [Table 6A] (hereinafter, referred to as "compound group SX396").

The compound (L-34), wherein $G^1$ represents CH, $R^{3b}$ and $R^{4b}$ represent a hydrogen atom, $R^6$ represents an ethyl group, T represents a substituent indicated in any of [Table 1A] to [Table 6A] (hereinafter, referred to as "compound group SX397").

The compound (L-34), wherein $G^1$ represents CH, $R^{3b}$ and $R^{4b}$ represent a hydrogen atom, $R^6$ represents a propyl group, T represents a substituent indicated in any of [Table 1A] to [Table 6A] (hereinafter, referred to as "compound group SX398").

The compound (L-34), wherein $G^1$ represents CH, $R^{3b}$ and $R^{4b}$ represent a hydrogen atom, $R^6$ represents an isopropyl group, T represents a substituent indicated in any of [Table 1A] to [Table 6A] (hereinafter, referred to as "compound group SX399").

The compound (L-34), wherein $G^1$ represents CH, $R^{3b}$ and $R^{4b}$ represent a hydrogen atom, $R^6$ represents a cyclopropyl group, T represents a substituent indicated in any of [Table 1A] to [Table 6A] (hereinafter, referred to as "compound group SX400").

The compound (L-34), wherein $G^1$ represents CH, $R^{3b}$ represents a bromine atom, $R^{4b}$ represents a hydrogen atom, $R^6$ represents a methyl group, T represents a substituent indicated in any of [Table 1A] to [Table 6A] (hereinafter, referred to as "compound group SX401").

The compound (L-34), wherein $G^1$ represents CH, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX402").

The compound (L-34), wherein $G^1$ represents CH, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX403").

The compound (L-34), wherein $G^1$ represents CH, $R^{3b}$ represents a bromine atom, $R^{4b}$ represents a hydrogen atom, $R^6$ represents a propyl group, T represents a substituent indicated in any of [Table 1A] to [Table 6A] (hereinafter, referred to as "compound group SX404").

The compound (L-34), wherein $G^1$ represents a nitrogen atom, $R^{3b}$ and $R^{4b}$ represent a hydrogen atom, $R^6$ represents a methyl group, T represents a substituent indicated in any of [Table 1A] to [Table 6A] (hereinafter, referred to as "compound group SX405").

The compound (L-34), wherein $G^1$ represents a nitrogen atom, $R^{3b}$ and $R^{4b}$ represent a hydrogen atom, $R^6$ represents an ethyl group, T represents a substituent indicated in any of [Table 1A] to [Table 6A] (hereinafter, referred to as "compound group SX406").

The compound (L-34), wherein $G^1$ represents a nitrogen atom, $R^{3b}$ and $R^{4b}$ represent a hydrogen atom, $R^6$ represents a propyl group, T represents a substituent indicated in any of [Table 1A] to [Table 6A] (hereinafter, referred to as "compound group SX407").

The compound (L-34), wherein $G^1$ represents a nitrogen atom, $R^{3b}$ and $R^{4b}$ represent a hydrogen atom, $R^6$ represents an isopropyl group, T represents a substituent indicated in any of [Table 1A] to [Table 6A] (hereinafter, referred to as "compound group SX408").

The compound (L-34), wherein $G^1$ represents a nitrogen atom, $R^{3b}$ and $R^{4b}$ represent a hydrogen atom, $R^6$ represents a cyclopropyl group, T represents a substituent indicated in any of [Table 1A] to [Table 6A] (hereinafter, referred to as "compound group SX409").

The compound (L-34), wherein $G^1$ represents a nitrogen atom, $R^{3b}$ represents a trifluoromethyl group, $R^{4b}$ represents a hydrogen atom, $R^6$ represents a methyl group, T represents a substituent indicated in any of [Table 1A] to [Table 6A] (hereinafter, referred to as "compound group SX410").

The compound (L-34), wherein $G^1$ represents a nitrogen atom, $R^{3b}$ represents a trifluoromethyl group, $R^{4b}$ represents a hydrogen atom, $R^6$ represents an ethyl group, T represents a substituent indicated in any of [Table 1A] to [Table 6A] (hereinafter, referred to as "compound group SX411").

The compound (L-34), wherein $G^1$ represents a nitrogen atom, $R^{3b}$ represents a trifluoromethyl group, $R^{4b}$ represents a hydrogen atom, $R^6$ represents an ethyl group, T represents a substituent indicated in any of [Table 1A] to [Table 6A] (hereinafter, referred to as "compound group SX412").

The compound (L-34), wherein $G^1$ represents a nitrogen atom, $R^{3b}$ represents a trifluoromethyl group, $R^{4b}$ represents a hydrogen atom, $R^6$ represents a propyl group, T represents a substituent indicated in any of [Table 1A] to [Table 6A] (hereinafter, referred to as "compound group SX413").

The compound (L-34), wherein $G^1$ represents a nitrogen atom, $R^{3b}$ represents a bromine atom, $R^{4b}$ represents a hydrogen atom, $R^6$ represents a methyl group, T represents a substituent indicated in any of [Table 1A] to [Table 6A](hereinafter, referred to as "compound group SX414").

The compound (L-34), wherein $G^1$ represents a nitrogen atom, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX415").

The compound (L-34), wherein $G^1$ represents a nitrogen atom, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX416").

The compound (L-34), wherein $G^1$ represents a nitrogen atom, $R^{3b}$ represents a bromine atom, $R^{4b}$ represents a hydrogen atom, $R^6$ represents a propyl group, T represents a substituent indicated in any of [Table 1A] to [Table 6A] (hereinafter, referred to as "compound group SX417").

The compound (L-34), wherein $G^1$ represents CH, $R^{3b}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX418").

The compound (L-34), wherein $G^1$ represents CH, $R^{3b}$ represents a bromine atom, $R^{4b}$ represents a chlorine atom, $R^6$ represents a methyl group, T represents a substituent indicated in any of [Table 1A] to [Table 6A] (hereinafter, referred to as "compound group SX419").

The compound (L-34), wherein $G^1$ represents a nitrogen atom, $R^{3b}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX420").

The compound (L-34), wherein $G^1$ represents a nitrogen atom, $R^{3b}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX421").

The compound (L-34), wherein $G^1$ represents a nitrogen atom, $R^{3b}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX422").

The compound (L-34), wherein $G^1$ represents a nitrogen atom, $R^{3b}$ represents a bromine atom, $R^{4b}$ represents a chlorine atom, $R^6$ represents a methyl group, T represents a substituent indicated in any of [Table 1A] to [Table 6A] (hereinafter, referred to as "compound group SX423").

A compound represented by formula (L-35):

(L-35)

(hereinafter, referred to as "compound (L-35)"),
wherein $G^1$ represents CH, $R^{3b}$ represents a hydrogen atom, $R^6$ represents a methyl group, T represents a substituent indicated in any of [Table 1A] to [Table 6A](hereinafter, referred to as "compound group SX424").

The compound (L-35), wherein $G^1$ represents CH, $R^{3b}$ represents a hydrogen atom, $R^6$ represents an ethyl group, T represents a substituent indicated in any of [Table 1A] to [Table 6A] (hereinafter, referred to as "compound group SX425").

The compound (L-35), wherein $G^1$ represents CH, $R^{3b}$ represents a hydrogen atom, $R^6$ represents a propyl group, T represents a substituent indicated in any of [Table 1A] to [Table 6A] (hereinafter, referred to as "compound group SX426").

The compound (L-35), wherein $G^1$ represents CH, $R^{3b}$ represents a hydrogen atom, $R^6$ represents an isopropyl group, T represents a substituent indicated in any of [Table 1A] to [Table 6A] (hereinafter, referred to as "compound group SX427").

The compound (L-35), wherein $G^1$ represents CH, $R^{3b}$ represents a hydrogen atom, $R^6$ represents a cyclopropyl group, T represents a substituent indicated in any of [Table 1A] to [Table 6A] (hereinafter, referred to as "compound group SX428").

The compound (L-35), wherein $G^1$ represents CH, $R^{3b}$ represents a bromine atom, $R^6$ represents a methyl group, T represents a substituent indicated in any of [Table 1A] to [Table 6A] (hereinafter, referred to as "compound group SX429").

The compound (L-35), wherein $G^1$ represents CH, $R^{3b}$ represents a bromine atom, $R^6$ represents an ethyl group, T represents a substituent indicated in any of [Table 1A] to [Table 6A] (hereinafter, referred to as "compound group SX430").

The compound (L-35), wherein $G^1$ represents CH, $R^{3b}$ represents a bromine atom, $R^6$ represents an ethyl group, T represents a substituent indicated in any of [Table 1A] to [Table 6A] (hereinafter, referred to as "compound group SX431").

The compound (L-35), wherein $G^1$ represents CH, $R^{3b}$ represents a bromine atom, $R^6$ represents a propyl group, T represents a substituent indicated in any of [Table 1A] to [Table 6A] (hereinafter, referred to as "compound group SX432").

The compound (L-35), wherein $G^1$ represents a nitrogen atom, $R^{3b}$ represents a hydrogen atom, $R^6$ represents a methyl group, T represents a substituent indicated in any of [Table 1A] to [Table 6A] (hereinafter, referred to as "compound group SX433").

The compound (L-35), wherein $G^1$ represents a nitrogen atom, $R^{3b}$ represents a hydrogen atom, $R^6$ represents an ethyl group, T represents a substituent indicated in any of [Table 1A] to [Table 6A] (hereinafter, referred to as "compound group SX434").

The compound (L-35), wherein $G^1$ represents a nitrogen atom, $R^{3b}$ represents a hydrogen atom, $R^6$ represents a propyl group, T represents a substituent indicated in any of [Table 1A] to [Table 6A] (hereinafter, referred to as "compound group SX435").

The compound (L-35), wherein $G^1$ represents a nitrogen atom, $R^{3b}$ represents a hydrogen atom, $R^6$ represents an isopropyl group, T represents a substituent indicated in any of [Table 1A] to [Table 6A] (hereinafter, referred to as "compound group SX436").

The compound (L-35), wherein $G^1$ represents a nitrogen atom, $R^{3b}$ represents a hydrogen atom, $R^6$ represents a cyclopropyl group, T represents a substituent indicated in any of [Table 1A] to [Table 6A] (hereinafter, referred to as "compound group SX437").

The compound (L-35), wherein $G^1$ represents a nitrogen atom, $R^{3b}$ represents a trifluoromethyl group, $R^6$ represents a methyl group, T represents a substituent indicated in any of [Table 1A] to [Table 6A] (hereinafter, referred to as "compound group SX438").

The compound (L-35), wherein $G^1$ represents a nitrogen atom, $R^2$ represents a trifluoromethyl group, $R^6$ represents an ethyl group, T represents a substituent indicated in any of [Table 1A] to [Table 6A] (hereinafter, referred to as "compound group SX439").

The compound (L-35), wherein $G^1$ represents a nitrogen atom, $R^{2b}$ represents a trifluoromethyl group, $R^6$ represents an ethyl group, T represents a substituent indicated in any of [Table 1A] to [Table 6A] (hereinafter, referred to as "compound group SX440").

The compound (L-35), wherein $G^1$ represents a nitrogen atom, $R^{2b}$ represents a trifluoromethyl group, $R^6$ represents a propyl group, T represents a substituent indicated in any of [Table 1A] to [Table 6A] (hereinafter, referred to as "compound group SX441").

The compound (L-35), wherein $G^1$ represents a nitrogen atom, $R^{3b}$ represents a bromine atom, $R^6$ represents a methyl group, T represents a substituent indicated in any of [Table 1A] to [Table 6A] (hereinafter, referred to as "compound group SX442").

The compound (L-35), wherein $G^1$ represents a nitrogen atom, $R^{3b}$ represents a bromine atom, $R^6$ represents an ethyl group, T represents a substituent indicated in any of [Table 1A] to [Table 6A] (hereinafter, referred to as "compound group SX443").

The compound (L-35), wherein $G^1$ represents a nitrogen atom, $R^2$ represents a bromine atom, $R^6$ represents an ethyl group, T represents a substituent indicated in any of [Table 1A] to [Table 6A] (hereinafter, referred to as "compound group SX444").

The compound (L-35), wherein $G^1$ represents a nitrogen atom, $R^{2b}$ represents a bromine atom, $R^6$ represents a propyl group, T represents a substituent indicated in any of [Table 1A] to [Table 6A] (hereinafter, referred to as "compound group SX445").

A compound represented by formula (L-36):

(L-36)

(hereinafter, referred to as "compound (L-36)"),
wherein $G^1$ represents CH, $R^{3b}$ and $R^{4b}$ represent a hydrogen atom, $R^6$ represents a methyl group, T represents a substituent indicated in any of [Table 1A] to [Table 6A] (hereinafter, referred to as "compound group SX446").

The compound (L-36), wherein $G^1$ represents CH, $R^{3b}$ and $R^{4b}$ represent a hydrogen atom, $R^6$ represents an ethyl group, T represents a substituent indicated in any of [Table 1A] to [Table 6A] (hereinafter, referred to as "compound group SX447").

The compound (L-36), wherein $G^1$ represents CH, $R^{3b}$ and $R^{4b}$ represent a hydrogen atom, $R^6$ represents a propyl group, T represents a substituent indicated in any of [Table 1A] to [Table 6A] (hereinafter, referred to as "compound group SX448").

The compound (L-36), wherein $G^1$ represents CH, $R^{3b}$ and $R^{4b}$ represent a hydrogen atom, $R^6$ represents an isopropyl group, T represents a substituent indicated in any of [Table 1A] to [Table 6A] (hereinafter, referred to as "compound group SX449").

The compound (L-36), wherein $G^1$ represents CH, $R^{3b}$ and $R^{4b}$ represent a hydrogen atom, $R^6$ represents a cyclopropyl group, T represents a substituent indicated in any of [Table 1A] to [Table 6A] (hereinafter, referred to as "compound group SX450").

The compound (L-36), wherein $G^1$ represents CH, $R^{3b}$ represents a bromine atom, $R^{4b}$ represents a hydrogen atom, $R^6$ represents a methyl group, T represents a substituent indicated in any of [Table 1A] to [Table 6A] (hereinafter, referred to as "compound group SX451").

The compound (L-36), wherein $G^1$ represents CH, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX452").

The compound (L-36), wherein $G^1$ represents CH, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX453").

The compound (L-36), wherein $G^1$ represents CH, $R^{3b}$ represents a bromine atom, $R^{4b}$ represents a hydrogen atom, $R^6$ represents a propyl group, T represents a substituent indicated in any of [Table 1A] to [Table 6A] (hereinafter, referred to as "compound group SX454").

The compound (L-36), wherein $G^1$ represents a nitrogen atom, $R^{3b}$ and $R^{4b}$ represent a hydrogen atom, $R^6$ represents a methyl group, T represents a substituent indicated in any of [Table 1A] to [Table 6A] (hereinafter, referred to as "compound group SX455").

The compound (L-36), wherein $G^1$ represents a nitrogen atom, $R^{3b}$ and $R^{4b}$ represent a hydrogen atom, $R^6$ represents an ethyl group, T represents a substituent indicated in any of [Table 1A] to [Table 6A] (hereinafter, referred to as "compound group SX456").

The compound (L-36), wherein $G^1$ represents a nitrogen atom, $R^{3b}$ and $R^{4b}$ represent a hydrogen atom, $R^6$ represents a propyl group, T represents a substituent indicated in any of [Table 1A] to [Table 6A] (hereinafter, referred to as "compound group SX457").

The compound (L-36), wherein $G^1$ represents a nitrogen atom, $R^{3b}$ and $R^{4b}$ represent a hydrogen atom, $R^6$ represents an isopropyl group, T represents a substituent indicated in any of [Table 1A] to [Table 6A] (hereinafter, referred to as "compound group SX458").

The compound (L-36), wherein $G^1$ represents a nitrogen atom, $R^{3b}$ and $R^{4b}$ represent a hydrogen atom, $R^6$ represents a cyclopropyl group, T represents a substituent indicated in any of [Table 1A] to [Table 6A] (hereinafter, referred to as "compound group SX459").

The compound (L-36), wherein $G^1$ represents a nitrogen atom, $R^{3b}$ represents a trifluoromethyl group, $R^{4b}$ represents a hydrogen atom, $R^6$ represents a methyl group, T represents a substituent indicated in any of [Table 1A] to [Table 6A] (hereinafter, referred to as "compound group SX460").

The compound (L-36), wherein $G^1$ represents a nitrogen atom, $R^{3b}$ represents a trifluoromethyl group, $R^{4b}$ represents a hydrogen atom, $R^6$ represents an ethyl group, T represents a substituent indicated in any of [Table 1A] to [Table 6A] (hereinafter, referred to as "compound group SX461").

The compound (L-36), wherein $G^1$ represents a nitrogen atom, $R^{3b}$ represents a trifluoromethyl group, $R^{4b}$ represents a hydrogen atom, $R^6$ represents an ethyl group, T represents a substituent indicated in any of [Table 1A] to [Table 6A] (hereinafter, referred to as "compound group SX462").

The compound (L-36), wherein $G^1$ represents a nitrogen atom, $R^{3b}$ represents a trifluoromethyl group, $R^{4b}$ represents a hydrogen atom, $R^6$ represents a propyl group, T represents a substituent indicated in any of [Table 1A] to [Table 6A] (hereinafter, referred to as "compound group SX463").

The compound (L-36), wherein $G^1$ represents a nitrogen atom, $R^{3b}$ represents a bromine atom, $R^{4b}$ represents a hydrogen atom, $R^6$ represents a methyl group, T represents a substituent indicated in any of [Table 1A] to [Table 6A](hereinafter, referred to as "compound group SX464").

The compound (L-36), wherein $G^1$ represents a nitrogen atom, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX465").

The compound (L-36), wherein $G^1$ represents a nitrogen atom, $R^{3b}$ represents a bromine atom, $R^{4b}$ represents a hydrogen atom, $R^6$ represents an ethyl group, T represents a substituent indicated in any of [Table 1A] to [Table 6A] (hereinafter, referred to as "compound group SX466").

The compound (L-36), wherein $G^1$ represents a nitrogen atom, $R^{3b}$ represents a bromine atom, $R^{4b}$ represents a hydrogen atom, $R^6$ represents a propyl group, T represents a substituent indicated in any of [Table 1A] to [Table 6A] (hereinafter, referred to as "compound group SX467").

The compound (L-36), wherein $G^1$ represents CH, $R^{3b}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX468").

The compound (L-36), wherein $G^1$ represents CH, $R^{3b}$ represents a bromine atom, $R^{4b}$ represents a chlorine atom, $R^6$ represents a methyl group, T represents a substituent indicated in any of [Table 1A] to [Table 6A] (hereinafter, referred to as "compound group SX469").

The compound (L-36), wherein $G^1$ represents a nitrogen atom, $R^{3b}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX470").

The compound (L-36), wherein $G^1$ represents a nitrogen atom, $R^{3b}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX471").

The compound (L-36), wherein $G^1$ represents a nitrogen atom, $R^{3b}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX472").

The compound (L-36), wherein $G^1$ represents a nitrogen atom, $R^{3b}$ represents a bromine atom, $R^{4b}$ represents a chlorine atom, $R^6$ represents a methyl group, T represents a substituent indicated in any of [Table 1A] to [Table 6A] (hereinafter, referred to as "compound group SX473").

A compound represented by formula (L-37):

(L-37)

[Chemical structure diagram showing formula L-37 with substituents $R^6$, T, $R^{4c}$, $(O)_2S$, $CH_3$, $G^1$, $R^{3b}$]

(hereinafter, referred to as "compound (L-37)"),
wherein $G^1$ represents CH, $R^{3b}$ and $R^{4c}$ represent a hydrogen atom, $R^6$ represents a methyl group, T represents a substituent indicated in any of [Table 1A] to [Table 6A] (hereinafter, referred to as "compound group SX474").

The compound (L-37), wherein $G^1$ represents CH, $R^{3b}$ and $R^{4c}$ represent a hydrogen atom, $R^6$ represents an ethyl group, T represents a substituent indicated in any of [Table 1A] to [Table 6A] (hereinafter, referred to as "compound group SX475").

The compound (L-37), wherein $G^1$ represents CH, $R^{3b}$ and $R^{4c}$ represent a hydrogen atom, $R^6$ represents a propyl group, T represents a substituent indicated in any of [Table 1A] to [Table 6A] (hereinafter, referred to as "compound group SX476").

The compound (L-37), wherein $G^1$ represents CH, $R^{3b}$ and $R^{4c}$ represent a hydrogen atom, $R^6$ represents an isopropyl group, T represents a substituent indicated in any of [Table 1A] to [Table 6A] (hereinafter, referred to as "compound group SX477").

The compound (L-37), wherein $G^1$ represents CH, $R^{3b}$ and $R^{4c}$ represent a hydrogen atom, $R^6$ represents a cyclopropyl group, T represents a substituent indicated in any of [Table 1A] to [Table 6A] (hereinafter, referred to as "compound group SX478").

The compound (L-37), wherein $G^1$ represents CH, $R^{3b}$ represents a bromine atom, $R^{4c}$ represents a hydrogen atom, $R^6$ represents a methyl group, T represents a substituent indicated in any of [Table 1A] to [Table 6A] (hereinafter, referred to as "compound group SX479").

The compound (L-37), wherein $G^1$ represents CH, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX480").

The compound (L-37), wherein $G^1$ represents CH, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX481").

The compound (L-37), wherein $G^1$ represents CH, $R^{3b}$ represents a bromine atom, $R^{4c}$ represents a hydrogen atom, $R^6$ represents a propyl group, T represents a substituent indicated in any of [Table 1A] to [Table 6A] (hereinafter, referred to as "compound group SX482").

The compound (L-37), wherein $G^1$ represents a nitrogen atom, $R^{3b}$ and $R^{4c}$ represent a hydrogen atom, $R^6$ represents a methyl group, T represents a substituent indicated in any of [Table 1A] to [Table 6A] (hereinafter, referred to as "compound group SX483").

The compound (L-37), wherein $G^1$ represents a nitrogen atom, $R^{3b}$ and $R^{4c}$ represent a hydrogen atom, $R^6$ represents an ethyl group, T represents a substituent indicated in any of [Table 1A] to [Table 6A] (hereinafter, referred to as "compound group SX484").

The compound (L-37), wherein $G^1$ represents a nitrogen atom, $R^{3b}$ and $R^{4c}$ represent a hydrogen atom, $R^6$ represents a propyl group, T represents a substituent indicated in any of [Table 1A] to [Table 6A] (hereinafter, referred to as "compound group SX485").

The compound (L-37), wherein $G^1$ represents a nitrogen atom, $R^{3b}$ and $R^{4c}$ represent a hydrogen atom, $R^6$ represents an isopropyl group, T represents a substituent indicated in any of [Table 1A] to [Table 6A] (hereinafter, referred to as "compound group SX486").

The compound (L-37), wherein $G^1$ represents a nitrogen atom, $R^{3b}$ and $R^{4c}$ represent a hydrogen atom, $R^6$ represents a cyclopropyl group, T represents a substituent indicated in any of [Table 1A] to [Table 6A] (hereinafter, referred to as "compound group SX487").

The compound (L-37), wherein $G^1$ represents a nitrogen atom, $R^{3b}$ represents a trifluoromethyl group, $R^{4c}$ represents a hydrogen atom, $R^6$ represents a methyl group, T represents a substituent indicated in any of [Table 1A] to [Table 6A] (hereinafter, referred to as "compound group SX488").

The compound (L-37), wherein $G^1$ represents a nitrogen atom, $R^{3b}$ represents a trifluoromethyl group, $R^{4c}$ represents a hydrogen atom, $R^6$ represents an ethyl group, T represents a substituent indicated in any of [Table 1A] to [Table 6A] (hereinafter, referred to as "compound group SX489").

The compound (L-37), wherein $G^1$ represents a nitrogen atom, $R^{3b}$ represents a trifluoromethyl group, $R^{4c}$ represents a hydrogen atom, $R^6$ represents an ethyl group, T represents a substituent indicated in any of [Table 1A] to [Table 6A] (hereinafter, referred to as "compound group SX490").

The compound (L-37), wherein $G^1$ represents a nitrogen atom, $R^{3b}$ represents a trifluoromethyl group, $R^{4c}$ represents a hydrogen atom, $R^6$ represents a propyl group, T represents a substituent indicated in any of [Table 1A] to [Table 6A] (hereinafter, referred to as "compound group SX491").

The compound (L-37), wherein $G^1$ represents a nitrogen atom, $R^{3b}$ represents a bromine atom, $R^{4c}$ represents a hydrogen atom, $R^6$ represents a methyl group, T represents a substituent indicated in any of [Table 1A] to [Table 6A](hereinafter, referred to as "compound group SX492").

The compound (L-37), wherein $G^1$ represents a nitrogen atom, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX493").

The compound (L-37), wherein $G^1$ represents a nitrogen atom, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX494").

The compound (L-37), wherein $G^1$ represents a nitrogen atom, $R^{3b}$ represents a bromine atom, $R^{4b}$ represents a hydrogen atom, $R^6$ represents a propyl group, T represents a substituent indicated in any of [Table 1A] to [Table 6A] (hereinafter, referred to as "compound group SX495").

The compound (L-37), wherein $G^1$ represents CH, $R^{3b}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX496").

The compound (L-37), wherein $G^1$ represents CH, $R^{3b}$ represents a bromine atom, $R^{4c}$ represents a chlorine atom, $R^6$ represents a methyl group, T represents a substituent indicated in any of [Table 1A] to [Table 6A] (hereinafter, referred to as "compound group SX497").

The compound (L-37), wherein $G^1$ represents a nitrogen atom, $R^{3b}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX498").

The compound (L-37), wherein $G^1$ represents a nitrogen atom, $R^{3b}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX499").

The compound (L-37), wherein $G^1$ represents a nitrogen atom, $R^{3b}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX500").

The compound (L-37), wherein $G^1$ represents a nitrogen atom, $R^{3b}$ represents a bromine atom, $R^{4b}$ represents a chlorine atom, $R^6$ represents a methyl group, T represents a substituent indicated in any of [Table 1A] to [Table 6A] (hereinafter, referred to as "compound group SX501").

A compound represented by formula (L-38):

(hereinafter, referred to as "compound (L-38)"), wherein $G^1$ represents CH, $R^{3b}$ represents a hydrogen atom, $R^6$ represents a methyl group, T represents a substituent indicated in any of [Table 1A] to [Table 6A](hereinafter, referred to as "compound group SX502").

The compound (L-38), wherein $G^1$ represents CH, $R^{3b}$ represents a hydrogen atom, $R^6$ represents an ethyl group, T represents a substituent indicated in any of [Table 1A] to [Table 6A] (hereinafter, referred to as "compound group SX503").

The compound (L-38), wherein $G^1$ represents CH, $R^{3b}$ represents a hydrogen atom, $R^6$ represents a propyl group, T represents a substituent indicated in any of [Table 1A] to [Table 6A] (hereinafter, referred to as "compound group SX504").

The compound (L-38), wherein $G^1$ represents CH, $R^{3b}$ represents a hydrogen atom, $R^6$ represents an isopropyl group, T represents a substituent indicated in any of [Table 1A] to [Table 6A] (hereinafter, referred to as "compound group SX505").

The compound (L-38), wherein $G^1$ represents CH, $R^{3b}$ represents a hydrogen atom, $R^6$ represents a cyclopropyl group, T represents a substituent indicated in any of [Table 1A] to [Table 6A] (hereinafter, referred to as "compound group SX506").

The compound (L-38), wherein $G^1$ represents CH, $R^{3b}$ represents a bromine atom, $R^6$ represents a methyl group, T represents a substituent indicated in any of [Table 1A] to [Table 6A] (hereinafter, referred to as "compound group SX507").

The compound (L-38), wherein $G^1$ represents CH, $R^{3b}$ represents a bromine atom, $R^6$ represents an ethyl group, T represents a substituent indicated in any of [Table 1A] to [Table 6A] (hereinafter, referred to as "compound group SX508").

The compound (L-38), wherein $G^1$ represents CH, $R^{3b}$ represents a bromine atom, $R^6$ represents an ethyl group, T represents a substituent indicated in any of [Table 1A] to [Table 6A] (hereinafter, referred to as "compound group SX509").

The compound (L-38), wherein $G^1$ represents CH, $R^{3b}$ represents a bromine atom, $R^6$ represents a propyl group, T represents a substituent indicated in any of [Table 1A] to [Table 6A] (hereinafter, referred to as "compound group SX510").

The compound (L-38), wherein $G^1$ represents a nitrogen atom, $R^{3b}$ represents a hydrogen atom, $R^6$ represents a methyl group, T represents a substituent indicated in any of [Table 1A] to [Table 6A] (hereinafter, referred to as "compound group SX511").

The compound (L-38), wherein $G^1$ represents a nitrogen atom, $R^{3b}$ represents a hydrogen atom, $R^6$ represents an ethyl group, T represents a substituent indicated in any of [Table 1A] to [Table 6A] (hereinafter, referred to as "compound group SX512").

The compound (L-38), wherein $G^1$ represents a nitrogen atom, $R^{3b}$ represents a hydrogen atom, $R^6$ represents a propyl group, T represents a substituent indicated in any of [Table 1A] to [Table 6A] (hereinafter, referred to as "compound group SX513").

The compound (L-38), wherein $G^1$ represents a nitrogen atom, $R^{3b}$ represents a hydrogen atom, $R^6$ represents an isopropyl group, T represents a substituent indicated in any of [Table 1A] to [Table 6A] (hereinafter, referred to as "compound group SX514").

The compound (L-38), wherein $G^1$ represents a nitrogen atom, $R^{3b}$ represents a hydrogen atom, $R^6$ represents a cyclopropyl group, T represents a substituent indicated in any of [Table 1A] to [Table 6A] (hereinafter, referred to as "compound group SX515").

The compound (L-38), wherein $G^1$ represents a nitrogen atom, $R^{3b}$ represents a trifluoromethyl group, $R^6$ represents a methyl group, T represents a substituent indicated in any of [Table 1A] to [Table 6A] (hereinafter, referred to as "compound group SX516").

The compound (L-38), wherein $G^1$ represents a nitrogen atom, $R^{3b}$ represents a trifluoromethyl group, $R^6$ represents an ethyl group, T represents a substituent indicated in any of [Table 1A] to [Table 6A] (hereinafter, referred to as "compound group SX517").

The compound (L-38), wherein $G^1$ represents a nitrogen atom, $R^{3b}$ represents a trifluoromethyl group, $R^6$ represents an ethyl group, T represents a substituent indicated in any of [Table 1A] to [Table 6A] (hereinafter, referred to as "compound group SX518").

The compound (L-38), wherein $G^1$ represents a nitrogen atom, $R^{3b}$ represents a trifluoromethyl group, $R^6$ represents a propyl group, T represents a substituent indicated in any of [Table 1A] to [Table 6A] (hereinafter, referred to as "compound group SX519").

The compound (L-38), wherein $G^1$ represents a nitrogen atom, $R^{3b}$ represents a bromine atom, $R^6$ represents a methyl group, T represents a substituent indicated in any of [Table 1A] to [Table 6A] (hereinafter, referred to as "compound group SX520").

The compound (L-38), wherein $G^1$ represents a nitrogen atom, $R^{3b}$ represents a bromine atom, $R^6$ represents an ethyl group, T represents a substituent indicated in any of [Table 1A] to [Table 6A] (hereinafter, referred to as "compound group SX521").

The compound (L-38), wherein $G^1$ represents a nitrogen atom, $R^{3b}$ represents a bromine atom, $R^6$ represents an ethyl group, T represents a substituent indicated in any of [Table 1A] to [Table 6A] (hereinafter, referred to as "compound group SX522").

The compound (L-38), wherein $G^1$ represents a nitrogen atom, $R^{3b}$ represents a bromine atom, $R^6$ represents a propyl group, T represents a substituent indicated in any of [Table 1A] to [Table 6A] (hereinafter, referred to as "compound group SX523").

A compound represented by formula (L-39):

(L-39)

$$\text{structure}$$

(hereinafter, referred to as "compound (L-39)"),
wherein $G^1$ represents CH, $R^{3b}$ and $R^{4c}$ represent a hydrogen atom, $R^6$ represents a methyl group, T represents a substituent indicated in any of [Table 1A] to [Table 6A] (hereinafter, referred to as "compound group SX524").

The compound (L-39), wherein $G^1$ represents CH, $R^{3b}$ and $R^{4c}$ represent a hydrogen atom, $R^6$ represents an ethyl group, T represents a substituent indicated in any of [Table 1A] to [Table 6A] (hereinafter, referred to as "compound group SX525").

The compound (L-39), wherein $G^1$ represents CH, $R^{3b}$ and $R^{4c}$ represent a hydrogen atom, $R^6$ represents a propyl group, T represents a substituent indicated in any of [Table 1A] to [Table 6A] (hereinafter, referred to as "compound group SX526").

The compound (L-39), wherein $G^1$ represents CH, $R^{3b}$ and $R^{4c}$ represent a hydrogen atom, $R^6$ represents an isopropyl group, T represents a substituent indicated in any of [Table 1A] to [Table 6A] (hereinafter, referred to as "compound group SX527").

The compound (L-39), wherein $G^1$ represents CH, $R^{3b}$ and $R^{4c}$ represent a hydrogen atom, $R^6$ represents a cyclopropyl group, T represents a substituent indicated in any of [Table 1A] to [Table 6A] (hereinafter, referred to as "compound group SX528").

The compound (L-39), wherein $G^1$ represents CH, $R^{3b}$ represents a bromine atom, $R^{4c}$ represents a hydrogen atom, $R^6$ represents a methyl group, T represents a substituent indicated in any of [Table 1A] to [Table 6A] (hereinafter, referred to as "compound group SX529").

The compound (L-39), wherein $G^1$ represents CH, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX530").

The compound (L-39), wherein $G^1$ represents CH, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX531").

The compound (L-39), wherein $G^1$ represents CH, $R^{3b}$ represents a bromine atom, $R^{4c}$ represents a hydrogen atom, $R^6$ represents a propyl group, T represents a substituent indicated in any of [Table 1A] to [Table 6A] (hereinafter, referred to as "compound group SX532").

The compound (L-39), wherein $G^1$ represents a nitrogen atom, $R^{3b}$ and $R^{4c}$ represent a hydrogen atom, $R^6$ represents a methyl group, T represents a substituent indicated in any of [Table 1A] to [Table 6A] (hereinafter, referred to as "compound group SX533").

The compound (L-39), wherein $G^1$ represents a nitrogen atom, $R^{3b}$ and $R^{4c}$ represent a hydrogen atom, $R^6$ represents an ethyl group, T represents a substituent indicated in any of [Table 1A] to [Table 6A] (hereinafter, referred to as "compound group SX534").

The compound (L-39), wherein $G^1$ represents a nitrogen atom, $R^{3b}$ and $R^{4c}$ represent a hydrogen atom, $R^6$ represents a propyl group, T represents a substituent indicated in any of [Table 1A] to [Table 6A] (hereinafter, referred to as "compound group SX535").

The compound (L-39), wherein $G^1$ represents a nitrogen atom, $R^{3b}$ and $R^{4c}$ represent a hydrogen atom, $R^6$ represents an isopropyl group, T represents a substituent indicated in any of [Table 1A] to [Table 6A] (hereinafter, referred to as "compound group SX536").

The compound (L-39), wherein $G^1$ represents a nitrogen atom, $R^{3b}$ and $R^{4c}$ represent a hydrogen atom, $R^6$ represents a cyclopropyl group, T represents a substituent indicated in any of [Table 1A] to [Table 6A] (hereinafter, referred to as "compound group SX537").

The compound (L-39), wherein $G^1$ represents a nitrogen atom, $R^{3b}$ represents a trifluoromethyl group, $R^{4c}$ represents a hydrogen atom, $R^6$ represents a methyl group, T represents a substituent indicated in any of [Table 1A] to [Table 6A] (hereinafter, referred to as "compound group SX538").

The compound (L-39), wherein $G^1$ represents a nitrogen atom, $R^{3b}$ represents a trifluoromethyl group, $R^{4c}$ represents a hydrogen atom, $R^6$ represents an ethyl group, T represents a substituent indicated in any of [Table 1A] to [Table 6A] (hereinafter, referred to as "compound group SX539").

The compound (L-39), wherein $G^1$ represents a nitrogen atom, $R^{3b}$ represents a trifluoromethyl group, $R^{4c}$ represents a hydrogen atom, $R^6$ represents an ethyl group, T represents a substituent indicated in any of [Table 1A] to [Table 6A] (hereinafter, referred to as "compound group SX540").

The compound (L-39), wherein $G^1$ represents a nitrogen atom, $R^{3b}$ represents a trifluoromethyl group, $R^{4c}$ represents a hydrogen atom, $R^6$ represents a propyl group, T represents a substituent indicated in any of [Table 1A] to [Table 6A] (hereinafter, referred to as "compound group SX541").

The compound (L-39), wherein $G^1$ represents a nitrogen atom, $R^{3b}$ represents a bromine atom, $R^{4c}$ represents a hydrogen atom, $R^6$ represents a methyl group, T represents a substituent indicated in any of [Table 1A] to [Table 6A](hereinafter, referred to as "compound group SX542").

The compound (L-39), wherein $G^1$ represents a nitrogen atom, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX543").

The compound (L-39), wherein $G^1$ represents a nitrogen atom, $R^{3b}$ represents a bromine atom, $R^{4c}$ represents a hydrogen atom, $R^6$ represents an ethyl group, T represents a substituent indicated in any of [Table 1A] to [Table 6A] (hereinafter, referred to as "compound group SX544").

The compound (L-39), wherein $G^1$ represents a nitrogen atom, $R^{3b}$ represents a bromine atom, $R^{4c}$ represents a hydrogen atom, $R^6$ represents a propyl group, T represents a substituent indicated in any of [Table 1A] to [Table 6A] (hereinafter, referred to as "compound group SX545").

The compound (L-39), wherein $G^1$ represents CH, $R^{3b}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX546").

The compound (L-39), wherein $G^1$ represents CH, $R^{3b}$ represents a bromine atom, $R^{4c}$ represents a chlorine atom, $R^6$ represents a methyl group, T represents a substituent indicated in any of [Table 1A] to [Table 6A] (hereinafter, referred to as "compound group SX547").

The compound (L-39), wherein $G^1$ represents a nitrogen atom, $R^{3b}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX548").

The compound (L-39), wherein $G^1$ represents a nitrogen atom, $R^{3b}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX549").

The compound (L-39), wherein $G^1$ represents a nitrogen atom, $R^{3b}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX550").

The compound (L-39), wherein $G^1$ represents a nitrogen atom, $R^{3b}$ represents a bromine atom, $R^{4b}$ represents a chlorine atom, $R^6$ represents a methyl group, T represents a substituent indicated in any of [Table 1A] to [Table 6A] (hereinafter, referred to as "compound group SX551").

A compound represented by formula (L-40):

(L-40)

(hereinafter, referred to as "compound (L-40)"),
wherein $G^1$ represents CH, $R^{3b}$ and $R^{4b}$ represent a hydrogen atom, T represents a substituent indicated in any of [Table 1A] to [Table 6A] (hereinafter, referred to as "compound group SX552").

The compound (L-40), wherein $G^1$ represents CH, $R^{3b}$ represents a bromine atom, $R^{4b}$ represents a hydrogen atom, T represents a substituent indicated in any of [Table 1A] to [Table 6A] (hereinafter, referred to as "compound group SX553").

The compound (L-40), wherein $G^1$ represents a nitrogen atom, $R^{3b}$ and $R^{4b}$ represent a hydrogen atom, T represents a substituent indicated in any of [Table 1A] to [Table 6A](hereinafter, referred to as "compound group SX554").

The compound (L-40), wherein $G^1$ represents a nitrogen atom, $R^{3b}$ represents a trifluoromethyl group, $R^{4b}$ represents a hydrogen atom, T represents a substituent indicated in any of [Table 1A] to [Table 6A] (hereinafter, referred to as "compound group SX555").

The compound (L-40), wherein $G^1$ represents a nitrogen atom, $R^{3b}$ represents a bromine atom, $R^{4b}$ represents a hydrogen atom, T represents a substituent indicated in any of [Table 1A] to [Table 6A] (hereinafter, referred to as "compound group SX556").

The compound (L-40), wherein $G^1$ represents CH, $R^{3b}$ represents a hydrogen atom, $R^{4b}$ represents a chlorine atom, T represents a substituent indicated in any of [Table 1A] to [Table 6A] (hereinafter, referred to as "compound group SX557").

The compound (L-40), wherein $G^1$ represents CH, $R^{3b}$ represents a bromine atom, $R^{4b}$ represents a chlorine atom, T represents a substituent indicated in any of [Table 1A] to [Table 6A] (hereinafter, referred to as "compound group SX558").

The compound (L-40), wherein $G^1$ represents a nitrogen atom, $R^{3b}$ represents a hydrogen atom, $R^{4b}$ represents a chlorine atom, T represents a substituent indicated in any of [Table 1A] to [Table 6A] (hereinafter, referred to as "compound group SX559").

The compound (L-40), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX560").

The compound (L-40), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX561").

The compound (L-40), wherein $G^1$ represents a nitrogen atom, $R^{3b}$ represents a bromine atom, $R^{4b}$ represents a chlorine atom, T represents a substituent indicated in any of [Table 1A] to [Table 6A] (hereinafter, referred to as "compound group SX562").

A compound represented by formula (L-41):

(L-41)

(hereinafter, referred to as "compound (L-41)"),
wherein $G^1$ represents CH, $R^{3b}$ and $R^{4b}$ represent a hydrogen atom, T represents a substituent indicated in any of [Table 1A] to [Table 6A] (hereinafter, referred to as "compound group SX563").

The compound (L-41), wherein $G^1$ represents CH, $R^{3b}$ represents a bromine atom, $R^{4b}$ represents a hydrogen atom, T represents a substituent indicated in any of [Table 1A] to [Table 6A] (hereinafter, referred to as "compound group SX564").

The compound (L-41), wherein $G^1$ represents a nitrogen atom, $R^{3b}$ and $R^{4b}$ represent a hydrogen atom, T represents a substituent indicated in any of [Table 1A] to [Table 6A](hereinafter, referred to as "compound group SX565").

The compound (L-41), wherein $G^1$ represents a nitrogen atom, $R^{3b}$ represents a trifluoromethyl group, $R^{4b}$ represents a hydrogen atom, T represents a substituent indicated in any of [Table 1A] to [Table 6A] (hereinafter, referred to as "compound group SX566").

The compound (L-41), wherein $G^1$ represents a nitrogen atom, $R^{3b}$ represents a bromine atom, $R^{4b}$ represents a hydrogen atom, T represents a substituent indicated in any of [Table 1A] to [Table 6A] (hereinafter, referred to as "compound group SX567").

The compound (L-41), wherein $G^1$ represents CH, $R^{3b}$ represents a hydrogen atom, $R^{4b}$ represents a chlorine atom, T represents a substituent indicated in any of [Table 1A] to [Table 6A] (hereinafter, referred to as "compound group SX568").

The compound (L-41), wherein $G^1$ represents CH, $R^{3b}$ represents a bromine atom, $R^{4b}$ represents a chlorine atom, T represents a substituent indicated in any of [Table 1A] to [Table 6A] (hereinafter, referred to as "compound group SX569").

The compound (L-41), wherein $G^1$ represents a nitrogen atom, $R^{3b}$ represents a hydrogen atom, $R^{4b}$ represents a chlorine atom, T represents a substituent indicated in any of [Table 1A] to [Table 6A] (hereinafter, referred to as "compound group SX570").

The compound (L-41), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX571").

The compound (L-41), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX572").

The compound (L-41), wherein $G^1$ represents a nitrogen atom, $R^{3b}$ represents a bromine atom, $R^{4b}$ represents a chlorine atom, T represents a substituent indicated in any of [Table 1A] to [Table 6A] (hereinafter, referred to as "compound group SX573").

A compound represented by formula (L-42):

(L-42)

(hereinafter, referred to as "compound (L-42)"), wherein $G^1$ represents CH, $R^{3b}$ and $R^{4a}$ represent a hydrogen atom, T represents a substituent indicated in any of [Table 1A] to [Table 6A] (hereinafter, referred to as "compound group SX574").

The compound (L-42), wherein $G^1$ represents CH, $R^{3b}$ represents a bromine atom, $R^{4a}$ represents a hydrogen atom, T represents a substituent indicated in any of [Table 1A] to [Table 6A] (hereinafter, referred to as "compound group SX575").

The compound (L-42), wherein $G^1$ represents a nitrogen atom, $R^{3b}$ and $R^{4a}$ represent a hydrogen atom, T represents a substituent indicated in any of [Table 1A] to [Table 6A](hereinafter, referred to as "compound group SX576").

The compound (L-42), wherein $G^1$ represents a nitrogen atom, $R^{3b}$ represents a trifluoromethyl group, $R^{4a}$ represents a hydrogen atom, T represents a substituent indicated in any of [Table 1A] to [Table 6A] (hereinafter, referred to as "compound group SX577").

The compound (L-42), wherein $G^1$ represents a nitrogen atom, $R^{3b}$ represents a bromine atom, $R^{4a}$ represents a hydrogen atom, T represents a substituent indicated in any of [Table 1A] to [Table 6A] (hereinafter, referred to as "compound group SX578").

The compound (L-42), wherein $G^1$ represents CH, $R^{3b}$ represents a hydrogen atom, $R^{4a}$ represents a chlorine atom, T represents a substituent indicated in any of [Table 1A] to [Table 6A] (hereinafter, referred to as "compound group SX579").

The compound (L-42), wherein $G^1$ represents CH, $R^{3b}$ represents a bromine atom, $R^{4a}$ represents a chlorine atom, T represents a substituent indicated in any of [Table 1A] to [Table 6A] (hereinafter, referred to as "compound group SX580").

The compound (L-42), wherein $G^1$ represents a nitrogen atom, $R^{3b}$ represents a hydrogen atom, $R^{4a}$ represents a chlorine atom, T represents a substituent indicated in any of [Table 1A] to [Table 6A] (hereinafter, referred to as "compound group SX581").

The compound (L-42), wherein $G^1$ represents a nitrogen atom, $R^{3b}$ represents a trifluoromethyl group, $R^{4a}$ represents a chlorine atom, T represents a substituent indicated in any of [Table 1A] to [Table 6A] (hereinafter, referred to as "compound group SX582").

The compound (L-42), wherein $G^1$ represents a nitrogen atom, $R^{3b}$ represents a trifluoromethyl group, $R^{4a}$ represents a chlorine atom, T represents a substituent indicated in any of [Table 1A] to [Table 6A] (hereinafter, referred to as "compound group SX583").

The compound (L-42), wherein $G^1$ represents a nitrogen atom, $R^{3b}$ represents a bromine atom, $R^{4a}$ represents a chlorine atom, T represents a substituent indicated in any of [Table 1A] to [Table 6A] (hereinafter, referred to as "compound group SX584").

A compound represented by formula (L-43):

(L-43)

(hereinafter, referred to as "compound (L-43)"), wherein $G^1$ represents CH, $R^{3b}$ and $R^{4c}$ represent a hydrogen atom, T represents a substituent indicated in any of [Table 1A] to [Table 6A] (hereinafter, referred to as "compound group SX585").

The compound (L-43), wherein $G^1$ represents CH, $R^{3b}$ represents a bromine atom, $R^{4c}$ represents a hydrogen atom, T represents a substituent indicated in any of [Table 1A] to [Table 6A] (hereinafter, referred to as "compound group SX586").

The compound (L-43), wherein $G^1$ represents a nitrogen atom, $R^{3b}$ and $R^{4c}$ represent a hydrogen atom, T represents a substituent indicated in any of [Table 1A] to [Table 6A](hereinafter, referred to as "compound group SX587").

The compound (L-43), wherein $G^1$ represents a nitrogen atom, $R^{3b}$ represents a trifluoromethyl group, $R^{4c}$ represents a hydrogen atom, T represents a substituent indicated in any of [Table 1A] to [Table 6A] (hereinafter, referred to as "compound group SX588").

The compound (L-43), wherein $G^1$ represents a nitrogen atom, $R^{3b}$ represents a bromine atom, $R^{4c}$ represents a hydrogen atom, T represents a substituent indicated in any of [Table 1A] to [Table 6A] (hereinafter, referred to as "compound group SX589").

The compound (L-43), wherein $G^1$ represents CH, $R^{3b}$ represents a hydrogen atom, $R^{4c}$ represents a chlorine atom, T represents a substituent indicated in any of [Table 1A] to [Table 6A] (hereinafter, referred to as "compound group SX590").

The compound (L-43), wherein $G^1$ represents CH, $R^{3b}$ represents a bromine atom, $R^{4c}$ represents a chlorine atom, T represents a substituent indicated in any of [Table 1A] to [Table 6A] (hereinafter, referred to as "compound group SX591").

The compound (L-43), wherein $G^1$ represents a nitrogen atom, $R^{3b}$ represents a hydrogen atom, $R^{4c}$ represents a chlorine atom, T represents a substituent indicated in any of [Table 1A] to [Table 6A] (hereinafter, referred to as "compound group SX592").

The compound (L-43), wherein $G^1$ represents a nitrogen atom, $R^{3b}$ represents a trifluoromethyl group, $R^{4c}$ represents a chlorine atom, T represents a substituent indicated in any of [Table 1A] to [Table 6A] (hereinafter, referred to as "compound group SX593").

The compound (L-43), wherein $G^1$ represents a nitrogen atom, $R^{3b}$ represents a trifluoromethyl group, $R^{4c}$ represents a chlorine atom, T represents a substituent indicated in any of [Table 1A] to [Table 6A] (hereinafter, referred to as "compound group SX594").

The compound (L-43), wherein $G^1$ represents a nitrogen atom, $R^{3b}$ represents a bromine atom, $R^{4c}$ represents a chlorine atom, T represents a substituent indicated in any of [Table 1A] to [Table 6A] (hereinafter, referred to as "compound group SX595").

A compound represented by formula (L-44):

(L-44)

(hereinafter, referred to as "compound (L-44)"), wherein $G^1$ represents CH, $R^{3b}$ and $R^{4b}$ represent a hydrogen atom, T represents a substituent indicated in any of [Table 1A] to [Table 6A] (hereinafter, referred to as "compound group SX596").

The compound (L-44), wherein $G^1$ represents CH, $R^{3b}$ represents a bromine atom, $R^{4b}$ represents a hydrogen atom, T represents a substituent indicated in any of [Table 1A] to [Table 6A] (hereinafter, referred to as "compound group SX597").

The compound (L-44), wherein $G^1$ represents a nitrogen atom, $R^{3b}$ and $R^{4b}$ represent a hydrogen atom, T represents a substituent indicated in any of [Table 1A] to [Table 6A](hereinafter, referred to as "compound group SX598").

The compound (L-44), wherein $G^1$ represents a nitrogen atom, $R^{3b}$ represents a trifluoromethyl group, $R^{4b}$ represents a hydrogen atom, T represents a substituent indicated in any of [Table 1A] to [Table 6A] (hereinafter, referred to as "compound group SX599").

The compound (L-44), wherein $G^1$ represents a nitrogen atom, $R^{3b}$ represents a bromine atom, $R^{4b}$ represents a hydrogen atom, T represents a substituent indicated in any of [Table 1A] to [Table 6A] (hereinafter, referred to as "compound group SX600").

The compound (L-44), wherein $G^1$ represents CH, $R^{3b}$ represents a hydrogen atom, $R^{4b}$ represents a chlorine atom, T represents a substituent indicated in any of [Table 1A] to [Table 6A] (hereinafter, referred to as "compound group SX601").

The compound (L-44), wherein $G^1$ represents CH, $R^{3b}$ represents a bromine atom, $R^{4b}$ represents a chlorine atom, T represents a substituent indicated in any of [Table 1A] to [Table 6A] (hereinafter, referred to as "compound group SX602").

The compound (L-44), wherein $G^1$ represents a nitrogen atom, $R^{3b}$ represents a hydrogen atom, $R^{4b}$ represents a chlorine atom, T represents a substituent indicated in any of [Table 1A] to [Table 6A] (hereinafter, referred to as "compound group SX603").

The compound (L-44), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX604").

The compound (L-44), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX605").

The compound (L-44), wherein $G^1$ represents a nitrogen atom, $R^{3b}$ represents a bromine atom, $R^{4b}$ represents a chlorine atom, T represents a substituent indicated in any of [Table 1A] to [Table 6A] (hereinafter, referred to as "compound group SX606").

A compound represented by formula (L-45):

(L-45)

(hereinafter, referred to as "compound (L-45)"), wherein $G^1$ represents CH, $R^{3b}$ and $R^{4b}$ represent a hydrogen atom, T represents a substituent indicated in any of [Table 1A] to [Table 6A] (hereinafter, referred to as "compound group SX607").

The compound (L-45), wherein $G^1$ represents CH, $R^{3b}$ represents a bromine atom, $R^{4b}$ represents a hydrogen atom, T represents a substituent indicated in any of [Table 1A] to [Table 6A] (hereinafter, referred to as "compound group SX608").

The compound (L-45), wherein $G^1$ represents a nitrogen atom, $R^{3b}$ and $R^{4b}$ represent a hydrogen atom, T represents a substituent indicated in any of [Table 1A] to [Table 6A](hereinafter, referred to as "compound group SX609").

The compound (L-45), wherein $G^1$ represents a nitrogen atom, $R^{3b}$ represents a trifluoromethyl group, $R^{4b}$ represents a hydrogen atom, T represents a substituent indicated in any of [Table 1A] to [Table 6A] (hereinafter, referred to as "compound group SX610").

The compound (L-45), wherein $G^1$ represents a nitrogen atom, $R^{3b}$ represents a bromine atom, $R^{4b}$ represents a hydrogen atom, T represents a substituent indicated in any of [Table 1A] to [Table 6A] (hereinafter, referred to as "compound group SX611").

The compound (L-45), wherein $G^1$ represents CH, $R^{3b}$ represents a hydrogen atom, $R^{4b}$ represents a chlorine atom, T represents a substituent indicated in any of [Table 1A] to [Table 6A] (hereinafter, referred to as "compound group SX612").

The compound (L-45), wherein $G^1$ represents CH, $R^{3b}$ represents a bromine atom, $R^{4b}$ represents a chlorine atom, T represents a substituent indicated in any of [Table 1A] to [Table 6A] (hereinafter, referred to as "compound group SX613").

The compound (L-45), wherein $G^1$ represents a nitrogen atom, $R^{3b}$ represents a hydrogen atom, $R^{4b}$ represents a chlorine atom, T represents a substituent indicated in any of [Table 1A] to [Table 6A] (hereinafter, referred to as "compound group SX614").

The compound (L-45), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX615").

The compound (L-45), wherein $G^1$ represents a nitrogen atom, $R^{3b}$ represents a trifluoromethyl group, $R^{4b}$ represents a chlorine atom, T represents a substituent indicated in any of [Table 1A] to [Table 6A] (hereinafter, referred to as "compound group SX616").

The compound (L-45), wherein $G^1$ represents a nitrogen atom, $R^{3b}$ represents a bromine atom, $R^{4b}$ represents a chlorine atom, T represents a substituent indicated in any of [Table 1A] to [Table 6A] (hereinafter, referred to as "compound group SX617").

A compound represented by formula (L-46):

(L-46)

(hereinafter, referred to as "compound (L-46)"), wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX618").

The compound (L-46), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX619").

The compound (L-46), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX620").

The compound (L-46), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX621").

The compound (L-46), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX622").

The compound (L-46), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A](hereinafter, referred to as "compound group SX623").

The compound (L-46), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A](hereinafter, referred to as "compound group SX624").

The compound (L-46), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A](hereinafter, referred to as "compound group SX625").

The compound (L-46), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX626").

The compound (L-46), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX627").

The compound (L-46), wherein $R^{3b}$ represents a bromine atom, $R^{3c}$ and $R^{4b}$ represent a hydrogen atom, $R^6$ represents a methyl group, T represents a substituent indicated in any of [Table 1A] to [Table 6A] (hereinafter, referred to as "compound group SX628").

The compound (L-46), wherein $R^{3b}$ represents a bromine atom, $R^{3c}$ and $R^{4b}$ represent a hydrogen atom, $R^6$ represents an ethyl group, T represents a substituent indicated in any of [Table 1A] to [Table 6A] (hereinafter, referred to as "compound group SX629").

The compound (L-46), wherein $R^{3b}$ represents a bromine atom, $R^{3c}$ and $R^{4b}$ represent a hydrogen atom, $R^6$ represents a propyl group, T represents a substituent indicated in any of [Table 1A] to [Table 6A] (hereinafter, referred to as "compound group SX630").

The compound (L-46), wherein $R^{3b}$ represents a bromine atom, $R^{3c}$ and $R^{4b}$ represent a hydrogen atom, $R^6$ represents an isopropyl group, T represents a substituent indicated in any of [Table 1A] to [Table 6A] (hereinafter, referred to as "compound group SX631").

The compound (L-46), wherein $R^{3b}$ represents a bromine atom, $R^{3c}$ and $R^{4b}$ represent a hydrogen atom, $R^6$ represents a cyclopropyl group, T represents a substituent indicated in any of [Table 1A] to [Table 6A] (hereinafter, referred to as "compound group SX632").

The compound (L-46), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX633").

The compound (L-46), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX634").

The compound (L-46), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX635").

The compound (L-46), wherein $R^{3b}$ and $R^{4b}$ represent a hydrogen atom, $R^{3c}$ represents a trifluoromethyl group, R represents an isopropyl group, T represents a substituent indicated in any of [Table 1A] to [Table 6A] (hereinafter, referred to as "compound group SX636").

The compound (L-46), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX637").

The compound (L-46), wherein $R^{3b}$ and $R^{4b}$ represent a hydrogen atom, $R^{3c}$ represents a bromine atom, $R^6$ represents a methyl group, T represents a substituent indicated in any of [Table 1A] to [Table 6A] (hereinafter, referred to as "compound group SX638").

The compound (L-46), wherein $R^{3b}$ and $R^{4b}$ represent a hydrogen atom, $R^{3c}$ represents a bromine atom, $R^6$ represents an ethyl group, T represents a substituent indicated in any of [Table 1A] to [Table 6A] (hereinafter, referred to as "compound group SX639").

The compound (L-46), wherein $R^{3b}$ and $R^{4b}$ represent a hydrogen atom, $R^{3c}$ represents a bromine atom, RE represents a propyl group, T represents a substituent indicated in any of [Table 1A] to [Table 6A] (hereinafter, referred to as "compound group SX640").

The compound (L-46), wherein $R^{3b}$ and $R^{4b}$ represent a hydrogen atom, $R^{3c}$ represents a bromine atom, RE represents an isopropyl group, T represents a substituent indicated in any of [Table 1A] to [Table 6A] (hereinafter, referred to as "compound group SX641").

The compound (L-46), wherein $R^{3b}$ and $R^{4b}$ represent a hydrogen atom, $R^{3c}$ represents a bromine atom, $R^6$ represents a cyclopropyl group, T represents a substituent indicated in any of [Table 1A] to [Table 6A] (hereinafter, referred to as "compound group SX642").

The compound (L-46), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX643").

The compound (L-46), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX644").

The compound (L-46), wherein $R^{3b}$ represents a bromine atom, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX645").

The compound (L-46), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX646").

The compound (L-46), wherein $R^{3b}$ represents a hydrogen atom, $R^{3c}$ represents a bromine atom, $R^{4b}$ represents a chlorine atom, $R^b$ represents a methyl group, T represents a substituent indicated in any of [Table 1A] to [Table 6A] (hereinafter, referred to as "compound group SX647").

A compound represented by formula (L-47):

(hereinafter, referred to as "compound (L-47)"),
wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX648").

The compound (L-47), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX649").

The compound (L-47), wherein $R^{3b}$ and $R^{3c}$ represent a hydrogen atom, $R^6$ represent a propyl group, T represents a substituent indicated in any of [Table 1A] to [Table 6A] (hereinafter, referred to as "compound group SX650").

The compound (L-47), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX651").

The compound (L-47), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX652").

The compound (L-47), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX653").

The compound (L-47), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX654").

The compound (L-47), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX655").

The compound (L-47), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX656").

The compound (L-47), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX657").

The compound (L-47), wherein $R^{3b}$ represents a bromine atom, $R^{3c}$ represents a hydrogen atom, $R^6$ represents a methyl group, T represents a substituent indicated in any of [Table 1A] to [Table 6A] (hereinafter, referred to as "compound group SX658").

The compound (L-47), wherein $R^{3b}$ represents a bromine atom, $R^{3c}$ represents a hydrogen atom, $R^6$ represents an ethyl group, T represents a substituent indicated in any of [Table 1A] to [Table 6A] (hereinafter, referred to as "compound group SX659").

The compound (L-47), wherein $R^{3b}$ represents a bromine atom, $R^{3c}$ represents a hydrogen atom, $R^6$ represents a propyl group, T represents a substituent indicated in any of [Table 1A] to [Table 6A] (hereinafter, referred to as "compound group SX660").

The compound (L-47), wherein $R^{3b}$ represents a bromine atom, $R^{3c}$ represents a hydrogen atom, $R^6$ represents an isopropyl group, T represents a substituent indicated in any of [Table 1A] to [Table 6A] (hereinafter, referred to as "compound group SX661").

The compound (L-47), wherein $R^{3b}$ represents a bromine atom, $R^{3c}$ represents a hydrogen atom, $R^6$ represents a cyclopropyl group, T represents a substituent indicated in any of [Table 1A] to [Table 6A] (hereinafter, referred to as "compound group SX662")

The compound (L-47), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX663").

The compound (L-47), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX664").

The compound (L-47), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX665").

The compound (L-47), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX666").

The compound (L-47), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX667").

The compound (L-47), wherein $R^{3b}$ represents a hydrogen atom, $R^{3c}$ represents a bromine atom, $R^6$ represents a methyl group, T represents a substituent indicated in any of [Table 1A] to [Table 6A] (hereinafter, referred to as "compound group SX668").

The compound (L-47), wherein $R^{3b}$ represents a hydrogen atom, $R^{3c}$ represents a bromine atom, $R^6$ represents an ethyl group, T represents a substituent indicated in any of [Table 1A] to [Table 6A] (hereinafter, referred to as "compound group SX669").

The compound (L-47), wherein $R^{3b}$ represents a hydrogen atom, $R^{3c}$ represents a bromine atom, $R^6$ represents a propyl group, T represents a substituent indicated in any of [Table 1A] to [Table 6A] (hereinafter, referred to as "compound group SX670").

The compound (L-47), wherein $R^{3b}$ represents a hydrogen atom, $R^{3c}$ represents a bromine atom, $R^6$ represents an isopropyl group, T represents a substituent indicated in any of [Table 1A] to [Table 6A] (hereinafter, referred to as "compound group SX671").

The compound (L-47), wherein $R^{3b}$ represents a hydrogen atom, $R^{3c}$ represents a bromine atom, $R^6$ represents a cyclopropyl group, T represents a substituent indicated in any of [Table 1A] to [Table 6A] (hereinafter, referred to as "compound group SX672").

A compound represented by formula (L-48):

(hereinafter, referred to as "compound (L-48)"),
wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX673").

The compound (L-48), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX674").

The compound (L-48), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX675").

The compound (L-48), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX676").

The compound (L-48), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX677").

The compound (L-48), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A] (hereinafter, referred to as "compound group SX678").

The compound (L-48), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A] (hereinafter, referred to as "compound group SX679").

The compound (L-48), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A] (hereinafter, referred to as "compound group SX680").

The compound (L-48), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A] (hereinafter, referred to as "compound group SX681").

The compound (L-48), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A] (hereinafter, referred to as "compound group SX682").

The compound (L-48), wherein $R^{3b}$ represents a bromine atom, $R^{3c}$ and $R^{4b}$ represent a hydrogen atom, $R^6$ represents a methyl group, T represents a substituent indicated in any of [Table 1A] to [Table 6A] (hereinafter, referred to as "compound group SX683").

The compound (L-48), wherein $R^{3b}$ represents a bromine atom, $R^{3c}$ and $R^{4b}$ represent a hydrogen atom, $R^6$ represents an ethyl group, T represents a substituent indicated in any of [Table 1A] to [Table 6A] (hereinafter, referred to as "compound group SX684").

The compound (L-48), wherein $R^{3b}$ represents a bromine atom, $R^{3c}$ and $R^{4b}$ represent a hydrogen atom, $R^6$ represents a propyl group, T represents a substituent indicated in any of [Table 1A] to [Table 6A] (hereinafter, referred to as "compound group SX685").

The compound (L-48), wherein $R^{3b}$ represents a bromine atom, $R^{3c}$ and $R^{4b}$ represent a hydrogen atom, $R^6$ represents an isopropyl group, T represents a substituent indicated in any of [Table 1A] to [Table 6A] (hereinafter, referred to as "compound group SX686").

The compound (L-48), wherein $R^{3b}$ represents a bromine atom, $R^{3c}$ and $R^{4b}$ represent a hydrogen atom, $R^6$ represents a cyclopropyl group, T represents a substituent indicated in any of [Table 1A] to [Table 6A] (hereinafter, referred to as "compound group SX687").

The compound (L-48), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX688").

The compound (L-48), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX689").

The compound (L-48), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX690").

The compound (L-48), wherein $R^{3b}$ and $R^{4b}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX691").

The compound (L-48), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX692").

The compound (L-48), wherein $R^{3b}$ and $R^{4b}$ represent a hydrogen atom, $R^{3c}$ represents a bromine atom, RE represents a methyl group, T represents a substituent indicated in any of [Table 1A] to [Table 6A] (hereinafter, referred to as "compound group SX693").

The compound (L-48), wherein $R^{3b}$ and $R^{4b}$ represent a hydrogen atom, $R^{3c}$ represents a bromine atom, $R^6$ represents an ethyl group, T represents a substituent indicated in any of [Table 1A] to [Table 6A] (hereinafter, referred to as "compound group SX694").

The compound (L-48), wherein $R^{3b}$ and $R^{4b}$ represent a hydrogen atom, $R^{3c}$ represents a bromine atom, $R^6$ represents a propyl group, T represents a substituent indicated in any of [Table 1A] to [Table 6A] (hereinafter, referred to as "compound group SX695").

The compound (L-48), wherein $R^{3b}$ and $R^{4b}$ represent a hydrogen atom, $R^{3c}$ represents a bromine atom, $R^6$ represents an isopropyl group, T represents a substituent indicated in any of [Table 1A] to [Table 6A] (hereinafter, referred to as "compound group SX696").

The compound (L-48), wherein $R^{3b}$ and $R^{4b}$ represent a hydrogen atom, $R^{3c}$ represents a bromine atom, RE represents a cyclopropyl group, T represents a substituent indicated in any of [Table 1A] to [Table 6A] (hereinafter, referred to as "compound group SX697")

The compound (L-48), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX698").

The compound (L-48), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX699").

The compound (L-48), wherein $R^{3b}$ represents a bromine atom, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX700").

The compound (L-48), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX701").

The compound (L-48), wherein $R^{3b}$ represents a hydrogen atom, $R^{3c}$ represents a bromine atom, $R^4$ represents a chlorine atom, $R^b$ represents a methyl group, T represents a substituent indicated in any of [Table 1A] to [Table 6A] (hereinafter, referred to as "compound group SX702").

A compound represented by formula (L-49):

(L-49)

[Chemical structure showing a pyridinone ring connected to a benzothiophene ring system with substituents T, $R^6$, $R^{4c}$, $R^{3b}$, $R^{3c}$, and an (O)$_2$S-CH$_2$-CH$_3$ group]

(hereinafter, referred to as "compound (L-49)"), wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX703").

The compound (L-49), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX704").

The compound (L-49), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX705").

The compound (L-49), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX706").

The compound (L-49), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX707").

The compound (L-49), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX708").

The compound (L-49), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX709").

The compound (L-49), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX710").

The compound (L-49), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX711").

The compound (L-49), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX712").

The compound (L-49), wherein $R^{3b}$ represents a bromine atom, $R^{3c}$ and $R^{4c}$ represent a hydrogen atom, $R^6$ represents a methyl group, T represents a substituent indicated in any of [Table 1A] to [Table 6A] (hereinafter, referred to as "compound group SX713").

The compound (L-49), wherein $R^{3b}$ represents a bromine atom, $R^{3c}$ and $R^{4c}$ represent a hydrogen atom, $R^6$ represents an ethyl group, T represents a substituent indicated in any of [Table 1A] to [Table 6A] (hereinafter, referred to as "compound group SX714").

The compound (L-49), wherein $R^{3b}$ represents a bromine atom, $R^{3c}$ and $R^{4c}$ represent a hydrogen atom, $R^6$ represents a propyl group, T represents a substituent indicated in any of [Table 1A] to [Table 6A] (hereinafter, referred to as "compound group SX715").

The compound (L-49), wherein $R^{3b}$ represents a bromine atom, $R^{3c}$ and $R^{4c}$ represent a hydrogen atom, $R^6$ represents an isopropyl group, T represents a substituent indicated in any of [Table 1A] to [Table 6A] (hereinafter, referred to as "compound group SX716").

The compound (L-49), wherein $R^{3b}$ represents a bromine atom, $R^{3c}$ and $R^{4c}$ represent a hydrogen atom, $R^6$ represents a cyclopropyl group, T represents a substituent indicated in any of [Table 1A] to [Table 6A] (hereinafter, referred to as "compound group SX717")

The compound (L-49), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX718").

The compound (L-49), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX719").

The compound (L-49), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX720").

The compound (L-49), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX721").

The compound (L-49), wherein $R^{3b}$ and $R^{4c}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX722").

The compound (L-49), wherein $R^{3b}$ and $R^{4c}$ represent a hydrogen atom, $R^{3c}$ represents a bromine atom, $R^6$ represents a methyl group, T represents a substituent indicated in any of [Table 1A] to [Table 6A] (hereinafter, referred to as "compound group SX723").

The compound (L-49), wherein $R^{3b}$ and $R^{4c}$ represent a hydrogen atom, $R^{3c}$ represents a bromine atom, $R^6$ represents an ethyl group, T represents a substituent indicated in any of [Table 1A] to [Table 6A] (hereinafter, referred to as "compound group SX724").

The compound (L-49), wherein $R^{3b}$ and $R^{4c}$ represent a hydrogen atom, $R^{3c}$ represents a bromine atom, $R^6$ represents a propyl group, T represents a substituent indicated in any of [Table 1A] to [Table 6A] (hereinafter, referred to as "compound group SX725").

The compound (L-49), wherein $R^{3b}$ and $R^{4c}$ represent a hydrogen atom, $R^{3c}$ represents a bromine atom, $R^6$ represents an isopropyl group, T represents a substituent indicated in any of [Table 1A] to [Table 6A] (hereinafter, referred to as "compound group SX726").

The compound (L-49), wherein $R^{3b}$ and $R^{4c}$ represent a hydrogen atom, $R^{3c}$ represents a bromine atom, $R^6$ represents a cyclopropyl group, T represents a substituent indicated in any of [Table 1A] to [Table 6A] (hereinafter, referred to as "compound group SX727").

The compound (L-49), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX728").

The compound (L-49), wherein $R^{3b}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX729").

The compound (L-49), wherein $R^{3b}$ represents a bromine atom, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX730").

The compound (L-49), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX731").

The compound (L-49), wherein $R^{3b}$ represents a hydrogen atom, $R^{3c}$ represents a bromine atom, $R^{4c}$ represents a chlorine atom, $R^6$ represents a methyl group, T represents a substituent indicated in any of [Table 1A] to [Table 6A] (hereinafter, referred to as "compound group SX732").

A compound represented by formula (L-50):

$$\text{(L-50)}$$

(hereinafter, referred to as "compound (L-50)"),
wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX733").

The compound (L-50), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX734").

The compound (L-50), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX735").

The compound (L-50), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX736").

The compound (L-50), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX737").

The compound (L-50), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX738").

The compound (L-50), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX739").

The compound (L-50), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX740").

The compound (L-50), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX741").

The compound (L-50), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX742").

The compound (L-50), wherein $R^{3b}$ represents a bromine atom, $R^{3c}$ represents a hydrogen atom, $R^6$ represents a methyl group, T represents a substituent indicated in any of [Table 1A] to [Table 6A] (hereinafter, referred to as "compound group SX743").

The compound (L-50), wherein $R^{3b}$ represents a bromine atom, $R^{3c}$ represents a hydrogen atom, $R^6$ represents an ethyl group, T represents a substituent indicated in any of [Table 1A] to [Table 6A] (hereinafter, referred to as "compound group SX744").

The compound (L-50), wherein $R^{3b}$ represents a bromine atom, $R^{3c}$ represents a hydrogen atom, $R^6$ represents a propyl group, T represents a substituent indicated in any of [Table 1A] to [Table 6A] (hereinafter, referred to as "compound group SX745").

The compound (L-50), wherein $R^{3b}$ represents a bromine atom, $R^{3c}$ represents a hydrogen atom, $R^6$ represents an isopropyl group, T represents a substituent indicated in any of [Table 1A] to [Table 6A] (hereinafter, referred to as "compound group SX746").

The compound (L-50), wherein $R^{3b}$ represents a bromine atom, $R^{3c}$ represents a hydrogen atom, $R^6$ represents a cyclopropyl group, T represents a substituent indicated in any of [Table 1A] to [Table 6A] (hereinafter, referred to as "compound group SX747").

The compound (L-50), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX748").

The compound (L-50), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX749").

The compound (L-50), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX750").

The compound (L-50), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX751").

The compound (L-50), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX752").

The compound (L-50), wherein $R^{2b}$ represents a hydrogen atom, $R^{3c}$ represents a bromine atom, $R^6$ represents a methyl group, T represents a substituent indicated of [Table 1A] to [Table 6A] (hereinafter, referred to as "compound group SX753").

The compound (L-50), wherein $R^{3b}$ represents a hydrogen atom, $R^{3c}$ represents a bromine atom, $R^6$ represents an ethyl group, T represents a substituent indicated in any of [Table 1A] to [Table 6A] (hereinafter, referred to as "compound group SX754").

The compound (L-50), wherein $R^{3b}$ represents a hydrogen atom, $R^{3c}$ represents a bromine atom, $R^6$ represents a propyl group, T represents a substituent indicated in any of [Table 1A] to [Table 6A] (hereinafter, referred to as "compound group SX755").

The compound (L-50), wherein $R^{3b}$ represents a hydrogen atom, $R^{3c}$ represents a bromine atom, $R^6$ represents an isopropyl group, T represents a substituent indicated in any of [Table 1A] to [Table 6A] (hereinafter, referred to as "compound group SX756").

The compound (L-50), wherein $R^{3b}$ represents a hydrogen atom, $R^{3c}$ represents a bromine atom, $R^6$ represents a cyclopropyl group, T represents a substituent indicated in any of [Table 1A] to [Table 6A] (hereinafter, referred to as "compound group SX757").

A compound represented by formula (L-51):

$$\text{(L-51)}$$

(hereinafter, referred to as "compound (L-51)"),
wherein $R^{3b}$, $R^{3c}$, and $R^{4c}$ represent a hydrogen atom, $R^6$ represents a methyl group, T represents a substituent indicated in any of [Table 1A] to [Table 6A] (hereinafter, referred to as "compound group SX758").

The compound (L-51), wherein $R^{3b}$, $R^{3c}$, and $R^{4c}$ represent a hydrogen atom, $R^6$ represents an ethyl group, T represents a substituent indicated in any of [Table 1A] to [Table 6A] (hereinafter, referred to as "compound group SX759").

The compound (L-51), wherein $R^{3b}$, $R^{3c}$, and $R^{4c}$ represent a hydrogen atom, $R^6$ represents a propyl group, T represents a substituent indicated in any of [Table 1A] to [Table 6A] (hereinafter, referred to as "compound group SX760").

The compound (L-51), wherein $R^{3b}$, $R^{3c}$, and $R^{4c}$ represent a hydrogen atom, $R^6$ represents an isopropyl group, T represents a substituent indicated in any of [Table 1A] to [Table 6A] (hereinafter, referred to as "compound group SX761").

The compound (L-51), wherein $R^{3b}$, $R^{3c}$, and $R^{4c}$ represent a hydrogen atom, $R^6$ represents a cyclopropyl group, T represents a substituent indicated in any of [Table 1A] to [Table 6A] (hereinafter, referred to as "compound group SX762").

The compound (L-51), wherein $R^{3b}$ represents a trifluoromethyl group, $R^{3c}$ and $R^{4c}$ represent a hydrogen atom, $R^6$ represents a methyl group, T represents a substituent indicated in any of [Table 1A] to [Table 6A](hereinafter, referred to as "compound group SX763").

The compound (L-51), wherein $R^{3b}$ represents a trifluoromethyl group, $R^{3c}$ and $R^{4c}$ represent a hydrogen atom, $R^6$ represents an ethyl group, T represents a substituent indicated in any of [Table 1A] to [Table 6A](hereinafter, referred to as "compound group SX764").

The compound (L-51), wherein $R^{3b}$ represents a trifluoromethyl group, $R^{3c}$ and $R^{4c}$ represent a hydrogen atom, $R^6$ represents a propyl group, T represents a substituent indicated in any of [Table 1A] to [Table 6A](hereinafter, referred to as "compound group SX765").

The compound (L-51), wherein $R^{3b}$ represents a trifluoromethyl group, $R^{3c}$ and $R^{4c}$ represent a hydrogen atom, $R^6$ represents an isopropyl group, T represents a substituent indicated in any of [Table 1A] to [Table 6A](hereinafter, referred to as "compound group SX766").

The compound (L-51), wherein $R^{3b}$ represents a trifluoromethyl group, $R^{3c}$ and $R^{4c}$ represent a hydrogen atom, $R^6$ represents a cyclopropyl group, T represents a substituent indicated in any of [Table 1A] to [Table 6A](hereinafter, referred to as "compound group SX767").

The compound (L-51), wherein $R^{3b}$ represents a bromine atom, $R^{3c}$ and $R^{4c}$ represent a hydrogen atom, $R^6$ represents a methyl group, T represents a substituent indicated in any of [Table 1A] to [Table 6A] (hereinafter, referred to as "compound group SX768").

The compound (L-51), wherein $R^{3b}$ represents a bromine atom, $R^{3c}$ and $R^{4c}$ represent a hydrogen atom, $R^6$ represents an ethyl group, T represents a substituent indicated in any of [Table 1A] to [Table 6A] (hereinafter, referred to as "compound group SX769").

The compound (L-51), wherein $R^{3b}$ represents a bromine atom, $R^{3c}$ and $R^{4c}$ represent a hydrogen atom, $R^6$ represents a propyl group, T represents a substituent indicated in any of [Table 1A] to [Table 6A] (hereinafter, referred to as "compound group SX770").

The compound (L-51), wherein $R^{3b}$ represents a bromine atom, $R^{3c}$ and $R^{4c}$ represent a hydrogen atom, $R^6$ represents an isopropyl group, T represents a substituent indicated in any of [Table 1A] to [Table 6A] (hereinafter, referred to as "compound group SX771").

The compound (L-51), wherein $R^{3b}$ represents a bromine atom, $R^{3c}$ and $R^{4c}$ represent a hydrogen atom, $R^6$ represents a cyclopropyl group, T represents a substituent indicated in any of [Table 1A] to [Table 6A] (hereinafter, referred to as "compound group SX772").

The compound (L-51), wherein $R^{3b}$ and $R^{4c}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX773").

The compound (L-51), wherein $R^{3b}$ and $R^{4c}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX774").

The compound (L-51), wherein $R^{3b}$ and $R^{4c}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX775").

The compound (L-51), wherein $R^{3b}$ and $R^{4c}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX776").

The compound (L-51), wherein $R^{3b}$ and $R^{4c}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX777").

The compound (L-51), wherein $R^{3b}$ and $R^{4c}$ represent a hydrogen atom, $R^{3c}$ represents a bromine atom, RE represents a methyl group, T represents a substituent indicated in any of [Table 1A] to [Table 6A] (hereinafter, referred to as "compound group SX778").

The compound (L-51), wherein $R^{3b}$ and $R^{4c}$ represent a hydrogen atom, $R^{3c}$ represents a bromine atom, RE represents an ethyl group, T represents a substituent indicated in any of [Table 1A] to [Table 6A] (hereinafter, referred to as "compound group SX779").

The compound (L-51), wherein $R^{3b}$ and $R^{4c}$ represent a hydrogen atom, $R^{3c}$ represents a bromine atom, $R^6$ represents a propyl group, T represents a substituent indicated in any of [Table 1A] to [Table 6A] (hereinafter, referred to as "compound group SX780").

The compound (L-51), wherein $R^{3b}$ and $R^{4c}$ represent a hydrogen atom, $R^{3c}$ represents a bromine atom, $R^6$ represents an isopropyl group, T represents a substituent indicated in any of [Table 1A] to [Table 6A] (hereinafter, referred to as "compound group SX781").

The compound (L-51), wherein $R^{3b}$ and $R^{4c}$ represent a hydrogen atom, $R^{3c}$ represents a bromine atom, $R^6$ represents a cyclopropyl group, T represents a substituent indicated in any of [Table 1A] to [Table 6A] (hereinafter, referred to as "compound group SX782").

The compound (L-51), wherein $R^{3b}$ and $R^{3c}$ represent a hydrogen atom, $R^{4c}$ represents a chlorine atom, $R^6$ represents a methyl group, T represents a substituent indicated in any of [Table 1A] to [Table 6A] (hereinafter, referred to as "compound group SX783").

The compound (L-51), wherein $R^{31}$ represents a trifluoromethyl group, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX784").

The compound (L-51), wherein $R^{3b}$ represents a bromine atom, $R^{3c}$ represents a hydrogen atom, $R^{4c}$ represents a chlorine atom, $R^6$ represents a methyl group, T represents a substituent indicated in any of [Table 1A] to [Table 6A] (hereinafter, referred to as "compound group SX785").

The compound (L-51), wherein $R^{3b}$ represents a hydrogen atom, $R^{3c}$ represents a trifluoromethyl group, $R^{4c}$ represents a chlorine atom, $R^6$ represents a methyl group, T represents a substituent indicated in any of [Table 1A] to [Table 6A] (hereinafter, referred to as "compound group SX786").

The compound (L-51), wherein $R^{3b}$ represents a hydrogen atom, $R^{3c}$ represents a bromine atom, $R^{4c}$ represents a chlorine atom, $R^6$ represents a methyl group, T represents a substituent indicated in any of [Table 1A] to [Table 6A] (hereinafter, referred to as "compound group SX787").

A compound represented by formula (L-52):

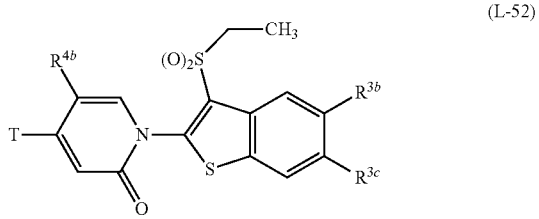

(L-52)

(hereinafter, referred to as "compound (L-52)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX788").

The compound (L-52), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX789").

The compound (L-52), wherein $R^{3b}$ represents a bromine atom, $R^{3c}$ and $R^{4b}$ represent a hydrogen atom, T represents a substituent indicated in any of [Table 1A] to [Table 6A](hereinafter, referred to as "compound group SX790").

The compound (L-52), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX791").

The compound (L-52), wherein $R^{3b}$ and $R^{4b}$ represent a hydrogen atom, $R^{3c}$ represents a bromine atom, T represents a substituent indicated in any of [Table 1A] to [Table 6A](hereinafter, referred to as "compound group SX792")

The compound (L-52), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX793").

The compound (L-52), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX794").

The compound (L-52), wherein $R^{3b}$ represents a bromine atom, $R^{3c}$ represents a hydrogen atom, $R^{4b}$ represents a chlorine atom, T represents a substituent indicated in any of [Table 1A] to [Table 6A] (hereinafter, referred to as "compound group SX795").

The compound (L-52), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX796").

The compound (L-52), wherein $R^{3b}$ represents a hydrogen atom, $R^{3c}$ represents a bromine atom, $R^{4b}$ represents a chlorine atom, T represents a substituent indicated in any of [Table 1A] to [Table 6A] (hereinafter, referred to as "compound group SX797").

A compound represented by formula (L-53):

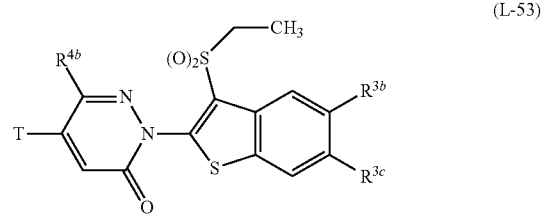

(L-53)

(hereinafter, referred to as "compound (L-53)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX798").

The compound (L-53), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX799").

The compound (L-53), wherein $R^{3b}$ represents a bromine atom, $R^{3c}$ and $R^{4b}$ represent a hydrogen atom, T represents a substituent indicated in any of [Table 1A] to [Table 6A](hereinafter, referred to as "compound group SX800").

The compound (L-53), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX801").

The compound (L-53), wherein $R^{3b}$ and $R^{4b}$ represent a hydrogen atom, $R^{3c}$ represents a bromine atom group, T represents a substituent indicated in any of [Table 1A] to [Table 6A] (hereinafter, referred to as "compound group SX802").

The compound (L-53), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX803").

The compound (L-53), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX804").

The compound (L-53), wherein $R^{2b}$ represents a bromine atom, $R^{3c}$ represents a hydrogen atom, $R^{4b}$ represents a chlorine atom, T represents a substituent indicated in any of [Table 1A] to [Table 6A] (hereinafter, referred to as "compound group SX805")

The compound (L-53), wherein $R^{2b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX806").

The compound (L-53), wherein $R^{3b}$ represents a hydrogen atom, $R^{3c}$ represents a bromine atom, $R^{4b}$ represents a chlorine atom, T represents a substituent indicated in any of [Table 1A] to [Table 6A] (hereinafter, referred to as "compound group SX807")

A compound represented by formula (L-54):

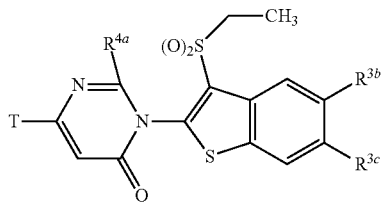

(L-54)

(hereinafter, referred to as "compound (L-54)"), wherein $R^{3b}$, $R^{3c}$, and $R^{4a}$ represent a hydrogen atom, T represents a substituent indicated in any of [Table 1A] to [Table 6A] (hereinafter, referred to as "compound group SX808").

The compound (L-54), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX809").

The compound (L-54), wherein $R^{3b}$ represents a bromine atom, $R^{3c}$ and $R^{4a}$ represent a hydrogen atom, T represents a substituent indicated in any of [Table 1A] to [Table 6A](hereinafter, referred to as "compound group SX810").

The compound (L-54), wherein $R^{3b}$ and $R^{4a}$ represent a hydrogen atom, $R^{3c}$ represents a trifluoromethyl group, T represents a substituent indicated in any of [Table 1A] to [Table 6A] (hereinafter, referred to as "compound group SX811").

The compound (L-54), wherein $R^{3b}$ and $R^{4a}$ represent a hydrogen atom, $R^{3c}$ represents a bromine atom, T represents a substituent indicated in any of [Table 1A] to [Table 6A](hereinafter, referred to as "compound group SX812").

The compound (L-54), wherein $R^{3b}$ and $R^{3c}$ represent a hydrogen atom, $R^{4a}$ represents a chlorine atom, T represents a substituent indicated in any of [Table 1A] to [Table 6A](hereinafter, referred to as "compound group SX813").

The compound (L-54), wherein $R^{3b}$ represents a trifluoromethyl group, $R^{3c}$ represents a hydrogen atom, $R^{4a}$ represents a chlorine atom, T represents a substituent indicated in any of [Table 1A] to [Table 6A] (hereinafter, referred to as "compound group SX814").

The compound (L-54), wherein $R^{3b}$ represents a bromine atom, $R^{3c}$ represents a hydrogen atom, $R^{4a}$ represents a chlorine atom, T represents a substituent indicated in any of [Table 1A] to [Table 6A] (hereinafter, referred to as "compound group SX815").

The compound (L-54), wherein $R^{3b}$ represents a hydrogen atom, $R^{3c}$ represents a trifluoromethyl group, $R^{4a}$ represents a chlorine atom, T represents a substituent indicated in any of [Table 1A] to [Table 6A] (hereinafter, referred to as "compound group SX816").

The compound (L-54), wherein $R^{3b}$ represents a hydrogen atom, $R^{3c}$ represents a bromine atom, $R^{4a}$ represents a chlorine atom, T represents a substituent indicated in any of [Table 1A] to [Table 6A] (hereinafter, referred to as "compound group SX817").

A compound represented by formula (L-55):

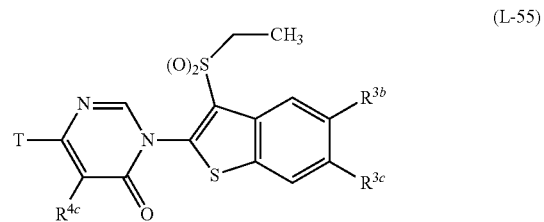

(L-55)

(hereinafter, referred to as "compound (L-55)"), wherein $R^{3b}$, $R^{3c}$, and $R^{4c}$ represent a hydrogen atom, T represents a substituent indicated in any of [Table 1A] to [Table 6A] (hereinafter, referred to as "compound group SX818").

The compound (L-55), wherein $R^{3b}$ represents a trifluoromethyl group, $R^{3c}$ and $R^{4c}$ represent a hydrogen atom, T represents a substituent indicated in any of [Table 1A] to [Table 6A] (hereinafter, referred to as "compound group SX819").

The compound (L-55), wherein $R^{3b}$ represents a bromine atom, $R^{3c}$ and $R^{4c}$ represent a hydrogen atom, T represents a substituent indicated in any of [Table 1A] to [Table 6A](hereinafter, referred to as "compound group SX820").

The compound (L-55), wherein $R^{3b}$ and $R^{4c}$ represent a hydrogen atom, $R^{3c}$ represents a trifluoromethyl group, T represents a substituent indicated in any of [Table 1A] to [Table 6A] (hereinafter, referred to as "compound group SX821").

The compound (L-55), wherein $R^{3b}$ and $R^{4c}$ represent a hydrogen atom, $R^{3c}$ represents a bromine atom, T represents a substituent indicated in any of [Table 1A] to [Table 6A](hereinafter, referred to as "compound group SX822").

The compound (L-55), wherein $R^{3b}$ and $R^{3c}$ represent a hydrogen atom, $R^{4c}$ represents a chlorine atom, T represents a substituent indicated in any of [Table 1A] to [Table 6A](hereinafter, referred to as "compound group SX823").

The compound (L-55), wherein $R^{3b}$ represents a trifluoromethyl group, $R^{3c}$ represents a hydrogen atom, $R^4$, represents a chlorine atom, T represents a substituent indicated in any of [Table 1A] to [Table 6A] (hereinafter, referred to as "compound group SX824").

The compound (L-55), wherein $R^{3b}$ represents a bromine atom, $R^{3c}$ represents a hydrogen atom, $R^{4c}$ represents a chlorine atom, T represents a substituent indicated in any of [Table 1A] to [Table 6A] (hereinafter, referred to as "compound group SX825").

The compound (L-55), wherein $R^{3b}$ represents a hydrogen atom, $R^{3c}$ represents a trifluoromethyl group, $R^{4c}$ represents a chlorine atom, T represents a substituent indicated in any of [Table 1A] to [Table 6A] (hereinafter, referred to as "compound group SX826").

The compound (L-55), wherein $R^{3b}$ represents a hydrogen atom, $R^{3c}$ represents a bromine atom, $R^{4c}$ represents a chlorine atom, T represents a substituent indicated in any of [Table 1A] to [Table 6A] (hereinafter, referred to as "compound group SX827").

A compound represented by formula (L-56):

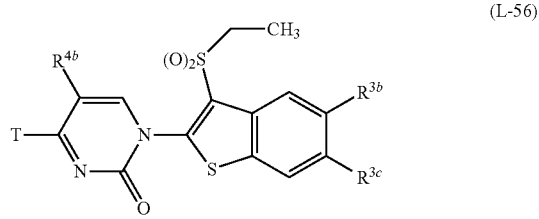

(L-56)

(hereinafter, referred to as "compound (L-56)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX828").

The compound (L-56), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX829").

The compound (L-56), wherein $R^{3b}$ represents a bromine atom, $R^{3c}$ and $R^{4b}$ represent a hydrogen atom, T represents a substituent indicated in any of [Table 1A] to [Table 6A](hereinafter, referred to as "compound group SX830").

The compound (L-56), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX831").

The compound (L-56), wherein $R^{3b}$ and $R^{4b}$ represent a hydrogen atom, $R^{3c}$ represents a bromine atom, T represents a substituent indicated in any of [Table 1A] to [Table 6A](hereinafter, referred to as "compound group SX832").

The compound (L-56), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX833").

The compound (L-56), wherein $R^{3b}$ represents a trifluoromethyl group, $R^{3c}$ represents a hydrogen atom, $R^{4b}$ represents a chlorine atom, T represents a substituent indicated in any of [Table 1A] to [Table 6A] (hereinafter, referred to as "compound group SX834").

The compound (L-56), wherein $R^{3b}$ represents a bromine atom, $R^{3c}$ represents a hydrogen atom, $R^{4b}$ represents a chlorine atom, T represents a substituent indicated in any of [Table 1A] to [Table 6A] (hereinafter, referred to as "compound group SX835").

The compound (L-56), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX836").

The compound (L-56), wherein $R^{3b}$ represents a hydrogen atom, $R^{3c}$ represents a bromine atom, $R^{4b}$ represents a chlorine atom, T represents a substituent indicated in any of [Table 1A] to [Table 6A] (hereinafter, referred to as "compound group SX837").

A compound represented by formula (L-57):

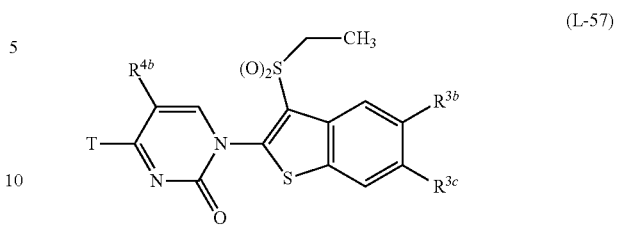

(L-57)

(hereinafter, referred to as "compound (L-57)"), wherein $R^{3b}$, $R^{3c}$, and $R^{4b}$ represent a hydrogen atom, T represents a substituent indicated in any of [Table 1A] to [Table 6A] (hereinafter, referred to as "compound group SX838").

The compound (L-57), wherein $R^{3b}$ represents a trifluoromethyl group, $R^{3c}$ and $R^{4b}$ represent a hydrogen atom, T represents a substituent indicated in any of [Table 1A] to [Table 6A] (hereinafter, referred to as "compound group SX839").

The compound (L-57), wherein $R^{3b}$ represents a bromine atom, $R^{3c}$ and $R^{4b}$ represent a hydrogen atom, T represents a substituent indicated in any of [Table 1A] to [Table 6A](hereinafter, referred to as "compound group SX840").

The compound (L-57), wherein $R^{3b}$ and $R^{4b}$ represent a hydrogen atom, $R^{3c}$ represents a trifluoromethyl group, T represents a substituent indicated in any of [Table 1A] to [Table 6A] (hereinafter, referred to as "compound group SX841").

The compound (L-57), wherein $R^{3b}$ and $R^{4b}$ represent a hydrogen atom, $R^{3c}$ represents a bromine atom, T represents a substituent indicated in any of [Table 1A] to [Table 6A](hereinafter, referred to as "compound group SX842").

The compound (L-57), wherein $R^{3b}$ and $R^{3c}$ represent a hydrogen atom, $R^{4b}$ represents a chlorine atom, T represents a substituent indicated in any of [Table 1A] to [Table 6A](hereinafter, referred to as "compound group SX843").

The compound (L-57), wherein $R^{3b}$ represents a trifluoromethyl group, RC represents a hydrogen atom, $R^{4b}$ represents a chlorine atom, T represents a substituent indicated in any of [Table 1A] to [Table 6A] (hereinafter, referred to as "compound group SX844").

The compound (L-57), wherein $R^{3b}$ represents a bromine atom, $R^{3c}$ represents a hydrogen atom, $R^{4b}$ represents a chlorine atom, T represents a substituent indicated in any of [Table 1A] to [Table 6A] (hereinafter, referred to as "compound group SX845").

The compound (L-57), wherein $R^{3b}$ represents a hydrogen atom, $R^{3c}$ represents a trifluoromethyl group, $R^{4b}$ represents a chlorine atom, T represents a substituent indicated in any of [Table 1A] to [Table 6A] (hereinafter, referred to as "compound group SX846").

The compound (L-57), wherein $R^{3b}$ represents a hydrogen atom, $R^{3c}$ represents a bromine atom, $R^{4b}$ represents a chlorine atom, T represents a substituent indicated in any of [Table 1A] to [Table 6A] (hereinafter, referred to as "compound group SX847").

A compound represented by formula (L-58):

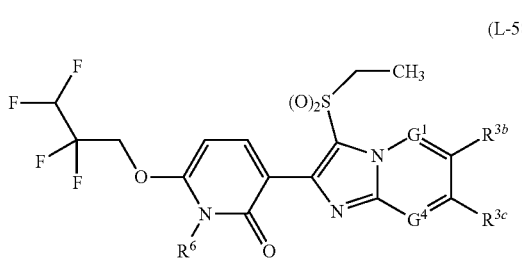

(hereinafter, referred to as "compound (L-58)"), wherein $G^1$ and $G^4$ represent CH, $R^6$ represents a methyl group, $R^{3b}$ represents a hydrogen atom, $R^{3b}$ represents a substituent indicated in any of [Table 7A] to [Table 15A] (hereinafter, referred to as "compound group SX848").

TABLE 7A

Cl
Br
I
Me
Et
Pr
i-Pr
c-Pr
1-CN-c-Pr
OMe
OEt
OPr
Oi-Pr
CN
C(O)OEt
CH=N—OH
CH=N—OMe
CH=N—OEt
CH=N—OCH$_2$CF$_3$
CMe=N—OH
CMe=N—OMe
CMe=N—OEt
CMe=N—OCH$_2$CF$_3$
C(NH$_2$)=N—OCH$_2$CF$_3$

TABLE 8A

Ph
2-F—Ph
3-F—Ph
4-F—Ph
3-Cl—Ph
4-Cl—Ph
3-CF$_3$—Ph
4-CF$_3$—Ph
3-NMe$_2$—Ph
4-NMe$_2$—Ph
3-CN—Ph
4-CN—Ph
4-C(O)NMe$_2$—Ph
4-NHC(O)Me—Ph
3,4-F$_2$—Ph
3,5-F$_2$—Ph
2,4-F$_2$—Ph
3,4,5-F$_3$—Ph
3,4-Cl$_2$—Ph
3,5-Cl$_2$—Ph
3,5-Cl$_2$-4-F—Ph
OPh
O-2-F—Ph
NH$_2$
NHCH$_2$CF$_3$

TABLE 9A

Py2
4-F-Py2
4-F-Py2
6-F-Py2
4-Cl-Py2
5-Cl-Py2
4-CF$_3$-Py2
5-CF$_3$-Py2
3-Me-Py2
4-Me-Py2
5-Me-Py2
6-Me-Py2
5-CN-Py2
5-OCH$_2$CF$_2$CF$_3$-Py2
3,5-F$_2$-Py2
Py3
6-CF$_3$-Py3
5-CF$_3$-Py3
6-F-Py3
6-Cl-Py3
Py4
OPy2
OPy3
NHC(O)c-Pr
NMeC(O)c-Pr

TABLE 10A

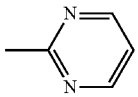

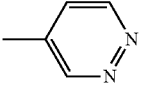

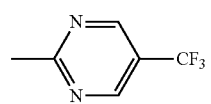

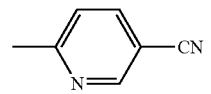

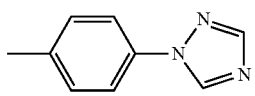

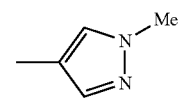

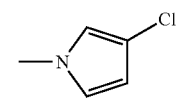

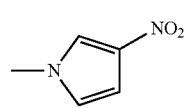

TABLE 11A
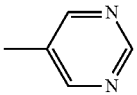
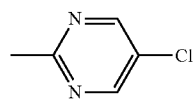
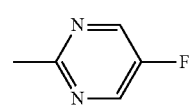
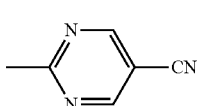
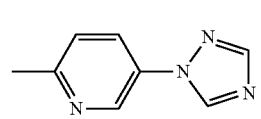
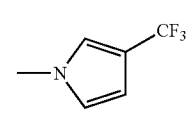
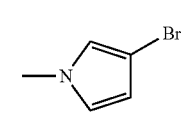
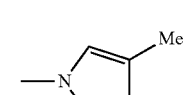
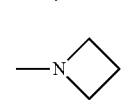
TABLE 12A
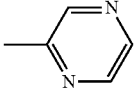
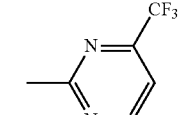
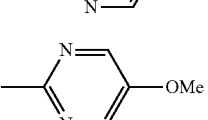
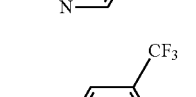
TABLE 12A-continued
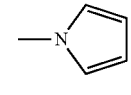
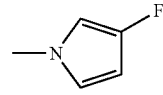
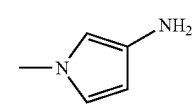
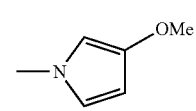
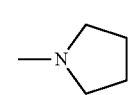
TABLE 13A
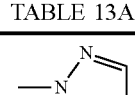
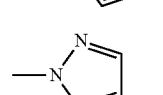
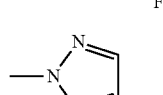
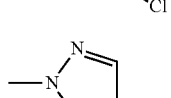
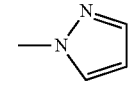
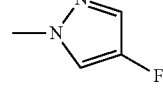
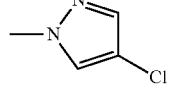
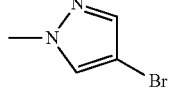
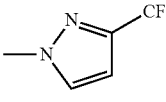

TABLE 13A-continued

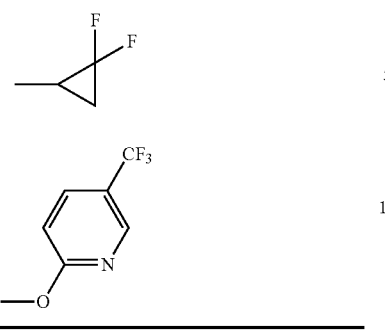

TABLE 14A

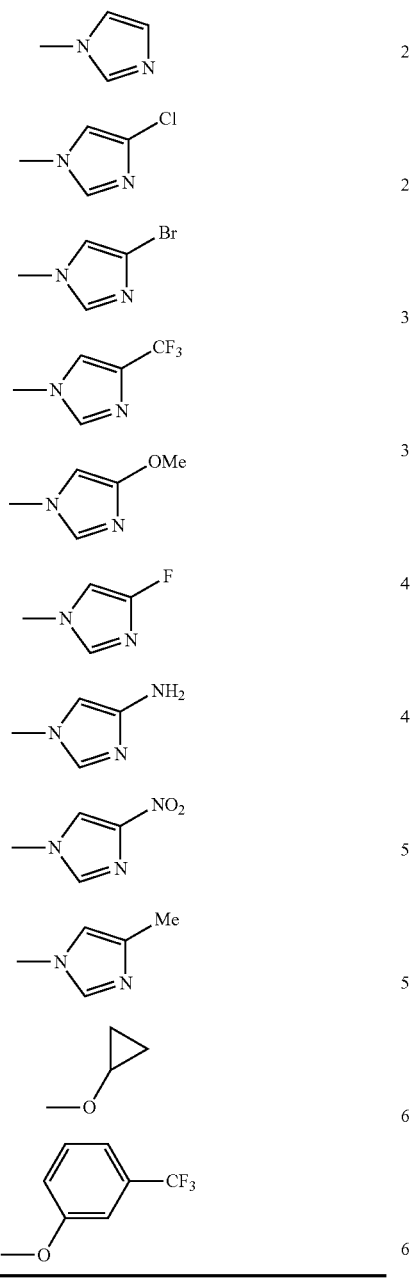

TABLE 15A

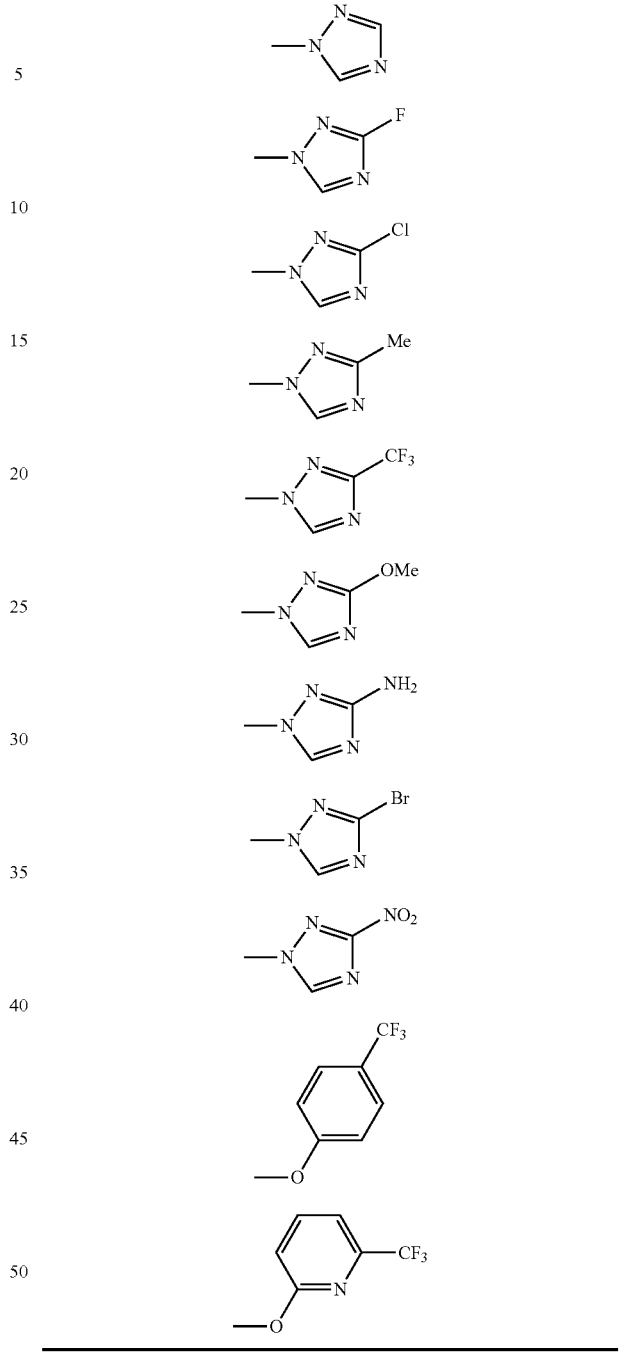

The compound (L-58), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX849").

The compound (L-58), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX850").

The compound (L-58), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX851").

The compound (L-58), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX852").

The compound (L-58), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX853").

The compound (L-58), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX854").

The compound (L-58), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX855").

The compound (L-58), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX856").

The compound (L-58), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX857").

The compound (L-58), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX858").

The compound (L-58), wherein $G^1$ represents CH, $G^4$ represents a nitrogen atom, $R^{3b}$ represents a hydrogen atom, $R^6$ represents an ethyl group, $R^{2'}$ represents a substituent indicated in any of [Table 7A] to [Table 15A] (hereinafter, referred to as "compound group SX859").

The compound (L-58), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX860").

The compound (L-58), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX861").

The compound (L-58), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX862").

The compound (L-58), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX863").

The compound (L-58), wherein $G^1$ represents CH, $G^4$ represents a nitrogen atom, $R^{3c}$ represents a hydrogen atom, $R^6$ represents an ethyl group, $R^{2b}$ represents a substituent indicated in any of [Table 7A] to [Table 15A] (hereinafter, referred to as "compound group SX864").

The compound (L-58), wherein $G^1$ represents CH, $G^4$ represents a nitrogen atom, $R^{3c}$ represents a hydrogen atom, $R^6$ represents a propyl group, $R^{2b}$ represents a substituent indicated in any of [Table 7A] to [Table 15A] (hereinafter, referred to as "compound group SX865").

The compound (L-58), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX866").

The compound (L-58), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX867").

The compound (L-58), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX868").

The compound (L-58), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX869").

The compound (L-58), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX870").

The compound (L-58), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX871").

The compound (L-58), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX872").

The compound (L-58), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX873").

The compound (L-58), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX874").

The compound (L-58), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX875").

The compound (L-58), wherein $G^1$ represents a nitrogen atom, $G^4$ represents CH, $R^{3c}$ represents a hydrogen atom, $R^5$ represents an isopropyl group, $R^{3b}$ represents a substituent indicated in any of [Table 7A] to [Table 15A] (hereinafter, referred to as "compound group SX876").

The compound (L-58), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX877").

A compound represented by formula (L-59):

(L-59)

(hereinafter, referred to as "compound (L-59)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX878").

The compound (L-59), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX879").

The compound (L-59), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX880").

The compound (L-59), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX881").

The compound (L-59), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX882").

The compound (L-59), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX883").

The compound (L-59), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX884").

The compound (L-59), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX885").

The compound (L-59), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX886").

The compound (L-59), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX887").

The compound (L-59), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX888").

The compound (L-59), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX889").

The compound (L-59), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX890").

The compound (L-59), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX891").

The compound (L-59), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX892").

The compound (L-59), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX893").

The compound (L-59), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX894").

The compound (L-59), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX895").

The compound (L-59), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX896").

The compound (L-59), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX897").

The compound (L-59), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX898").

The compound (L-59), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX899").

The compound (L-59), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX900").

The compound (L-59), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX901").

The compound (L-59), wherein G¹ represents a nitrogen atom, G⁴ represents CH, R³ᵇ represents a hydrogen atom, R⁶ represents a cyclopropyl group, R³ᶜ represents a substituent indicated in any of [Table 7A] to [Table 15A](hereinafter, referred to as "compound group SX902").

The compound (L-59), wherein G¹ represents a nitrogen atom, G⁴ represents CH, R³ᶜ represents a hydrogen atom, R⁶ represents a methyl group, R³ᵇ represents a substituent indicated in any of [Table 7A] to [Table 15A] (hereinafter, referred to as "compound group SX903").

The compound (L-59), wherein G¹ represents a nitrogen atom, G⁴ represents CH, R³ᶜ represents a hydrogen atom, R⁶ represents an ethyl group, R³ᵇ represents a substituent indicated in any of [Table 7A] to [Table 15A] (hereinafter, referred to as "compound group SX904").

The compound (L-59), wherein G¹ represents a nitrogen atom, G⁴ represents CH, R³ᶜ represents a hydrogen atom, R⁶ represents a propyl group, R³ᵇ represents a substituent indicated in any of [Table 7A] to [Table 15A] (hereinafter, referred to as "compound group SX905").

The compound (L-59), wherein G¹ represents a nitrogen atom, G⁴ represents CH, R³ᶜ represents a hydrogen atom, R⁶ represents an isopropyl group, R³ᵇ represents a substituent indicated in any of [Table 7A] to [Table 15A] (hereinafter, referred to as "compound group SX906").

The compound (L-59), wherein G¹ represents a nitrogen atom, G⁴ represents CH, R³ᶜ represents a hydrogen atom, R⁶ represents a cyclopropyl group, R³ᵇ represents a substituent indicated in any of [Table 7A] to [Table 15A](hereinafter, referred to as "compound group SX907").

A compound represented by formula (L-60):

(L-60)

(hereinafter, referred to as "compound (L-60)"), wherein G¹ and G⁴ represent CH, R⁶ represents a methyl group, R³ᵇ represents a hydrogen atom, R³ᶜ represents a substituent indicated in any of [Table 7A] to [Table 15A] (hereinafter, referred to as "compound group SX908").

The compound (L-60), wherein G¹ and G⁴ represent CH, R³ᵇ represents a hydrogen atom, R⁶ represents an ethyl group, R³ᶜ represents a substituent indicated in any of [Table 7A] to [Table 15A] (hereinafter, referred to as "compound group SX909").

The compound (L-60), wherein G¹ and G⁴ represent CH, R³ᵇ represents a hydrogen atom, R⁶ represents a propyl group, R³ᶜ represents a substituent indicated in any of [Table 7A] to [Table 15A] (hereinafter, referred to as "compound group SX910").

The compound (L-60), wherein G¹ and G⁴ represent CH, R³ᵇ represents a hydrogen atom, R⁶ represents an isopropyl group, R³ᶜ represents a substituent indicated in any of [Table 7A] to [Table 15A] (hereinafter, referred to as "compound group SX911").

The compound (L-60), wherein G¹ and G⁴ represent CH, R³ᵇ represents a hydrogen atom, R⁶ represents a cyclopropyl group, R³ᶜ represents a substituent indicated in any of [Table 7A] to [Table 15A] (hereinafter, referred to as "compound group SX912").

The compound (L-60), wherein G¹ and G⁴ represent CH, R³ᶜ represents a hydrogen atom, R⁶ represents a methyl group, R³ᵇ represents a substituent indicated in any of [Table 7A] to [Table 15A] (hereinafter, referred to as "compound group SX913").

The compound (L-60), wherein G¹ and G⁴ represent CH, R³ᶜ represents a hydrogen atom, R⁶ represents an ethyl group, R³ᵇ represents a substituent indicated in any of [Table 7A] to [Table 15A] (hereinafter, referred to as "compound group SX914").

The compound (L-60), wherein G¹ and G⁴ represent CH, R³ᶜ represents a hydrogen atom, R⁶ represents a propyl group, R³ᵇ represents a substituent indicated in any of [Table 7A] to [Table 15A] (hereinafter, referred to as "compound group SX915").

The compound (L-60), wherein G¹ and G⁴ represent CH, R³ᶜ represents a hydrogen atom, R⁶ represents an isopropyl group, R³ᵇ represents a substituent indicated in any of [Table 7A] to [Table 15A] (hereinafter, referred to as "compound group SX916").

The compound (L-60), wherein G¹ and G⁴ represent CH, R³ᶜ represents a hydrogen atom, R⁶ represents a cyclopropyl group, R³ᵇ represents a substituent indicated in any of [Table 7A] to [Table 15A] (hereinafter, referred to as "compound group SX917").

The compound (L-60), wherein G¹ represents CH, G⁴ represents a nitrogen atom, R³ᵇ represents a hydrogen atom, R⁶ represents a methyl group, R³ᶜ represents a substituent indicated in any of [Table 7A] to [Table 15A] (hereinafter, referred to as "compound group SX918").

The compound (L-60), wherein G¹ represents CH, G⁴ represents a nitrogen atom, R³ᵇ represents a hydrogen atom, R⁶ represents an ethyl group, R³ᶜ represents a substituent indicated in any of [Table 7A] to [Table 15A] (hereinafter, referred to as "compound group SX919").

The compound (L-60), wherein G¹ represents CH, G⁴ represents a nitrogen atom, R³ᵇ represents a hydrogen atom, R⁶ represents a propyl group, R³ᶜ represents a substituent indicated in any of [Table 7A] to [Table 15A] (hereinafter, referred to as "compound group SX920").

The compound (L-60), wherein G¹ represents CH, G⁴ represents a nitrogen atom, R³ᵇ represents a hydrogen atom, R⁶ represents an isopropyl group, R³ᶜ represents a substituent indicated in any of [Table 7A] to [Table 15A](hereinafter, referred to as "compound group SX921").

The compound (L-60), wherein G¹ represents CH, G⁴ represents a nitrogen atom, R³ᵇ represents a hydrogen atom, R⁶ represents a cyclopropyl group, R³ᶜ represents a substituent indicated in any of [Table 7A] to [Table 15A](hereinafter, referred to as "compound group SX922").

The compound (L-60), wherein G¹ represents CH, G⁴ represents a nitrogen atom, R³ᶜ represents a hydrogen atom, R⁶ represents a methyl group, R³ᵇ represents a substituent indicated in any of [Table 7A] to [Table 15A] (hereinafter, referred to as "compound group SX923").

The compound (L-60), wherein G¹ represents CH, G⁴ represents a nitrogen atom, R³ᶜ represents a hydrogen atom, R⁶ represents an ethyl group, R³ᵇ represents a substituent indicated in any of [Table 7A] to [Table 15A] (hereinafter, referred to as "compound group SX924").

The compound (L-60), wherein G¹ represents CH, G⁴ represents a nitrogen atom, R³ᶜ represents a hydrogen atom, R⁶ represents a propyl group, R³ᵇ represents a substituent indicated in any of [Table 7A] to [Table 15A] (hereinafter, referred to as "compound group SX925").

The compound (L-60), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX926").

The compound (L-60), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX927").

The compound (L-60), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX928").

The compound (L-60), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX929").

The compound (L-60), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX930").

The compound (L-60), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX931").

The compound (L-60), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX932").

The compound (L-60), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX933").

The compound (L-60), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX934").

The compound (L-60), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX935").

The compound (L-60), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX936").

The compound (L-60), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX937").

A compound represented by formula (L-61):

$$(L-61)$$

(hereinafter, referred to as "compound (L-61)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX938").

The compound (L-61), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX939").

The compound (L-61), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX940").

The compound (L-61), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX941").

The compound (L-61), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX942").

The compound (L-61), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX943").

The compound (L-61), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX944").

The compound (L-61), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX945").

The compound (L-61), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX946").

The compound (L-61), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX947").

The compound (L-61), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX948").

The compound (L-61), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX949").

The compound (L-61), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX950").

The compound (L-61), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX951").

The compound (L-61), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX952").

The compound (L-61), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX953").

The compound (L-61), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX954").

The compound (L-61), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX955").

The compound (L-61), wherein $G^1$ represents CH, $G^4$ represents a nitrogen atom, $R^{3c}$ represents a hydrogen atom, $R^6$ represents an isopropyl group, $R^3$ represents a substituent indicated in any of [Table 7A] to [Table 15A](hereinafter, referred to as "compound group SX956").

The compound (L-61), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX957").

The compound (L-61), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX958").

The compound (L-61), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX959").

The compound (L-61), wherein $G^1$ represents a nitrogen atom, $G^4$ represents CH, $R^3$ represents a hydrogen atom, $R^6$ represents a propyl group, $R^{3c}$ represents a substituent indicated in any of [Table 7A] to [Table 15A] (hereinafter, referred to as "compound group SX960").

The compound (L-61), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX961").

The compound (L-61), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX962").

The compound (L-61), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX963").

The compound (L-61), wherein $G^1$ represents a nitrogen atom, $G^4$ represents CH, $R^{3c}$ represents a hydrogen atom, R represents an ethyl group, $R^{3b}$ represents a substituent indicated in any of [Table 7A] to [Table 15A] (hereinafter, referred to as "compound group SX964").

The compound (L-61), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX965").

The compound (L-61), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX966").

The compound (L-61), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX967").

A compound represented by formula (L-62):

(hereinafter, referred to as "compound (L-62)"), wherein $G^1$ and $G^4$ represent CH, $R^{3b}$ represents a hydrogen atom, $R^3$ represents a substituent indicated in any of [Table 7A] to [Table 15A] (hereinafter, referred to as "compound group SX968").

The compound (L-62), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX969").

The compound (L-62), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX970").

The compound (L-62), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX971").

The compound (L-62), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX972").

The compound (L-62), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX973").

A compound represented by formula (L-63):

(L-63)

(hereinafter, referred to as "compound (L-63)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX974").

The compound (L-63), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX975").

The compound (L-63), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX976").

The compound (L-63), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX977").

The compound (L-63), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX978").

The compound (L-63), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX979").

A compound represented by formula (L-64):

(L-64)

(hereinafter, referred to as "compound (L-64)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX980").

The compound (L-64), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX981").

The compound (L-64), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX982").

The compound (L-64), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX983").

The compound (L-64), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX984").

The compound (L-64), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX985").

The compound (L-64), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX986").

The compound (L-64), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX987").

The compound (L-64), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX988").

The compound (L-64), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX989").

The compound (L-64), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX990").

The compound (L-64), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX991").

The compound (L-64), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX992").

The compound (L-64), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX993").

The compound (L-64), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX994").

The compound (L-64), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX995").

The compound (L-64), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX996").

The compound (L-64), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX997").

The compound (L-64), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX998").

The compound (L-64), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX999").

The compound (L-64), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1000").

The compound (L-64), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1001").

The compound (L-64), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1002").

The compound (L-64), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1003").

The compound (L-64), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1004").

The compound (L-64), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1005").

The compound (L-64), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1006").

The compound (L-64), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1007").

The compound (L-64), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1008").

The compound (L-64), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1009"). WO 2019/124548

A compound represented by formula (L-65):

(L-65)

(hereinafter, referred to as "compound (L-65)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1010").

The compound (L-65), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1011").

The compound (L-65), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1012").

The compound (L-65), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1013").

The compound (L-65), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1014").

The compound (L-65), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1015").

The compound (L-65), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1016").

The compound (L-65), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1017").

The compound (L-65), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1018").

The compound (L-65), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1019").

The compound (L-65), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1020").

The compound (L-65), wherein $G^1$ represents CH, $G^4$ represents a nitrogen atom, $R^{3b}$ represents a hydrogen atom, $R^6$ represents an ethyl group, $R^{2'}$ represents a substituent indicated in any of [Table 7A] to [Table 15A] (hereinafter, referred to as "compound group SX1021").

The compound (L-65), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1022").

The compound (L-65), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1023").

The compound (L-65), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1024").

The compound (L-65), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1025").

The compound (L-65), wherein $G^1$ represents CH, $G^4$ represents a nitrogen atom, $R^{3c}$ represents a hydrogen atom, $R^6$ represents an ethyl group, $R^{2b}$ represents a substituent indicated in any of [Table 7A] to [Table 15A] (hereinafter, referred to as "compound group SX1026").

The compound (L-65), wherein $G^1$ represents CH, $G^4$ represents a nitrogen atom, $R^{3c}$ represents a hydrogen atom, $R^6$ represents a propyl group, $R^{2b}$ represents a substituent indicated in any of [Table 7A] to [Table 15A] (hereinafter, referred to as "compound group SX1027").

The compound (L-65), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1028").

The compound (L-65), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1029").

The compound (L-65), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1030").

The compound (L-65), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1031").

The compound (L-65), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1032").

The compound (L-65), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1033").

The compound (L-65), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1034").

The compound (L-65), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1035").

The compound (L-65), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1036").

The compound (L-65), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1037").

The compound (L-65), wherein $G^1$ represents a nitrogen atom, $G^4$ represents CH, $R^{3c}$ represents a hydrogen atom, $R^5$ represents an isopropyl group, $R^{3b}$ represents a substituent indicated in any of [Table 7A] to [Table 15A] (hereinafter, referred to as "compound group SX1038").

The compound (L-65), wherein $G^1$ represents a nitrogen atom, $G^4$ represents CH, $R^{3c}$ represents a hydrogen atom, Re represents a cyclopropyl group, $R^{3b}$ represents a substituent indicated in any of [Table 7A] to [Table 15A](hereinafter, referred to as "compound group SX1039").

A compound represented by formula (L-66):

(L-66)

(hereinafter, referred to as "compound (L-66)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1040").

The compound (L-66), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1041").

The compound (L-66), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1042").

The compound (L-66), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1043").

The compound (L-66), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1044").

The compound (L-66), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1045").

The compound (L-66), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1046").

The compound (L-66), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1047").

The compound (L-66), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1048").

The compound (L-66), wherein $G^1$ and $G^4$ represent CH, $R^3$ represents a hydrogen atom, $R^6$ represents a cyclopropyl group, $R^{3b}$ represents a substituent indicated in any of [Table 7A] to [Table 15A] (hereinafter, referred to as "compound group SX1049").

The compound (L-66), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1050").

The compound (L-66), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1051").

The compound (L-66), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1052").

The compound (L-66), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1053").

The compound (L-66), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1054").

The compound (L-66), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1055").

The compound (L-66), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1056").

The compound (L-66), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1057").

The compound (L-66), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1058").

The compound (L-66), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1059").

The compound (L-66), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1060").

The compound (L-66), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1061").

The compound (L-66), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1062").

The compound (L-66), wherein $G^1$ represents a nitrogen atom, $G^4$ represents CH, $R^{2b}$ represents a hydrogen atom, $R^6$ represents an isopropyl group, $R^{3c}$ represents a substituent indicated in any of [Table 7A] to [Table 15A] (hereinafter, referred to as "compound group SX1063").

The compound (L-66), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1064").

The compound (L-66), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1065").

The compound (L-66), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1066").

The compound (L-66), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1067").

The compound (L-66), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1068").

The compound (L-66), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1069").

A compound represented by formula (L-67):

(L-67)

[Chemical structure]

(hereinafter, referred to as "compound (L-67)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1070").

The compound (L-67), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1071").

The compound (L-67), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1072").

The compound (L-67), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1073").

The compound (L-67), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1074").

The compound (L-67), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1075").

The compound (L-67), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1076").

The compound (L-67), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1077").

The compound (L-67), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1078").

The compound (L-67), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1079").

The compound (L-67), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1080").

The compound (L-67), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1081").

The compound (L-67), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1082").

The compound (L-67), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1083").

The compound (L-67), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1084").

The compound (L-67), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1085").

The compound (L-67), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1086").

The compound (L-67), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1087").

The compound (L-67), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1088").

The compound (L-67), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1089").

The compound (L-67), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1090").

The compound (L-67), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1091").

The compound (L-67), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1092").

The compound (L-67), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1093").

The compound (L-67), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1094").

The compound (L-67), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1095").

The compound (L-67), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1096").

The compound (L-67), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1097").

The compound (L-67), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1098").

The compound (L-67), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1099").

A compound represented by formula (L-68):

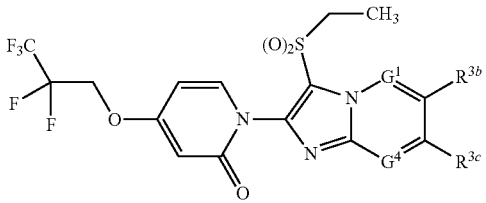

(L-68)

(hereinafter, referred to as "compound (L-68)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1100").

The compound (L-68), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1101").

The compound (L-68), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1102").

The compound (L-68), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1103").

The compound (L-68), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1104").

The compound (L-68), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1105").

A compound represented by formula (L-69):

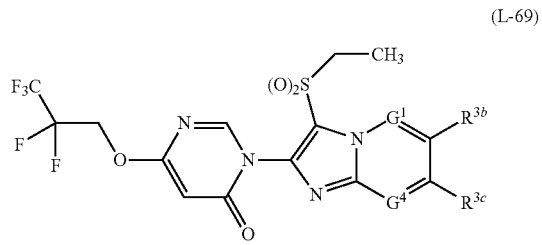

(L-69)

(hereinafter, referred to as "compound (L-69)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1106").

The compound (L-69), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1107").

The compound (L-69), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1108").

The compound (L-69), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1109").

The compound (L-69), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1110").

The compound (L-69), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1111").

A compound represented by formula (L-70):

$$\text{(L-70)}$$

(hereinafter, referred to as "compound (L-70)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1112").

The compound (L-70), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1113").

The compound (L-70), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1114").

The compound (L-70), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1115").

The compound (L-70), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1116").

The compound (L-70), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1117").

The compound (L-70), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1118").

The compound (L-70), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1119").

The compound (L-70), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1120").

The compound (L-70), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1121").

The compound (L-70), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1122").

The compound (L-70), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1123").

The compound (L-70), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1124").

The compound (L-70), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1125").

The compound (L-70), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1126").

The compound (L-70), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1127").

The compound (L-70), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1128").

The compound (L-70), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1129").

The compound (L-70), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1130").

The compound (L-70), wherein $G^1$ represents CH, $G^4$ represents a nitrogen atom, $R^{3c}$ represents a hydrogen atom, $R^6$ represents a cyclopropyl group, $R^3$ represents a substituent indicated in any of [Table 7A] to [Table 15A](hereinafter, referred to as "compound group SX1131").

The compound (L-70), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1132").

The compound (L-70), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1133").

The compound (L-70), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1134").

The compound (L-70), wherein $G^1$ represents a nitrogen atom, $G^4$ represents CH, $R^3$ represents a hydrogen atom, $R^6$ represents an isopropyl group, $R^{3c}$ represents a substituent indicated in any of [Table 7A] to [Table 15A] (hereinafter, referred to as "compound group SX1135").

The compound (L-70), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1136").

The compound (L-70), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1137").

The compound (L-70), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1138").

The compound (L-70), wherein $G^1$ represents a nitrogen atom, $G^4$ represents CH, $R^{3c}$ represents a hydrogen atom, R represents a propyl group, $R^{3b}$ represents a substituent indicated in any of [Table 7A] to [Table 15A] (hereinafter, referred to as "compound group SX1139").

The compound (L-70), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1140").

The compound (L-70), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1141").

A compound represented by formula (L-71):

(L-71)

(hereinafter, referred to as "compound (L-71)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1142").

The compound (L-71), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1143").

The compound (L-71), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1144").

The compound (L-71), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1145").

The compound (L-71), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1146").

The compound (L-71), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1147").

The compound (L-71), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1148").

The compound (L-71), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1149").

The compound (L-71), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1150").

The compound (L-71), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1151").

The compound (L-71), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1152").

The compound (L-71), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1153").

The compound (L-71), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1154").

The compound (L-71), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1155").

The compound (L-71), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1156").

The compound (L-71), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1157").

The compound (L-71), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1158").

The compound (L-71), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1159").

The compound (L-71), wherein $G^1$ represents CH, $G^4$ represents a nitrogen atom, $R^{3c}$ represents a hydrogen atom,

245

$R^6$ represents an isopropyl group, $R^{3b}$ represents a substituent indicated in any of [Table 7A] to [Table 15A](hereinafter, referred to as "compound group SX1160").

The compound (L-71), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1161").

The compound (L-71), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1162").

The compound (L-71), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1163").

The compound (L-71), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1164").

The compound (L-71), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1165").

The compound (L-71), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1166").

The compound (L-71), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1167").

The compound (L-71), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1168").

The compound (L-71), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1169").

The compound (L-71), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1170").

The compound (L-71), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1171").

246

A compound represented by formula (L-72):

(L-72)

(hereinafter, referred to as "compound (L-72)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1172").

The compound (L-72), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1173").

The compound (L-72), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1174").

The compound (L-72), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1175").

The compound (L-72), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1176").

The compound (L-72), wherein $G^1$ and $G^4$ represent CH, $R^{3c}$ represents a hydrogen atom, $R^6$ represents a methyl group, $R^{3c}$ represents a substituent indicated in any of [Table 7A] to [Table 15A] (hereinafter, referred to as "compound group SX1177").

The compound (L-72), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1178").

The compound (L-72), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1179").

The compound (L-72), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1180").

The compound (L-72), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1181").

The compound (L-72), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1182").

The compound (L-72), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1183").

The compound (L-72), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1184").

The compound (L-72), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1185").

The compound (L-72), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1186").

The compound (L-72), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1187").

The compound (L-72), wherein $G^1$ represents CH, $G^4$ represents a nitrogen atom, $R^{3c}$ represents a hydrogen atom, $R^6$ represents an ethyl group, $R^{2b}$ represents a substituent indicated in any of [Table 7A] to [Table 15A] (hereinafter, referred to as "compound group SX1188").

The compound (L-72), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1189").

The compound (L-72), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1190").

The compound (L-72), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1191").

The compound (L-72), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1192").

The compound (L-72), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1193").

The compound (L-72), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1194").

The compound (L-72), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1195").

The compound (L-72), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1196").

The compound (L-72), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1197").

The compound (L-72), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1198").

The compound (L-72), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1199").

The compound (L-72), wherein $G^1$ represents a nitrogen atom, $G^4$ represents CH, $R^{3c}$ represents a hydrogen atom, $R^5$ represents an isopropyl group, $R^{3b}$ represents a substituent indicated in any of [Table 7A] to [Table 15A] (hereinafter, referred to as "compound group SX1200").

The compound (L-72), wherein $G^1$ represents a nitrogen atom, $G^4$ represents CH, $R^{3c}$ represents a hydrogen atom, Re represents a cyclopropyl group, $R^{3b}$ represents a substituent indicated in any of [Table 7A] to [Table 15A] (hereinafter, referred to as "compound group SX1201").

A compound represented by formula (L-73):

(L-73)

(hereinafter, referred to as "compound (L-73)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1202").

The compound (L-73), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1203").

The compound (L-73), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1204").

The compound (L-73), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1205").

The compound (L-73), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1206").

The compound (L-73), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1207").

The compound (L-73), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1208").

The compound (L-73), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1209").

The compound (L-73), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1210").

The compound (L-73), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1211").

The compound (L-73), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1212").

The compound (L-73), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1213").

The compound (L-73), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1214").

The compound (L-73), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1215").

The compound (L-73), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1216").

The compound (L-73), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1217").

The compound (L-73), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1218").

The compound (L-73), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1219").

The compound (L-73), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1220").

The compound (L-73), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1221").

The compound (L-73), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1222").

The compound (L-73), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1223").

The compound (L-73), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1224").

The compound (L-73), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1225").

The compound (L-73), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1226").

The compound (L-73), wherein $G^1$ represents a nitrogen atom, $G^4$ represents CH, $R^{3c}$ represents a hydrogen atom, Re represents a methyl group, $R^{3b}$ represents a substituent indicated in any of [Table 7A] to [Table 15A] (hereinafter, referred to as "compound group SX1227").

The compound (L-73), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1228").

The compound (L-73), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1229").

The compound (L-73), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1230").

The compound (L-73), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1231").

A compound represented by formula (L-7):

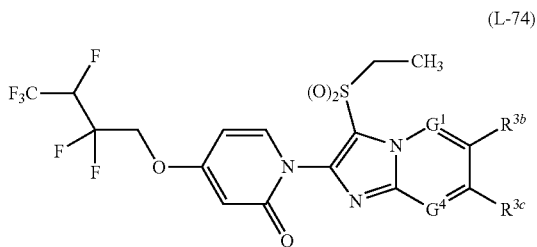

(hereinafter, referred to as "compound (L-74)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1232").

The compound (L-74), wherein $G^1$ and $G^4$ represent CH, $R^{3c}$ represent a hydrogen atom, $R^2$ represent a substituent indicated in any of [Table 7A] to [Table 15A] (hereinafter, referred to as "compound group SX1233").

The compound (L-74), wherein G represent CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1234").

The compound (L-74), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1235").

The compound (L-74), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1236").

The compound (L-74), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1237").

A compound represented by formula (L-75):

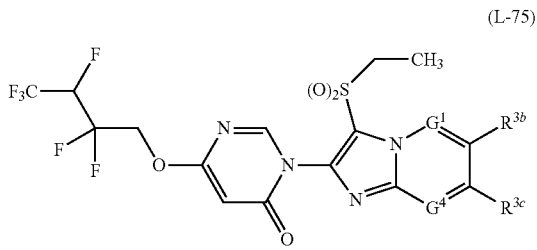

(hereinafter, referred to as "compound (L-75)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1238").

The compound (L-75), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1239").

The compound (L-75), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1240").

The compound (L-75), wherein $G^1$ represents CH, $G^4$ represents a nitrogen atom, $R^{3'}$ represents a hydrogen atom, $R^{3c}$ represents a substituent indicated in any of [Table 7A] to [Table 15A] (hereinafter, referred to as "compound group SX1241").

The compound (L-75), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1242").

The compound (L-75), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1243").

A compound represented by formula (L-76):

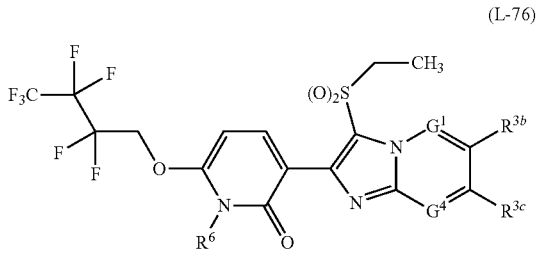

(hereinafter, referred to as "compound (L-76)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1244").

The compound (L-76), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1245").

The compound (L-76), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1246").

The compound (L-76), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1247").

The compound (L-76), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1248").

The compound (L-76), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1249").

The compound (L-76), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1250").

The compound (L-76), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1251").

The compound (L-76), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1252").

The compound (L-76), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1253").

The compound (L-76), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1254").

The compound (L-76), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1255").

The compound (L-76), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1256").

The compound (L-76), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1257").

The compound (L-76), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1258").

The compound (L-76), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1259").

The compound (L-76), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1260").

The compound (L-76), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1261").

The compound (L-76), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1262").

The compound (L-76), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1263").

The compound (L-76), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1264").

The compound (L-76), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1265").

The compound (L-76), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1266").

The compound (L-76), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1267").

The compound (L-76), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1268").

The compound (L-76), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1269").

The compound (L-76), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1270").

The compound (L-76), wherein $G^1$ represents a nitrogen atom, $G^4$ represents CH, $R^{3c}$ represents a hydrogen atom, $R^6$ represents a propyl group, $R^{2b}$ represents a substituent indicated in any of [Table 7A] to [Table 15A] (hereinafter, referred to as "compound group SX1271").

The compound (L-76), wherein $G^1$ represents a nitrogen atom, $G^4$ represents CH, $R^{3c}$ represents a hydrogen atom, R represents an isopropyl group, $R^{3b}$ represents a substituent indicated in any of [Table 7A] to [Table 15A] (hereinafter, referred to as "compound group SX1272").

The compound (L-76), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1273").

A compound represented by formula (L-77):

(L-77)

(hereinafter, referred to as "compound (L-77)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1274").

The compound (L-77), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1275").

The compound (L-77), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1276").

The compound (L-77), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1277").

The compound (L-77), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1278").

The compound (L-77), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1279").

The compound (L-77), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1280").

The compound (L-77), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1281").

The compound (L-77), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1282").

The compound (L-77), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1283").

The compound (L-77), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1284").

The compound (L-77), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1285").

The compound (L-77), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1286").

The compound (L-77), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1287").

The compound (L-77), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1288").

The compound (L-77), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1289").

The compound (L-77), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1290").

The compound (L-77), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1291").

The compound (L-77), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1292").

The compound (L-77), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1293").

The compound (L-77), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1294").

The compound (L-77), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1295").

The compound (L-77), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1296").

The compound (L-77), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1297").

The compound (L-77), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1298").

The compound (L-77), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1299").

The compound (L-77), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1300").

The compound (L-77), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1301").

The compound (L-77), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1302").

The compound (L-77), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1303").

A compound represented by formula (L-78):

(L-78)

[Chemical structure showing F₃C-CF₂-CF₂-CH₂-O- connected to a pyridone ring with R⁶-N, which connects to an imidazo-pyridine system bearing (O)₂S-CH₃, $G^1$, $R^{3b}$, $G^4$, $R^{3c}$]

(hereinafter, referred to as "compound (L-78)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1304").

The compound (L-78), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1305").

The compound (L-78), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1306").

The compound (L-78), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1307").

The compound (L-78), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1308").

The compound (L-78), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1309").

The compound (L-78), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1310").

The compound (L-78), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1311").

The compound (L-78), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1312").

The compound (L-78), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1313").

The compound (L-78), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1314").

The compound (L-78), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1315").

The compound (L-78), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1316").

The compound (L-78), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1317").

The compound (L-78), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1318").

The compound (L-78), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1319").

The compound (L-78), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1320").

The compound (L-78), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1321").

The compound (L-78), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1322").

The compound (L-78), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1323").

The compound (L-78), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1324").

The compound (L-78), wherein $G^1$ represents a nitrogen atom, $G^4$ represents CH, $R^3$ represents a hydrogen atom, $R^6$ represents an ethyl group, $R^{3c}$ represents a substituent indicated in any of [Table 7A] to [Table 15A] (hereinafter, referred to as "compound group SX1325").

The compound (L-78), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1326").

The compound (L-78), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1327").

The compound (L-78), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1328").

The compound (L-78), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1329").

The compound (L-78), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1330").

The compound (L-78), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1331").

The compound (L-78), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1332").

The compound (L-78), wherein $G^1$ represents a nitrogen atom, $G^4$ represents CH, $R^{3c}$ represents a hydrogen atom, $R^6$ represents a cyclopropyl group, $R^3$ represents a substituent indicated in any of [Table 7A] to [Table 15A](hereinafter, referred to as "compound group SX1333").

A compound represented by formula (L-79):

(L-79)

(hereinafter, referred to as "compound (L-79)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1334").

The compound (L-79), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1335").

The compound (L-79), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1336").

The compound (L-79), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1337").

The compound (L-79), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1338").

The compound (L-79), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1339").

The compound (L-79), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1340").

The compound (L-79), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1341").

The compound (L-79), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1342").

The compound (L-79), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1343").

The compound (L-79), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1344").

The compound (L-79), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1345").

The compound (L-79), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1346").

The compound (L-79), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1347").

The compound (L-79), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1348").

The compound (L-79), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1349").

The compound (L-79), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1350").

The compound (L-79), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1351").

The compound (L-79), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1352").

The compound (L-79), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1353").

The compound (L-79), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1354").

The compound (L-79), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1355").

The compound (L-79), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1356").

The compound (L-79), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1357").

The compound (L-79), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1358").

The compound (L-79), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1359").

The compound (L-79), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1360").

The compound (L-79), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1361").

The compound (L-79), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1362").

The compound (L-79), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1363").

A compound represented by formula (L-80):

(L-80)

(hereinafter, referred to as "compound (L-80)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1364").

The compound (L-80), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1365").

The compound (L-80), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1366").

The compound (L-80), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1367").

The compound (L-80), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1368").

The compound (L-80), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1369").

A compound represented by formula (L-81):

(L-81)

(hereinafter, referred to as "compound (L-81)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1370").

The compound (L-81), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1371").

The compound (L-81), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1372").

The compound (L-81), wherein $G^1$ represents CH, $G^4$ represents a nitrogen atom, $R^{3'}$ represents a hydrogen atom, $R^{3b}$ represents a substituent indicated in any of [Table 7A] to [Table 15A] (hereinafter, referred to as "compound group SX1373").

The compound (L-81), wherein $G^1$ represents a nitrogen atom, $G^4$ represents CH, $R^{3b}$ represents a hydrogen atom, $R^3$ represents a substituent indicated in any of [Table 7A] to [Table 15A] (hereinafter, referred to as "compound group SX1374").

The compound (L-81), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1375").

A compound represented by formula (L-82):

(L-82)

(hereinafter, referred to as "compound (L-82)"),
wherein wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1376").

The compound (L-82), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1377").

The compound (L-82), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1378").

The compound (L-82), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1379").

The compound (L-82), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1380").

The compound (L-82), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1381").

The compound (L-82), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1382").

The compound (L-82), wherein $G^1$ and $G^4$ represent CH, $R^{3c}$ represents a hydrogen atom, $R^5$ represents a propyl group, $R^{3b}$ represents a substituent indicated in any of [Table 7A] to [Table 15A] (hereinafter, referred to as "compound group SX1383").

The compound (L-82), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1384").

The compound (L-82), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1385").

The compound (L-82), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1386").

The compound (L-82), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1387").

The compound (L-82), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1388").

The compound (L-82), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1389").

The compound (L-82), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1390").

The compound (L-82), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1391").

The compound (L-82), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1392").

The compound (L-82), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1393").

The compound (L-82), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1394").

The compound (L-82), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1395").

The compound (L-82), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1396").

The compound (L-82), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1397").

The compound (L-82), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1398").

The compound (L-82), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1399").

The compound (L-82), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1400").

The compound (L-82), wherein $G^1$ represents a nitrogen atom, $G^4$ represents CH, $R^{3c}$ represents a hydrogen atom, $R^6$ represents a methyl group, $R^3$ represents a substituent indicated in any of [Table 7A] to [Table 15A] (hereinafter, referred to as "compound group SX1401").

The compound (L-82), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1402").

The compound (L-82), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1403").

The compound (L-82), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1404").

The compound (L-82), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1405").

A compound represented by formula (L-83):

(L-83)

(hereinafter, referred to as "compound (L-83)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1406").

The compound (L-83), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1407").

The compound (L-83), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1408").

The compound (L-83), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1409").

The compound (L-83), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1410").

The compound (L-83), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1411").

The compound (L-83), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1412").

The compound (L-83), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1413").

The compound (L-83), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1414").

The compound (L-83), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1415").

The compound (L-83), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1416").

The compound (L-83), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1417").

The compound (L-83), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1418").

The compound (L-83), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1419").

The compound (L-83), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1420").

The compound (L-83), wherein $G^1$ represents CH, $G^4$ represents a nitrogen atom, $R^{3c}$ represents a hydrogen atom, $R^6$ represents a methyl group, $R^{2b}$ represents a substituent indicated in any of [Table 7A] to [Table 15A] (hereinafter, referred to as "compound group SX1421").

The compound (L-83), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1422").

The compound (L-83), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1423").

The compound (L-83), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1424").

The compound (L-83), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1425").

The compound (L-83), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1426").

The compound (L-83), wherein $G^1$ represents a nitrogen atom, $G^4$ represents CH, $R^{3b}$ represents a hydrogen atom, Re represents an ethyl group, $R^{3c}$ represents a substituent indicated in any of [Table 7A] to [Table 15A] (hereinafter, referred to as "compound group SX1427").

The compound (L-83), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1428").

The compound (L-83), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1429").

The compound (L-83), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1430").

The compound (L-83), wherein $G^1$ represents a nitrogen atom, $G^4$ represents CH, $R^{3c}$ represents a hydrogen atom, $R^5$ represents a methyl group, $R^{3b}$ represents a substituent indicated in any of [Table 7A] to [Table 15A] (hereinafter, referred to as "compound group SX1431").

The compound (L-83), wherein $G^1$ represents a nitrogen atom, $G^4$ represents CH, $R^{3c}$ represents a hydrogen atom, Re represents an ethyl group, $R^{3b}$ represents a substituent indicated in any of [Table 7A] to [Table 15A] (hereinafter, referred to as "compound group SX1432").

The compound (L-83), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1433").

The compound (L-83), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1434").

The compound (L-83), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1435").

A compound represented by formula (L-84):

(L-84)

(hereinafter, referred to as "compound (L-84)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1436").

The compound (L-84), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1437").

The compound (L-84), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1438").

The compound (L-84), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1439").

The compound (L-84), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1440").

The compound (L-84), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1441").

The compound (L-84), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1442").

The compound (L-84), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1443").

The compound (L-84), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1444").

The compound (L-84), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1445").

The compound (L-84), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1446").

The compound (L-84), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1447").

The compound (L-84), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1448").

The compound (L-84), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1449").

The compound (L-84), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1450").

The compound (L-84), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1451").

The compound (L-84), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1452").

The compound (L-84), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1453").

The compound (L-84), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1454").

The compound (L-84), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1455").

The compound (L-84), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1456").

The compound (L-84), wherein $G^1$ represents a nitrogen atom, $G^4$ represents CH, $R^3$ represents a hydrogen atom, $R^6$ represents an ethyl group, $R^{3c}$ represents a substituent indicated in any of [Table 7A] to [Table 15A] (hereinafter, referred to as "compound group SX1457").

The compound (L-84), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1458").

The compound (L-84), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1459").

The compound (L-84), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1460").

The compound (L-84), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1461").

The compound (L-84), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1462").

The compound (L-84), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1463").

The compound (L-84), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1464").

The compound (L-84), wherein $G^1$ represents a nitrogen atom, $G^4$ represents CH, $R^{3c}$ represents a hydrogen atom, $R^5$ represents a cyclopropyl group, $R^3$ represents a substituent indicated in any of [Table 7A] to [Table 15A](hereinafter, referred to as "compound group SX1465").

A compound represented by formula (L-85):

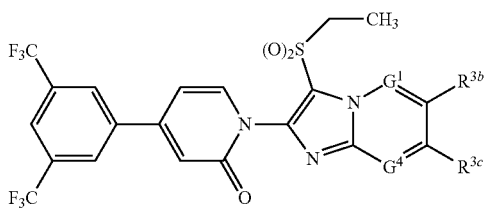

(L-85)

(hereinafter, referred to as "compound (L-85)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1466").

The compound (L-85), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1467").

The compound (L-85), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1468").

The compound (L-85), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1469").

The compound (L-85), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1470").

The compound (L-85), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1471").

A compound represented by formula (L-86):

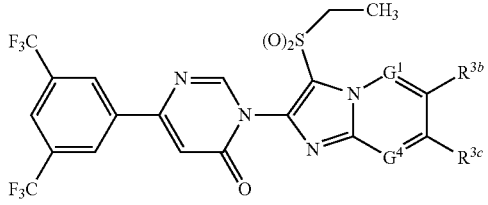

(L-86)

(hereinafter, referred to as "compound (L-86)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1472").

The compound (L-86), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1473").

The compound (L-86), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1474").

The compound (L-86), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1475").

The compound (L-86), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1476").

The compound (L-86), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1477").

A compound represented by formula (L-87):

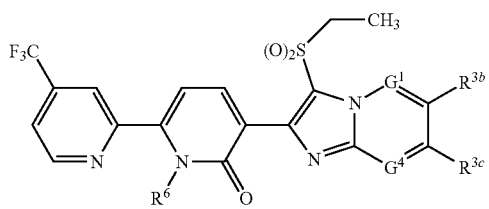

(L-87)

(hereinafter, referred to as "compound (L-87)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1478").

The compound (L-87), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1479").

The compound (L-87), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1480").

The compound (L-87), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1481").

The compound (L-87), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1482").

The compound (L-87), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1483").

The compound (L-87), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1484").

The compound (L-87), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1485").

The compound (L-87), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1486").

The compound (L-87), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1487").

The compound (L-87), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1488").

The compound (L-87), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1489").

The compound (L-87), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1490").

The compound (L-87), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1491").

The compound (L-87), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1492").

The compound (L-87), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1493").

The compound (L-87), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1494").

The compound (L-87), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1495").

The compound (L-87), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1496").

The compound (L-87), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1497").

The compound (L-87), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1498").

The compound (L-87), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1499").

The compound (L-87), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1500").

The compound (L-87), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1501").

The compound (L-87), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1502").

The compound (L-87), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1503").

The compound (L-87), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1504").

The compound (L-87), wherein $G^1$ represents a nitrogen atom, $G^4$ represents CH, $R^{3c}$ represents a hydrogen atom, $R^6$ represents a propyl group, $R^3$ represents a substituent indicated in any of [Table 7A] to [Table 15A] (hereinafter, referred to as "compound group SX1505").

The compound (L-87), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1506").

The compound (L-87), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1507").

A compound represented by formula (L-88):

(L-88)

(hereinafter, referred to as "compound (L-88)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1508").

The compound (L-88), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1509").

The compound (L-88), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1510").

The compound (L-88), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1511").

The compound (L-88), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1512").

The compound (L-88), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1513").

The compound (L-88), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1514").

The compound (L-88), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1515").

The compound (L-88), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1516").

The compound (L-88), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1517").

The compound (L-88), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1518").

The compound (L-88), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1519").

The compound (L-88), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1520").

The compound (L-88), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1521").

The compound (L-88), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1522").

The compound (L-88), wherein $G^1$ represents CH, $G^4$ represents a nitrogen atom, $R^{3c}$ represents a hydrogen atom, $R^6$ represents a methyl group, $R^{2b}$ represents a substituent indicated in any of [Table 7A] to [Table 15A] (hereinafter, referred to as "compound group SX1523").

The compound (L-88), wherein $G^1$ represents CH, $G^4$ represents a nitrogen atom, $R^{3c}$ represents a hydrogen atom, $R^6$ represents an ethyl group, $R^{2b}$ represents a substituent indicated in any of [Table 7A] to [Table 15A] (hereinafter, referred to as "compound group SX1524").

The compound (L-88), wherein $G^1$ represents CH, $G^4$ represents a nitrogen atom, $R^{3c}$ represents a hydrogen atom, $R^6$ represents a propyl group, $R^{2b}$ represents a substituent indicated in any of [Table 7A] to [Table 15A] (hereinafter, referred to as "compound group SX1525").

The compound (L-88), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1526").

The compound (L-88), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1527").

The compound (L-88), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1528").

The compound (L-88), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1529").

The compound (L-88), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1530").

The compound (L-88), wherein $G^1$ represents a nitrogen atom, $G^4$ represents CH, $R^{3b}$ represents a hydrogen atom, Re represents an isopropyl group, $R^{3c}$ represents a substituent indicated in any of [Table 7A] to [Table 15A] (hereinafter, referred to as "compound group SX1531").

The compound (L-88), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1532").

The compound (L-88), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1533").

The compound (L-88), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1534").

The compound (L-88), wherein $G^1$ represents a nitrogen atom, $G^4$ represents CH, $R^{3c}$ represents a hydrogen atom, $R^5$ represents a propyl group, $R^{3b}$ represents a substituent indicated in any of [Table 7A] to [Table 15A] (hereinafter, referred to as "compound group SX1535").

The compound (L-88), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1536").

The compound (L-88), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1537").

A compound represented by formula (L-89):

(L-89)

(hereinafter, referred to as "compound (L-89)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1538").

The compound (L-89), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1539").

The compound (L-89), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1540").

The compound (L-89), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1541").

The compound (L-89), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1542").

The compound (L-89), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1543").

The compound (L-89), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1544").

The compound (L-89), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1545").

The compound (L-89), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1546").

The compound (L-89), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1547").

The compound (L-89), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1548").

The compound (L-89), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1549").

The compound (L-89), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1550").

The compound (L-89), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1551").

The compound (L-89), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1552").

The compound (L-89), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1553").

The compound (L-89), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1554").

The compound (L-89), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1555").

The compound (L-89), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1556").

The compound (L-89), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1557").

The compound (L-89), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1558").

The compound (L-89), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1559").

The compound (L-89), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1560").

The compound (L-89), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1561").

The compound (L-89), wherein $G^1$ represents a nitrogen atom, $G^4$ represents CH, $R^{3b}$ represents a hydrogen atom, Re represents a cyclopropyl group, $R^{3c}$ represents a substituent indicated in any of [Table 7A] to [Table 15A](hereinafter, referred to as "compound group SX1562").

The compound (L-89), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1563").

The compound (L-89), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1564").

The compound (L-89), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1565").

The compound (L-89), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1566").

The compound (L-89), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1567").

A compound represented by formula (L-90):

(L-90)

[Chemical structure of compound (L-90)]

(hereinafter, referred to as "compound (L-90)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1568").

The compound (L-90), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1569").

The compound (L-90), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1570").

The compound (L-90), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1571").

The compound (L-90), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1572").

The compound (L-90), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1573").

The compound (L-90), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1574").

The compound (L-90), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1575").

The compound (L-90), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1576").

The compound (L-90), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1577").

The compound (L-90), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1578").

The compound (L-90), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1579").

The compound (L-90), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1580").

The compound (L-90), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1581").

The compound (L-90), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1582").

The compound (L-90), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1583").

The compound (L-90), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1584").

The compound (L-90), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1585").

The compound (L-90), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1586").

The compound (L-90), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1587").

The compound (L-90), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1588").

The compound (L-90), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1589").

The compound (L-90), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1590").

The compound (L-90), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1591").

The compound (L-90), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1592").

The compound (L-90), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1593").

The compound (L-90), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1594").

The compound (L-90), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1595").

The compound (L-90), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1596").

The compound (L-90), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1597").

A compound represented by formula (L-91):

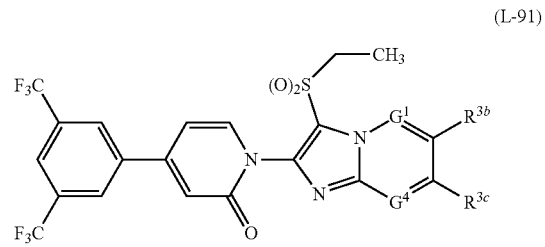

(L-91)

(hereinafter, referred to as "compound (L-91)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1598").

The compound (L-91), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1599").

The compound (L-91), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1600").

The compound (L-91), wherein $G^1$ represents CH, $G^4$ represents a nitrogen atom, $R^{3'}$ represents a hydrogen atom, $R^{3b}$ represents a substituent indicated in any of [Table 7A] to [Table 15A] (hereinafter, referred to as "compound group SX1601").

The compound (L-91), wherein $G^1$ represents a nitrogen atom, $G^4$ represents CH, $R^{3b}$ represents a hydrogen atom, $R^3$ represents a substituent indicated in any of [Table 7A] to [Table 15A] (hereinafter, referred to as "compound group SX1602").

The compound (L-91), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1603").

A compound represented by formula (L-92):

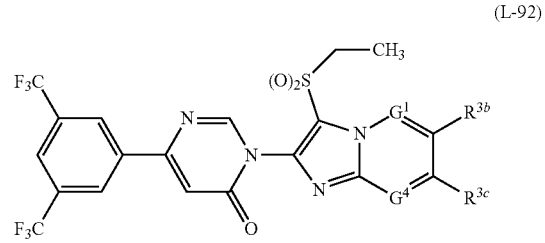

(L-92)

(hereinafter, referred to as "compound (L-92)"),
wherein $G^1$ and $G^4$ represent CH, $R^{3b}$ represent a hydrogen atom, $R^{3c}$ represents a substituent indicated in any of [Table 7A] to [Table 15A] (hereinafter, referred to as "compound group SX1604").

The compound (L-92), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1605").

The compound (L-92), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1606").

The compound (L-92), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1607").

The compound (L-92), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1608").

The compound (L-92), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1609").

A compound represented by formula (L-93):

(L-93)

(hereinafter, referred to as "compound (L-93)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1610").

The compound (L-93), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1611").

The compound (L-93), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1612").

The compound (L-93), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1613").

The compound (L-93), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1614").

The compound (L-93), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1615").

The compound (L-93), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1616").

The compound (L-93), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1617").

The compound (L-93), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1618").

The compound (L-93), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1619").

The compound (L-93), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1620").

The compound (L-93), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1621").

The compound (L-93), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1622").

The compound (L-93), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1623").

The compound (L-93), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1624").

The compound (L-93), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1625").

The compound (L-93), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1626").

The compound (L-93), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1627").

The compound (L-93), wherein $G^1$ represents CH, $G^4$ represents a nitrogen atom, $R^{3c}$ represents a hydrogen atom, $R^6$ represents an isopropyl group, $R^3$ represents a substituent indicated in any of [Table 7A] to [Table 15A](hereinafter, referred to as "compound group SX1628").

The compound (L-93), wherein $G^1$ represents CH, $G^4$ represents a nitrogen atom, $R^{3c}$ represents a hydrogen atom, $R^6$ represents a cyclopropyl group, $R^3$ represents a substituent indicated in any of [Table 7A] to [Table 15A](hereinafter, referred to as "compound group SX1629").

The compound (L-93), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1630").

The compound (L-93), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1631").

The compound (L-93), wherein $G^1$ represents a nitrogen atom, $G^4$ represents CH, $R^3$ represents a hydrogen atom, $R^6$ represents a propyl group, $R^{3c}$ represents a substituent indicated in any of [Table 7A] to [Table 15A] (hereinafter, referred to as "compound group SX1632").

The compound (L-93), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1633").

The compound (L-93), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1634").

The compound (L-93), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1635").

The compound (L-93), wherein $G^1$ represents a nitrogen atom, $G^4$ represents CH, $R^{3c}$ represents a hydrogen atom, R represents an ethyl group, $R^{3b}$ represents a substituent indicated in any of [Table 7A] to [Table 15A] (hereinafter, referred to as "compound group SX1636").

The compound (L-93), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1637").

The compound (L-93), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1638").

The compound (L-93), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1639").

A compound represented by formula (L-94):

(L-94)

(hereinafter, referred to as "compound (L-94)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1640").

The compound (L-94), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1641").

The compound (L-94), wherein $G^1$ and $G^4$ represent CH, $R^3$ represents a hydrogen atom, $R^6$ represents a propyl group, $R^{3c}$ represents a substituent indicated in any of [Table 7A] to [Table 15A] (hereinafter, referred to as "compound group SX1642").

The compound (L-94), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1643").

The compound (L-94), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1644").

The compound (L-94), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1645").

The compound (L-94), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1646").

The compound (L-94), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1647").

The compound (L-94), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1648").

The compound (L-94), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1649").

The compound (L-94), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1650").

The compound (L-94), wherein G¹ represents CH, G⁴ represents a nitrogen atom, R³ᵇ represents a hydrogen atom, R⁶ represents an ethyl group, R³ᶜ represents a substituent indicated in any of [Table 7A] to [Table 15A] (hereinafter, referred to as "compound group SX1651").

The compound (L-94), wherein G¹ represents CH, G⁴ represents a nitrogen atom, R³ᵇ represents a hydrogen atom, R⁶ represents a propyl group, R³ᶜ represents a substituent indicated in any of [Table 7A] to [Table 15A] (hereinafter, referred to as "compound group SX1652").

The compound (L-94), wherein G¹ represents CH, G⁴ represents a nitrogen atom, R³ᵇ represents a hydrogen atom, R⁶ represents an isopropyl group, R³ᶜ represents a substituent indicated in any of [Table 7A] to [Table 15A](hereinafter, referred to as "compound group SX1653").

The compound (L-94), wherein G¹ represents CH, G⁴ represents a nitrogen atom, R³ᵇ represents a hydrogen atom, R⁶ represents a cyclopropyl group, R³ᶜ represents a substituent indicated in any of [Table 7A] to [Table 15A](hereinafter, referred to as "compound group SX1654").

The compound (L-94), wherein G¹ represents CH, G⁴ represents a nitrogen atom, R³ᶜ represents a hydrogen atom, R⁶ represents a methyl group, R³ᵇ represents a substituent indicated in any of [Table 7A] to [Table 15A] (hereinafter, referred to as "compound group SX1655").

The compound (L-94), wherein G¹ represents CH, G⁴ represents a nitrogen atom, R³ᶜ represents a hydrogen atom, R⁶ represents an ethyl group, R³ᵇ represents a substituent indicated in any of [Table 7A] to [Table 15A] (hereinafter, referred to as "compound group SX1656").

The compound (L-94), wherein G¹ represents CH, G⁴ represents a nitrogen atom, R³ᶜ represents a hydrogen atom, R⁶ represents a propyl group, R³ᵇ represents a substituent indicated in any of [Table 7A] to [Table 15A] (hereinafter, referred to as "compound group SX1657").

The compound (L-94), wherein G¹ represents CH, G⁴ represents a nitrogen atom, R³ represents a hydrogen atom, R⁶ represents an isopropyl group, R³ᵇ represents a substituent indicated in any of [Table 7A] to [Table 15A](hereinafter, referred to as "compound group SX1658").

The compound (L-94), wherein G¹ represents CH, G⁴ represents a nitrogen atom, R³ᶜ represents a hydrogen atom, R⁶ represents a cyclopropyl group, R³ᵇ represents a substituent indicated in any of [Table 7A] to [Table 15A](hereinafter, referred to as "compound group SX1659").

The compound (L-94), wherein G¹ represents a nitrogen atom, G⁴ represents CH, R³ᵇ represents a hydrogen atom, R⁶ represents a methyl group, R³ᶜ represents a substituent indicated in any of [Table 7A] to [Table 15A] (hereinafter, referred to as "compound group SX1660").

The compound (L-94), wherein G¹ represents a nitrogen atom, G⁴ represents CH, R³ᵇ represents a hydrogen atom, R⁶ represents an ethyl group, R³ᶜ represents a substituent indicated in any of [Table 7A] to [Table 15A] (hereinafter, referred to as "compound group SX1661").

The compound (L-94), wherein G¹ represents a nitrogen atom, G⁴ represents CH, R³ᵇ represents a hydrogen atom, R⁶ represents a propyl group, R³ᶜ represents a substituent indicated in any of [Table 7A] to [Table 15A] (hereinafter, referred to as "compound group SX1662").

The compound (L-94), wherein G¹ represents a nitrogen atom, G⁴ represents CH, R³ᵇ represents a hydrogen atom, R⁶ represents an isopropyl group, R³ᶜ represents a substituent indicated in any of [Table 7A] to [Table 15A] (hereinafter, referred to as "compound group SX1663").

The compound (L-94), wherein G¹ represents a nitrogen atom, G⁴ represents CH, R³ᵇ represents a hydrogen atom, R⁶ represents a cyclopropyl group, R³ᶜ represents a substituent indicated in any of [Table 7A] to [Table 15A](hereinafter, referred to as "compound group SX1664").

The compound (L-94), wherein G¹ represents a nitrogen atom, G⁴ represents CH, R³ᶜ represents a hydrogen atom, R⁶ represents a methyl group, R³ᵇ represents a substituent indicated in any of [Table 7A] to [Table 15A] (hereinafter, referred to as "compound group SX1665").

The compound (L-94), wherein G¹ represents a nitrogen atom, G⁴ represents CH, R³ᶜ represents a hydrogen atom, R⁶ represents an ethyl group, R³ᵇ represents a substituent indicated in any of [Table 7A] to [Table 15A] (hereinafter, referred to as "compound group SX1666").

The compound (L-94), wherein G¹ represents a nitrogen atom, G⁴ represents CH, R³ᶜ represents a hydrogen atom, R⁶ represents a propyl group, R³ᵇ represents a substituent indicated in any of [Table 7A] to [Table 15A] (hereinafter, referred to as "compound group SX1667").

The compound (L-94), wherein G¹ represents a nitrogen atom, G⁴ represents CH, R³ᶜ represents a hydrogen atom, R⁶ represents an isopropyl group, R³ᵇ represents a substituent indicated in any of [Table 7A] to [Table 15A] (hereinafter, referred to as "compound group SX1668").

The compound (L-94), wherein G¹ represents a nitrogen atom, G⁴ represents CH, R³ᶜ represents a hydrogen atom, R⁶ represents a cyclopropyl group, R³ᵇ represents a substituent indicated in any of [Table 7A] to [Table 15A](hereinafter, referred to as "compound group SX1669").

A compound represented by formula (L-95):

(L-95)

(hereinafter, referred to as "compound (L-95)"),
wherein G¹ and G⁴ represent CH, R⁶ represents a methyl group, R³ᵇ represents a hydrogen atom, R³ᶜ represents a substituent indicated in any of [Table 7A] to [Table 15A] (hereinafter, referred to as "compound group SX1670").

The compound (L-95), wherein G¹ and G⁴ represent CH, R³ᵇ represents a hydrogen atom, R⁶ represents an ethyl group, R³ᶜ represents a substituent indicated in any of [Table 7A] to [Table 15A] (hereinafter, referred to as "compound group SX1671").

The compound (L-95), wherein G¹ and G⁴ represent CH, R³ᵇ represents a hydrogen atom, R⁶ represents a propyl group, R³ᶜ represents a substituent indicated in any of [Table 7A] to [Table 15A] (hereinafter, referred to as "compound group SX1672").

The compound (L-95), wherein G¹ and G⁴ represent CH, R³ᵇ represents a hydrogen atom, R⁶ represents an isopropyl group, R³ᶜ represents a substituent indicated in any of [Table 7A] to [Table 15A] (hereinafter, referred to as "compound group SX1673").

The compound (L-95), wherein G¹ and G⁴ represent CH, R³ᵇ represents a hydrogen atom, R⁶ represents a cyclopropyl group, R³ᶜ represents a substituent indicated in any of [Table 7A] to [Table 15A] (hereinafter, referred to as "compound group SX1674").

The compound (L-95), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1675").

The compound (L-95), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1676").

The compound (L-95), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1677").

The compound (L-95), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1678").

The compound (L-95), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1679").

The compound (L-95), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1680").

The compound (L-95), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1681").

The compound (L-95), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1682").

The compound (L-95), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1683").

The compound (L-95), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1684").

The compound (L-95), wherein $G^1$ represents CH, $G^4$ represents a nitrogen atom, $R^{3c}$ represents a hydrogen atom, $R^6$ represents a methyl group, $R^{2b}$ represents a substituent indicated in any of [Table 7A] to [Table 15A] (hereinafter, referred to as "compound group SX1685").

The compound (L-95), wherein $G^1$ represents CH, $G^4$ represents a nitrogen atom, $R^{3c}$ represents a hydrogen atom, $R^6$ represents an ethyl group, $R^{2b}$ represents a substituent indicated in any of [Table 7A] to [Table 15A] (hereinafter, referred to as "compound group SX1686").

The compound (L-95), wherein $G^1$ represents CH, $G^4$ represents a nitrogen atom, $R^{3c}$ represents a hydrogen atom, $R^6$ represents a propyl group, $R^{2b}$ represents a substituent indicated in any of [Table 7A] to [Table 15A] (hereinafter, referred to as "compound group SX1687").

The compound (L-95), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1688").

The compound (L-95), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1689").

The compound (L-95), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1690").

The compound (L-95), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1691").

The compound (L-95), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1692").

The compound (L-95), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1693").

The compound (L-95), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1694").

The compound (L-95), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1695").

The compound (L-95), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1696").

The compound (L-95), wherein $G^1$ represents a nitrogen atom, $G^4$ represents CH, $R^{3c}$ represents a hydrogen atom, $R^5$ represents a propyl group, $R^{3b}$ represents a substituent indicated in any of [Table 7A] to [Table 15A] (hereinafter, referred to as "compound group SX1697").

The compound (L-95), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1698").

The compound (L-95), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1699").

A compound represented by formula (L-96):

$$\text{(L-96)}$$

(hereinafter, referred to as "compound (L-96)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1700").

The compound (L-96), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1701").

The compound (L-96), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1702").

The compound (L-96), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1703").

The compound (L-96), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1704").

The compound (L-96), wherein $G^1$ and $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1705").

The compound (L-96), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1706").

The compound (L-96), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1707").

The compound (L-96), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1708").

The compound (L-96), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1709").

The compound (L-96), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1710").

The compound (L-96), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1711").

The compound (L-96), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1712").

The compound (L-96), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1713").

The compound (L-96), wherein $G^1$ represents CH, $G^4$ represents a nitrogen atom, $R^{3b}$ represents a hydrogen atom, $R^6$ represents a cyclopropyl group, $R^{3'}$ represents a substituent indicated in any of [Table 7A] to [Table 15A] (hereinafter, referred to as "compound group SX1714").

The compound (L-96), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1715").

The compound (L-96), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1716").

The compound (L-96), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1717").

The compound (L-96), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1718").

The compound (L-96), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1719").

The compound (L-96), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1720").

The compound (L-96), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1721").

The compound (L-96), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1722").

The compound (L-96), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1723").

The compound (L-96), wherein $G^1$ represents a nitrogen atom, $G^4$ represents CH, $R^{3b}$ represents a hydrogen atom, Re represents a cyclopropyl group, $R^{3c}$ represents a substituent indicated in any of [Table 7A] to [Table 15A](hereinafter, referred to as "compound group SX1724").

The compound (L-96), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1725").

The compound (L-96), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1726").

The compound (L-96), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1727").

The compound (L-96), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1728").

The compound (L-96), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1729").

A compound represented by formula (L-97):

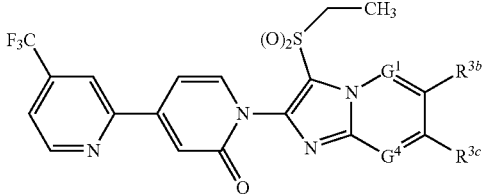

(L-97)

(hereinafter, referred to as "compound (L-97)"), wherein $G^1$ and $G^4$ represent CH, $R^{2b}$ represents a hydrogen atom, $R^{3c}$ represents a substituent indicated in any of [Table 7A] to [Table 15A] (hereinafter, referred to as "compound group SX1730").

The compound (L-97), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1731").

The compound (L-97), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1732").

The compound (L-97), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1733").

The compound (L-97), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1734").

The compound (L-97), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1735").

A compound represented by formula (L-98):

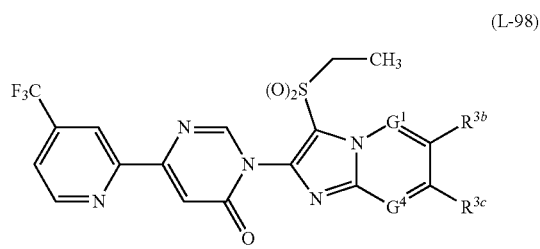

(L-98)

(hereinafter, referred to as "compound (L-98)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1736").

The compound (L-98), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1737").

The compound (L-98), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1738").

The compound (L-98), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1739").

The compound (L-98), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1740").

The compound (L-98), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1741").

A compound represented by formula (L-99):

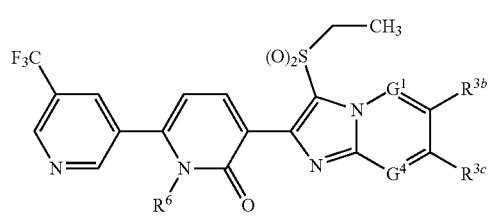

(L-99)

(hereinafter, referred to as "compound (L-99)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1742").

The compound (L-99), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1743").

The compound (L-99), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1744").

The compound (L-99), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1745").

The compound (L-99), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1746").

The compound (L-99), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1747").

The compound (L-99), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1748").

The compound (L-99), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1749").

The compound (L-99), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1750").

The compound (L-99), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1751").

The compound (L-99), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1752").

The compound (L-99), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1753").

The compound (L-99), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1754").

The compound (L-99), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1755").

The compound (L-99), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1756").

The compound (L-99), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1757").

The compound (L-99), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1758").

The compound (L-99), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1759").

The compound (L-99), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1760").

The compound (L-99), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1761").

The compound (L-99), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1762").

The compound (L-99), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1763").

The compound (L-99), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1764").

The compound (L-99), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1765").

The compound (L-99), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1766").

The compound (L-99), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1767").

The compound (L-99), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1768").

The compound (L-99), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1769").

The compound (L-99), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1770").

The compound (L-99), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1771").

A compound represented by formula (L-100):

(L-100)

[Chemical structure diagram showing a compound with F₃C, (O)₂S, CH₃, N, G¹, R³ᵇ, G⁴, R³ᶜ, R⁶, O groups]

(hereinafter, referred to as "compound (L-100)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1772").

The compound (L-100), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1773").

The compound (L-100), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1774").

The compound (L-100), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1775").

The compound (L-100), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1776").

The compound (L-100), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1777").

The compound (L-100), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1778").

The compound (L-100), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1779").

The compound (L-100), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1780").

The compound (L-100), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1781").

The compound (L-100), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1782").

The compound (L-100), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1783").

The compound (L-100), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1784").

The compound (L-100), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1785").

The compound (L-100), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1786").

The compound (L-100), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1787").

The compound (L-100), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1788").

The compound (L-100), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1789").

The compound (L-100), wherein $G^1$ represents CH, $G^4$ represents a nitrogen atom, $R^{3c}$ represents a hydrogen atom, $R^6$ represents an isopropyl group, $R^3$ represents a substituent indicated in any of [Table 7A] to [Table 15A](hereinafter, referred to as "compound group SX1790").

The compound (L-100), wherein $G^1$ represents CH, $G^4$ represents a nitrogen atom, $R^{3c}$ represents a hydrogen atom, $R^6$ represents a cyclopropyl group, $R^3$ represents a substituent indicated in any of [Table 7A] to [Table 15A](hereinafter, referred to as "compound group SX1791").

The compound (L-100), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1792").

The compound (L-100), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1793").

The compound (L-100), wherein $G^1$ represents a nitrogen atom, $G^4$ represents CH, $R^3$ represents a hydrogen atom, $R^6$ represents a propyl group, $R^{3c}$ represents a substituent indicated in any of [Table 7A] to [Table 15A] (hereinafter, referred to as "compound group SX1794").

The compound (L-100), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1795").

The compound (L-100), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1796").

The compound (L-100), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1797").

The compound (L-100), wherein $G^1$ represents a nitrogen atom, $G^4$ represents CH, $R^{3c}$ represents a hydrogen atom, R represents an ethyl group, $R^{3b}$ represents a substituent indicated in any of [Table 7A] to [Table 15A] (hereinafter, referred to as "compound group SX1798").

The compound (L-100), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1799").

The compound (L-100), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1800").

The compound (L-100), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1801").

A compound represented by formula (L-101):

(L-101)

(hereinafter, referred to as "compound (L-101)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1802").

The compound (L-101), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1803").

The compound (L-101), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1804").

The compound (L-101), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1805").

The compound (L-101), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1806").

The compound (L-101), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1807").

The compound (L-101), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1808").

The compound (L-101), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1809").

The compound (L-101), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1810").

The compound (L-101), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1811").

The compound (L-101), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1812").

The compound (L-101), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1813").

The compound (L-101), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1814").

The compound (L-101), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1815").

The compound (L-101), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1816").

The compound (L-101), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1817").

The compound (L-101), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1818").

The compound (L-101), wherein $G^1$ represents CH, $G^4$ represents a nitrogen atom, $R^{3b}$ represents a hydrogen atom, $R^6$ represents a propyl group, $R^{3b}$ represents a substituent indicated in any of [Table 7A] to [Table 15A] (hereinafter, referred to as "compound group SX1819").

The compound (L-101), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1820").

The compound (L-101), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1821").

The compound (L-101), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1822").

The compound (L-101), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1823").

The compound (L-101), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1824").

The compound (L-101), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1825").

The compound (L-101), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1826").

The compound (L-101), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1827").

The compound (L-101), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1828").

The compound (L-101), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1829").

The compound (L-101), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1830").

The compound (L-101), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1831").

A compound represented by formula (L-102):

(L-102)

(hereinafter, referred to as "compound (L-102)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1832").

The compound (L-102), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1833").

The compound (L-102), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1834").

The compound (L-102), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1835").

The compound (L-102), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1836").

The compound (L-102), wherein G. and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1837").

The compound (L-102), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1838").

The compound (L-102), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1839").

The compound (L-102), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1840").

The compound (L-102), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1841").

The compound (L-102), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1842").

The compound (L-102), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1843").

The compound (L-102), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1844").

The compound (L-102), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1845").

The compound (L-102), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1846").

The compound (L-102), wherein $G^1$ represents CH, $G^4$ represents a nitrogen atom, $R^{3c}$ represents a hydrogen atom, $R^6$ represents a methyl group, $R^{2b}$ represents a substituent indicated in any of [Table 7A] to [Table 15A] (hereinafter, referred to as "compound group SX1847").

The compound (L-102), wherein $G^1$ represents CH, $G^4$ represents a nitrogen atom, $R^{3c}$ represents a hydrogen atom, $R^6$ represents an ethyl group, $R^{2b}$ represents a substituent indicated in any of [Table 7A] to [Table 15A] (hereinafter, referred to as "compound group SX1848").

The compound (L-102), wherein $G^1$ represents CH, $G^4$ represents a nitrogen atom, $R^{3c}$ represents a hydrogen atom, $R^6$ represents a propyl group, $R^{2b}$ represents a substituent indicated in any of [Table 7A] to [Table 15A] (hereinafter, referred to as "compound group SX1849").

The compound (L-102), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1850").

The compound (L-102), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1851").

The compound (L-102), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1852").

The compound (L-102), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1853").

The compound (L-102), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1854").

The compound (L-102), wherein $G^1$ represents a nitrogen atom, $G^4$ represents CH, $R^{3c}$ represents a hydrogen atom, $R^6$ represents an isopropyl group, $R^{3c}$ represents a substituent indicated in any of [Table 7A] to [Table 15A] (hereinafter, referred to as "compound group SX1855").

The compound (L-102), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1856").

The compound (L-102), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1857").

The compound (L-102), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1858").

The compound (L-102), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1859").

The compound (L-102), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1860").

The compound (L-102), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1861").

A compound represented by formula (L-103):

(L-103)

(hereinafter, referred to as "compound (L-103)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1862").

The compound (L-103), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1863").

The compound (L-103), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1864").

The compound (L-103), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1865").

The compound (L-103), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1866").

The compound (L-103), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1867").

A compound represented by formula (L-104):

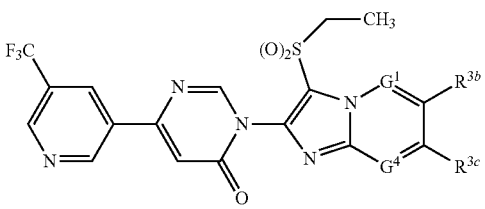

(L-104)

(hereinafter, referred to as "compound (L-104)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1868").

The compound (L-104), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1869").

The compound (L-104), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1870").

The compound (L-104), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1871").

The compound (L-104), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1872").

The compound (L-104), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1873").

A compound represented by formula (L-105):

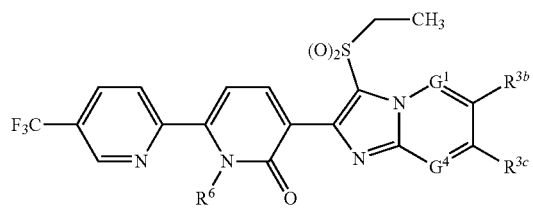

(L-105)

(hereinafter, referred to as "compound (L-105)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1874").

The compound (L-105), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1875").

The compound (L-105), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1876").

The compound (L-105), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1877").

The compound (L-105), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1878").

The compound (L-105), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1879").

The compound (L-105), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1880").

The compound (L-105), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1881").

The compound (L-105), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1882").

The compound (L-105), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1883").

The compound (L-105), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1884").

The compound (L-105), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1885").

The compound (L-105), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1886").

The compound (L-105), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1887").

The compound (L-105), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1888").

The compound (L-105), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1889").

The compound (L-105), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1890").

The compound (L-105), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1891").

The compound (L-105), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1892").

The compound (L-105), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1893").

The compound (L-105), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1894").

The compound (L-105), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1895").

The compound (L-105), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1896").

The compound (L-105), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1897").

The compound (L-105), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1898").

The compound (L-105), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1899").

The compound (L-105), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1900").

The compound (L-105), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1901").

The compound (L-105), wherein $G^1$ represents a nitrogen atom, $G^4$ represents CH, $R^{3c}$ represents a hydrogen atom, R represents an isopropyl group, $R^{3b}$ represents a substituent indicated in any of [Table 7A] to [Table 15A] (hereinafter, referred to as "compound group SX1902").

The compound (L-105), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1903").

A compound represented by formula (L-106):

(hereinafter, referred to as "compound (L-106)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1904").

The compound (L-106), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1905").

The compound (L-106), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1906").

The compound (L-106), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1907").

The compound (L-106), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1908").

The compound (L-106), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1909").

The compound (L-106), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1910").

The compound (L-106), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1911").

The compound (L-106), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1912").

The compound (L-106), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1913").

The compound (L-106), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1914").

The compound (L-106), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1915").

The compound (L-106), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1916").

The compound (L-106), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1917").

The compound (L-106), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1918").

The compound (L-106), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1919").

The compound (L-106), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1920").

The compound (L-106), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1921").

The compound (L-106), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1922").

The compound (L-106), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1923").

The compound (L-106), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1924").

The compound (L-106), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1925").

The compound (L-106), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1926").

The compound (L-106), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1927").

The compound (L-106), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1928").

The compound (L-106), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1929").

The compound (L-106), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1930").

The compound (L-106), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1931").

The compound (L-106), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1932").

The compound (L-106), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1933").

A compound represented by formula (L-107):

$$\text{(L-107)}$$

(structure showing pyridine with F₃C substituent, connected to pyridinone bearing R⁶ and (O)₂S-CH₂CH₃ groups, linked to imidazo-fused ring with G¹, G⁴, R³ᵇ, R³ᶜ substituents)

(hereinafter, referred to as "compound (L-107)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1934").

The compound (L-107), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1935").

The compound (L-107), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1936").

The compound (L-107), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1937").

The compound (L-107), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1938").

The compound (L-107), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1939").

The compound (L-107), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1940").

The compound (L-107), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1941").

The compound (L-107), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1942").

The compound (L-107), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1943").

The compound (L-107), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1944").

The compound (L-107), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1945").

The compound (L-107), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1946").

The compound (L-107), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1947").

The compound (L-107), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1948").

The compound (L-107), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1949").

The compound (L-107), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1950").

The compound (L-107), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1951").

The compound (L-107), wherein $G^1$ represents CH, $G^4$ represents a nitrogen atom, $R^{3c}$ represents a hydrogen atom, $R^6$ represents an isopropyl group, $R^3$ represents a substituent indicated in any of [Table 7A] to [Table 15A](hereinafter, referred to as "compound group SX1952").

The compound (L-107), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1953").

The compound (L-107), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1954").

The compound (L-107), wherein $G^1$ represents a nitrogen atom, $G^4$ represents CH, $R^3$ represents a hydrogen atom, $R^6$ represents an ethyl group, $R^{3c}$ represents a substituent indicated in any of [Table 7A] to [Table 15A] (hereinafter, referred to as "compound group SX1955").

The compound (L-107), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1956").

The compound (L-107), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1957").

The compound (L-107), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1958").

The compound (L-107), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1959").

The compound (L-107), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1960").

The compound (L-107), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1961").

The compound (L-107), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1962").

The compound (L-107), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1963").

A compound represented by formula (L-108):

(L-108)

(hereinafter, referred to as "compound (L-108)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX1964").

The compound (L-108), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1965").

The compound (L-108), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1966").

The compound (L-108), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1967").

The compound (L-108), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX1968").

The compound (L-108), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1969").

The compound (L-108), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1970").

The compound (L-108), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1971").

The compound (L-108), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1972").

The compound (L-108), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX1973").

The compound (L-108), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX1974").

The compound (L-108), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1975").

The compound (L-108), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX1976").

The compound (L-108), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX1977").

The compound (L-108), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1978").

The compound (L-108), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX1979").

The compound (L-108), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX1980").

The compound (L-108), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX1981").

The compound (L-108), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX1982").

The compound (L-108), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1983").

The compound (L-108), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX1984").

The compound (L-108), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX1985").

The compound (L-108), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX1986").

The compound (L-108), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX1987").

The compound (L-108), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX1988").

The compound (L-108), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX1989").

The compound (L-108), wherein $G^1$ represents a nitrogen atom, $G^4$ represents CH, $R^{3c}$ represents a hydrogen atom, $R^6$ represents an ethyl group, $R^3$ represents a substituent indicated in any of [Table 7A] to [Table 15A] (hereinafter, referred to as "compound group SX1990").

The compound (L-108), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX1991").

The compound (L-108), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX1992").

The compound (L-108), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX1993").

A compound represented by formula (L-109):

(L-109)

[Chemical structure showing F₃C-pyridine connected to pyridinone connected to imidazo ring system with (O)₂S-CH₃ group, G¹, G⁴, R³ᵇ, R³ᶜ substituents]

(hereinafter, referred to as "compound (L-109)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX1994").

The compound (L-109), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX1995").

The compound (L-109), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX1996").

The compound (L-109), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX1997").

The compound (L-109), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX1998").

The compound (L-109), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX1999").

A compound represented by formula (L-110):

(L-110)

[Chemical structure showing F₃C-pyridine connected to pyrimidinone connected to imidazo ring system with (O)₂S-CH₃ group, G¹, G⁴, R³ᵇ, R³ᶜ substituents]

(hereinafter, referred to as "compound (L-110)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX2000").

The compound (L-110), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX2001").

The compound (L-110), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX2002").

The compound (L-110), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX2003").

The compound (L-110), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX2004").

The compound (L-110), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX2005").

A compound represented by formula (L-111):

(L-111)

[Chemical structure: F₃C-pyrazole-pyridinone(N-R⁶)-imidazopyrimidine with $G^1$, $G^4$, $R^{3b}$, $R^{3c}$ substituents and (O)₂S-CH₂-CH₃ group]

(hereinafter, referred to as "compound (L-111)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2006").

The compound (L-111), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2007").

The compound (L-111), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2008").

The compound (L-111), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2009").

The compound (L-111), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2010").

The compound (L-111), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2011").

The compound (L-111), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2012").

The compound (L-111), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2013").

The compound (L-111), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2014").

The compound (L-111), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2015").

The compound (L-111), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2016").

The compound (L-111), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2017").

The compound (L-111), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2018").

The compound (L-111), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX2019").

The compound (L-111), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2020").

The compound (L-111), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2021").

The compound (L-111), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2022").

The compound (L-111), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2023").

The compound (L-111), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX2024").

The compound (L-111), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2025").

The compound (L-111), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2026").

The compound (L-111), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2027").

The compound (L-111), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2028").

The compound (L-111), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2029").

The compound (L-111), wherein $G^1$ represents a nitrogen atom, $G^4$ represents CH, $R^3$ represents a hydrogen atom, $R^6$ represents a cyclopropyl group, $R^{3c}$ represents a substituent indicated in any of [Table 7A] to [Table 15A](hereinafter, referred to as "compound group SX2030").

The compound (L-111), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2031").

The compound (L-111), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2032").

The compound (L-111), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2033").

The compound (L-111), wherein $G^1$ represents a nitrogen atom, $G^4$ represents CH, $R^{3c}$ represents a hydrogen atom, R represents an isopropyl group, $R^{3b}$ represents a substituent indicated in any of [Table 7A] to [Table 15A] (hereinafter, referred to as "compound group SX2034").

The compound (L-111), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2035").

A compound represented by formula (L-112):

(L-112)

(hereinafter, referred to as "compound (L-112)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2036").

The compound (L-112), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2037").

The compound (L-112), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2038").

The compound (L-112), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2039").

The compound (L-112), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2040").

The compound (L-112), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2041").

The compound (L-112), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2042").

The compound (L-112), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2043").

The compound (L-112), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2044").

The compound (L-112), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2045").

The compound (L-112), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2046").

The compound (L-112), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2047").

The compound (L-112), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2048").

The compound (L-112), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX2049").

The compound (L-112), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2050").

The compound (L-112), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2051").

The compound (L-112), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2052").

The compound (L-112), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2053").

The compound (L-112), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX2054").

The compound (L-112), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2055").

The compound (L-112), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2056").

The compound (L-112), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2057").

The compound (L-112), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2058").

The compound (L-112), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2059").

The compound (L-112), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2060").

The compound (L-112), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2061").

The compound (L-112), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2062").

The compound (L-112), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2063").

The compound (L-112), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2064").

The compound (L-112), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2065").

A compound represented by formula (L-113):

(L-113)

(hereinafter, referred to as "compound (L-113)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2066").

The compound (L-113), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2067").

The compound (L-113), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2068").

The compound (L-113), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2069").

The compound (L-113), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2070").

The compound (L-113), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2071").

The compound (L-113), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2072").

The compound (L-113), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2073").

The compound (L-113), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2074").

The compound (L-113), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2075").

The compound (L-113), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2076").

The compound (L-113), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2077").

The compound (L-113), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2078").

The compound (L-113), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX2079").

The compound (L-113), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2080").

The compound (L-113), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2081").

The compound (L-113), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2082").

The compound (L-113), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2083").

The compound (L-113), wherein $G^1$ represents CH, $G^4$ represents a nitrogen atom, $R^{3c}$ represents a hydrogen atom, $R^6$ represents an isopropyl group, $R^3$ represents a substituent indicated in any of [Table 7A] to [Table 15A](hereinafter, referred to as "compound group SX2084").

The compound (L-113), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2085").

The compound (L-113), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2086").

The compound (L-113), wherein $G^1$ represents a nitrogen atom, $G^4$ represents CH, $R^3$ represents a hydrogen atom, $R^6$ represents an ethyl group, $R^{3c}$ represents a substituent indicated in any of [Table 7A] to [Table 15A] (hereinafter, referred to as "compound group SX2087").

The compound (L-113), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2088").

The compound (L-113), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2089").

The compound (L-113), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2090").

The compound (L-113), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2091").

The compound (L-113), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2092").

The compound (L-113), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2093").

The compound (L-113), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2094").

The compound (L-113), wherein $G^1$ represents a nitrogen atom, $G^4$ represents CH, $R^{3c}$ represents a hydrogen atom, $R^6$ represents a cyclopropyl group, $R^3$ represents a substituent indicated in any of [Table 7A] to [Table 15A](hereinafter, referred to as "compound group SX2095").

A compound represented by formula (L-114):

(L-114)

(hereinafter, referred to as "compound (L-114)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2096").

The compound (L-114), wherein $G^1$ and $G^4$ represent CH, $R^3$ represents a hydrogen atom, $R^6$ represents an ethyl group, $R^{3c}$ represents a substituent indicated in any of [Table 7A] to [Table 15A] (hereinafter, referred to as "compound group SX2097").

The compound (L-114), wherein $G^1$ and $G^4$ represent CH, $R^3$ represents a hydrogen atom, $R^6$ represents a propyl group, $R^{3c}$ represents a substituent indicated in any of [Table 7A] to [Table 15A] (hereinafter, referred to as "compound group SX2098").

The compound (L-114), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2099").

The compound (L-114), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2100").

The compound (L-114), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2101").

The compound (L-114), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2102").

The compound (L-114), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2103").

The compound (L-114), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2104").

The compound (L-114), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2105").

The compound (L-114), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2106").

The compound (L-114), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2107").

The compound (L-114), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2108").

The compound (L-114), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2109").

The compound (L-114), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2110").

The compound (L-114), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2111").

The compound (L-114), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2112").

The compound (L-114), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2113").

The compound (L-114), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2114").

The compound (L-114), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2115").

The compound (L-114), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2116").

The compound (L-114), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2117").

The compound (L-114), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2118").

The compound (L-114), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2119").

The compound (L-114), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2120").

The compound (L-114), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2121").

The compound (L-114), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2122").

The compound (L-114), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2123").

The compound (L-114), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2124").

The compound (L-114), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2125").

A compound represented by formula (L-115):

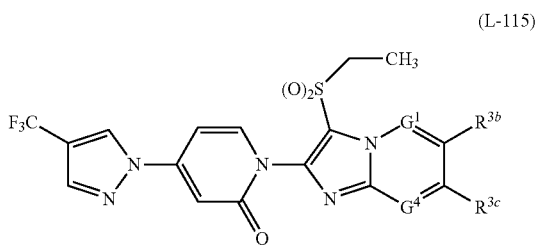

(L-115)

(hereinafter, referred to as "compound (L-115)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX2126").

The compound (L-115), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX2127").

The compound (L-115), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX2128").

The compound (L-115), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX2129").

The compound (L-115), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX2130").

The compound (L-115), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX2131").

A compound represented by formula (L-116):

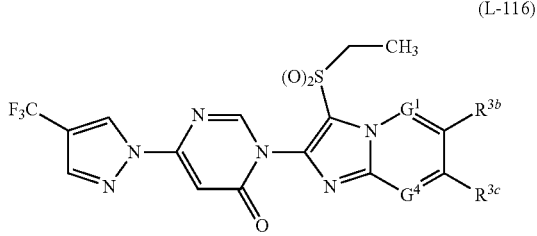

(L-116)

(hereinafter, referred to as "compound (L-116)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX2132").

The compound (L-116), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX2133").

The compound (L-116), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX2134").

The compound (L-116), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX2135").

The compound (L-116), wherein $G^1$ represents a nitrogen atom, $G^4$ represents CH, $R^{3b}$ represents a hydrogen atom, $R^3$ represents a substituent indicated in any of [Table 7A] to [Table 15A] (hereinafter, referred to as "compound group SX2136").

The compound (L-116), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX2137").

A compound represented by formula (L-117):

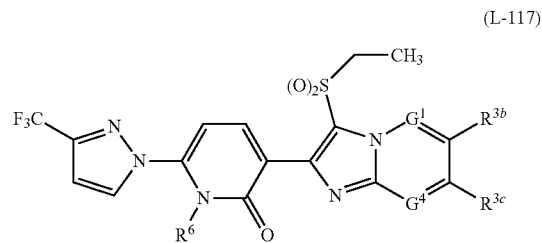

(L-117)

(hereinafter, referred to as "compound (L-117)"),
wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2138").

The compound (L-117), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2139").

The compound (L-117), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2140").

The compound (L-117), wherein $G^1$ and $G^4$ represent CH, $R^{3b}$ represents a hydrogen atom, $R^6$ represents an isopropyl C group, $R^{3c}$ represents a substituent indicated in any of [Table 7A] to [Table 15A] (hereinafter, referred to as "compound group SX2141").

The compound (L-117), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2142").

The compound (L-117), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2143").

The compound (L-117), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2144").

The compound (L-117), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2145").

The compound (L-117), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2146").

The compound (L-117), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2147").

The compound (L-117), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2148").

The compound (L-117), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2149").

The compound (L-117), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2150").

The compound (L-117), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2151").

The compound (L-117), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2152").

The compound (L-117), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2153").

The compound (L-117), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2154").

The compound (L-117), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2155").

The compound (L-117), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2156").

The compound (L-117), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2157").

The compound (L-117), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2158").

The compound (L-117), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2159").

The compound (L-117), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2160").

The compound (L-117), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2161").

The compound (L-117), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2162").

The compound (L-117), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2163").

The compound (L-117), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2164").

The compound (L-117), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2165").

The compound (L-117), wherein $G^1$ represents a nitrogen atom, $G^4$ represents CH, $R^{3c}$ represents a hydrogen atom, R represents an isopropyl group, $R^{3b}$ represents a substituent indicated in any of [Table 7A] to [Table 15A] (hereinafter, referred to as "compound group SX2166").

The compound (L-117), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2167").

A compound represented by formula (L-118):

$$\text{(L-118)}$$

(chemical structure of compound L-118: F₃C-substituted pyrazole linked to a pyrimidinone bearing an SO₂CH₂CH₃ group, connected to an imidazo-fused ring with G¹, G⁴, R³ᵇ, R³ᶜ substituents and N-R⁶)

(hereinafter, referred to as "compound (118)"),
wherein G¹ and G⁴ represent CH, R⁶ represents a methyl group, R³ᵇ represents a hydrogen atom, R³ᶜ represents a substituent indicated in any of [Table 7A] to [Table 15A] (hereinafter, referred to as "compound group SX2168").

The compound (L-118), wherein G¹ and G⁴ represent CH, R³ᵇ represents a hydrogen atom, R⁶ represents an ethyl group, R³ᶜ represents a substituent indicated in any of [Table 7A] to [Table 15A] (hereinafter, referred to as "compound group SX2169").

The compound (L-118), wherein G¹ and G⁴ represent CH, R³ᵇ represents a hydrogen atom, R⁶ represents a propyl group, R³ᶜ represents a substituent indicated in any of [Table 7A] to [Table 15A] (hereinafter, referred to as "compound group SX2170").

The compound (L-118), wherein G¹ and G⁴ represent CH, R³ᵇ represents a hydrogen atom, R⁶ represents an isopropyl group, R³ᶜ represents a substituent indicated in any of [Table 7A] to [Table 15A] (hereinafter, referred to as "compound group SX2171").

The compound (L-118), wherein G¹ and G⁴ represent CH, R³ᵇ represents a hydrogen atom, R⁶ represents a cyclopropyl group, R³ᶜ represents a substituent indicated in any of [Table 7A] to [Table 15A] (hereinafter, referred to as "compound group SX2172").

The compound (L-118), wherein G¹ and G⁴ represent CH, R³ᶜ represents a hydrogen atom, R⁶ represents a methyl group, R³ᵇ represents a substituent indicated in any of [Table 7A] to [Table 15A] (hereinafter, referred to as "compound group SX2173").

The compound (L-118), wherein G¹ and G⁴ represent CH, R³ᶜ represents a hydrogen atom, R⁶ represents an ethyl group, R³ᵇ represents a substituent indicated in any of [Table 7A] to [Table 15A] (hereinafter, referred to as "compound group SX2174").

The compound (L-118), wherein G¹ and G⁴ represent CH, R³ᶜ represents a hydrogen atom, R⁶ represents a propyl group, R³ᵇ represents a substituent indicated in any of [Table 7A] to [Table 15A] (hereinafter, referred to as "compound group SX2175").

The compound (L-118), wherein G¹ and G⁴ represent CH, R³ᶜ represents a hydrogen atom, R⁶ represents an isopropyl group, R³ᵇ represents a substituent indicated in any of [Table 7A] to [Table 15A] (hereinafter, referred to as "compound group SX2176").

The compound (L-118), wherein G¹ and G⁴ represent CH, R³ᶜ represents a hydrogen atom, R⁶ represents a cyclopropyl group, R³ᵇ represents a substituent indicated in any of [Table 7A] to [Table 15A] (hereinafter, referred to as "compound group SX2177").

The compound (L-118), wherein G¹ represents CH, G⁴ represents a nitrogen atom, R³ᵇ represents a hydrogen atom, R⁶ represents a methyl group, R³ᶜ represents a substituent indicated in any of [Table 7A] to [Table 15A] (hereinafter, referred to as "compound group SX2178").

The compound (L-118), wherein G¹ represents CH, G⁴ represents a nitrogen atom, R³ᵇ represents a hydrogen atom, R⁶ represents an ethyl group, R³ᶜ represents a substituent indicated in any of [Table 7A] to [Table 15A] (hereinafter, referred to as "compound group SX2179").

The compound (L-118), wherein G¹ represents CH, G⁴ represents a nitrogen atom, R³ᵇ represents a hydrogen atom, R⁶ represents a propyl group, R³ᶜ represents a substituent indicated in any of [Table 7A] to [Table 15A] (hereinafter, referred to as "compound group SX2180").

The compound (L-118), wherein G¹ represents CH, G⁴ represents a nitrogen atom, R³ᵇ represents a hydrogen atom, R⁶ represents an isopropyl group, R³ᶜ represents a substituent indicated in any of [Table 7A] to [Table 15A](hereinafter, referred to as "compound group SX2181").

The compound (L-118), wherein G¹ represents CH, G⁴ represents a nitrogen atom, R³ᵇ represents a hydrogen atom, R⁶ represents a cyclopropyl group, R³ᶜ represents a substituent indicated in any of [Table 7A] to [Table 15A](hereinafter, referred to as "compound group SX2182").

The compound (L-118), wherein G¹ represents CH, G⁴ represents a nitrogen atom, R³ᶜ represents a hydrogen atom, R⁶ represents a methyl group, R³ᵇ represents a substituent indicated in any of [Table 7A] to [Table 15A] (hereinafter, referred to as "compound group SX2183").

The compound (L-118), wherein G¹ represents CH, G⁴ represents a nitrogen atom, R³ᶜ represents a hydrogen atom, R⁶ represents an ethyl group, R³ᵇ represents a substituent indicated in any of [Table 7A] to [Table 15A] (hereinafter, referred to as "compound group SX2184").

The compound (L-118), wherein G¹ represents CH, G⁴ represents a nitrogen atom, R³ᶜ represents a hydrogen atom, R⁶ represents a propyl group, R³ᵇ represents a substituent indicated in any of [Table 7A] to [Table 15A] (hereinafter, referred to as "compound group SX2185").

The compound (L-118), wherein G¹ represents CH, G⁴ represents a nitrogen atom, R³ᶜ represents a hydrogen atom, R⁶ represents an isopropyl group, R³ᵇ represents a substituent indicated in any of [Table 7A] to [Table 15A](hereinafter, referred to as "compound group SX2186").

The compound (L-118), wherein G¹ represents CH, G⁴ represents a nitrogen atom, R³ᶜ represents a hydrogen atom, R⁶ represents a cyclopropyl group, R³ᵇ represents a substituent indicated in any of [Table 7A] to [Table 15A](hereinafter, referred to as "compound group SX2187").

The compound (L-118), wherein G¹ represents a nitrogen atom, G⁴ represents CH, R³ᵇ represents a hydrogen atom, R⁶ represents a methyl group, R³ᶜ represents a substituent indicated in any of [Table 7A] to [Table 15A] (hereinafter, referred to as "compound group SX2188").

The compound (L-118), wherein G¹ represents a nitrogen atom, G⁴ represents CH, R³ᵇ represents a hydrogen atom, R⁶ represents an ethyl group, R³ᶜ represents a substituent indicated in any of [Table 7A] to [Table 15A] (hereinafter, referred to as "compound group SX2189").

The compound (L-118), wherein G¹ represents a nitrogen atom, G⁴ represents CH, R³ᵇ represents a hydrogen atom, R⁶ represents a propyl group, R³ᶜ represents a substituent indicated in any of [Table 7A] to [Table 15A] (hereinafter, referred to as "compound group SX2190").

The compound (L-118), wherein G¹ represents a nitrogen atom, G⁴ represents CH, R³ᵇ represents a hydrogen atom, R⁶ represents an isopropyl group, R³ᶜ represents a substituent indicated in any of [Table 7A] to [Table 15A] (hereinafter, referred to as "compound group SX2191").

The compound (L-118), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2192").

The compound (L-118), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2193").

The compound (L-118), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2194").

The compound (L-118), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2195").

The compound (L-118), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2196").

The compound (L-118), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2197").

A compound represented by formula (L-119):

(L-119)

(hereinafter, referred to as "compound (L-119)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2198").

The compound (L-119), wherein $G^1$ and $G^4$ represent CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2199").

The compound (L-119), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2200").

The compound (L-119), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2201").

The compound (L-119), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2202").

The compound (L-119), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2203").

The compound (L-119), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2204").

The compound (L-119), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2205").

The compound (L-119), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2206").

The compound (L-119), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2207").

The compound (L-119), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2208").

The compound (L-119), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2209").

The compound (L-119), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2210").

The compound (L-119), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A](hereinafter, referred to as "compound group SX2211").

The compound (L-119), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2212").

The compound (L-119), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2213").

The compound (L-119), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2214").

The compound (L-119), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2215").

The compound (L-119), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A](hereinafter, referred to as "compound group SX2216").

The compound (L-119), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2217").

The compound (L-119), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2218").

The compound (L-119), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2219").

The compound (L-119), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2220").

The compound (L-119), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2221").

The compound (L-119), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A](hereinafter, referred to as "compound group SX2222").

The compound (L-119), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2223").

The compound (L-119), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2224").

The compound (L-119), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2225").

The compound (L-119), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2226").

The compound (L-119), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A](hereinafter, referred to as "compound group SX2227").

A compound represented by formula (L-120):

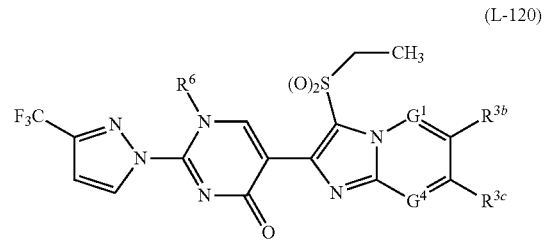

(L-120)

(hereinafter, referred to as "compound (L-120)"), wherein $G^1$ and $G^4$ represent CH, $R^6$ represents a methyl group, $R^{3b}$ represents a hydrogen atom, $R^{3c}$ represents a substituent indicated in any of [Table 7A] to [Table 15A] (hereinafter, referred to as "compound group SX2228").

The compound (L-120), wherein $G^1$ and $G^4$ represent CH, $R^3$ represents a hydrogen atom, $R^6$ represents an ethyl group, $R^{3c}$ represents a substituent indicated in any of [Table 7A] to [Table 15A] (hereinafter, referred to as "compound group SX2229").

The compound (L-120), wherein $G^1$ and $G^4$ represent CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2230").

The compound (L-120), wherein $G^1$ and $G^4$ represent CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2231").

The compound (L-120), wherein $G^1$ and $G^4$ represent CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2232").

The compound (L-120), wherein $G^1$ and $G^4$ represent CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2233").

The compound (L-120), wherein $G^1$ and $G^4$ represent CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2234").

The compound (L-120), wherein $G^1$ and $G^4$ represent CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2235").

The compound (L-120), wherein $G^1$ and $G^4$ represent CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2236").

The compound (L-120), wherein $G^1$ and $G^4$ represent CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2237").

The compound (L-120), wherein $G^1$ represents CH, $G^4$ represents a nitrogen atom, $R^{3b}$ represents a hydrogen atom, $R^6$ represents a methyl group, $R^{3c}$ represents a substituent indicated in any of [Table 7A] to [Table 15A] (hereinafter, referred to as "compound group SX2238").

The compound (L-120), wherein $G^1$ represents CH, $G^4$ represents a nitrogen atom, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2239").

The compound (L-120), wherein $G^1$ represents CH, $G^4$ represents a nitrogen atom, $R^{3b}$ represents a hydrogen atom, $R^6$ represents a propyl group, $R^{3c}$ represents a substituent indicated in any of [Table 7A] to [Table 15A] (hereinafter, referred to as "compound group SX2240").

The compound (L-120), wherein $G^1$ represents CH, $G^4$ represents a nitrogen atom, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2241").

The compound (L-120), wherein $G^1$ represents CH, $G^4$ represents a nitrogen atom, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2242").

The compound (L-120), wherein $G^1$ represents CH, $G^4$ represents a nitrogen atom, $R^{3c}$ represents a hydrogen atom, $R^6$ represents a methyl group, $R^{3b}$ represents a substituent indicated in any of [Table 7A] to [Table 15A] (hereinafter, referred to as "compound group SX2243").

The compound (L-120), wherein $G^1$ represents CH, $G^4$ represents a nitrogen atom, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2244").

The compound (L-120), wherein $G^1$ represents CH, $G^4$ represents a nitrogen atom, $R^{3c}$ represents a hydrogen atom, $R^6$ represents a propyl group, $R^{3b}$ represents a substituent indicated in any of [Table 7A] to [Table 15A] (hereinafter, referred to as "compound group SX2245").

The compound (L-120), wherein $G^1$ represents CH, $G^4$ represents a nitrogen atom, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2246").

The compound (L-120), wherein $G^1$ represents CH, $G^4$ represents a nitrogen atom, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2247").

The compound (L-120), wherein $G^1$ represents a nitrogen atom, $G^4$ represents CH, $R^{3b}$ represents a hydrogen atom, $R^6$ represents a methyl group, $R^{3c}$ represents a substituent indicated in any of [Table 7A] to [Table 15A] (hereinafter, referred to as "compound group SX2248").

The compound (L-120), wherein $G^1$ represents a nitrogen atom, $G^4$ represents CH, $R^{3b}$ represents a hydrogen atom, $R^6$ represents an ethyl group, $R^{3c}$ represents a substituent indicated in any of [Table 7A] to [Table 15A] (hereinafter, referred to as "compound group SX2249").

The compound (L-120), wherein $G^1$ represents a nitrogen atom, $G^4$ represents CH, $R^{3b}$ represents a hydrogen atom, $R^6$ represents a propyl group, $R^{3c}$ represents a substituent indicated in any of [Table 7A] to [Table 15A] (hereinafter, referred to as "compound group SX2250").

The compound (L-120), wherein $G^1$ represents a nitrogen atom, $G^4$ represents CH, $R^{3b}$ represents a hydrogen atom, $R^6$ represents an isopropyl group, $R^{3c}$ represents a substituent indicated in any of [Table 7A] to [Table 15A] (hereinafter, referred to as "compound group SX2251").

The compound (L-120), wherein $G^1$ represents a nitrogen atom, $G^4$ represents CH, $R^{3b}$ represents a hydrogen atom, $R^6$ represents a cyclopropyl group, $R^{3c}$ represents a substituent indicated in any of [Table 7A] to [Table 15A] (hereinafter, referred to as "compound group SX2252").

The compound (L-120), wherein $G^1$ represents a nitrogen atom, $G^4$ represents CH, $R^{3c}$ represents a hydrogen atom, $R^6$ represents a methyl group, $R^{3b}$ represents a substituent indicated in any of [Table 7A] to [Table 15A] (hereinafter, referred to as "compound group SX2253").

The compound (L-120), wherein $G^1$ represents a nitrogen atom, $G^4$ represents CH, $R^{3c}$ represents a hydrogen atom, $R^6$ represents an ethyl group, $R^{3b}$ represents a substituent indicated in any of [Table 7A] to [Table 15A] (hereinafter, referred to as "compound group SX2254").

The compound (L-120), wherein $G^1$ represents a nitrogen atom, $G^4$ represents CH, $R^{3c}$ represents a hydrogen atom, $R^6$ represents a propyl group, $R^{3b}$ represents a substituent indicated in any of [Table 7A] to [Table 15A] (hereinafter, referred to as "compound group SX2255").

The compound (L-120), wherein $G^1$ represents a nitrogen atom, $G^4$ represents CH, $R^{3c}$ represents a hydrogen atom, $R^6$ represents an isopropyl group, $R^{3b}$ represents a substituent indicated in any of [Table 7A] to [Table 15A] (hereinafter, referred to as "compound group SX2256").

The compound (L-120), wherein $G^1$ represents a nitrogen atom, $G^4$ represents CH, $R^{3c}$ represents a hydrogen atom, $R^6$ represents a cyclopropyl group, $R^{3b}$ represents a substituent indicated in any of [Table 7A] to [Table 15A] (hereinafter, referred to as "compound group SX2257").

A compound represented by formula (L-121):

(hereinafter, referred to as "compound (L-121)"), wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX2258").

The compound (L-121), wherein $G^1$ and $G^4$ represent CH, $R^{3c}$ represents a hydrogen atom, $R^{3b}$ represents a substituent indicated in any of [Table 7A] to [Table 15A] (hereinafter, referred to as "compound group SX2259").

The compound (L-121), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX2260").

The compound (L-121), wherein $G^1$ represents CH, $G^4$ represents a nitrogen atom, $R^{3c}$ represents a hydrogen atom, $R^{3b}$ represents a substituent indicated in any of [Table 7A] to [Table 15A] (hereinafter, referred to as "compound group SX2261").

The compound (L-121), wherein $G^1$ represents a nitrogen atom, $G^4$ represents CH, $R^{3b}$ represents a hydrogen atom, $R^{3c}$ represents a substituent indicated in any of [Table 7A] to [Table 15A] (hereinafter, referred to as "compound group SX2262").

The compound (L-121), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX2263").

A compound represented by formula (L-122):

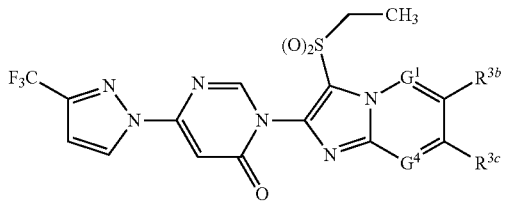

(L-122)

(hereinafter, referred to as "compound (L-122)"),
wherein $G^1$ and $G^4$ represent CH, $R^{3b}$ represents a hydrogen atom, $R^{3c}$ represents a substituent indicated in any of [Table 7A] to [Table 15A] (hereinafter, referred to as "compound group SX2264").

The compound (L-122), wherein $G^1$ and $G^4$ represent CH, $R^{3c}$ represents a hydrogen atom, $R^{3b}$ represents a substituent indicated in any of [Table 7A] to [Table 15A](hereinafter, referred to as "compound group SX2265").

The compound (L-122), wherein $G^1$ represents CH, $G^4$ represents a nitrogen atom, $R^{3b}$ represents a hydrogen atom, $R^{3c}$ represents a substituent indicated in any of [Table 7A] to [Table 15A] (hereinafter, referred to as "compound group SX2266").

The compound (L-122), wherein $G^1$ represents CH, $G^4$ represents a nitrogen atom, $R^{3'}$ represents a hydrogen atom, $R^{3b}$ represents a substituent indicated in any of [Table 7A] to [Table 15A] (hereinafter, referred to as "compound group SX2267").

The compound (L-122), wherein $G^1$ represents a nitrogen atom, $G^4$ represents CH, $R^{3b}$ represents a hydrogen atom, $R^3$ represents a substituent indicated in any of [Table 7A] to [Table 15A] (hereinafter, referred to as "compound group SX2268").

The compound (L-122), wherein $G^1$ represents a nitrogen atom, $G^4$ represents CH, $R^{3c}$ represents a hydrogen atom, $R^{3b}$ represents a substituent indicated in any of [Table 7A] to [Table 15A] (hereinafter, referred to as "compound group SX2269").

A compound represented by formula (L-123):

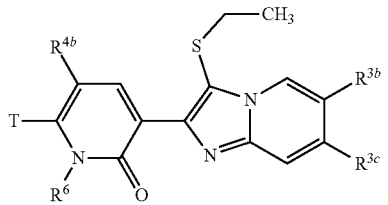

(L-123)

(hereinafter, referred to as "compound (L-123)"),
wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX2312").

The compound (L-123), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX2313").

The compound (L-123), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX2314").

The compound (L-123), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX2315").

The compound (L-123), wherein $R^{3b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX2316").

The compound (L-123), wherein $R^{3b}$ represents a trifluoromethyl group, $R^{3a}$ and $R^{4b}$ represent a hydrogen atom, $R^6$ represents a methyl group, T represents a substituent indicated in any of [Table 1A] to [Table 6A] (hereinafter, referred to as "compound group SX2317").

The compound (L-123), wherein $R^{3b}$ represents a trifluoromethyl group, $R^{3a}$ and $R^{4b}$ represent a hydrogen atom, $R^6$ represents an ethyl group, T represents a substituent indicated in any of [Table 1A] to [Table 6A] (hereinafter, referred to as "compound group SX2318").

The compound (L-123), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A] (hereinafter, referred to as "compound group SX2319").

The compound (L-123), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX2320").

The compound (L-123), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX2321").

The compound (L-123), wherein $R^{3b}$ and $R^{4b}$ represent a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX2322").

The compound (L-123), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX2323").

The compound (L-123), wherein $R^{3b}$ and $R^{4b}$ represent a hydrogen atom, $R^{3c}$ represents a trifluoromethyl group, R represents a propyl group, T represents a substituent indicated in any of [Table 1A] to [Table 6A] (hereinafter, referred to as "compound group SX2324").

The compound (L-123), wherein $R^{3b}$ and $R^{4b}$ represent a hydrogen atom, $R^{3c}$ represents a trifluoromethyl group, R represents an isopropyl group, T represents a substituent indicated in any of [Table 1A] to [Table 6A] (hereinafter, referred to as "compound group SX2325").

The compound (L-123), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX2326").

The compound (L-123), wherein $R^{3b}$ and $R^{3c}$ represent a hydrogen atom, $R^{4b}$ represents a chlorine atom, $R^6$ represents a methyl group, T represents a substituent indicated in any of [Table 1A] to [Table 6A] (hereinafter, referred to as "compound group SX2327").

The compound (L-123), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX2328").

The compound (L-123), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX2329").

The compound (L-123), wherein $R^{3b}$ represents a chlorine atom, $R^{3c}$ represents a hydrogen atom $R^{4b}$ represents a hydrogen atom, $R^6$ represents a hydrogen atom, T represents a substituent indicated in any of [Table 1A] to [Table 6A](hereinafter, referred to as "compound group SX2330").

The compound (L-123), wherein $R^{3b}$ represents a chlorine atom, $R^{3c}$ represents a hydrogen atom, $R^{4b}$ represents a hydrogen atom, $R^6$ represents a methyl group, T represents a substituent indicated in any of [Table 1A] to [Table 6A] (hereinafter, referred to as "compound group SX2331").

The compound (L-123), wherein $R^{3b}$ represents a chlorine atom, $R^{3c}$ represents a hydroxy group, $R^{4b}$ represents a hydrogen atom, $R^6$ represents a methyl group, T represents a substituent indicated in any of [Table 1A] to [Table 6A] (hereinafter, referred to as "compound group SX2332").

The compound (L-123), wherein $R^{3b}$ represents a chlorine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2333").

The compound (L-123), wherein $R^{3b}$ represents a chlorine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2334").

The compound (L-123), wherein $R^{3b}$ represents a chlorine atom, $R^{3c}$ represents a hydrogen atom, $R^{4b}$ represents a hydrogen atom, $R^1$ represents an isopropyl group, T represents a substituent indicated in any of [Table 1A] to [Table 6A] (hereinafter, referred to as "compound group SX2335").

The compound (L-123), wherein $R^{3b}$ represents a chlorine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2336").

The compound (L-123), wherein $R^{3b}$ represents a bromine atom, $R^{3c}$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2337").

The compound (L-123), wherein $R^{2b}$ represents a bromine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2338").

The compound (L-123), wherein $R^{2b}$ represents a bromine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2339").

The compound (L-123), wherein $R^{2b}$ represents a bromine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2340").

The compound (L-123), wherein $R^{3b}$ represents a bromine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2341").

The compound (L-123), wherein $R^{3b}$ represents a bromine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2342").

The compound (L-123), wherein $R^{3b}$ represents a bromine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2343").

The compound (L-123), wherein $R^{3b}$ represents an iodine atom, $R^3$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2344").

The compound (L-123), wherein $R^{3b}$ represents an iodine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2345").

The compound (L-123), wherein $R^{3b}$ represents an iodine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2346").

The compound (L-123), wherein $R^{2b}$ represents an iodine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2347").

The compound (L-123), wherein $R^{3b}$ represents an iodine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2348").

The compound (L-123), wherein $R^{3'}$ represents an iodine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2349").

The compound (L-123), wherein $R^{3b}$ represents an iodine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2350").

A compound represented by formula (L-124):

(L-124)

(hereinafter, referred to as "compound (L-124)"),
wherein $R^{3b}$, $R^{3c}$, and $R^{4b}$ represent a hydrogen atom, $R^6$ represents a methyl group, T represents a substituent indicated in any of [Table 1A] to [Table 6A] (hereinafter, referred to as "compound group SX2351").

The compound (L-124), wherein $R^{3b}$, $R^{3c}$, and $R^{4b}$ represent a hydrogen atom, $R^6$ represents an ethyl group, T represents a substituent indicated in any of [Table 1A] to [Table 6A] (hereinafter, referred to as "compound group SX2352").

The compound (L-124), wherein $R^{3b}$, $R^{3c}$, and $R^{4b}$ represent a hydrogen atom, $R^6$ represents a propyl group, T represents a substituent indicated in any of [Table 1A] to [Table 6A] (hereinafter, referred to as "compound group SX2353").

The compound (L-124), wherein $R^{3b}$, $R^{3c}$, and $R^{4b}$ represent a hydrogen atom, $R^6$ represents an isopropyl group, T represents a substituent indicated in any of [Table 1A] to [Table 6A] (hereinafter, referred to as "compound group SX2354").

The compound (L-124), wherein $R^{4b}$, $R^{3c}$, and $R^{4b}$ represent a hydrogen atom, $R^6$ represents a cyclopropyl group, T represents a substituent indicated in any of [Table 1A] to [Table 6A] (hereinafter, referred to as "compound group SX2355").

The compound (L-124), wherein $R^{3b}$ represents a trifluoromethyl group, $R^{3c}$ and $R^{4b}$ represent a hydrogen atom, $R^6$ represents a methyl group, T represents a substituent indicated in any of [Table 1A] to [Table 6A] (hereinafter, referred to as "compound group SX2356").

The compound (L-124), wherein $R^{3b}$ represents a trifluoromethyl group, $R^{3c}$ and $R^{4b}$ represent a hydrogen atom, $R^6$ represents an ethyl group, T represents a substituent indicated in any of [Table 1A] to [Table 6A] (hereinafter, referred to as "compound group SX2356").

The compound (L-124), wherein $R^{3b}$ represents a trifluoromethyl group, $R^{3c}$ and $R^{4b}$ represent a hydrogen atom, $R^6$ represents a propyl group, T represents a substituent indicated in any of [Table 1A] to [Table 6A] (hereinafter, referred to as "compound group SX2357").

The compound (L-124), wherein $R^{3b}$ represents a trifluoromethyl group, $R^{3c}$ and $R^{4b}$ represent a hydrogen atom, $R^6$ represents an isopropyl group, T represents a substituent indicated in any of [Table 1A] to [Table 6A](hereinafter, referred to as "compound group SX2358").

The compound (L-124), wherein $R^{3b}$ represents a trifluoromethyl group, $R^{3c}$ and $R^{4b}$ represent a hydrogen atom, $R^6$ represents a cyclopropyl group, T represents a substituent indicated in any of [Table 1A] to [Table 6A](hereinafter, referred to as "compound group SX2359").

The compound (L-124), wherein $R^{3b}$ and $R^{4b}$ represent a hydrogen atom, $R^{3'}$ represents a trifluoromethyl group, $R^6$ represents a methyl group, T represents a substituent indicated in any of [Table 1A] to [Table 6A] (hereinafter, referred to as "compound group SX2360").

The compound (L-124), wherein $R^{3b}$ and $R^{4b}$ represent a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX2361").

The compound (L-124), wherein $R^{3b}$ and $R^{4b}$ represent a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX2362").

The compound (L-124), wherein $R^{3b}$ and $R^{4b}$ represent a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX2363").

The compound (L-124), wherein $R^{3b}$ and $R^{4b}$ represent a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX2364").

The compound (L-124), wherein $R^{3b}$ and $R^{3c}$ represent a hydrogen atom, $R^{4b}$ represents a chlorine atom, RE represents a methyl group, T represents a substituent indicated in any of [Table 1A] to [Table 6A] (hereinafter, referred to as "compound group SX2365").

The compound (L-124), wherein $R^{3b}$ represents a trifluoromethyl group, $R^{3c}$ represents a hydrogen atom, $R^{4b}$ represents a chlorine atom, $R^6$ represents a methyl group, T represents a substituent indicated in any of [Table 1A] to [Table 6A] (hereinafter, referred to as "compound group SX2366").

The compound (L-124), wherein $R^{3b}$ represents a hydrogen atom, $R^{3c}$ represents a trifluoromethyl group, $R^{4b}$ represents a chlorine atom, $R^6$ represents a methyl group, T represents a substituent indicated in any of [Table 1A] to [Table 6A] (hereinafter, referred to as "compound group SX2367").

The compound (L-124), wherein $R^{3b}$ represents a chlorine atom, $R^{3c}$ represents a hydrogen atom, $R^{4b}$ represents a hydrogen atom, $R^6$ represents a hydrogen atom, T represents a substituent indicated in any of [Table 1A] to [Table 6A] (hereinafter, referred to as "compound group SX2368").

The compound (L-124), wherein $R^{3b}$ represents a chlorine atom, $R^{3c}$ represents a hydrogen atom, $R^{4b}$ represents a hydrogen atom, $R^6$ represents a methyl group, T represents a substituent indicated in any of [Table 1A] to [Table 6A] (hereinafter, referred to as "compound group SX2369").

The compound (L-124), wherein $R^{4b}$ represents a chlorine atom, $R^{3c}$ represents a hydroxy group, $R^{4b}$ represents a hydrogen atom, $R^6$ represents a methyl group, T represents a substituent indicated in any of [Table 1A] to [Table 6A] (hereinafter, referred to as "compound group SX2370").

The compound (L-124), wherein $R^{4b}$ represents a chlorine atom, $R^1$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2371").

The compound (L-124), wherein $R^{4b}$ represents a chlorine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2372").

The compound (L-124), wherein $R^{3b}$ represents a chlorine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2373").

The compound (L-124), wherein $R^{3b}$ represents a chlorine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2374").

The compound (L-124), wherein $R^{3b}$ represents a bromine atom, $R^{3c}$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2375").

The compound (L-124), wherein $R^{3b}$ represents a bromine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2376").

The compound (L-124), wherein $R^{3b}$ represents a bromine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2377").

The compound (L-124), wherein $R^{3b}$ represents a bromine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2378").

The compound (L-124), wherein $R^{3b}$ represents a bromine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2379").

The compound (L-124), wherein $R^{3b}$ represents a bromine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2380").

The compound (L-124), wherein $R^{3b}$ represents a bromine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2381").

The compound (L-124), wherein $R^{3b}$ represents an iodine atom, $R^{3c}$ represents a hydrogen atom, $R^{4b}$ represents a hydrogen atom, $R^6$ represents a hydrogen atom, T represents a substituent indicated in any of [Table 1A] to [Table 6A](hereinafter, referred to as "compound group SX2382").

The compound (L-124), wherein $R^{3b}$ represents an iodine atom, $R^{3c}$ represents a hydrogen atom, $R^{4b}$ represents a hydrogen atom, $R^6$ represents a methyl group, T represents a substituent indicated in any of [Table 1A] to [Table 6A](hereinafter, referred to as "compound group SX2383").

The compound (L-124), wherein $R^{3b}$ represents an iodine atom, $R^{3c}$ represents a hydroxy group, $R^{4b}$ represents a hydrogen atom, $R^6$ represents a methyl group, T represents a substituent indicated in any of [Table 1A] to [Table 6A](hereinafter, referred to as "compound group SX2384").

The compound (L-124), wherein $R^{3b}$ represents an iodine atom, $R^{3c}$ represents a hydrogen atom, $R^{4b}$ represents a hydrogen atom, $R^6$ represents an ethyl group, T represents a substituent indicated in any of [Table 1A] to [Table 6A] (hereinafter, referred to as "compound group SX2385").

The compound (L-124), wherein $R^{3b}$ represents an iodine atom, $R^{3c}$ represents a hydrogen atom, $R^{4b}$ represents a hydrogen atom, $R^6$ represents a propyl group, T represents a substituent indicated in any of [Table 1A] to [Table 6A] (hereinafter, referred to as "compound group SX2386").

The compound (L-124), wherein $R^{3b}$ represents an iodine atom, $R^{3c}$ represents a hydrogen atom, $R^{4b}$ represents a hydrogen atom, $R^6$ represents an isopropyl group, T represents a substituent indicated in any of [Table 1A] to [Table 6A] (hereinafter, referred to as "compound group SX2387").

The compound (L-124), wherein $R^{3b}$ represents an iodine atom, $R^{3c}$ represents a hydrogen atom, $R^{4b}$ represents a hydrogen atom, $R^6$ represents a cyclopropyl group, T represents a substituent indicated in any of [Table 1A] to [Table 6A] (hereinafter, referred to as "compound group SX2388").

A compound represented by formula (L-125):

(L-125)

(hereinafter, referred to as "compound (L-125)"), wherein $R^{3b}$ and $R^{3c}$ represent a hydrogen atom, $R^6$ represents a methyl group, T represents a substituent indicated in any of [Table 1A] to [Table 6A] (hereinafter, referred to as "compound group SX2389").

The compound (L-125), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX2390").

The compound (L-125), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX2391").

The compound (L-125), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX2392").

The compound (L-125), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX2393").

The compound (L-125), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX2394").

The compound (L-125), wherein $R^{3b}$ represents a trifluoromethyl group, $R^{3c}$ represents a hydrogen atom, $R^5$ represents an ethyl group, T represents a substituent indicated in any of [Table 1A] to [Table 6A] (hereinafter, referred to as "compound group SX2395").

The compound (L-125), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX2396").

The compound (L-125), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX2397").

The compound (L-125), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX2398").

The compound (L-125), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX2399").

The compound (L-125), wherein $R^{3b}$ represents a hydrogen atom, $R^{3c}$ represents a trifluoromethyl group, $R^5$ represents an ethyl group, T represents a substituent indicated in any of [Table 1A] to [Table 6A] (hereinafter, referred to as "compound group SX2400").

The compound (L-125), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX2401").

The compound (L-125), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX2402").

The compound (L-125), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX2403").

The compound (L-125), wherein $R^{3b}$ represents a chlorine atom, $R^{3c}$ represents a hydrogen atom, $R^6$ represents a hydrogen atom, T represents a substituent indicated in any of [Table 1A] to [Table 6A] (hereinafter, referred to as "compound group SX2404").

The compound (L-125), wherein $R^{3b}$ represents a chlorine atom, $R^{3c}$ represents a hydrogen atom, RE represents a methyl group, T represents a substituent indicated in any of [Table 1A] to [Table 6A] (hereinafter, referred to as "compound group SX2405").

The compound (L-125), wherein $R^{3b}$ represents a chlorine atom, $R^{3c}$ represents a hydroxy group, $R^b$ represents a methyl group, T represents a substituent indicated in any of [Table 1A] to [Table 6A] (hereinafter, referred to as "compound group SX2406").

The compound (L-125), wherein $R^{3b}$ represents a chlorine atom, $R^{3c}$ represents a hydrogen atom, $R^6$ represents an ethyl group, T represents a substituent indicated in any of [Table 1A] to [Table 6A] (hereinafter, referred to as "compound group SX2407").

The compound (L-125), wherein $R^{3b}$ represents a chlorine atom, $R^{3c}$ represents a hydrogen atom, $R^6$ represents a propyl group, T represents a substituent indicated in any of [Table 1A] to [Table 6A] (hereinafter, referred to as "compound group SX2408").

The compound (L-125), wherein $R^{3b}$ represents a chlorine atom, $R^{3c}$ represents a hydrogen atom, $R^6$ represents an isopropyl group, T represents a substituent indicated in any of [Table 1A] to [Table 6A] (hereinafter, referred to as "compound group SX2409").

The compound (L-125), wherein $R^{3b}$ represents a chlorine atom, $R^{3c}$ represents a hydrogen atom, $R^6$ represents a cyclopropyl group, T represents a substituent indicated in any of [Table 1A] to [Table 6A] (hereinafter, referred to as "compound group SX2410").

The compound (L-125), wherein $R^{3b}$ represents a bromine atom, $R^{3c}$ represents a hydrogen atom, $R^6$ represents a hydrogen atom, T represents a substituent indicated in any of [Table 1A] to [Table 6A] (hereinafter, referred to as "compound group SX2411").

The compound (L-125), wherein $R^{3b}$ represents a bromine atom, $R^3$ represents a hydrogen atom, $R^6$ represents a methyl group, T represents a substituent indicated in any of [Table 1A] to [Table 6A] (hereinafter, referred to as "compound group SX2412").

The compound (L-125), wherein $R^{3b}$ represents a bromine atom, $R^3$ represents a hydroxy group, $R^6$ represents a methyl group, T represents a substituent indicated in any of [Table 1A] to [Table 6A] (hereinafter, referred to as "compound group SX2413").

The compound (L-125), wherein $R^{3b}$ represents a bromine atom, $R^{3c}$ represents a hydrogen atom, $R^6$ represents an ethyl group, T represents a substituent indicated in any of [Table 1A] to [Table 6A] (hereinafter, referred to as "compound group SX2414").

The compound (L-125), wherein $R^{3b}$ represents a bromine atom, $R^{3c}$ represents a hydrogen atom, $R^6$ represents a propyl group, T represents a substituent indicated in any of [Table 1A] to [Table 6A] (hereinafter, referred to as "compound group SX2415").

The compound (L-125), wherein $R^{3b}$ represents a bromine atom, $R^{3c}$ represents a hydrogen atom, $R^6$ represents an isopropyl group, T represents a substituent indicated in any of [Table 1A] to [Table 6A] (hereinafter, referred to as "compound group SX2416").

The compound (L-125), wherein $R^{3b}$ represents a bromine atom, $R^{3c}$ represents a hydrogen atom, $R^6$ represents a cyclopropyl group, T represents a substituent indicated in any of [Table 1A] to [Table 6A] (hereinafter, referred to as "compound group SX2417").

The compound (L-125), wherein $R^{3b}$ represents an iodine atom, $R^{3c}$ represents a hydrogen atom, $R^6$ represents a hydrogen atom, T represents a substituent indicated in any of [Table 1A] to [Table 6A] (hereinafter, referred to as "compound group SX2418").

The compound (L-125), wherein $R^{3b}$ represents an iodine atom, $R^{3c}$ represents a hydrogen atom, $R^6$ represents a methyl group, T represents a substituent indicated in any of [Table 1A] to [Table 6A] (hereinafter, referred to as "compound group SX2419").

The compound (L-125), wherein $R^{3b}$ represents an iodine atom, $R^{3c}$ represents a hydroxy group, $R^6$ represents a methyl group, T represents a substituent indicated in any of [Table 1A] to [Table 6A] (hereinafter, referred to as "compound group SX2420").

The compound (L-125), wherein $R^{3b}$ represents an iodine atom, $R^{3c}$ represents a hydrogen atom, $R^6$ represents an ethyl group, T represents a substituent indicated in any of [Table 1A] to [Table 6A] (hereinafter, referred to as "compound group SX2421").

The compound (L-125), wherein $R^{3b}$ represents an iodine atom, $R^{3c}$ represents a hydrogen atom, $R^6$ represents a propyl group, T represents a substituent indicated in any of [Table 1A] to [Table 6A] (hereinafter, referred to as "compound group SX2422").

The compound (L-125), wherein $R^{3b}$ represents an iodine atom, $R^{3c}$ represents a hydrogen atom, $R^6$ represents an isopropyl group, T represents a substituent indicated in any of [Table 1A] to [Table 6A] (hereinafter, referred to as "compound group SX2423").

The compound (L-125), wherein $R^{3b}$ represents an iodine atom, $R^{3c}$ represents a hydrogen atom, $R^5$ represents a cyclopropyl group, T represents a substituent indicated in any of [Table 1A] to [Table 6A] (hereinafter, referred to as "compound group SX2424").

A compound represented by formula (L-126):

(L-126)

(hereinafter, referred to as "compound (L-126)"),
wherein $R^{3b}$ and $R^{3c}$ represent a hydrogen atom, $R^5$ represents a methyl group, T represents a substituent indicated in any of [Table 1A] to [Table 6A] (hereinafter, referred to as "compound group SX2425").

The compound (L-126), wherein $R^{3b}$ and $R^{3c}$ represent a hydrogen atom, $R^6$ represents an ethyl group, T represents a substituent indicated in any of [Table 1A] to [Table 6A] (hereinafter, referred to as "compound group SX2426").

The compound (L-126), wherein $R^{3b}$ and $R^{3c}$ represent a hydrogen atom, $R^6$ represents a propyl group, T represents a substituent indicated in any of [Table 1A] to [Table 6A] (hereinafter, referred to as "compound group SX2427").

The compound (L-126), wherein $R^{3b}$ and $R^{3c}$ represent a hydrogen atom, $R^6$ represents an isopropyl group, T represents a substituent indicated in any of [Table 1A] to [Table 6A] (hereinafter, referred to as "compound group SX2428").

The compound (L-126), wherein $R^{3b}$ and $R^{3c}$ represent a hydrogen atom, $R^6$ represents a cyclopropyl group, T represents a substituent indicated in any of [Table 1A] to [Table 6A] (hereinafter, referred to as "compound group SX2429").

The compound (L-126), wherein $R^{3b}$ represents a trifluoromethyl group, $R^{3c}$ represents a hydrogen atom, $R^6$ represents a methyl group, T represents a substituent indicated in any of [Table 1A] to [Table 6A] (hereinafter, referred to as "compound group SX2430").

The compound (L-126), wherein $R^{3b}$ represents a trifluoromethyl group, $R^{3c}$ represents a hydrogen atom, $R^6$ represents an ethyl group, T represents a substituent indicated in any of [Table 1A] to [Table 6A] (hereinafter, referred to as "compound group SX2431").

The compound (L-126), wherein $R^{3b}$ represents a trifluoromethyl group, $R^{3c}$ represents a hydrogen atom, $R^6$ represents a propyl group, T represents a substituent indicated in any of [Table 1A] to [Table 6A] (hereinafter, referred to as "compound group SX2432").

The compound (L-126), wherein $R^{3b}$ represents a trifluoromethyl group, $R^{3c}$ represents a hydrogen atom, $R^6$ represents an isopropyl group, T represents a substituent indicated in any of [Table 1A] to [Table 6A] (hereinafter, referred to as "compound group SX2433").

The compound (L-126), wherein $R^{3b}$ represents a trifluoromethyl group, $R^{3c}$ represents a hydrogen atom, $R^6$ represents a cyclopropyl group, T represents a substituent indicated in any of [Table 1A] to [Table 6A] (hereinafter, referred to as "compound group SX2434").

The compound (L-126), wherein $R^{3b}$ represents a hydrogen atom, $R^{3c}$ represents a trifluoromethyl group, $R^6$ represents a methyl group, T represents a substituent indicated in any of [Table 1A] to [Table 6A] (hereinafter, referred to as "compound group SX2435").

The compound (L-126), wherein $R^{3b}$ represents a hydrogen atom, $R^{3c}$ represents a trifluoromethyl group, $R^6$ represents an ethyl group, T represents a substituent indicated in any of [Table 1A] to [Table 6A] (hereinafter, referred to as "compound group SX2436").

The compound (L-126), wherein $R^{3b}$ represents a hydrogen atom, $R^{3c}$ represents a trifluoromethyl group, $R^6$ represents a propyl group, T represents a substituent indicated in any of [Table 1A] to [Table 6A] (hereinafter, referred to as "compound group SX2437").

The compound (L-126), wherein $R^{3b}$ represents a hydrogen atom, $R^{3c}$ represents a trifluoromethyl group, $R^6$ represents an isopropyl group, T represents a substituent indicated in any of [Table 1A] to [Table 6A] (hereinafter, referred to as "compound group SX2438").

The compound (L-126), wherein $R^{3b}$ represents a hydrogen atom, $R^{3c}$ represents a trifluoromethyl group, $R^6$ represents a cyclopropyl group, T represents a substituent indicated in any of [Table 1A] to [Table 6A] (hereinafter, referred to as "compound group SX2439").

The compound (L-126), wherein $R^{3b}$ represents a chlorine atom, $R^{3c}$ represents a hydrogen atom, $R^6$ represents a hydrogen atom, T represents a substituent indicated in any of [Table 1A] to [Table 6A] (hereinafter, referred to as "compound group SX2440").

The compound (L-126), wherein $R^{3b}$ represents a chlorine atom, $R^{3c}$ represents a hydrogen atom, $R^6$ represents a methyl group, T represents a substituent indicated in any of [Table 1A] to [Table 6A] (hereinafter, referred to as "compound group SX2441").

The compound (L-126), wherein $R^{3b}$ represents a chlorine atom, $R^{3c}$ represents a hydroxy group, $R^6$ represents a methyl group, T represents a substituent indicated in any of [Table 1A] to [Table 6A] (hereinafter, referred to as "compound group SX2442").

The compound (L-126), wherein $R^{3b}$ represents a chlorine atom, $R^{3c}$ represents a hydrogen atom, $R^6$ represents an ethyl group, T represents a substituent indicated in any of [Table 1A] to [Table 6A] (hereinafter, referred to as "compound group SX2443").

The compound (L-126), wherein $R^{3b}$ represents a chlorine atom, $R^{3c}$ represents a hydrogen atom, $R^6$ represents a propyl group, T represents a substituent indicated in any of [Table 1A] to [Table 6A] (hereinafter, referred to as "compound group SX2444").

The compound (L-126), wherein $R^{3b}$ represents a chlorine atom, $R^{3c}$ represents a hydrogen atom, $R^6$ represents an isopropyl group, T represents a substituent indicated in any of [Table 1A] to [Table 6A] (hereinafter, referred to as "compound group SX2445").

The compound (L-126), wherein $R^{3b}$ represents a chlorine atom, $R^{3c}$ represents a hydrogen atom, $R^6$ represents a cyclopropyl group, T represents a substituent indicated in any of [Table 1A] to [Table 6A] (hereinafter, referred to as "compound group SX2446").

The compound (L-126), wherein $R^{3b}$ represents a bromine atom, $R^{2c}$ represents a hydrogen atom, $R^6$ represents a hydrogen atom, T represents a substituent indicated in any of [Table 1A] to [Table 6A] (hereinafter, referred to as "compound group SX2447").

The compound (L-126), wherein $R^{3b}$ represents a bromine atom, $R^{3c}$ represents a hydrogen atom, $R^6$ represents a methyl group, T represents a substituent indicated in any of [Table 1A] to [Table 6A] (hereinafter, referred to as "compound group SX2448").

The compound (L-126), wherein $R^{3b}$ represents a bromine atom, $R^{3c}$ represents a hydroxy group, $R^6$ represents a methyl group, T represents a substituent indicated in any of [Table 1A] to [Table 6A] (hereinafter, referred to as "compound group SX2449").

The compound (L-126), wherein $R^{3b}$ represents a bromine atom, $R^{3c}$ represents a hydrogen atom, $R^6$ represents an ethyl group, T represents a substituent indicated in any of [Table 1A] to [Table 6A] (hereinafter, referred to as "compound group SX2450").

The compound (L-126), wherein $R^{3b}$ represents a bromine atom, $R^{3c}$ represents a hydrogen atom, $R^6$ represents a propyl group, T represents a substituent indicated in any of [Table 1A] to [Table 6A] (hereinafter, referred to as "compound group SX2451").

The compound (L-126), wherein $R^{3b}$ represents a bromine atom, $R^{3c}$ represents a hydrogen atom, $R^6$ represents an isopropyl group, T represents a substituent indicated in any of [Table 1A] to [Table 6A] (hereinafter, referred to as "compound group SX2452").

The compound (L-126), wherein $R^{3b}$ represents a bromine atom, $R^{3c}$ represents a hydrogen atom, $R^6$ represents a cyclopropyl group, T represents a substituent indicated in any of [Table 1A] to [Table 6A] (hereinafter, referred to as "compound group SX2453").

The compound (L-126), wherein $R^{3b}$ represents an iodine atom, $R^{3c}$ represents a hydrogen atom, $R^6$ represents a hydrogen atom, T represents a substituent indicated in any of [Table 1A] to [Table 6A] (hereinafter, referred to as "compound group SX2454").

The compound (L-126), wherein $R^{2b}$ represents an iodine atom, $R^{3c}$ represents a hydrogen atom, $R^1$ represents a methyl group, T represents a substituent indicated in any of [Table 1A] to [Table 6A] (hereinafter, referred to as "compound group SX2455").

The compound (L-126), wherein $R^{3b}$ represents an iodine atom, $R^{3c}$ represents a hydroxy group, $R^6$ represents a methyl group, T represents a substituent indicated in any of [Table 1A] to [Table 6A] (hereinafter, referred to as "compound group SX2456").

The compound (L-126), wherein $R^{3b}$ represents an iodine atom, $R^{3c}$ represents a hydrogen atom, $R^6$ represents an ethyl group, T represents a substituent indicated in any of [Table 1A] to [Table 6A] (hereinafter, referred to as "compound group SX2457").

The compound (L-126), wherein $R^{3b}$ represents an iodine atom, $R^{3c}$ represents a hydrogen atom, $R^6$ represents a propyl group, T represents a substituent indicated in any of [Table 1A] to [Table 6A] (hereinafter, referred to as "compound group SX2458").

The compound (L-126), wherein $R^{3b}$ represents an iodine atom, $R^{3c}$ represents a hydrogen atom, $R^6$ represents an isopropyl group, T represents a substituent indicated in any of [Table 1A] to [Table 6A] (hereinafter, referred to as "compound group SX2459").

The compound (L-126), wherein $R^{2b}$ represents an iodine atom, $R^{3c}$ represents a hydrogen atom, $R^6$ represents a cyclopropyl group, T represents a substituent indicated in any of [Table 1A] to [Table 6A] (hereinafter, referred to as "compound group SX2460").

A compound represented by formula (L-127):

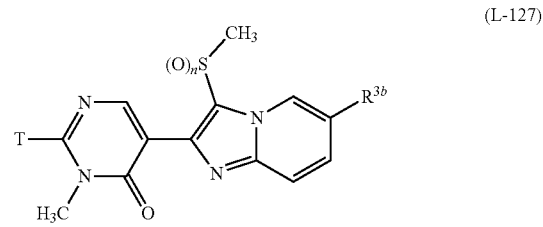

(L-127)

(hereinafter, referred to as "compound (L-127)"), wherein n represents 0, $R^{3b}$ represents a chlorine atom, T represents a substituent indicated in any of [Table 1A] to [Table 6A] (hereinafter, referred to as "compound group SX2461").

The compound (L-127), wherein n represents 1, $R^{3b}$ represents a chlorine atom, T represents a substituent indicated in any of [Table 1A] to [Table 6A] (hereinafter, referred to as "compound group SX2462").

The compound (L-127), wherein n represents 2, $R^{3b}$ represents a chlorine atom, T represents a substituent indicated in any of [Table 1A] to [Table 6A] (hereinafter, referred to as "compound group SX2463").

The compound (L-127), wherein n represents 0, $R^{3b}$ represents a bromine atom, T represents a substituent indicated in any of [Table 1A] to [Table 6A] (hereinafter, referred to as "compound group SX2464").

The compound (L-127), wherein n represents 1, $R^{3b}$ represents a bromine atom, T represents a substituent indicated in any of [Table 1A] to [Table 6A] (hereinafter, referred to as "compound group SX2465").

The compound (L-127), wherein n represents 2, $R^{3b}$ represents a bromine atom, T represents a substituent indicated in any of [Table 1A] to [Table 6A] (hereinafter, referred to as "compound group SX2466").

The compound (L-127), wherein n represents 0, $R^{3b}$ represents an iodine atom, T represents a substituent indicated in any of [Table 1A] to [Table 6A] (hereinafter, referred to as "compound group SX2467").

The compound (L-127), wherein n represents 1, $R^{3b}$ represents an iodine atom, T represents a substituent indicated in any of [Table 1A] to [Table 6A] (hereinafter, referred to as "compound group SX2468").

The compound (L-127), wherein n represents 2, $R^{3b}$ represents an iodine atom, T represents a substituent indicated in any of [Table 1A] to [Table 6A] (hereinafter, referred to as "compound group SX2469").

A compound represented by formula (L-128):

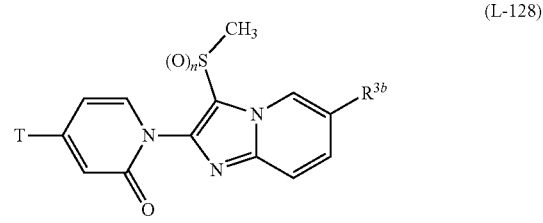

(L-128)

(hereinafter, referred to as "compound (L-128)"), wherein n represents 0, $R^{3b}$ represents a chlorine atom, T represents a substituent indicated in any of [Table 1A] to [Table 6A] (hereinafter, referred to as "compound group SX2470").

The compound (L-128), wherein n represents 1, $R^{3b}$ represents a chlorine atom, T represents a substituent indicated in any of [Table 1A] to [Table 6A] (hereinafter, referred to as "compound group SX2471").

The compound (L-128), wherein n represents 2, $R^{3b}$ represents a chlorine atom, T represents a substituent indicated in any of [Table 1A] to [Table 6A] (hereinafter, referred to as "compound group SX2472").

The compound (L-128), wherein n represents 0, $R^{3b}$ represents a bromine atom, T represents a substituent indicated in any of [Table 1A] to [Table 6A] (hereinafter, referred to as "compound group SX2473").

The compound (L-128), wherein n represents 1, $R^{3b}$ represents a bromine atom, T represents a substituent indicated in any of [Table 1A] to [Table 6A] (hereinafter, referred to as "compound group SX2474").

The compound (L-128), wherein n represents 2, $R^{3b}$ represents a bromine atom, T represents a substituent indicated in any of [Table 1A] to [Table 6A] (hereinafter, referred to as "compound group SX2475").

The compound (L-128), wherein n represents 0, $R^{3b}$ represents an iodine atom, T represents a substituent indicated in any of [Table 1A] to [Table 6A] (hereinafter, referred to as "compound group SX2476").

The compound (L-128), wherein n represents 1, $R^{3b}$ represents an iodine atom, T represents a substituent indicated in any of [Table 1A] to [Table 6A] (hereinafter, referred to as "compound group SX2477").

The compound (L-128), wherein n represents 2, $R^{3b}$ represents an iodine atom, T represents a substituent indicated in any of [Table 1A] to [Table 6A] (hereinafter, referred to as "compound group SX2478").

A compound represented by formula (L-129):

(L-129)

(hereinafter, referred to as "compound (L-129)"), wherein n represents 0, $R^{3b}$ represents a chlorine atom, T represents a substituent indicated in any of [Table 1A] to [Table 6A] (hereinafter, referred to as "compound group SX2479").

The compound (L-129), wherein n represents 1, $R^{3b}$ represents a chlorine atom, T represents a substituent indicated in any of [Table 1A] to [Table 6A] (hereinafter, referred to as "compound group SX2480").

The compound (L-129), wherein n represents 2, $R^{3b}$ represents a chlorine atom, T represents a substituent indicated in any of [Table 1A] to [Table 6A] (hereinafter, referred to as "compound group SX2481").

The compound (L-129), wherein n represents 0, $R^{3b}$ represents a bromine atom, T represents a substituent indicated in any of [Table 1A] to [Table 6A] (hereinafter, referred to as "compound group SX2482").

The compound (L-129), wherein n represents 1, $R^{3b}$ represents a bromine atom, T represents a substituent indicated in any of [Table 1A] to [Table 6A] (hereinafter, referred to as "compound group SX2483").

The compound (L-129), wherein n represents 2, $R^{3b}$ represents a bromine atom, T represents a substituent indicated in any of [Table 1A] to [Table 6A] (hereinafter, referred to as "compound group SX2484").

The compound (L-129), wherein n represents 0, $R^{3b}$ represents an iodine atom, T represents a substituent indicated in any of [Table 1A] to [Table 6A] (hereinafter, referred to as "compound group SX2485").

The compound (L-129), wherein n represents 1, $R^{3b}$ represents an iodine atom, T represents a substituent indicated in any of [Table 1A] to [Table 6A] (hereinafter, referred to as "compound group SX2486").

The compound (L-129), wherein n represents 2, $R^{3b}$ represents an iodine atom, T represents a substituent indicated in any of [Table 1A] to [Table 6A] (hereinafter, referred to as "compound group SX2487").

A compound represented by formula (L-130):

(L-130)

(hereinafter, referred to as "compound (L-130)"), wherein n represents 0, $R^{3b}$ represents a chlorine atom, T represents a substituent indicated in any of [Table 1A] to [Table 6A] (hereinafter, referred to as "compound group SX2488").

The compound (L-130), wherein n represents 1, $R^{3b}$ represents a chlorine atom, T represents a substituent indicated in any of [Table 1A] to [Table 6A] (hereinafter, referred to as "compound group SX2489").

The compound (L-130), wherein n represents 2, $R^{3b}$ represents a chlorine atom, T represents a substituent indicated in any of [Table 1A] to [Table 6A] (hereinafter, referred to as "compound group SX2490").

The compound (L-130), wherein n represents 0, $R^{3b}$ represents a bromine atom, T represents a substituent indicated in any of [Table 1A] to [Table 6A] (hereinafter, referred to as "compound group SX2491").

The compound (L-130), wherein n represents 1, $R^{3b}$ represents a bromine atom, T represents a substituent indicated in any of [Table 1A] to [Table 6A] (hereinafter, referred to as "compound group SX2492").

The compound (L-130), wherein n represents 2, $R^{3b}$ represents a bromine atom, T represents a substituent indicated in any of [Table 1A] to [Table 6A] (hereinafter, referred to as "compound group SX2493").

The compound (L-130), wherein n represents 0, $R^{3b}$ represents an iodine atom, T represents a substituent indicated in any of [Table 1A] to [Table 6A] (hereinafter, referred to as "compound group SX2494").

The compound (L-130), wherein n represents 1, $R^{3b}$ represents an iodine atom, T represents a substituent indicated in any of [Table 1A] to [Table 6A] (hereinafter, referred to as "compound group SX2495").

The compound (L-130), wherein n represents 2, $R^{3b}$ represents an iodine atom, T represents a substituent indicated in any of [Table 1A] to [Table 6A] (hereinafter, referred to as "compound group SX2496").

Next, the Formulation examples of the present compound X are shown below. The "parts" represents "part by weight". Further, the present compound S represents the compounds described as the compound groups SX1 to SX2496.

Formulation Example 1

Into a mixture of 10 parts of any one of the present compounds S, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of wet process silica, and 54 parts of diatomaceous earth are mixed, and further 20 parts of any one of the present compounds S is added thereto, followed by mixing them to obtain each formulation.

Formulation Example 3

To 2 parts of any one of the present compounds S, 1 part of wet process silica, 2 parts of calcium lignin sulfonate, 30 parts of bentonite, and 65 parts of kaolin clay are added, followed by mixing them. To the mixtures is then added an appropriate amount of water, and the mixtures are further stirred, granulated with a granulator, and forced-air dried to obtain each formulation.

Formulation Example 4

Into an appropriate amount of acetone, 1 part of any one of the present compounds S is mixed, and then 5 parts of wet process silica, 0.3 parts of isopropyl acid phosphate, and 93.7 parts of kaolin clay are added, following by mixing them with stirring thoroughly and removal of acetone from the mixture by evaporation to obtain each formulation.

Formulation Example 5

A mixture of 35 parts of polyoxyethylene alkyl ether sulfate ammonium salt and wet process silica (weight ratio of 1:1), 20 parts of any one of the present compounds S, and 45 parts of water are enough mixed to obtain each formulation.

Formulation Example 6

Into a mixture of 5 parts of xylene and 5 parts of trichloroethane, 0.1 parts of any one of the present compounds S are mixed, and the resulting mixture is then mixed with 89.9 parts of kerosene to obtain each solution.

Formulation Example 7

Into 0.5 ml of acetone, 10 mg of any one of the present compounds S is mixed, and the solution is added dropwise to 5 g of a solid feed powder for an animal (solid feed powder for rearing and breeding CE-2, manufactured by CLEA Japan, Inc.), followed by mixing the resulting mixtures uniformly, and then by drying them by evaporation of acetone to obtain each poison bait.

Formulation Example 8

Into an aerosol can, 0.1 parts of any one of the present compounds S and 49.9 parts of Neothiozole (manufactured by Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 parts of any one of the present compounds S, 0.01 parts of 2,6-di-tert-butyl-4-methylphenol, 5 parts of xylene, 3.39 parts of kerosene, and 1 part of Rheodol (registered trademark) MO-60 (manufactured by Kao Corporation), and 50 parts of distilled water are filled into an aerosol container, and a valve part of the container is attached. Then, 40 parts of LPG is filled therein through the valve under pressure to obtain each aqueous aerosol.

Formulation Example 10

Zero point one (0.1) g of any one of the present compounds S is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 11

Five (5) parts of any one of the present compounds S, and 95 parts of ethylene-methyl methacrylate copolymer (the ratio of the methyl methacrylate in the copolymer: 10 weight %) are melted and kneaded, and the resulting kneaded product is extruded from an extrusion molding machine to obtain each rod-shaped molded product having a length of 15 cm and a diameter of 3 mm.

Formulation Example 12

Five (5) parts of any one of the present compounds S, and 95 parts of plasticized polyvinyl chloride resin are melted and kneaded, and the resulting kneaded product is extruded from an extrusion molding machine to obtain each rod-shaped molded product having a length of 15 cm and a diameter of 3 mm.

Formulation Example 13

One-hundred (100) mg of any one of the present compounds S, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 14

Twenty-five (25) mg of any one of the present compounds S, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 15

To 100 mg of any one of the present compounds S, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum (registered trademark) K (manufactured by Vanderbilt Co.), 35 mg of a perfume, and 500 mg of a coloring agent, distilled water is added so that a final volume is set to be 100 mL, followed by mixing the mixtures to obtain each suspension for oral administration.

Formulation Example 16

Into a mixture of 5 parts of an emulsifier, 3 parts of benzyl alcohol and 30 parts of propylene glycol, 5 parts of any one of the present compounds S is mixed, and phosphate buffer is added thereto so that a pH of the solution is set to be 6.0 to 6.5, and water is added as the rest parts to obtain each solution for oral administration.

Formulation Example 17

To a mixture of 57 parts of fractional distilled palm oil and 3 parts of polysorbate 85, 5 parts of aluminium distearate is added, and heated to disperse it. The resulting mixture is cooled to room temperature, and 25 parts of saccharin is dispersed in an oil vehicle. Ten (10) parts of any one of the present compounds S is divided thereto to obtain each paste for oral administration.

Formulation Example 18

Five (5) parts of any one of the present compounds S is mixed with 95 parts of limestone filler, followed by a wet-granulation of the resulting mixture to obtain each granule for oral administration.

Formulation Example 19

Into 80 parts of diethylene glycol monoethyl ether, 5 parts of any one of the present compounds S is mixed, and 15 parts of propylene carbonate is added thereto, and the resulting mixture is mixed to obtain each spot-on solution.

Formulation Example 20

Into 70 parts of diethylene glycol monoethyl ether, 10 parts of any one of the present compounds S is mixed, and 20 parts of 2-octyldodecanol is added thereto, and the resulting mixture is mixed to obtain each pour-on solution.

Formulation Example 21

To 0.1 parts of any one of the present compounds S, 40 parts of sodium polyoxyethylene laurylether sulfate (25% aqueous solution), 5 parts of lauramidopropyl betaine, 5 parts of coconut fatty acid monoethanolamide, 0.5 parts of carboxy vinyl polymer, and 49.4 parts of purified water are added, and the resulting mixture is enough mixed to obtain each shampoo formulation.

Formulation Example 22

Zero point fifteen (0.15) parts of any one of the present compounds S, 95 parts of animal feed, as well as 4.85 parts of a mixture of dibasic calcium phosphate, diatomaceous earth, Aerosil (registered trademark), and carbonate (or chalk) are enough mixed to obtain each premix for animal feed.

Formulation Example 23

Seven point two (7.2) g of any one of the present compounds S, and 92.8 g of Hosco (registered trademark) S-55 are mixed at 100° C., and the resulting mixture is poured into a suppository mold, followed by performing a cooling solidification to obtain each suppository.

Next, the test examples are used to show an efficacy of the present compound X on controlling harmful arthropods. The following test examples were conducted at 25° C.

Test Method 1

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cucumber (*Cucumber sativus*) seedling (on the developmental stage of the second true leaf) is planted in a cup, and approximately 30 cotton aphids (*Aphis gossypii*) (all stages of life) are released onto the seedling. After one day, the diluted solutions are sprayed into the seedling at a ratio of 10 mL/seedling. After 5 days, the number of the surviving insects is examined and the controlling value is calculated by the following equation.

$$\text{Controlling value (\%)} = \{1 - (Cb \times Tai)/(Cai \times Tb)\} \times 100$$

wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group;

Here the "untreated group" represents a group where a similar treatment procedure to that of treated group except not using the test compound is done.

Test Example 1

The test was conducted according to the Test method 1 by making the prescribed concentration 500 ppm and using the below-mentioned present compounds as a test compound, and, as the result of the test, the below-mentioned present compounds showed 90% or more as the controlling value. Present compound Nos: 1, 2, 4, 7 to 13, 22 to 33, 35 to 49, 51, 59, 60, 62 to 65, 68 to 85, 92, 93, 97, and 107

Test Method 2

Test compounds are made to a formulation according to a similar method to that described in the Formulation example 5, and thereto is added water to prepare a diluted solution containing a prescribed concentration of the test compound.

Cucumber (*Cucumber sativus*) seedling (on the developmental stage of the second true leaf) is planted in a cup, and the diluted solutions are drenched to the foot of the seedling at a ratio of 5 mL/seedling. After 7 days, approximately 30 cotton aphids (*Aphis gossypii*) (all stages of life) are released onto the leaf of the seedling. After 6 days, the number of the surviving insects is examined and the controlling value is calculated by the following equation.

$$\text{Controlling value (\%)} = \{1 - (Cb \times Tai)/(Cai \times Tb)\} \times 100$$

wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group;
Here the "untreated group" represents a group where a similar treatment procedure to that of treated group except not using the test compound is done.

Test Example 2

The test was conducted according to the Test method 2 by making the prescribed concentration 1000 ppm and using the below-mentioned present compounds as a test compound, and, as the result of the test, the below-mentioned present compounds showed 90% or more as the controlling value. Present compound Nos: 7, 8, 10, 11, 23, 24, 25, 27, 29, 30, 35 to 40, 42 to 44, 62, 68, 69, 76, 78, and 91
Test Method 3

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) tobacco cutworms (*Spodoptera litura*) at the second instar larval stage are released into the cup. After 5 days, the number of the surviving insects is counted, and the mortality of insects is calculated by the following equation.

Mortality (%)=(1−Number of surviving insects/5)×100

Test Example 3

The test was conducted according to the Test method 3 by making the prescribed concentration 500 ppm and using the below-mentioned present compounds as a test compound, and, as the result of the test, the below-mentioned present compounds showed 80% or more as the mortality of insects. Present compound Nos: 1, 3, 4, 6 to 12, 23, 25 to 30, 32, 35 to 43, 47 to 49, 92, 93, 97, and 107
Test Method 4

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) cabbage moths (*Plutella xylostella*) at the second instar larval stage are released into the cup. After 5 days, the number of the surviving insects is counted, and the mortality of insects is calculated by the following equation.

Mortality (%)=(1−Number of surviving insects/5)×100

Test Example 4

The test was conducted according to the Test method 4 by making the prescribed concentration 500 ppm and using the below-mentioned present compounds as a test compound, and, as the result of the test, the below-mentioned present compounds showed 80 or more as the mortality of insects. Present compound Nos: 1 to 4, 6 to 13, 22 to 49, 51, 59, 60, 63 to 65, 68 to 83, 85 to 87, 90 to 93, 97, 99, 100, and 107
Test Method 5

Each 1 mg of the test compounds is dissolved into 50 μL of a mixed solution of polyoxyethylene sorbitan mono-cocoate and acetone (polyoxyethylene sorbitan mono-cocoate:acetone=5:95 (v/v ratio)). Thereto is added water containing 0.03% by volume of Shindain (registered trademark) to prepare a diluted solution containing a prescribed concentration of the test compound.

A young entire seedling of Corns (*Zea mays*) is immersed into the diluted solution for 30 seconds. Thereafter, each two grains of the seedlings are installed in a plastic petri dish (90 mm radius), and 10 Western corn rootworms (*Diabrotica virgifera virgifera*) at the second instar larval stage are released into the dish. After 5 days, the number of the dead insects is counted, and the mortality of insects is calculated by the following equation.

Mortality (%)={Number of dead insects/10}×100

Test Example 5

The test was conducted according to the Test method 5 by making the prescribed concentration 500 ppm and using the below-mentioned present compounds as a test compound, and, as the result of the test, the below-mentioned present compounds showed 80% or more as the mortality of insects. Present compound Nos: 1, 4, 7, 9 to 13, 23, 24, 26 to 29, 32, 33, 35, 38, 39, 41, 43, 44, 47, 48, 59, 60, 62, 63, 67 to 70, 73 to 83, and 96
Test Method 6

Test compounds are made to a formulation according to a similar method to that described in the Formulation example 5, and thereto is added water to prepare a diluted solution containing a prescribed concentration of the test compound.

A filter paper having a diameter of 5.5 cm in diameter is spread on the bottom of the cup, and then 0.7 ml of the diluted solutions are added dropwise to the filter paper and 30 mg of sucrose is uniformly placed on the filter paper as a bait. Ten (10) housefly (*Musca domestica*) female adults are released into the cup, and the cup is then covered with the lid. After 24 hours, the number of the dead insects is counted, and the mortality of insects is calculated by the following equation.

Mortality (%)=(Number of dead insects/Number of tested insects)×100

Test Example 6

The test was conducted according to the Test method 6 by making the prescribed concentration 500 ppm and using the below-mentioned present compounds as a test compound, and, as the result of the test, the below-mentioned present compounds showed 100% or more as the mortality of insects. Present compound Nos: 9, 11 to 13, 22, 27 to 30, 59, 60, 63, 68, 69, 75, 78, 79, 82, and 83

Test Method 7

Test compounds are made to a formulation according to a similar method to that described in the Formulation example 5, and thereto is added water to prepare a diluted solution containing a prescribed concentration of the test compound.

A filter paper having a diameter of 5.5 cm is spread on the bottom of the cup, and then 0.7 ml of the diluted solutions are added dropwise to the filter paper and 30 mg of sucrose is uniformly placed on the filter paper as a bait. Two (2) German cockroach (*Blattella germanica*) male adults are released into the cup, and the cup is covered with the lid. After 6 days, the number of the dead insects is counted, and the mortality of insects is calculated by the following equation.

Mortality (%)=(Number of dead insects/Number of tested insects)×100

Test Example 7

The test was conducted according to the Test method 7 by making the prescribed concentration 500 ppm and using the below-mentioned present compounds as a test compound, and, as the result of the test, the below-mentioned present compounds showed 100% or more as the mortality of insects. Present compound Nos: 10, 25, 27, 28, 30, 59, 60, 63, 68, 69, 75, 78, 79, 82, and 83

Test Method 8

Each 1 mg of the present compounds is dissolved into 10 μL of a mixed solution of xylene, DMF, and a surfactant (xylene:DMF:surfactant=4:4:1 (v/v ratio)). Thereto is added water containing 0.02% by volume of a spreader to prepare diluted solution A containing a prescribed concentration of the present compound.

Each 1 mg of the present ingredients is dissolved into 10 μL of a mixed solution of xylene, DMF, and a surfactant (xylene:DMF:surfactant=4:4:1 (v/v ratio)). Thereto is added water containing 0.02% s by volume of a spreader to prepare diluted solution B containing a prescribed concentration of the present ingredient.

The diluted solution A is mixed with the diluted solution B to prepare diluted solution C.

Leaf discs of Cucumber (*Cucumber sativus*) cotyledon (length 1.5 cm) are placed in each well of 24-well microplate. Two (2) apterous adults and 8 larvae of cotton aphids (*Aphis gossypii*) per one well are released and the diluted solution C is sprayed at 20 μL per one well. The group is defined as "treated group". A well that is sprayed with 20 μL of water containing 0.02% by volume of a spreader instead of the diluted solution C is defined as "untreated group".

After drying the diluted solution C, the upper microplate is covered with a film sheet. After 5 days, the number of the surviving insects in each well is examined.

The controlling value is calculated by the following equation.

Controlling value (%)={1−(Tai)/(Cai)}×100 wherein the symbols in the equation represent the following descriptions.

Cai: Number of the surviving insects at the time of the examination in untreated group;

Tai: Number of the surviving insects at the time of the examination in treated group.

Specific diluted solutions C, which can confirm their effect according to the Test method 8, are described in the following 1) to 5).

1) The diluted solution C comprises the combination recited in List A wherein a concentration of the present compound is 200 ppm and a concentration of the present ingredient is 2000 ppm. In List A, Comp X represents any compound selected from the present compounds 1 to 83.

List A:

Comp X+Clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA-11; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the present compound is 200 ppm, and a concentration of the present ingredient is 200 ppm.

3) The diluted solution C comprises the combination recited in List A wherein a concentration of the present compound is 500 ppm, and a concentration of the present ingredient is 50 ppm.

4) The diluted solution C comprises the combination recited in List A wherein a concentration of the present compound is 500 ppm, and a concentration of the present ingredient is 5 ppm.

5) The diluted solution C comprises the combination recited in List A wherein a concentration of the present compound is 500 ppm, and a concentration of the present ingredient is 0.5 ppm.

INDUSTRIAL APPLICABILITY

The present compound X shows an excellent control effect against a harmful arthropod.

The invention claimed is:

1. A compound represented by formula (I):

Q-Het  (I)

wherein,

Q represents Q1 or Q2:

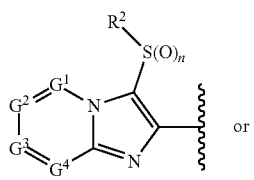

Q2

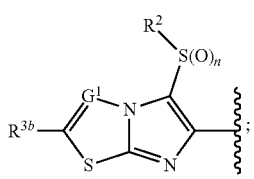

wherein:

(Q1)

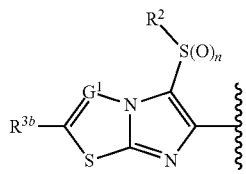

represents:

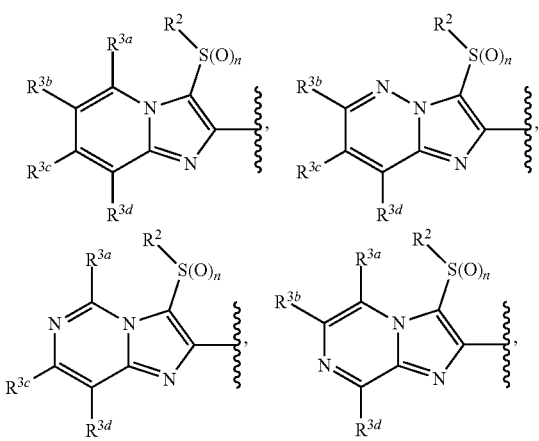

(Q2)

represents $R^2$ represents $C_1$-$C_6$ alkyl, wherein the $C_1$-$C_6$ alkyl is optionally substituted with one or more substituents independently selected from the group consisting of halogen, $CH_2$-cyclopropyl, and cyclopropyl;

$R^{3a}$ represents H, halogen, CN, $NO_2$, a $C_1$-$C_6$ hydrocarbon chain, $C(NOR^{17})R^{30}$, $C(O)R^{13}$, $C(O)NR^{31}R^{32}$, $C(O)NR^{11}S(O)_2R^{23}$, $C(O)OR^{17}$, $NR^{11}R^{12}$, $NR^{11a}R^{12a}$, $NR^{11}C(O)R^{13}$, $NR^{11}C(O)NR^{31}R^{32}$, $NR^{11}C(O)OR^{14}$, $N{=}CHNR^{31}R^{32}$, $NR^{24}NR^{11}R^{12}$, $NR^{24}NR^{11}C(O)R^{13}$, $NR^{24}NR^{11}C(O)NR^{31}R^{32}$, $NR^{24}NR^{11}C(O)OR^{14}$, $NR^{24}OR^{11}$, $N{=}S(O)_pR^{15}R^{16}$, $OR^{12}$, $C_3$-$C_7$ cycloalkyl, phenyl, or 5- or 6-membered heteroaryl, wherein the $C_1$-$C_6$ hydrocarbon chain is optionally substituted with one or more independently selected Group B substituents, and further wherein the $C_3$-$C_7$ cycloalkyl is optionally substituted with one or more independently selected Group E substituents, and the phenyl or 5- or 6-membered heteroaryl is optionally substituted with one or more independently selected Group H substituents;

$R^{3b}$ represents H, halogen, CN, $NO_2$, a $C_1$-$C_6$ hydrocarbon chain, $C(NOR^{17})R^{30}$, $C(O)R^{13}$, $C(O)NR^{31}R^{32}$, $C(O)NR^{11}S(O)_2R^{23}$, $C(O)OR^{17}$, $NR^{11}R^{12}$, $NR^{11a}R^{12a}$, $NR^{11}C(O)R^{13}$, $NR^{11}C(O)NR^{31}R^{32}$, $NR^{11}C(O)OR^{14}$, $N{=}CHNR^{31}R^{32}$, $NR^{24}NR^{11}R^{12}$, $NR^{24}NR^{11}C(O)R^{13}$, $NR^{24}NR^{11}C(O)NR^{31}R^{32}$, $NR^{24}NR^{11}C(O)OR^{14}$, $NR^{24}OR^{11}$, $N{=}S(O)_pR^{15}R^{16}$, $OR^{12}$, $C_3$-$C_7$ cycloalkyl, phenyl, or 5- or 6-membered heteroaryl, wherein the $C_1$-$C_6$ hydrocarbon chain is optionally substituted with one or more independently selected Group B substituents, and further wherein the $C_3$-$C_7$ cycloalkyl is optionally substituted with one or more independently selected Group E substituents, and the phenyl or 5- or 6-membered heteroaryl is optionally substituted with one or more independently selected Group H substituents;

$R^{3c}$ represents H, halogen, CN, $NO_2$, a $C_1$-$C_6$ hydrocarbon chain, $C(NOR^{17})R^{30}$, $C(O)R^{13}$, $C(O)NR^{31}R^{32}$, $C(O)NR^{11}S(O)_2R^{23}$, $C(O)OR^{17}$, $NR^{11}R^{12}$, $NR^{11a}R^{12a}$, $NR^{11}C(O)R^{13}$, $NR^{11}C(O)NR^{31}R^{32}$, $NR^{11}C(O)OR^{14}$, $N{=}CHNR^{31}R^{32}$, $NR^{24}NR^{11}R^{12}$, $NR^{24}NR^{11}C(O)R^{13}$, $NR^{24}NR^{11}C(O)NR^{31}R^{32}$, $NR^{24}NR^{11}C(O)OR^{14}$, $NR^{24}OR^{11}$, $N{=}S(O)_pR^{15}R^{16}$, $OR^{12}$, $C_3$-$C_7$ cycloalkyl, phenyl, or 5- or 6-membered heteroaryl, wherein the $C_1$-$C_6$ hydrocarbon chain is optionally substituted with one or more independently selected Group B substituents, and further wherein the $C_3$-$C_7$ cycloalkyl is optionally substituted with one or more independently selected Group E substituents, and the phenyl or 5- or 6-membered heteroaryl is optionally substituted with one or more independently selected Group H substituents;

$R^{3d}$ represents H, halogen, CN, $NO_2$, a $C_1$-$C_6$ hydrocarbon chain, $C(NOR^{17})R^{30}$, $C(O)R^{13}$, $C(O)NR^{31}R^{32}$, $C(O)NR^{11}S(O)_2R^{23}$, $C(O)OR^{17}$, $NR^{11}R^{12}$, $NR^{11a}R^{12a}$, $NR^{11}C(O)R^{13}$, $NR^{11}C(O)NR^{31}R^{32}$, $NR^{11}C(O)OR^{14}$, $N=CHNR^{31}R^{32}$, $NR^{24}R^{11}R^{12}$, $NR^{24}NR^{11}C(O)R^{13}$, $NR^{24}NR^{11}C(O)NR^{13}R^{32}$, $NR^{24}NR^{11}C(O)OR^{14}$, $NR^{24}OR^{11}$, $N=S(O)_pR^{15}R^{16}$, $OR^{12}$, $C_3$-$C_7$ cycloalkyl, phenyl, or 5- or 6-membered heteroaryl, wherein the $C_1$-$C_6$ hydrocarbon chain is optionally substituted with one or more independently selected Group B substituents, and further wherein the $C_3$-$C_7$ cycloalkyl is optionally substituted with one or more independently selected Group E substituents, and the phenyl or 5- or 6-membered heteroaryl is optionally substituted with one or more independently selected Group H substituents;

each $R^{11}$ independently represents H or a $C_1$-$C_6$ hydrocarbon chain, wherein each $C_1$-$C_6$ hydrocarbon chain is optionally and independently substituted with one or more independently selected halogen substituents;

each $R^{12}$ independently represents H, a $C_1$-$C_6$ hydrocarbon chain, $S(O)_2R^{23}$, $C_3$-$C_7$ cycloalkyl, $C_3$-$C_7$ cycloalkenyl, phenyl, or 6-membered heteroaryl, wherein each $C_1$-$C_6$ hydrocarbon chain is optionally and independently substituted with one or more independently selected Group F substituents, and further wherein each $C_3$-$C_7$ cycloalkyl and $C_3$-$C_7$ cycloalkenyl is optionally and independently substituted with one or more independently selected Group J substituents, and each phenyl and 6-membered heteroaryl is optionally and independently substituted with one or more independently selected Group D substituents;

each $R^{11a}$ and $R^{12a}$ taken together with the N atom to which they are attached, independently represents a non-aromatic 3- to 7-membered heterocyclyl, wherein each non-aromatic 3- to 7-membered heterocyclyl is optionally and independently substituted with one or more independently selected Group E substituents;

each $R^{13}$ independently represents H, a $C_1$-$C_6$ hydrocarbon chain, $C_1$-$C_3$ alkylene-$C_3$-$C_6$ cycloalkyl, $C_3$-$C_7$ cycloalkyl, phenyl, or 5- or 6-membered heteroaryl, wherein each $C_1$-$C_6$ hydrocarbon chain, $C_1$-$C_3$ alkylene-$C_3$-$C_6$ cycloalkyl, and $C_3$-$C_7$ cycloalkyl is optionally and independently substituted with one or more independently selected halogen substituents, and further wherein each phenyl and 5- or 6-membered heteroaryl is optionally and independently substituted with one or more independently selected Group D substituents;

each $R^{14}$ independently represents a $C_1$-$C_6$ hydrocarbon chain, $C_1$-$C_3$ alkylene-$C_3$-$C_6$ cycloalkyl, $C_1$-$C_3$ alkylene-phenyl, or $C_3$-$C_7$ cycloalkyl, wherein each $C_1$-$C_6$ hydrocarbon chain, $C_1$-$C_3$ alkylene-$C_3$-$C_6$ cycloalkyl, and $C_3$-$C_7$ cycloalkyl is optionally and independently substituted with one or more independently selected halogen substituents, and further wherein each phenyl of each $C_1$-$C_3$ alkylene-phenyl is optionally and independently substituted with one or more independently selected Group D substituents;

each $R^{15}$ independently represents $C_1$-$C_6$ alkyl, wherein each $C_1$-$C_6$ alkyl is optionally and independently substituted with one or more independently selected halogen substituents;

each $R^{16}$ independently represents $C_1$-$C_6$ alkyl, wherein each $C_1$-$C_6$ alkyl is optionally and independently substituted with one or more independently selected halogen substituents;

each $R^{17}$ independently represents H, a $C_1$-$C_6$ hydrocarbon chain, or phenyl, wherein each $C_1$-$C_6$ hydrocarbon chain is optionally and independently substituted with one or more independently selected halogen substituents, and further wherein each phenyl is optionally and independently substituted with one or more independently selected Group D substituents;

each $R^{23}$ independently represents a $C_1$-$C_6$ hydrocarbon chain or phenyl, wherein each $C_1$-$C_6$ hydrocarbon chain is optionally and independently substituted with one or more independently selected halogen substituents, and wherein each phenyl is optionally and independently substituted with one or more independently selected Group D substituents;

each $R^{24}$ independently represents H or a $C_1$-$C_6$ hydrocarbon chain, wherein each $C_1$-$C_6$ hydrocarbon chain is optionally and independently substituted with one or more independently selected halogen substituents;

each $R^{31}$ independently represents H or $C_1$-$C_6$ alkyl, wherein each $C_1$-$C_6$ alkyl is optionally and independently substituted with one or more independently selected halogen substituents;

each $R^{32}$ independently represents H, a $C_1$-$C_6$ hydrocarbon chain, $S(O)_2R^{23}$, or $C_3$-$C_7$ cycloalkyl, wherein each $C_1$-$C_6$ hydrocarbon chain is optionally and independently substituted with one or more independently selected Group F substituents, and further wherein each $C_3$-$C_7$ cycloalkyl is optionally and independently substituted with one or more independently selected Group J substituents;

n represents 0, 1, or 2; and each p independently represents 0 or 1;

Het represents Het1, Het2, or Het3:

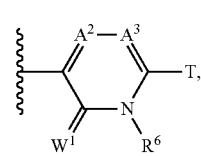

Het1

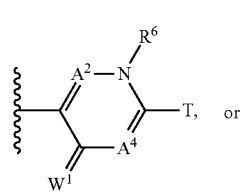

Het2

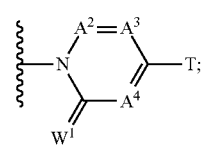

Het3 wherein:

$W^1$ represents O or S;

$A^2$ represents N or $CR^{4a}$, $A^3$ represents N or $CR^{4b}$, $A^4$ represents N or $CR^{4c}$, $R^{4a}$ represents H, halogen, CN, $NO_2$, a $C_1$-$C_6$ hydrocarbon chain, $NH_2$, $NR^{18}R^{19}$, or $OR^{18}$, wherein the $C_1$-$C_6$ hydrocarbon chain is optionally substituted with one or more independently selected halogen substituents;

$R^{4b}$ represents H, halogen, CN, $NO_2$, a $C_1$-$C_6$ hydrocarbon chain, NH, $NR^{18}R^{19}$, or $OR^{18}$, wherein the $C_1$-$C_6$ hydrocarbon chain is optionally substituted with one or more independently selected halogen substituents;

$R^{4c}$ represents H, halogen, CN, $NO_2$, a $C_1$-$C_6$ hydrocarbon chain, NH, $NR^{18}R^{19}$, or $OR^{18}$, wherein the $C_1$-$C_6$ hydrocarbon chain is optionally substituted with one or more independently selected halogen substituents;

$R^6$ represents a $C_1$-$C_6$ hydrocarbon chain, $C_3$-$C_6$ cycloalkyl, phenyl, or 5- or 6-membered heteroaryl, wherein the $C_1$-$C_6$ hydrocarbon chain is optionally substituted with one or more independently selected Group F substituents, and further wherein the $C_3$-$C_6$ cycloalkyl is optionally substituted with one or more independently selected Group J substituents, and the phenyl or 5- or 6-membered heteroaryl is optionally substituted with one or more independently selected Group H substituents;

each $R^{18}$ independently represents a $C_1$-$C_6$ hydrocarbon chain, wherein each $C_1$-$C_6$ hydrocarbon chain is optionally and independently substituted with one or more independently selected halogen substituents;

each $R^{19}$ independently represents H or a $C_1$-$C_6$ hydrocarbon chain, wherein each $C_1$-$C_6$ hydrocarbon chain is optionally and independently substituted with one or more independently selected halogen substituents;

(i) T represents a $C_1$-$C_{10}$ hydrocarbon chain, a $C_1$-$C_5$ alkylene-C(O)—$C_1$-$C_5$ alkyl, $CH_2OR^1$, $C_2$-$C_5$ alkylene-$OC_1$-$C_5$ alkyl, $C_2$-$C_5$ alkylene-$OC_3$-$C_5$ alkenyl, $C_2$-$C_5$ alkylene-$OC_3$-$C_5$ alkynyl, $C_2$-$C_5$ alkylene-$S(O)_w$—$C_1$-$C_5$ alkyl, $C_2$-$C_5$ alkylene-$S(O)_w$—$C_3$-$C_5$ alkenyl, $C_2$-$C_5$ alkylene-$S(O)_w$—$C_3$-$C_5$ alkynyl, $C_1$-$C_3$ alkylene-$C_3$-$C_7$ cycloalkyl, $C(O)R^1$, $C(O)NR^1R^{29}$, $NR^1R^{29}$, $NR^{29}C(O)R^1$, $N=CR^1R^{30}$, $OR^1$, $OS(O)_2R^1$, $S(O)_vR^1$, or $C_3$-$C_7$ cycloalkyl, wherein the $C_1$-$C_{10}$ hydrocarbon chain, $C_1$-$C_5$ alkylene-C(O)—$C_1$-$C_5$ alkyl, $C_2$-$C_5$ alkylene-$OC_1$-$C_5$ alkyl, $C_2$-$C_5$ alkylene-$OC_3$-$C_5$ alkenyl, $C_2$-$C_5$ alkylene-$OC_3$-$C_5$ alkynyl, $C_2$-$C_5$ alkylene-$S(O)_w$—$C_1$-$C_5$ alkyl, $C_2$-$C_5$ alkylene-$S(O)_w$—$C_3$-$C_5$ alkenyl, or $C_2$-$C_5$ alkylene-$S(O)_w$—$C_3$-$C_5$ alkynyl is optionally substituted with one or more substituents independently selected from the group consisting of halogen and CN, and further wherein the $C_1$-$C_3$ alkylene-$C_3$-$C_7$ cycloalkyl or $C_3$-$C_7$ cycloalkyl is optionally substituted with one or more independently selected Group G substituents;

$R^1$ represents a $C_1$-$C_{10}$ hydrocarbon chain, $C_1$-$C_5$ alkylene-C(O)—$C_1$-$C_5$ alkyl, $C_2$-$C_5$ alkylene-$OC_1$-$C_5$ alkyl, $C_2$-$C_5$ alkylene-$OC_3$-$C_5$ alkenyl, $C_2$-$C_5$ alkylene-$OC_3$-$C_5$ alkynyl, $C_2$-$C_5$ alkylene-$S(O)_t$—$C_1$-$C_5$ alkyl, $C_2$-$C_5$ alkylene-$S(O)_t$—$C_3$-$C_5$ alkenyl, $C_2$-$C_5$ alkylene-$S(O)_t$—$C_3$-$C_5$ alkynyl, $C_1$-$C_3$ alkylene-$C_3$-$C_7$ cycloalkyl, or $C_3$-$C_7$ cycloalkyl, wherein the $C_1$-$C_{10}$ hydrocarbon chain, $C_1$-$C_5$ alkylene-C(O)—$C_1$-$C_5$ alkyl, $C_2$-$C_5$ alkylene-$OC_1$-$C_5$ alkyl, $C_2$-$C_5$ alkylene-$OC_3$-$C_5$ alkenyl, $C_2$-$C_5$ alkylene-$OC_3$-$C_5$ alkynyl, $C_2$-$C_5$ alkylene-$S(O)_t$—$C_1$-$C_5$ alkyl, $C_2$-$C_5$ alkylene-$S(O)_t$—$C_3$-$C_5$ alkenyl, or $C_2$-$C_5$ alkylene-$S(O)_t$—$C_3$-$C_5$ alkynyl is optionally substituted with one or more substituents independently selected from the group consisting of halogen and CN, and further wherein the $C_1$-$C_3$ alkylene-$C_3$-$C_7$ cycloalkyl or $C_3$-$C_7$ cycloalkyl is optionally substituted with one or more independently selected Group G substituents;

$R^{29}$ represents H or a $C_1$-$C_6$ hydrocarbon chain, wherein the $C_1$-$C_6$ hydrocarbon chain is optionally substituted with one or more independently selected halogen substituents;

each $R^{30}$ independently represents H, halogen, a $C_1$-$C_6$ hydrocarbon chain, $NR^{36}R^{37}$, or $OR^{35}$, wherein each $C_1$-$C_6$ hydrocarbon chain is optionally and independently substituted with one or more independently selected halogen substituents;

$R^{35}$ represents a $C_1$-$C_6$ hydrocarbon chain, wherein the $C_1$-$C_6$ hydrocarbon chain is optionally substituted with one or more independently selected halogen substituents;

$R^{36}$ represents H or a $C_1$-$C_6$ hydrocarbon chain, wherein the $C_1$-$C_6$ hydrocarbon chain is optionally substituted with one or more independently selected halogen substituents;

$R^{37}$ represents H or a $C_1$-$C_6$ hydrocarbon chain, wherein the $C_1$-$C_6$ hydrocarbon chain is optionally substituted with one or more independently selected halogen substituents; and v represents 0, 1 or 2; and w represents 0, 1 or 2; or (ii) T represents T-1, T-2, T-3, T-4, T-5, T-6, T-7, T-8, T-9, T-10, T-11, or T-12:

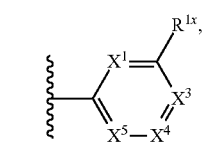

T-1

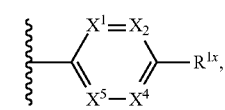

T-2

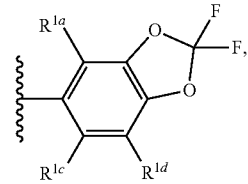

T-3

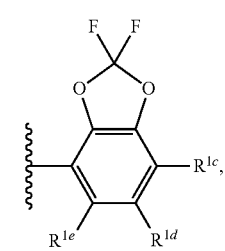

T-4

-continued

T-5: [structure with N, X², R¹ᶜ, R¹ˣ, R¹ᵉ, O]

T-6: [structure with N, X², X⁴, R¹ᶜ, R¹ᵉ, O]

T-7: [structure with N, X⁴, R¹ˣ, R¹ᶜ, R¹ᵉ, O]

T-8: [structure with N, Y², Y³, Y⁴, R¹ʸ]

T-9: [structure with Y², Y³, Y⁴, N, R¹ᵃʸ]

T-10: [structure with Y², Y³, Y¹, R¹ʸ]

T-11: [structure with Y¹, Y², Y³, R¹ʸ]

T-12: [structure with Y¹, Y², Y³, R¹ʸ]

$X^1$ represents N or $CR^{1a}$;
$X^2$ represents N or $CR^{1b}$;
$X^3$ represents N or $CR^{1c}$;
$X^4$ represents N or $CR^{1d}$;
$X^5$ represents N or $CR^{1e}$;
$Y^1$ represents —$NR^{25}$—, —O—, or —S—;
$Y^2$ represents N or $CR^{26}$;
$Y^3$ represents N or $CR^{27}$;
$Y^4$ represents N or $CR^{28}$;
$R^{1a}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
$R^{1b}$ represents H, halogen, a $C_1$-$C_6$ hydrocarbon chain, or $C_3$-$C_6$ cycloalkyl, wherein the $C_1$-$C_6$, hydrocarbon chain or $C_3$-$C_6$ cycloalkyl is optionally substituted with one or more independently selected halogen substituents;
$R^{1c}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
$R^{1d}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
$R^{1e}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
$R^{1x}$ represents halogen, a $C_1$-$C_5$ hydrocarbon chain, $NR^8S(O)_2R^7$, $OR^7$, $OS(O)_2R^7$, or $S(O)_mR^7$, wherein the $C_1$-$C_5$ hydrocarbon chain is substituted with one or more independently selected halogen substituents;
$R^{1y}$ represents halogen, CN, a $C_1$-$C_5$ hydrocarbon chain, $NR^8S(O)_2R^7$, $OR^7$, $OS(O)_2R^7$, or $S(O)_mR^7$, wherein the $C_1$-$C_5$ hydrocarbon chain is substituted with one or more independently selected halogen substituents;
$R^{1ay}$ represents a $C_1$-$C_6$ hydrocarbon chain, wherein the $C_1$-$C_6$ hydrocarbon chain is substituted with one or more independently selected halogen substituents;
$R^7$ represents a $C_1$-$C_6$ hydrocarbon chain, wherein the $C_1$-$C_6$ hydrocarbon chain is substituted with one or more independently selected halogen substituents;
$R^8$ represents H or a $C_1$-$C_6$ hydrocarbon chain, wherein the $C_1$-$C_6$ hydrocarbon chain is optionally substituted with one or more independently selected halogen substituents;
$R^{25}$ represents H, a $C_1$-$C_6$ hydrocarbon chain, $C_1$-$C_6$ alkylene-$C_3$-$C_7$ cycloalkyl, $OC_1$-$C_6$ alkyl, or $C_3$-$C_7$ cycloalkyl, wherein the $C_1$-$C_6$ hydrocarbon chain, $C_1$-$C_6$ alkylene-$C_3$-$C_7$ cycloalkyl, $OC_1$-$C_6$ alkyl, or $C_3$-$C_7$ cycloalkyl is optionally substituted with one or more independently selected halogen substituents;
$R^{26}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
$R^{27}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
$R^{28}$ represents H, halogen, a $C_1$-$C_6$ hydrocarbon chain, or $C_3$-$C_6$ cycloalkyl, wherein the $C_1$-$C_6$ hydrocarbon chain or $C_3$-$C_6$ cycloalkyl is optionally substituted with one or more independently selected halogen substituents;
m represents 0, 1, or 2; and
t represents 0, 1, or 2;
each Group B substituent independently represents halogen, CN, OH, $OC_1$-$C_6$ alkyl, $OC_3$-$C_6$ alkenyl, $OC_3$-$C_6$ alkynyl, $SC_1$-$C_6$ alkyl, $S(O)C_1$-$C_6$ alkyl, $S(O)_2C_1$-$C_6$ alkyl, or $C_3$-$C_6$ cycloalkyl, wherein each $OC_1$-$C_6$ alkyl, $OC_3$-$C_6$ alkenyl, $OC_3$-$C_6$ alkynyl, $SC_1$-$C_6$ alkyl, $S(O)C_1$-$C_6$ alkyl, $S(O)_2C_1$-$C_6$ alkyl, and $C_3$-$C_6$ cycloalkyl is optionally and independently substituted with one or more independently selected halogen substituents;
each Group C substituent independently represents halogen, a $C_1$-$C_6$ hydrocarbon chain, $OC_1$-$C_6$ alkyl, $OC_3$-$C_6$ alkenyl, or $OC_3$-$C_6$ alkynyl, wherein each $C_1$-$C_6$ hydrocarbon chain, $OC_1$-$C_6$ alky, $OC_3$-$C_6$ alkenyl, and $OC_3$-$C_6$ alkynyl is optionally and independently substituted with one or more independently selected halogen substituents;

each Group D substituent independently represents halogen, CN, $NO_2$, a $C_1$-$C_6$ hydrocarbon chain, $C(O)R^{21}$, $C(O)OR^{21}$, $NH_2$, $NHR^{21}$, $NR^{21}R^{22}$, OH, $OC_1$-$C_6$ alkyl, $OC_3$-$C_6$ alkenyl, $OC_3$-$C_6$ alkynyl, $OC(O)R^{21}$, SH, $SC_1$-$C_6$ alkyl, $S(O)C_1$-$C_6$ alkyl, or $S(O)_2C_1$-$C_6$ alkyl, wherein each $C_1$-$C_6$ hydrocarbon chain, $OC_1$-$C_6$ alkyl, $OC_3$-$C_6$ alkenyl, $OC_3$-$C_6$ alkynyl, $SC_1$-$C_6$ alkyl, $S(O)C_1$-$C_6$ alkyl, and $S(O)_2C_1$-$C_6$ alkyl is optionally and independently substituted with one or more independently selected halogen substituents;

each Group E substituent independently represents halogen, CN, $NO_2$, a $C_1$-$C_6$ hydrocarbon chain, OH, $OC_1$-$C_6$ alkyl, $OC_3$-$C_6$ alkenyl, $OC_3$-$C_6$ alkynyl, or =O, wherein each $C_1$-$C_6$ hydrocarbon chain, $OC_1$-$C_6$ alkyl, $OC_3$-$C_6$ alkenyl, and $OC_3$-$C_6$ alkynyl is optionally and independently substituted with one or more independently selected halogen substituents;

each Group F substituent independently represents halogen, CN, $NH_2$, $NHR^{21}$, $NR^{21}R^{22}$, $OC_1$-$C_6$ alkyl, $C_3$-$C_7$ cycloalkyl, a non-aromatic 3- to 7-membered heterocyclyl, phenyl, or 5- or 6-membered heteroaryl, wherein each $OC_1$-$C_6$ alkyl is optionally and independently substituted with one or more independently selected halogen substituents, and further wherein each non-aromatic 3- to 7-membered heterocyclyl is optionally and independently substituted with one or more independently selected Group C substituents, and each $C_3$-$C_7$ cycloalkyl, phenyl, and 5- or 6-membered heteroaryl is optionally and independently substituted with one or more independently selected Group D substituents;

each Group G substituent independently represents halogen, CN, or $C_1$-$C_6$ haloalkyl;

each Group H substituent independently represents halogen, CN, $NO_2$, $C_1$-$C_6$ alkyl, $C(O)R^{10}$, $C(O)NR^9R^{10}$, $C(O)OR^{10}$, $NH_2NR^9R^{10}$, $NR^{10}C(O)R^9$, $NR^{10}C(O)OR^9$, $OR^{10}$, $OC(O)R^9$, $OC(O)OR^9$, or 5- or 6-membered heteroaryl, wherein each $C_1$-$C_6$ alkyl is optionally and independently substituted with one or more independently selected halogen substituents;

each Group J substituent independently represents halogen, CN, or $C_1$-$C_6$ alkyl, wherein each $C_1$-$C_6$ alkyl is optionally and independently substituted with one or more independently selected halogen substituents;

each $R^9$ independently represents $C_1$-$C_6$ alkyl or $C_3$-$C_6$ cycloalkyl, wherein each $C_1$-$C_6$ alkyl and $C_3$-$C_6$ cycloalkyl is optionally and independently substituted with one or more independently selected halogen substituents;

each $R^{10}$ independently represents H, $C_1$-$C_6$ alkyl, or $C_3$-$C_6$ cycloalkyl, wherein each $C_1$-$C_6$ alkyl and $C_3$-$C_6$ cycloalkyl is optionally and independently substituted with one or more independently selected halogen substituents;

each $R^{21}$ independently represents $C_1$-$C_6$ alkyl, wherein each $C_1$-$C_6$ alkyl is optionally and independently substituted with one or more independently selected halogen substituents; and each $R^{22}$ independently represents $C_1$-$C_6$ alkyl, wherein each $C_1$-$C_6$ alkyl is optionally and independently substituted with one or more independently selected halogen substituents.

2. The compound according to claim 1, wherein:

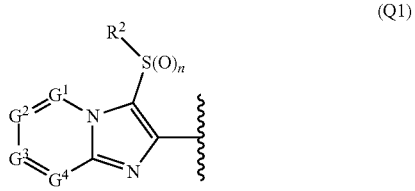

(Q1)

represents:

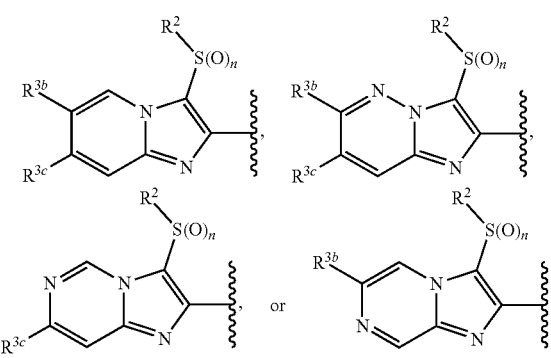

wherein:

$R^{3b}$ represents H, halogen, $C_1$-$C_6$ alkyl, $OR^{12}$, or $C_3$-$C_7$ cycloalkyl, wherein the $C_1$-$C_6$ alkyl or $C_3$-$C_7$ cycloalkyl is optionally substituted with one or more substituents independently selected from the group consisting of halogen and CN;

$R^{3c}$ represents H, halogen, $C_1$-$C_6$ alkyl, $OR^{12}$, or $C_3$-$C_7$ cycloalkyl, wherein the $C_1$-$C_6$ alky or $C_3$-$C_7$ cycloalkyl is optionally substituted with one or more substituents independently selected from the group consisting of halogen and CN;

$R^{4a}$ represents H;

$R^{4b}$ represents H; and $R^{4c}$ represents H.

3. The compound according to claim 1, wherein:

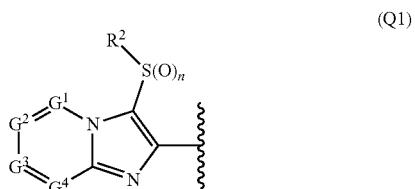

(Q1)

represents:

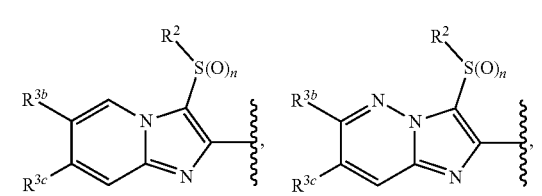

-continued

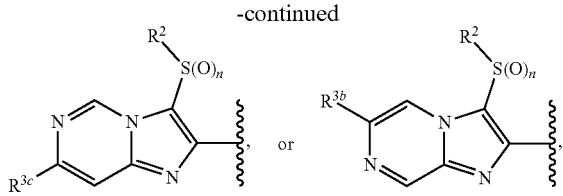

wherein:

R³ᵇ represents H or $C_1$-$C_6$ alkyl wherein the $C_1$-$C_6$ alkyl is optionally substituted with one or more independently selected halogen substituents; and R³ᶜ represents H or $C_1$-$C_6$ alkyl, wherein the $C_1$-$C_6$ alkyl is optionally substituted with one or more independently selected halogen substituents.

4. The compound according to claim 1, wherein Q represents Q1;

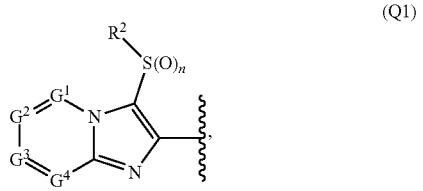

wherein Q1 represents:

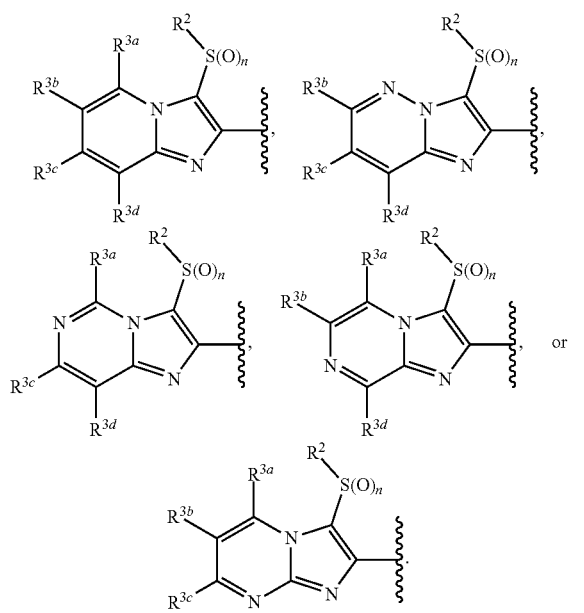

5. The compound according to claim 1, wherein Q represents Q2:

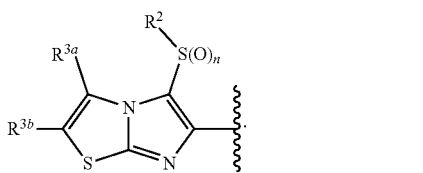

6. The compound according to claim 1, wherein $R^2$ represents $CH_2CH_3$.

7. The compound according to claim 1, wherein:

$R^{3a}$ represents H, halogen, $C_1$-$C_6$alkyl, $C(NOR^{17})R^{30}$, $OR^{12}$, $C_3$-$C_7$ cycloalkyl, phenyl, pyridinyl, or pyrimidinyl, wherein the $C_1$-$C_6$ alkyl or $C_3$-$C_7$ cycloalkyl is optionally substituted with one or more substituents independently selected from the group consisting of halogen and CN, and further wherein the phenyl, pyridinyl, or pyrimidinyl is optionally substituted with one or more independently selected Group H substituents;

$R^{3b}$ represents H, halogen, $C_1$-$C_6$ alkyl, $C(NOR^{17})R^{30}$, $OR^{12}$, $C_3$-$C_7$ cycloalkyl, phenyl, pyridinyl, or pyrimidinyl, wherein the $C_1$-$C_6$ alkyl or $C_3$-$C_7$ cycloalkyl is optionally substituted with one or more substituents independently selected from the group consisting of halogen and CN, and further wherein the phenyl, pyridinyl, or primidinyl is optionally substituted with one or more independently selected Group H substituents;

$R^{3c}$ represents H, halogen, $C_1$-$C_6$ alkyl, $C(NOR^{17})R^{30}$, $OR^{12}$, $C_3$-$C_7$ cycloalkyl, phenyl, pyridinyl, or pyrimidinyl, wherein the $C_1$-$C_6$ alkyl or $C_3$-$C_7$ cycloalkyl is optionally substituted with one or more substituents independently selected from the group consisting of halogen and CN, and further wherein the phenyl, pyridinyl, or pyrimidinyl is optionally substituted with one or more independently selected Group H substituents;

$R^{3d}$ represents H, halogen, $C_1$-$C_6$alkyl, $C(NOR^{17})R^{30}$, $OR^{12}$, $C_3$-$C_7$ cycloalkyl, phenyl, pyridinyl, or pyrimidinyl, wherein the $C_1$-$C_6$ alkyl or $C_3$-$C_7$ cycloalkyl is optionally substituted with one or more substituents independently selected from the group consisting of halogen and CN, and further wherein the phenyl, pyridinyl, or pyrimidinyl is optionally substituted with one or more independently selected Group H substituents;

$R^{4a}$ represents H, halogen, CN, $C_1$-$C_3$ alkyl, or $OR^{18}$;

$R^{4b}$ represents H, halogen, CN, $C_1$-$C_3$ alkyl, or $OR^{18}$;

$R^{4c}$ represents H, halogen, CN, $C_1$-$C_3$ alkyl, or $OR^{18}$; and each $R^{18}$ independently represents $C_1$-$C_3$ alkyl.

8. The compound according to claim 1, wherein Het represents Het2:

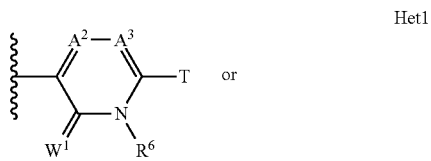

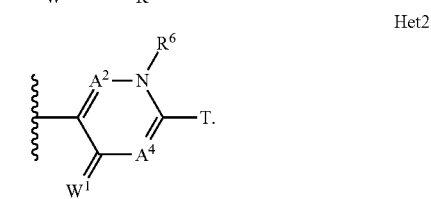

9. The compound according to claim 1, wherein Het represents a group represented by Het1:

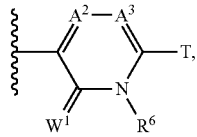

Het1 wherein:
$A^2$ represents $CR^{4a}$,
$A^3$ represents $CR^{4b}$.

10. The compound according to claim 1, wherein Het represents Het1:

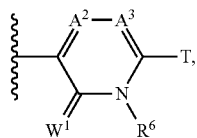

Het1 wherein:
$A^2$ represents $CR^{4a}$,
$A^3$ represents N.

11. The compound according to claim 1, wherein:
(i) T represents a $C_1$-$C_{10}$ hydrocarbon chain, $CH_2OR^1$, $C_2$-$C_5$ alkylene-$OC_1$-$C_5$ alkyl, $C_2$-$C_5$ alkylene-$S(O)_w$—$C_1$-$C_5$ alkyl, $C_1$-$C_3$ alkylene-$C_3$-$C_7$ cycloalkyl, $C(O)R^1$, $C(O)NR^1R^{29}$, $NR^1R^{29}$, $NR^{29}C(O)R^1$, $N=CR^1R^{30}$, $OR^1$, $OS(O)_2R^1$, $S(O)_yR^1$, or $C_3$-$C_7$ cycloalkyl, wherein the $C_1$-$C_{10}$ hydrocarbon chain, $C_2$-$C_5$ alkylene-$OC_1$-$C_5$ alkyl, or $C_2$-$C_5$ alkylene-$S(O)_w$—$C_1$-$C_5$ alkyl is optionally substituted with one or more independently selected halogen substituents, and further wherein the $C_1$-$C_3$ alkylene-$C_3$-$C_7$ cycloalkyl or $C_3$-$C_7$ cycloalkyl is optionally substituted with one or more independently selected Group G substituents; and
$R^1$ represents a $C_1$-$C_{10}$ hydrocarbon chain, $C_2$-$C_5$ alkylene-$OC_1$-$C_5$ alkyl, $C_2$-$C_5$ alkylene-$S(O)_t$—$C_1$-$C_5$ alkyl, $C_1$-$C_3$ alkylene-$C_3$-$C_7$ cycloalkyl, or $C_3$-$C_7$ cycloalkyl, wherein the $C_1$-$C_{10}$ hydrocarbon chain, $C_2$-$C_5$ alkylene-$OC_1$-$C_5$ alkyl or $C_2$-$C_5$ alkylene-$S(O)_t$—$C_1$-$C_5$ alkyl is optionally substituted with one or more independently selected halogen substituents, and further wherein the $C_1$-$C_3$ alkylene-$C_3$-$C_7$ cycloalkyl or $C_3$-$C_7$ cycloalkyl is optionally substituted with one or more independently selected Group G substituents; or
(ii) T represents T-1, T-2, T-3, T-4, T-5, T-6, T-7, T-8, T-9, T-10, T-11, or T-12:

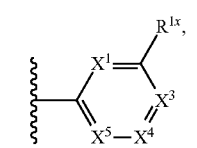

T-1

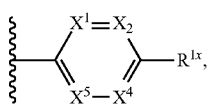

T-2

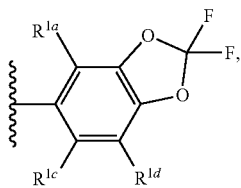

T-3

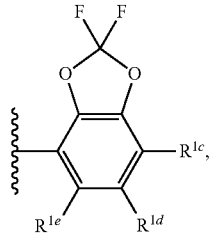

T-4

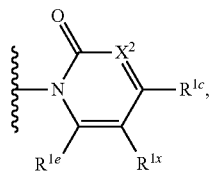

T-5

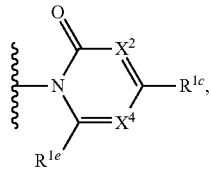

T-6

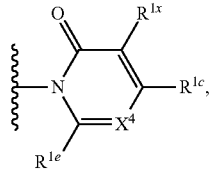

T-7

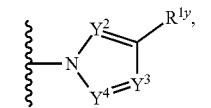

T-8

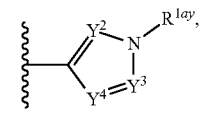

T-9

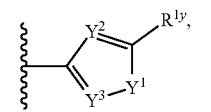

T-10

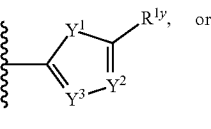

T-11

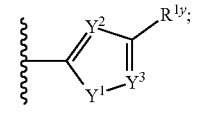

T-12 each Group F substituent independently represents CN, $NH_2$, $NHR^{21}$, $NR^{21}R^{22}$, $OC_1$-$C_6$ alkyl, $C_3$-$C_7$ cycloalkyl, a non-aromatic 3- to 7-membered heterocyclyl, phenyl, or 5- or 6-membered heteroaryl, wherein each $OC_1$-$C_6$ alkyl is optionally and independently substituted with one or more independently selected halogen substituents, and further wherein each $C_3$-$C_7$ cycloalkyl is optionally and independently substituted with one or more independently selected halogen substituents, each non-aromatic 3- to 7-membered heterocyclyl is optionally and independently substituted with one or more independently selected Group C substituents, and each phenyl and 5- or 6-membered heteroaryl is optionally and independently substituted with one or more independently selected Group D substituents; and each Group G substituent independently represents halogen or $C_1$-$C_6$ haloalkyl.

12. The compound according to claim 1, wherein T represents a $C_1$-$C_{10}$ hydrocarbon chain, $C_2$-$C_5$ alkylene-$OC_1$-$C_5$ alkyl, $C_2$-$C_5$ alkylene-$S(O)_w$—$C_1$-$C_5$ alkyl, $C_1$-$C_3$ alkylene-$C_3$-$C_7$ cycloalkyl, $NR^1R^{29}$, $OR^1$, $OS(O)_2R^1$, $S(O)_y R^1$, or $C_3$-$C_7$ cycloalkyl, wherein the $C_1$-$C_{10}$ hydrocarbon chain, $C_2$-$C_5$ alkylene-$OC_1$-$C_5$ alkyl, or $C_2$-$C_5$ alkylene-$S(O)_w$—$C_1$-$C_5$ alkyl is optionally substituted with one or more independently selected halogen substituents, and further wherein the $C_1$-$C_3$ alkylene-$C_3$-$C_7$ cycloalkyl or $C_3$-$C_7$ cycloalkyl is optionally substituted with one or more independently selected Group G substituents.

13. The compound according to claim 1, wherein:
T represents $OR^1$ and
$R^1$ represents a $C_1$-$C_5$ alkyl group, wherein the $C_1$-$C_5$ alkyl is substituted with three or more F substituents.

14. A seed or vegetative reproductive organ comprising an effective amount of the compound according to claim 1.

15. A composition comprising an inert carrier and the compound according to claim 1.

16. A composition comprising the compound according to claim 1 and one or more ingredients selected from the group consisting of a fungicidal ingredient, an insecticidal ingredient, a miticidal ingredient, and a nematicidal ingredient.

17. A method for controlling a harmful arthropod, wherein the method comprises applying to a harmful arthropod or applying to a habitat where the harmful arthropod lives an effective amount of the compound according to claim 1.

18. A method for controlling a harmful arthropod, wherein the method comprises applying to a harmful arthropod or applying to a habitat where the harmful arthropod lives an effective amount of the composition according to claim 15.

* * * * *